United States Patent
Wang et al.

(10) Patent No.: US 12,156,466 B2
(45) Date of Patent: Nov. 26, 2024

(54) ORGANIC ELECTROLUMINESCENT MATERIAL AND DEVICE

(71) Applicant: BEIJING SUMMER SPROUT TECHNOLOGY CO., LTD., Beijing (CN)

(72) Inventors: Qiang Wang, Beijing (CN); Le Wang, Beijing (CN); Junfei Wang, Beijing (CN); Chi Yuen Raymond Kwong, Beijing (CN); Chuanjun Xia, Beijing (CN)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 893 days.

(21) Appl. No.: 17/103,151

(22) Filed: Nov. 24, 2020

(65) Prior Publication Data
US 2021/0167297 A1 Jun. 3, 2021

(30) Foreign Application Priority Data

Nov. 29, 2019 (CN) .......................... 201911201966.0
Apr. 13, 2020 (CN) .......................... 202010270250.2

(51) Int. Cl.
*H10K 85/60* (2023.01)
*C07D 487/16* (2006.01)
(Continued)

(52) U.S. Cl.
CPC ....... *H10K 85/6572* (2023.02); *C07D 487/16* (2013.01); *C09K 11/02* (2013.01);
(Continued)

(58) Field of Classification Search
CPC ............. H10K 85/6572; H10K 85/342; H10K 2101/10; H10K 50/11; H10K 2211/1007;
(Continued)

(56) References Cited

U.S. PATENT DOCUMENTS 5,703,436 A 12/1997 Forrest et al.
5,707,745 A 1/1998 Forrest et al.
(Continued)

FOREIGN PATENT DOCUMENTS

CN 108391433 8/2018
JP 2019529340 10/2019
(Continued)

OTHER PUBLICATIONS

Nagata, R. et al. "Organic Light-Emitting Diodes (OLEDs): Materials, Photophysics, and Device Physics" in "Organic Electronics Materials and Devices" ed. S. Ogawa. pp. 73-118 (Year: 2024).*
(Continued)

*Primary Examiner* — Michael M Dollinger
*Assistant Examiner* — Christina H. W. Rosebach
(74) *Attorney, Agent, or Firm* — Workman Nydegger

(57) ABSTRACT

Provided are an organic electroluminescent material and a device comprising the same. The organic electroluminescent material is a novel compound having a parent core structure formed by fusing indole and pyrrole with an azamacrocycle and bonded with benzoquinazoline or benzoquinoxaline and similar structures thereof. The organic electroluminescent material may be used as a host material in an electroluminescent device. The novel compound can provide better device performance in the electroluminescent device. Further provided are an electroluminescent device and a compound formulation.

26 Claims, 2 Drawing Sheets

(51) Int. Cl.
  *C09K 11/02* (2006.01)
  *C09K 11/06* (2006.01)
  *H10K 85/30* (2023.01)
  *H10K 50/11* (2023.01)
  *H10K 101/10* (2023.01)

(52) U.S. Cl.
  CPC ............ *C09K 11/06* (2013.01); *H10K 85/342* (2023.02); *C09K 2211/1007* (2013.01); *C09K 2211/1029* (2013.01); *C09K 2211/185* (2013.01); *H10K 50/11* (2023.02); *H10K 2101/10* (2023.02)

(58) Field of Classification Search
  CPC ...... H10K 2211/1029; H10K 2211/185; C07D 487/16; C09K 11/02; C09K 11/06; C09K 2211/1007; C09K 2211/1029; C09K 2211/185
  See application file for complete search history.

(56) References Cited

U.S. PATENT DOCUMENTS

| | | | |
|---|---|---|---|
| 5,844,363 | A | 12/1998 | Gu et al. |
| 6,097,147 | A | 8/2000 | Baldo et al. |
| 6,303,238 | B1 | 10/2001 | Thompson et al. |
| 7,279,704 | B2 | 10/2007 | Walters et al. |
| 7,968,146 | B2 | 6/2011 | Wagner et al. |
| 2003/0230980 | A1 | 12/2003 | Forrest et al. |
| 2004/0174116 | A1 | 9/2004 | Lu et al. |
| 2015/0349273 | A1 | 12/2015 | Hung et al. |
| 2016/0359122 | A1 | 12/2016 | Boudreault et al. |
| 2018/0175306 | A1 | 6/2018 | Dyatkin et al. |
| 2018/0269405 | A1* | 9/2018 | Mun ............... H10K 85/657 |
| 2018/0337340 | A1* | 11/2018 | Moon ............. C07D 487/16 |

FOREIGN PATENT DOCUMENTS

| | | | |
|---|---|---|---|
| KR | 20150077220 | 7/2015 | |
| KR | 20170066241 | 6/2017 | |
| KR | 20180008336 | 1/2018 | |
| KR | 20180012709 | 2/2018 | |
| KR | 20190088624 | 7/2019 | |
| WO | WO2017095156 | 6/2017 | |
| WO | WO2019143184 | 7/2019 | |
| WO | WO-2020032424 A1 * | 2/2020 | ......... H01L 51/0071 |

OTHER PUBLICATIONS

Translation of WO 2020032424 A1 by Park et al. (Year: 2020).*
Chinese Second Office Action for Chinese Application No. 202010270250.2, dated Apr. 7, 2022, 12 pages with translation.
Japanese Notice of Reasons for Refusal for Japanese Application No. 2020-198355, dated May 10, 2022, 6 pages with English translation.
Korean Written Opinion for Korean Application No. 10-2020-0163107 dated Sep. 19, 2022, 21 pages with English translation.
Joyama et al., "Highly efficient organic light-emitting diodes from delayed fluorescence" Nature vol. 492, (Dec. 13, 2012), pp. 234-238.
Chinese Office Action cited in Application No. or Publication No. 202010270250.2 dated Nov. 3, 2021.
Search Report issued in Application No. 2020102702502 dated Apr. 13, 2020.
Germany Office Action issued in 102020131491.4 dated Mar. 5, 2021.
Japanese Office Action issued in 2020-198355 dated Oct. 18, 2021.
Tang, C.W., et al., "Organic electroluminescent diodes", Applied Physics Letters, accepted for publication Jul. 20, 1987.

* cited by examiner

ORGANIC ELECTROLUMINESCENT MATERIAL AND DEVICE

CROSS-REFERENCE TO RELATED APPLICATION(S)

This application claims priority to Chinese Patent Application No. CN 201911201966.0 filed on Nov. 29, 2019 and Chinese Patent Application No. CN 202010270250.2 filed on Apr. 13, 2020, the disclosures of which are incorporated herein by reference in their entirety.

TECHNICAL FIELD

The present disclosure relates to compounds for organic electronic devices, for example, organic electroluminescent devices. More particularly, the present disclosure relates to a novel compound with a parent core structure formed by fusing indole and pyrrole with an azamacrocycle and bonded with benzoquinazoline or benzoquinoxaline and similar structures thereof, and an organic electroluminescent device and a compound formulation containing the compound.

BACKGROUND

Organic electronic devices include, but are not limited to, the following types: organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12): 913-915). Once a bias is applied to the device, green light was emitted from the device. This device laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since the OLED is a self-emitting solid state device, it offers tremendous potential for display and lighting applications. In addition, the inherent properties of organic materials, such as their flexibility, may make them well suited for particular applications such as fabrication on flexible substrates.

The OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of the fluorescent OLED is only 25%. This limitation hindered the commercialization of OLED. In 1997, Forrest and Thompson reported phosphorescent OLED, which uses triplet emission from heavy metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. A small molecule refers to any organic or organometallic material that is not a polymer. The molecular weight of the small molecule can be large as long as it has well defined structure. Dendrimers with well-defined structures are considered as small molecules. Polymer OLEDs include conjugated polymers and non-conjugated polymers with pendant emitting groups. Small molecule OLED can become the polymer OLED if post polymerization occurred during the fabrication process.

There are various methods for OLED fabrication. Small molecule OLEDs are generally fabricated by vacuum thermal evaporation. Polymer OLEDs are fabricated by solution process such as spin-coating, inkjet printing, and slit printing. If the material can be dissolved or dispersed in a solvent, the small molecule OLED can also be produced by solution process.

The emitting color of the OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent device still suffers from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime.

US20180337340A1 has disclosed an organic electroluminescent compound and an organic electroluminescent device containing the same, which includes an organic layer containing one or more hosts, where a first host is an organic optical compound having the following structure:

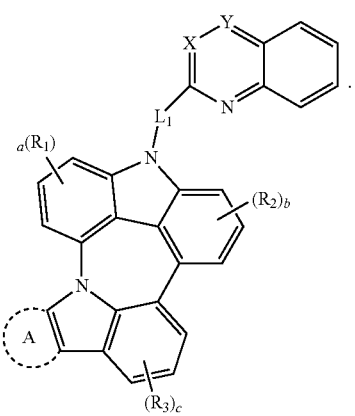

However, the disclosed compound must have a structural unit of quinazoline or quinoxaline, and no organic compound including a structural unit of benzoquinazoline or benzoquinoxaline and similar structures thereof has been disclosed and instructed.

However, various host materials reported so far are still need to be further improved. In order to meet the increasing requirements of the industry, a novel material still needs to be further researched and developed.

SUMMARY

The present disclosure aims to provide a novel compound having a parent core that has an indole- and pyrrole-fused azamacrocycle structure and is bonded with benzoquinazoline or benzoquinoxaline and similar structures thereof, so as to solve at least part of the above-mentioned problems. The novel compound can serve as a host material in an electroluminescent device, provide an electroluminescent device with better device performance, such as higher efficiency/lifetime. The present disclosure discloses a bipolar compound with a novel structure, where the compound has an electron transporting unit comprising benzoquinazoline or benzoquinoxaline and a hole transporting unit formed by fusing indole and pyrrole with an azamacrocycle. The compound exhibits unexpectedly excellent characteristics in the balance of hole and electron transport and higher efficiency in a device, so that the device can provide better device performance.

According to an embodiment of the present disclosure, disclosed is a compound having a structure of H-L$_1$-E;

wherein H has a structure represented by Formula 1:

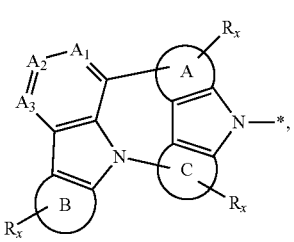

Formula 1 in Formula 1, A$_1$, A$_2$ and A$_3$ are, at each occurrence identically or differently, selected from CR; and the ring A, the ring B and the ring C are, at each occurrence identically or differently, selected from an aromatic ring having 6 to 18 carbon atoms or a hetero-aromatic ring having 3 to 18 carbon atoms;

R$_x$ represents mono-substitution, multiple substitutions or non-substitution; and adjacent substituents R, R$_x$ can be optionally joined to form a ring;

wherein E has a structure represented by Formula 2:

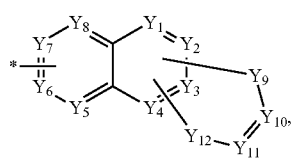

Formula 2 wherein Y$_1$ to Y$_{12}$ are, at each occurrence identically or differently, selected from N, C or CR$_y$; and any two of Y$_5$ to Y$_8$ are selected from nitrogen, the other two of Y$_5$ to Y$_8$ are selected from C or CR$_y$, respectively; and any adjacent two of Y$_1$ to Y$_4$ are C and joined to Y$_9$ and Y$_{12}$, respectively;

L$_1$ is selected from a single bond, substituted or unsubstituted arylene having 6 to 30 carbon atoms, substituted or unsubstituted heteroarylene having 3 to 30 carbon atoms or combinations thereof;

wherein R, R$_x$ and R$_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

According to an embodiment of the present disclosure, further disclosed is an electroluminescent device, including:
an anode,
a cathode, and
an organic layer disposed between the anode and the cathode, wherein the organic layer comprises a compound having a structure of H-L$_1$-E;

wherein H has a structure represented by Formula 1:

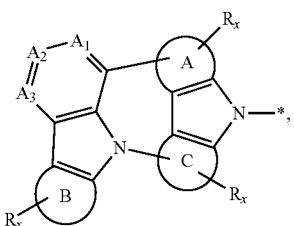

Formula 1 in Formula 1, A$_1$, A$_2$ and A$_3$ are, at each occurrence identically or differently, selected from CR; and the ring A, the ring B and the ring C are, at each occurrence identically or differently, selected from an aromatic ring having 6 to 18 carbon atoms or a hetero-aromatic ring having 3 to 18 carbon atoms;

R$_x$ represents mono-substitution, multiple substitutions or non-substitution; and adjacent substituents R, R$_x$ can be optionally joined to form a ring;

wherein E has a structure represented by Formula 2:

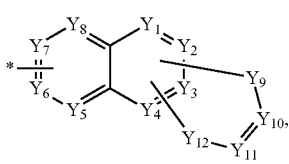

Formula 2 wherein $Y_1$ to $Y_{12}$ are, at each occurrence identically or differently, selected from N, C or $CR_y$; and any two of $Y_5$ to $Y_8$ are selected from nitrogen, the other two of $Y_5$ to $Y_8$ are selected from C or $CR_y$, respectively; and any adjacent two of $Y_1$ to $Y_4$ are C and joined to $Y_9$ and $Y_{12}$, respectively;

$L_1$ is selected from a single bond, substituted or unsubstituted arylene having 6 to 30 carbon atoms, substituted or unsubstituted heteroarylene having 3 to 30 carbon atoms or combinations thereof;

wherein R, $R_x$ and $R_y$ are, at each occurrence identically or differently, selected from the group consisting of hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

According to an embodiment of the present disclosure, further disclosed is a compound formulation comprising the compound having a structure of H-$L_1$-E.

The present disclosure discloses a novel compound that has a parent core having an indole- and pyrrole-fused azamacrocycle structure and bonded with benzoquinazoline or benzoquinoxaline and similar structures thereof. The novel compound can serve as the host material in the electroluminescent device, provide electroluminescent devices with better device performance, such as higher efficiency/lifetime.

DETAILED DESCRIPTION

Figure 1:
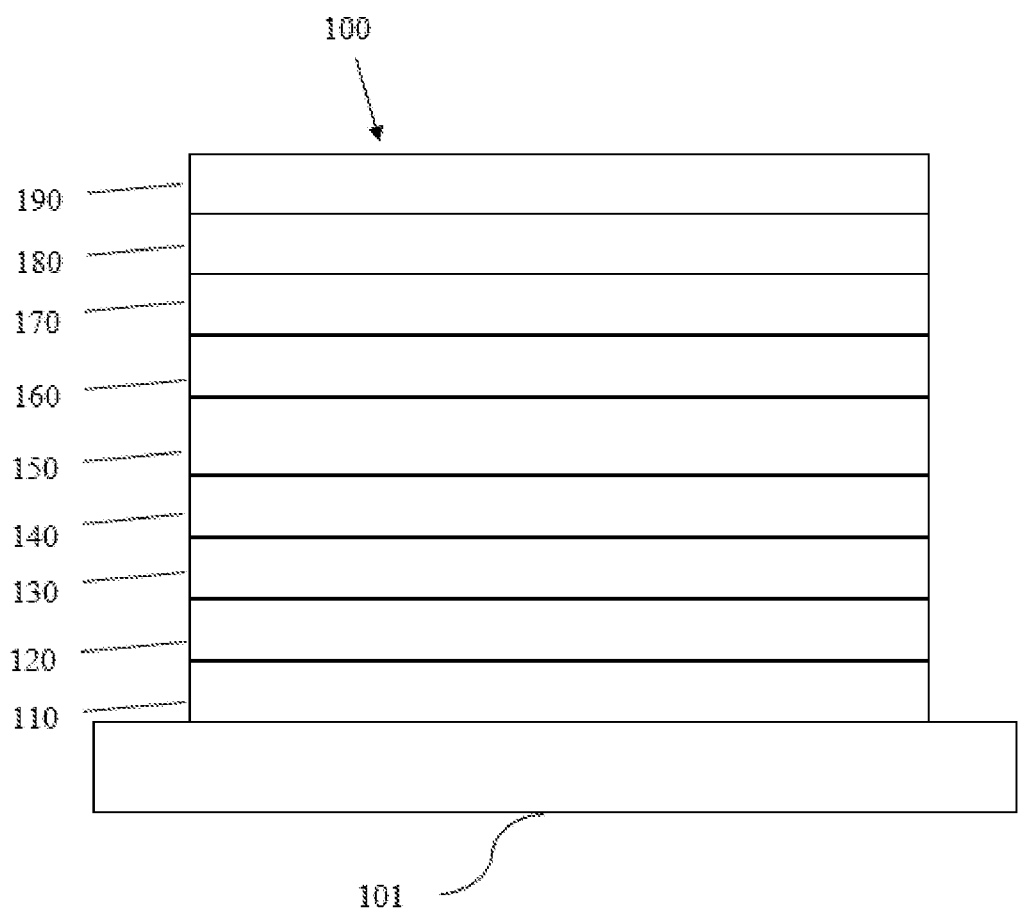
FIG. 1 is a schematic diagram of an organic light-emitting apparatus that may include a compound and a compound formulation disclosed by the present disclosure.

OLEDs can be fabricated on various types of substrates such as glass, plastic, and metal foil. FIG. 1 schematically shows the organic light emitting device 100 without limitation. The figures are not necessarily drawn to scale. Some of the layers in the figures can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, the contents of which are incorporated by reference herein in its entirety.

More examples for each of these layers are available. For example, a flexible and transparent substrate-anode combination is disclosed in U.S. Pat. No. 5,844,363, which is incorporated by reference herein in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference herein in its entirety. Examples of host materials are disclosed in U.S. Pat. No. 6,303,238 to Thompson et al., which is incorporated by reference herein in its entirety. An example of an n-doped electron transport layer is BPhen doped with Li at a molar ratio of 1:1, as disclosed in U.S. Patent Application Publication No. 2003/0230980, which is incorporated by reference herein in its entirety. U.S. Pat. Nos. 5,703,436 and 5,707,745, which are incorporated by reference herein in their entireties, disclose examples of cathodes including composite cathodes having a thin layer of metal such as Mg:Ag with an overlying transparent, electrically-conductive, sputter-deposited ITO layer. The theory and use of blocking layers are described in more detail in U.S. Pat. No. 6,097,147 and U.S. Patent Application Publication No. 2003/0230980, which are incorporated by reference herein in their entireties. Examples of injection layers are provided in U.S. Patent Application Publication No. 2004/0174116, which is incorporated by reference herein in its entirety. A description of protective layers may be found in U.S. Patent Application Publication No. 2004/0174116, which is incorporated by reference herein in its entirety.

The layered structure described above is provided by way of non-limiting example. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have two layers of different emitting materials to achieve desired emission spectrum.

In one embodiment, an OLED may be described as having an "organic layer" disposed between a cathode and an anode. This organic layer may comprise a single layer or multiple layers.

Figure 2:
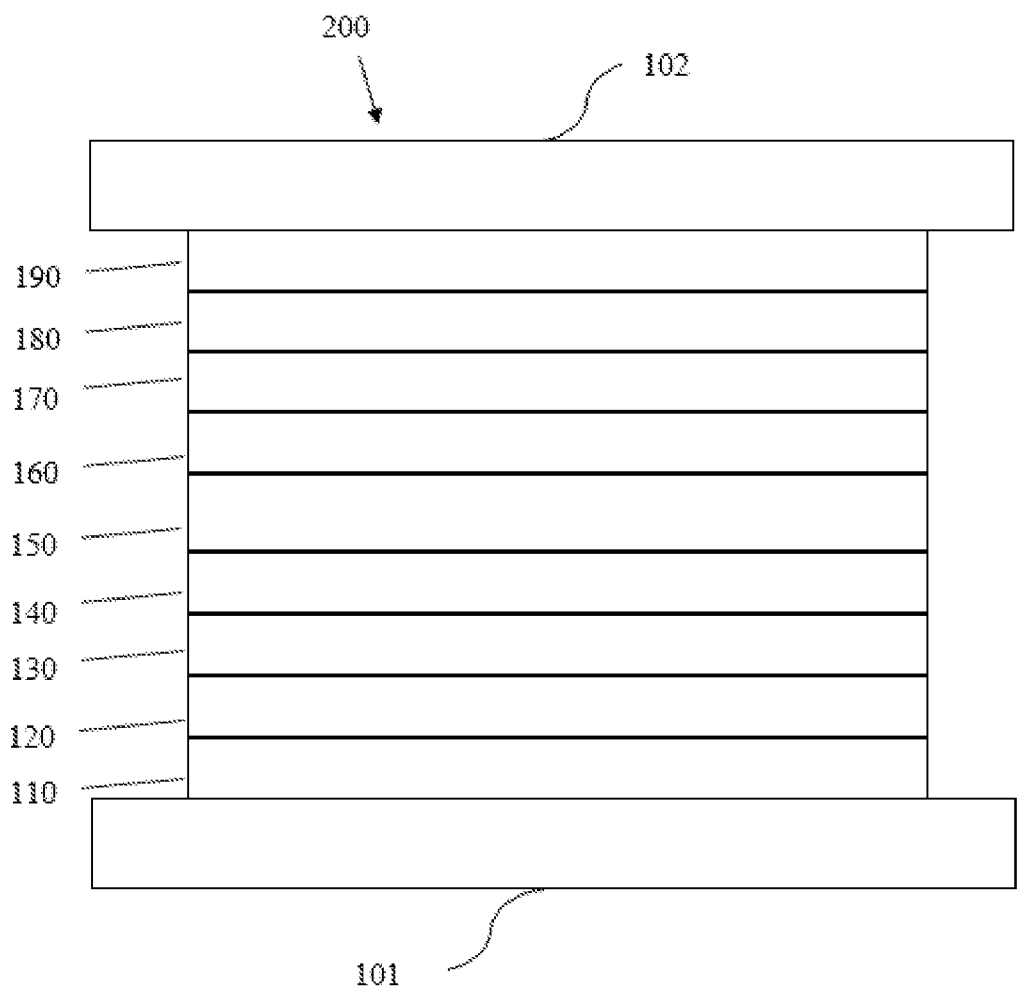
FIG. 2 is a schematic diagram of another organic light-emitting apparatus that may include a compound and a compound formulation disclosed by the present disclosure.

An OLED can be encapsulated by a barrier layer. FIG. 2 schematically shows the organic light emitting device 200 without limitation. FIG. 2 differs from FIG. 1 in that the organic light emitting device include a barrier layer 102, which is above the cathode 190, to protect it from harmful species from the environment such as moisture and oxygen. Any material that can provide the barrier function can be used as the barrier layer such as glass and organic-inorganic hybrid layers. The barrier layer should be placed directly or indirectly outside of the OLED device. Multilayer thin film encapsulation was described in U.S. Pat. No. 7,968,146, which is herein incorporated by reference in its entirety.

Devices fabricated in accordance with embodiments of the present disclosure can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small $\Delta E_{S-T}$. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents

Halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, and 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing 2 to 15 carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing 2 to 15 carbon atoms. Additionally, the alkynyl group may be optionally substituted.

Aryl or aromatic group—as used herein includes noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein includes aromatic and non-aromatic cyclic groups. Heteroaromatic also means heteroaryl. Preferred non-aromatic heterocyclic groups are those containing 3 to 7 ring atoms which include at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein includes noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro-2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline, dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

In the present disclosure, unless otherwise defined, when any term of the group consisting of substituted alkyl, substituted cycloalkyl, substituted heteroalkyl, substituted aralkyl, substituted alkoxy, substituted aryloxy, substituted alkenyl, substituted aryl, substituted heteroaryl, substituted alkylsilyl, substituted arylsilyl, substituted amine, substituted acyl, substituted carbonyl, substituted carboxylic acid group, substituted ester group, substituted sulfinyl, substituted sulfonyl and substituted phosphino is used, it means that any group of alkyl, cycloalkyl, heteroalkyl, aralkyl, alkoxy, aryloxy, alkenyl, aryl, heteroaryl, alkylsilyl, arylsilyl, amine, acyl, carbonyl, carboxylic acid group, ester group, sulfinyl, sulfonyl and phosphino may be substituted with one or more groups selected from the group consisting of deuterium, halogen, an unsubstituted alkyl group having 1 to 20 carbon atoms, an unsubstituted cycloalkyl group having 3 to 20 ring carbon atoms, an unsubstituted heteroalkyl group having 1 to 20 carbon atoms, an unsubstituted aralkyl group having 7 to 30 carbon atoms, an unsubstituted alkoxy group having 1 to 20 carbon atoms, an unsubstituted aryloxy group having 6 to 30 carbon atoms, an unsubstituted alkenyl group having 2 to 20 carbon atoms, an unsubstituted aryl group having 6 to 30 carbon atoms, an unsubstituted heteroaryl group having 3 to 30 carbon atoms, an unsubstituted alkylsilyl group having 3 to 20 carbon atoms, an unsubstituted arylsilyl group having 6 to 20 carbon atoms, an unsubstituted amino group having 0 to 20 carbon atoms, an acyl group, a carbonyl group, a carboxylic acid group, an ester group, a cyano group, an isocyano group, a sulfanyl group, a sulfinyl group, a sulfonyl group and a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, multiple substitutions refer to a range that includes a double substitution, up to the maximum available substitutions. When a substitution in the compounds mentioned in this disclosure represents multiple substitutions (including di, tri, tetra substitutions etc.), that means the substituent may exist at a plurality of available substitution positions on its linking structure, the substituents present at a plurality of available substitution positions may be the same structure or different structures.

In the compounds mentioned in the present disclosure, adjacent substituents in the compounds cannot be joined to form a ring unless otherwise explicitly defined, for example, adjacent substituents can be optionally joined to form a ring.

In the compounds mentioned in the present disclosure, adjacent substituents can be optionally joined to form a ring, including the case where adjacent substituents can be connected to form a ring, and the case where adjacent substituents are not connected to form a ring. When adjacent substituents can be optionally joined to form a ring, the ring formed may be monocyclic or polycyclic, as well as alicyclic, heteroalicyclic, aromatic or heteroaromatic. In such expression, adjacent substituents may refer to substituents bonded to the same atom, substituents bonded to carbon atoms which are directly bonded to each other, or substituents bonded to carbon atoms which are more distant from each other. Preferably, adjacent substituents refer to substituents bonded to the same carbon atom and substituents bonded to carbon atoms which are directly bonded to each other.

The expression that adjacent substituents can be optionally joined to form a ring is also intended to mean that two substituents bonded to the same carbon atom are joined to each other via a chemical bond to form a ring, which can be exemplified by the following formula:

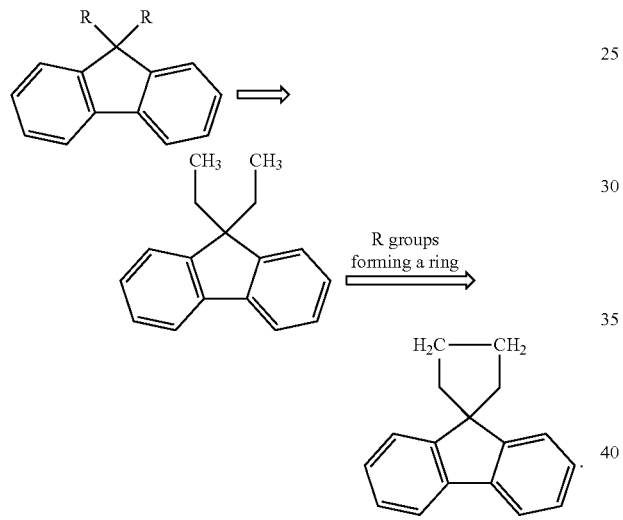

The expression that adjacent substituents can be optionally joined to form a ring is also intended to mean that two substituents bonded to carbon atoms which are directly bonded to each other are joined to each other via a chemical bond to form a ring, which can be exemplified by the following formula:

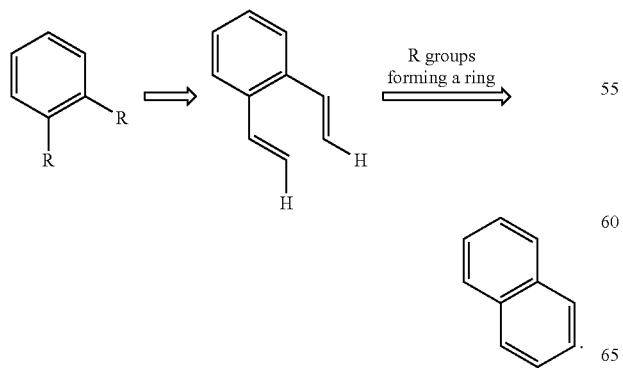

Furthermore, the expression that adjacent substituents can be optionally joined to form a ring is also intended to mean that, in the case where one of the two substituents bonded to carbon atoms which are directly bonded to each other represents hydrogen, the second substituent is bonded at a position at which the hydrogen atom is bonded, thereby forming a ring. This is exemplified by the following formula:

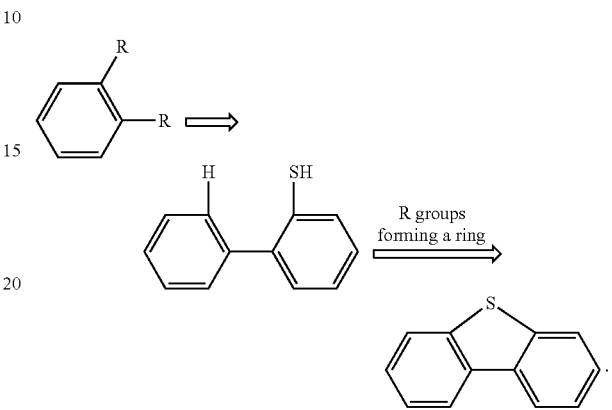

According to an embodiment of the present disclosure, disclosed is a compound having a structure of H-L$_1$-E;

wherein H has a structure represented by Formula 1:

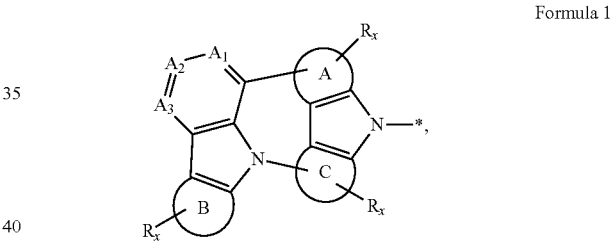

Formula 1 in Formula 1, A$_1$, A$_2$ and A$_3$ are, at each occurrence identically or differently, selected from CR; and the ring A, the ring B and the ring C are, at each occurrence identically or differently, selected from an aromatic ring having 6 to 18 carbon atoms or a hetero-aromatic ring having 3 to 18 carbon atoms;

R$_x$ represents, at each occurrence identically or differently, mono-substitution, multiple substitutions or non-substitution;

adjacent substituents R, R$_x$ can be optionally joined to form a ring;

wherein E has a structure represented by Formula 2:

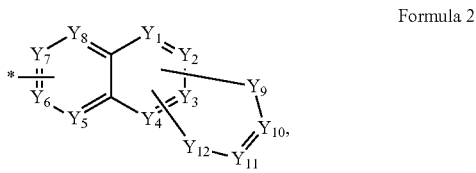

Formula 2 wherein Y$_1$ to Y$_{12}$ are, at each occurrence identically or differently, selected from N, C or CR$_y$; and any two of Y$_5$ to Y$_8$ are selected from nitrogen, the other two of Y$_5$ to $Y_8$ are selected from C or $CR_y$, respectively; and any adjacent two of $Y_1$ to $Y_4$ are C and joined to $Y_9$ and $Y_{12}$, respectively;

$L_1$ is selected from a single bond, substituted or unsubstituted arylene having 6 to 30 carbon atoms, substituted or unsubstituted heteroarylene having 3 to 30 carbon atoms or combinations thereof;

wherein R, $R_x$ and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

In this embodiment, the expression that adjacent substituents R, $R_x$ can be optionally joined to form a ring is intended to mean that adjacent substituents R can be optionally joined to form a ring; also intended to mean that when multiple $R_x$ are present on the ring A, adjacent substituents $R_x$ can be optionally joined to form a ring; also intended to mean that when multiple $R_x$ are present on the ring B, adjacent substituents $R_x$ can be optionally joined to form a ring; also intended to mean that when multiple $R_x$ are present on the ring C, adjacent substituents $R_x$ can be optionally joined to form a ring; and, also intended to mean that adjacent substituents R and $R_x$ can be optionally joined to form a ring. It is obvious for those skilled in the art that adjacent substituents R, $R_x$ may not be joined to form a ring. In this case, adjacent substituents R are not joined to form a ring, and/or adjacent substituents $R_x$ are not joined to form a ring, and/or adjacent substituents R and $R_x$ are also not joined to form a ring.

According to an embodiment of the present disclosure, wherein the H has a structure represented by Formula 1-a:

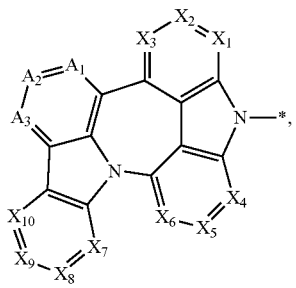

Formula 1-a wherein $A_1$ to $A_3$ are, at each occurrence identically or differently, selected from CR; and $X_1$ to $X_{10}$ are, at each occurrence identically or differently, selected from $CR_x$; wherein R and $R_x$ are, at each occurrence identically or differently, selected from the group consisting of hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group, and combinations thereof; and wherein adjacent substituents R, $R_x$ can be optionally joined to form a ring.

In this embodiment, the expression that adjacent substituents R, $R_x$ can be optionally joined to form a ring is intended to mean that adjacent substituents R can be optionally joined to form a ring; also intended to mean that adjacent substituents $R_x$ in $X_1$ to $X_3$ can be optionally joined to form a ring; also intended to mean that adjacent substituents $R_x$ in $X_4$ to $X_6$ can be optionally joined to form a ring; also intended to mean that adjacent substituents $R_x$ in $X_7$ to $X_{10}$ can be optionally joined to form a ring; and, also intended to mean that adjacent substituents $R_x$, R and $R_x$ can be optionally joined to form a ring. For example, adjacent substituents in $A_1$ and $X_3$, and/or $A_3$ and $X_{10}$, and/or $X_6$ and $X_7$ can be optionally joined to form a ring. It is obvious for those skilled in the art that adjacent substituents R and $R_x$ may not be joined to form a ring. In this case, adjacent substituents R are not joined to form a ring, and/or adjacent substituents $R_x$ are not joined to form a ring, and/or adjacent substituents R and $R_x$ are also not joined to form a ring.

According to an embodiment of the present disclosure, in the Formula 1-a, R and $R_x$ are, at each occurrence identically or differently, selected from the group consisting of hydrogen, deuterium, halogen, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a sulfanyl group and combinations thereof; and adjacent substituents R, $R_x$ can be optionally joined to form a ring.

In this embodiment, the expression that adjacent substituents R, $R_x$ can be optionally joined to form a ring is intended to mean that adjacent substituents R can be optionally joined to form a ring; also intended to mean that adjacent substituents $R_x$ in $X_1$ to $X_3$ can be optionally joined to form a ring; also intended to mean that adjacent substituents $R_x$ in $X_4$ to $X_6$ can be optionally joined to form a ring; also intended to mean that adjacent substituents $R_x$ in $X_7$ to $X_{10}$ can be optionally joined to form a ring; and, also intended to mean that adjacent substituents $R_x$, R and $R_x$ can be optionally joined to form a ring. For example, adjacent substituents in $A_1$ and $X_3$, and/or $A_3$ and $X_{10}$, and/or $X_6$ and $X_7$ can be optionally joined to form a ring. It is obvious for those skilled in the art that adjacent substituents R and $R_x$ may not be joined to form a ring. In this case, adjacent substituents R are not joined to form a ring, and/or adjacent substituents $R_x$ are not joined to form a ring, and/or adjacent substituents R and $R_x$ are also not joined to form a ring.

According to an embodiment of the present disclosure, in the Formula 1-a, at least one of R and $R_x$ is selected from deuterium, substituted or unsubstituted aryl having 6 to 30 carbon atoms, or substituted or unsubstituted heteroaryl having 3 to 30 carbon atoms.

According to an embodiment of the present disclosure, in the Formula 1-a, at least one of R and $R_x$ is selected from deuterium, phenyl, biphenyl or pyridyl.

According to an embodiment of the present disclosure, in the Formula 1-a, for adjacent substituents R in $A_1$ to $A_3$, adjacent substituents $R_x$ in $X_1$ to $X_3$, adjacent substituents $R_x$ in $X_4$ to $X_6$, and adjacent substituents $R_x$ in $X_7$ to $X_{10}$, at least one of these groups of adjacent substituents is joined to form a ring.

In this embodiment, the expression that at least one group of these groups of adjacent substituents is joined to form a ring is intended to mean that for groups of adjacent substituents present in Formula 1-a, for example, two adjacent substituents R in $A_1$ and $A_2$, two adjacent substituents R in $A_2$ and $A_3$, two adjacent substituents $R_x$ in $X_1$ and $X_2$, two adjacent substituents $R_x$ in $X_2$ and $X_3$, two adjacent substituents $R_x$ in $X_4$ and $X_5$, two adjacent substituents $R_x$ in $X_5$ and $X_6$, two adjacent substituents $R_x$ in $X_7$ and $X_8$, two adjacent substituents $R_x$ in $X_8$ and $X_9$, and two adjacent substituents $R_x$ in $X_9$ and $X_{10}$, at least one group of these groups of substituents is joined to form a ring.

According to an embodiment of the present disclosure, the H is selected from the group consisting of the following structures:

H-1

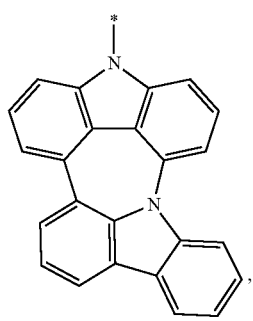

H-2

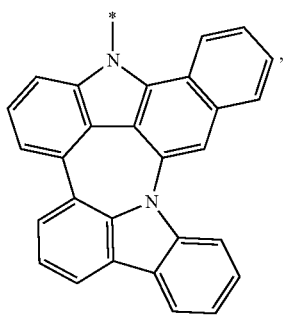

H-3

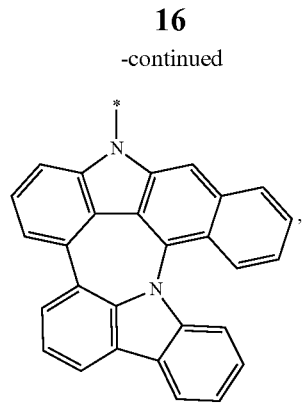

H-4

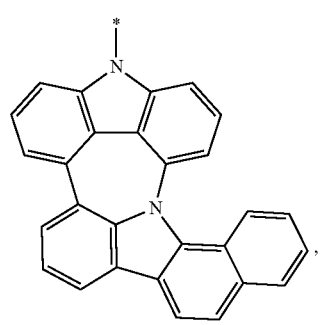

H-5

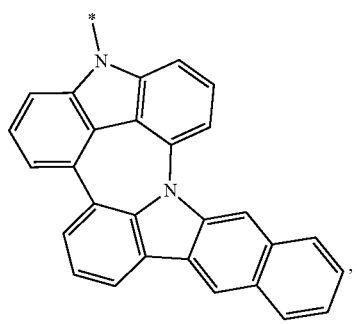

H-6

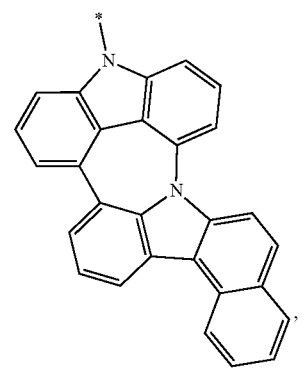

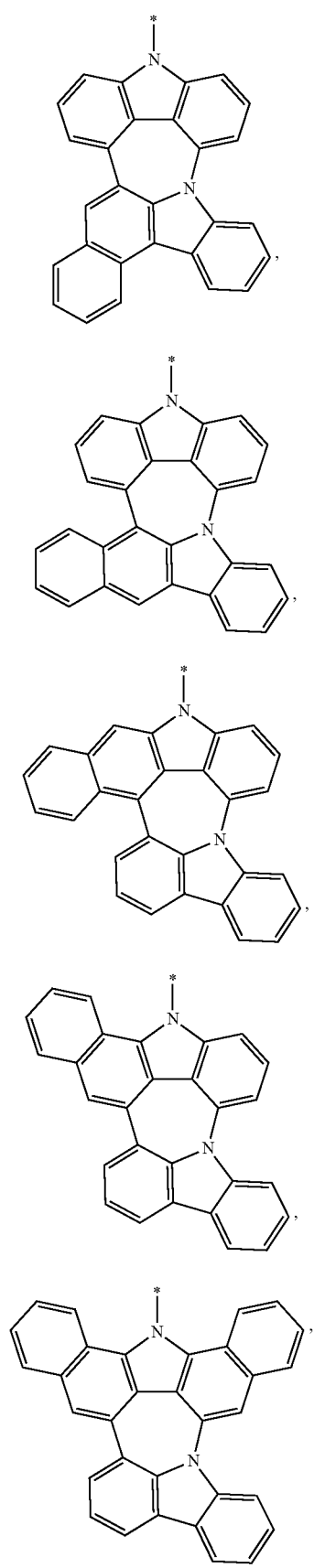
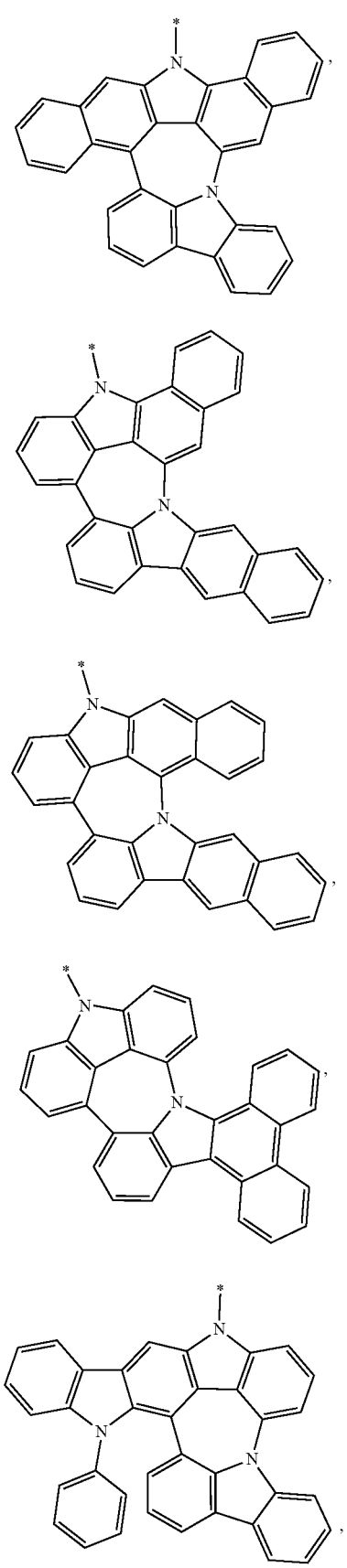

H-17
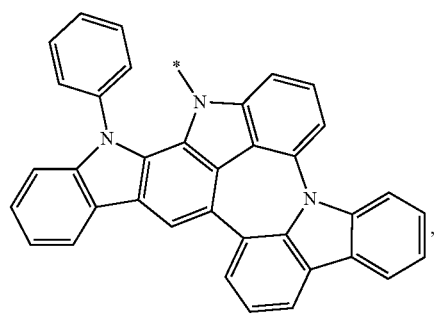
H-18
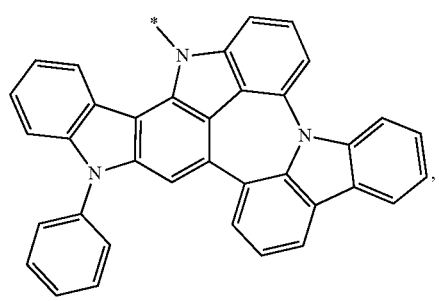
H-19
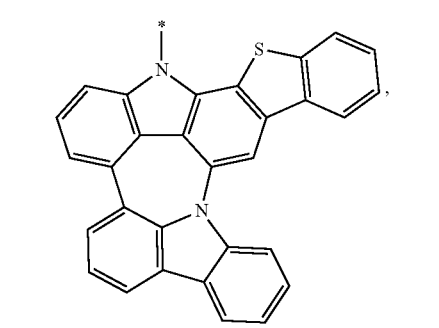
H-20
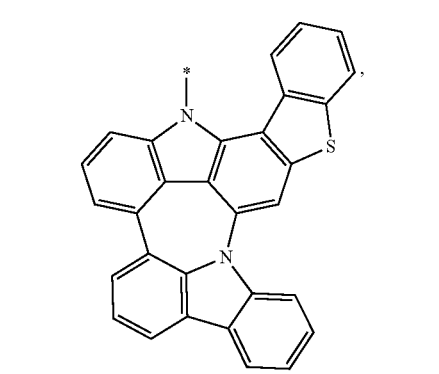
H-21
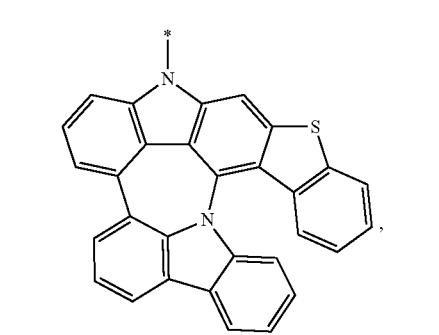
H-22
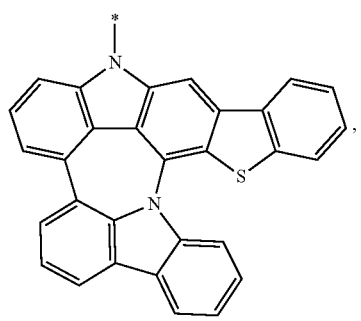
H-23
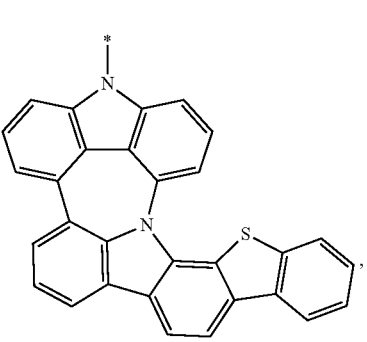
H-24
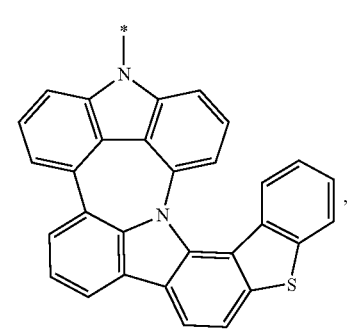
H-25
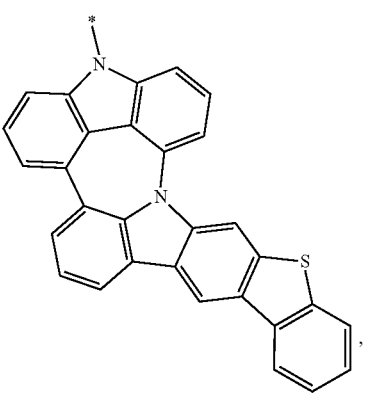

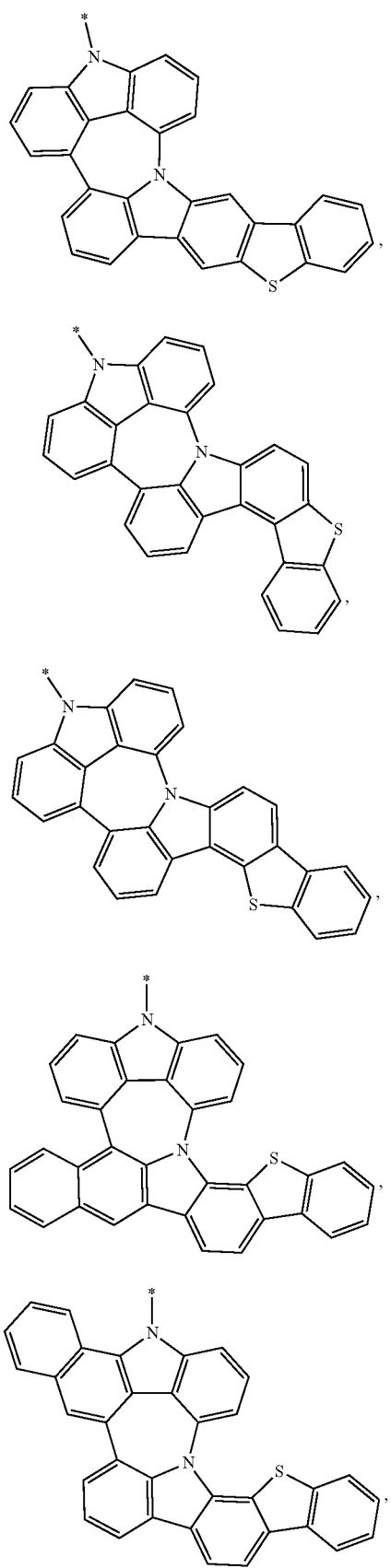
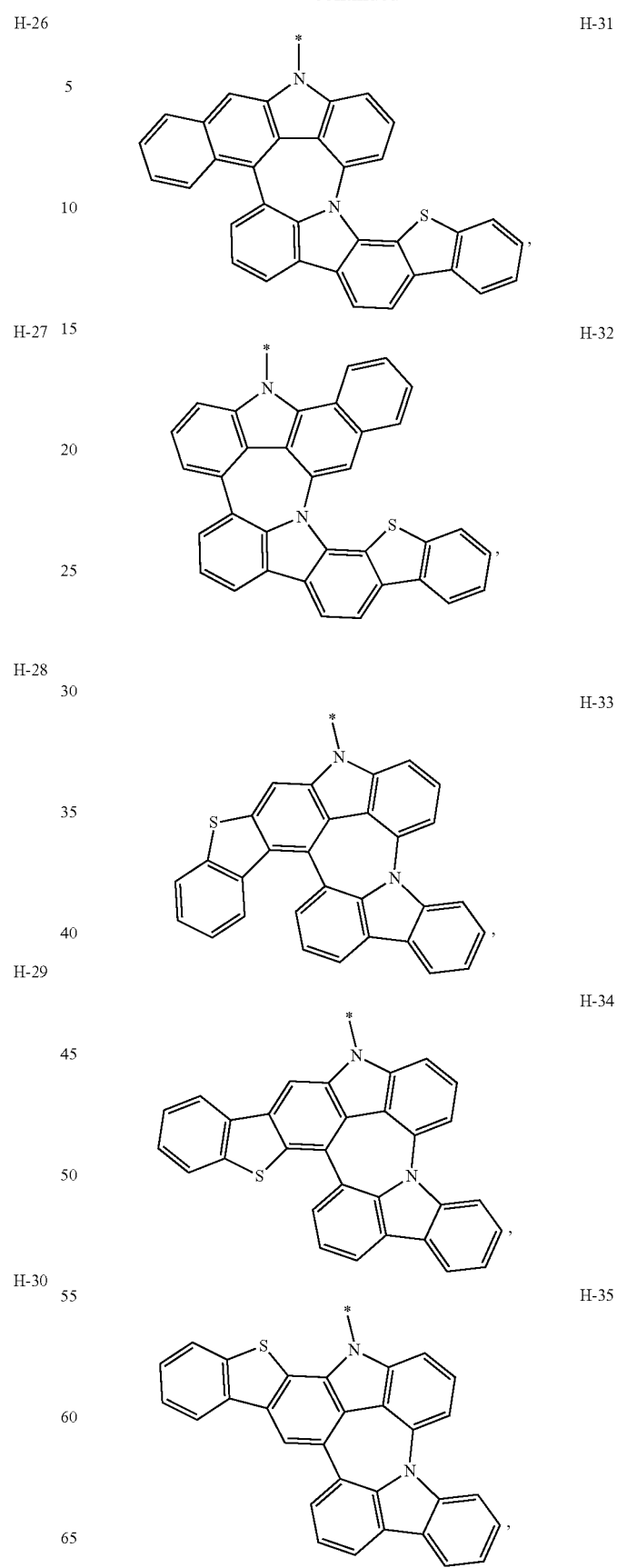

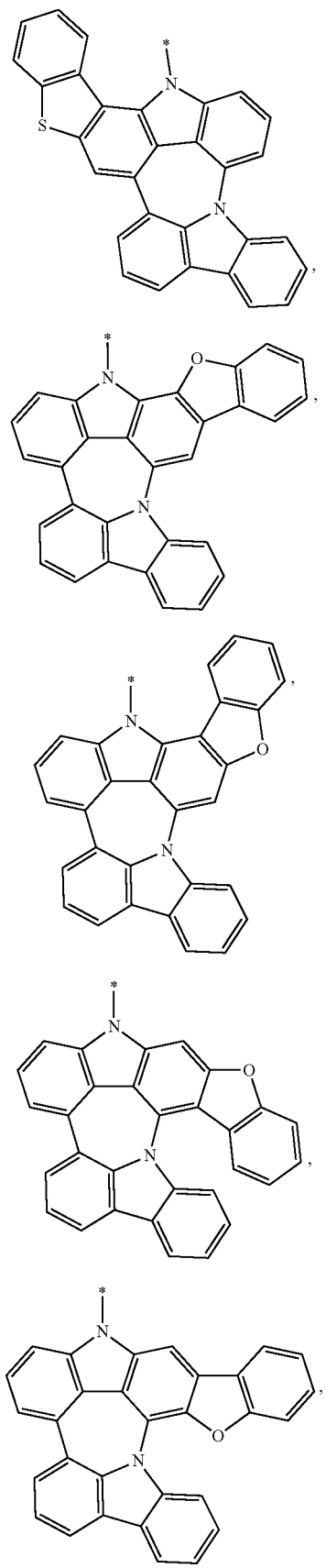
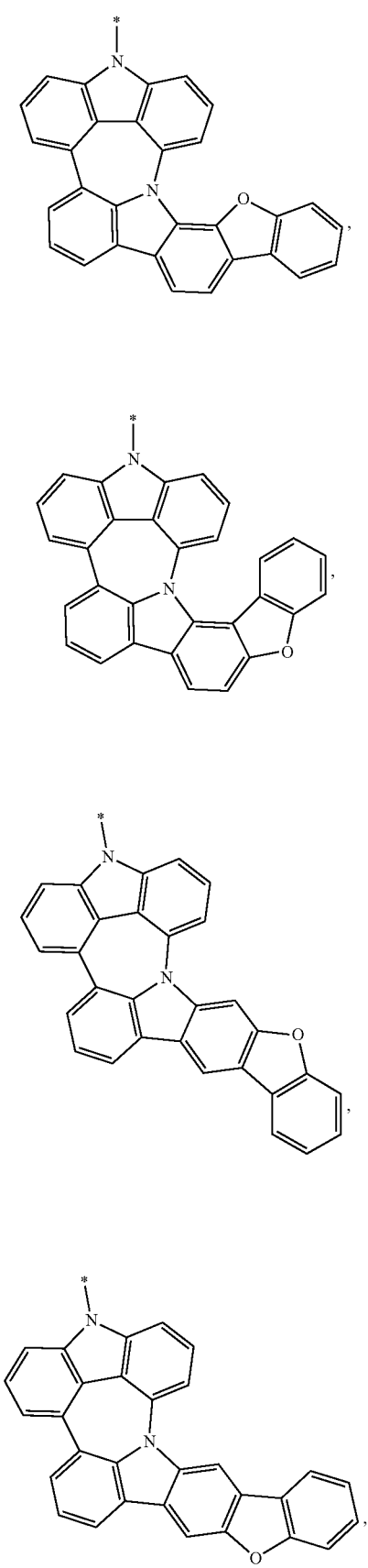

H-45
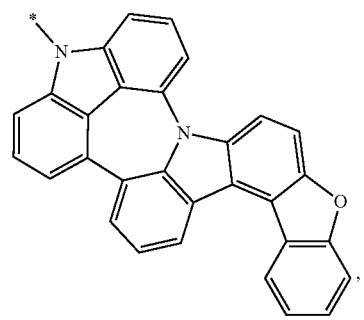
H-46
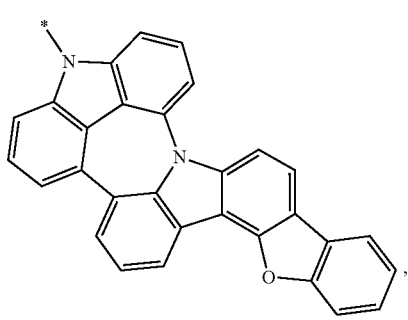
H-47
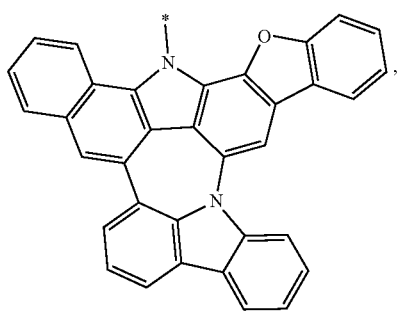
H-48
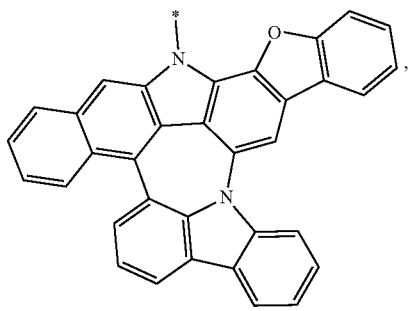
H-49
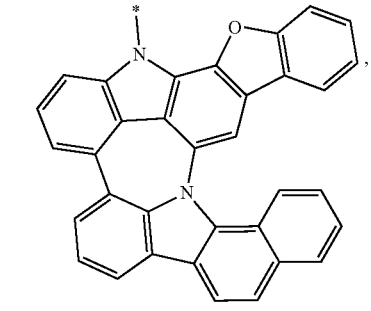
H-50
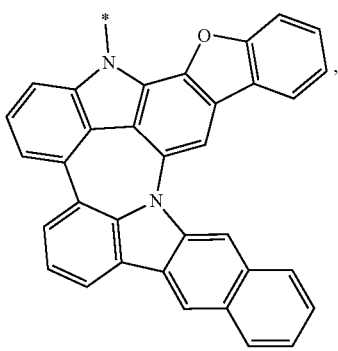
H-51
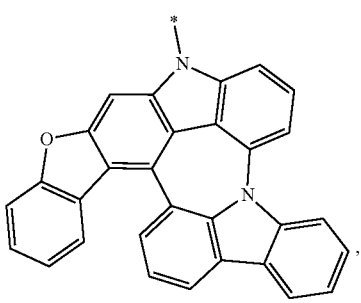
H-52
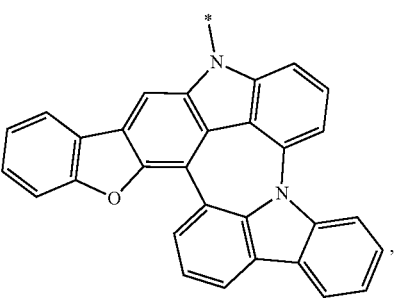
H-53
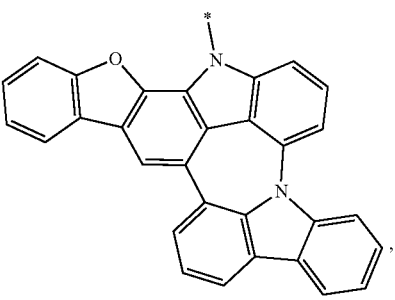
H-54
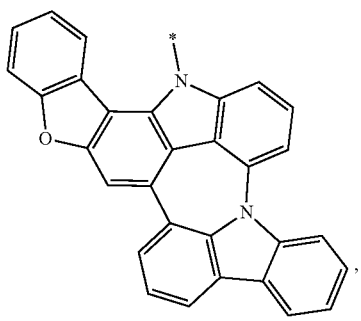

H-55 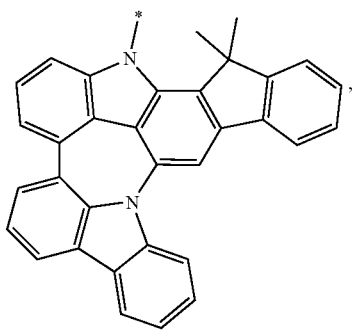
H-56 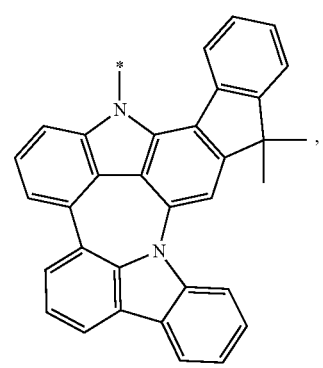
H-57 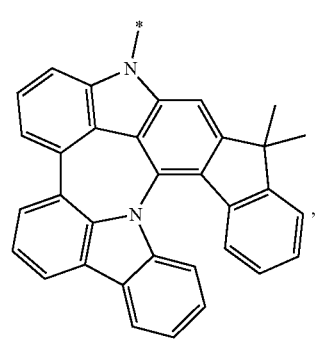
H-58 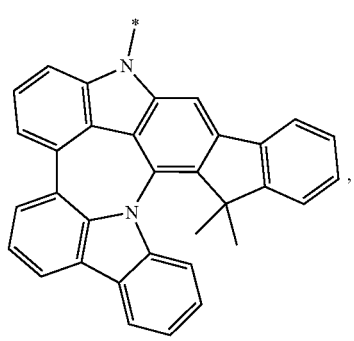
H-59 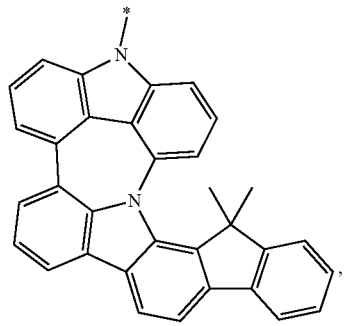
H-60 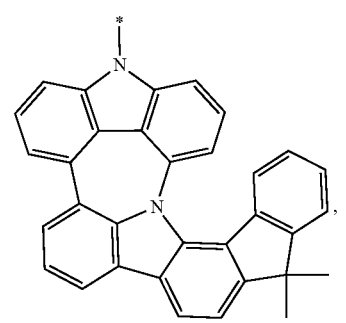
H-61 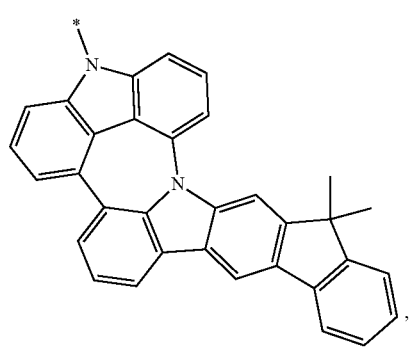
H-62 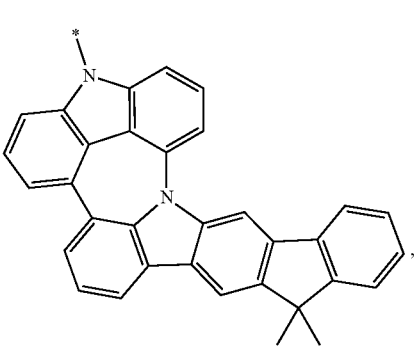
H-63 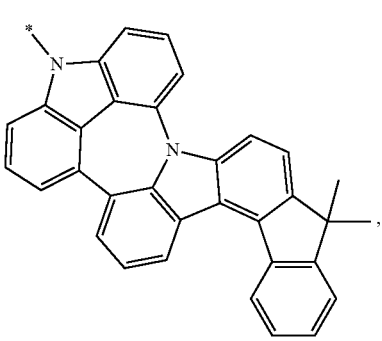

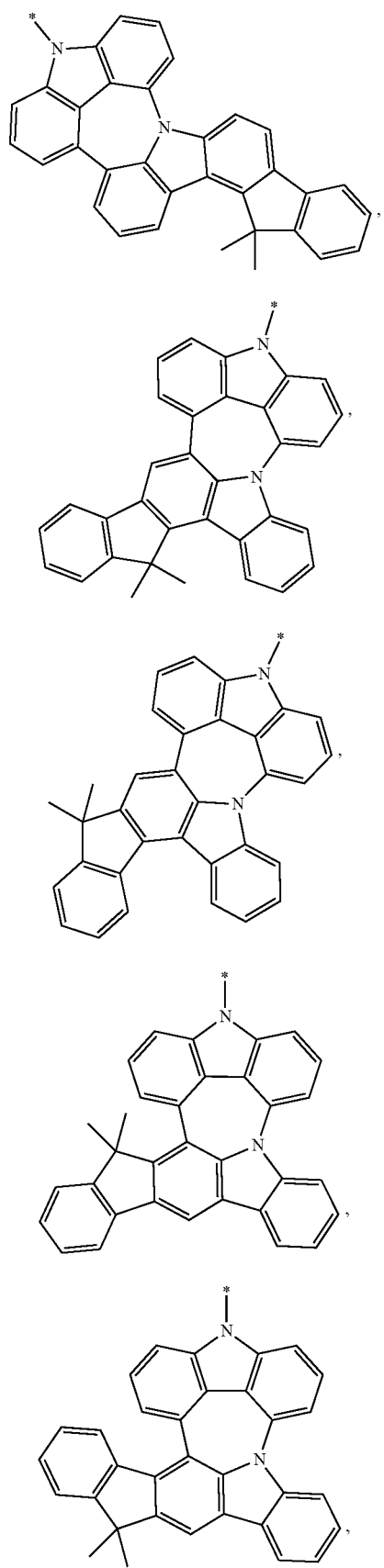
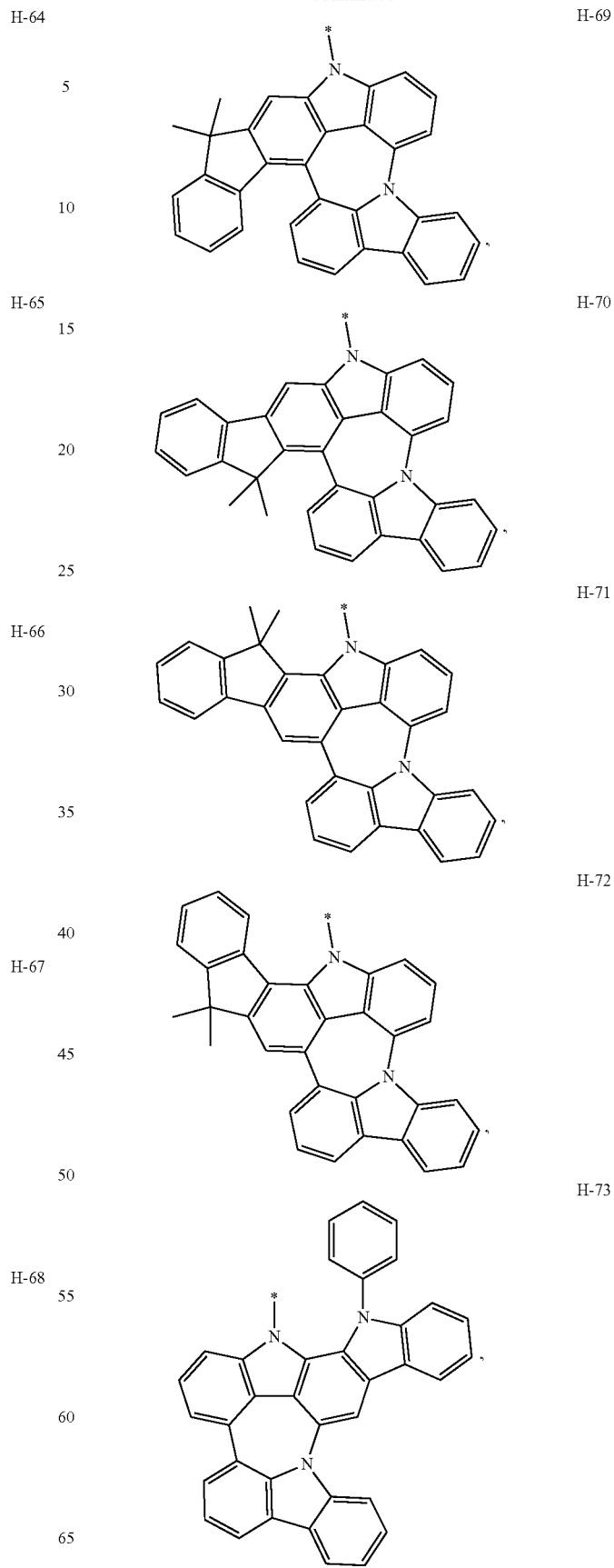

-continued
H-74
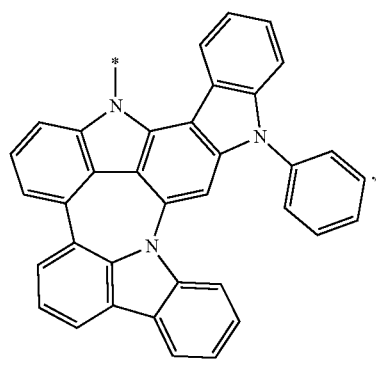
H-75
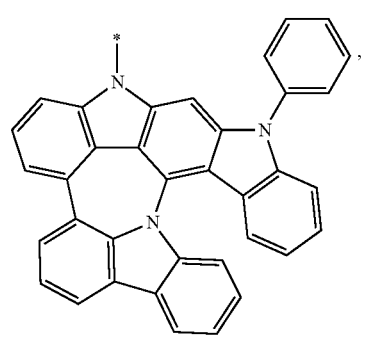
H-76
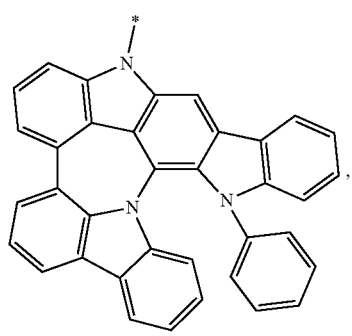
H-77
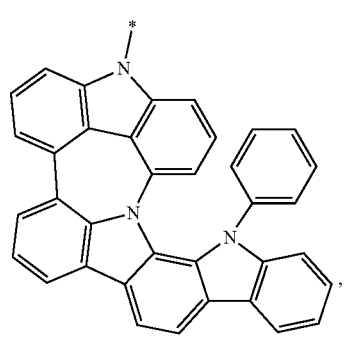
-continued
H-78
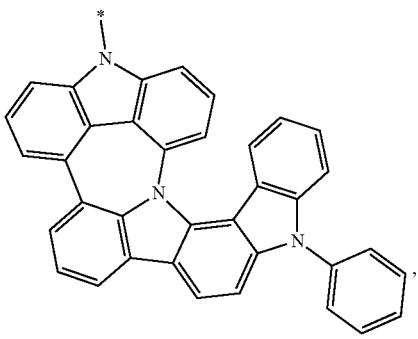
H-79
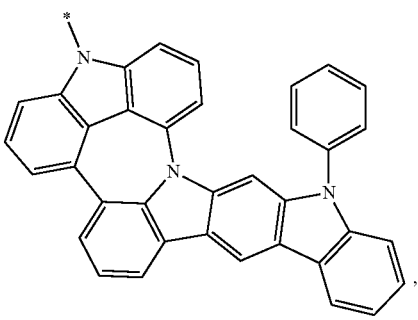
H-80
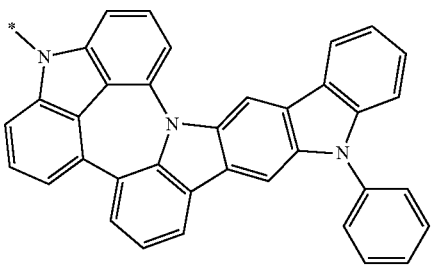
H-81
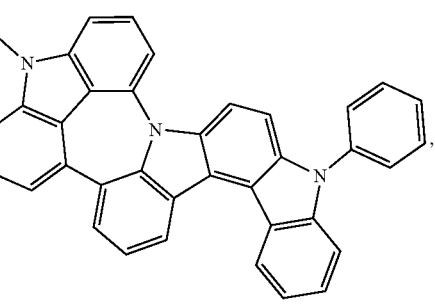
H-82
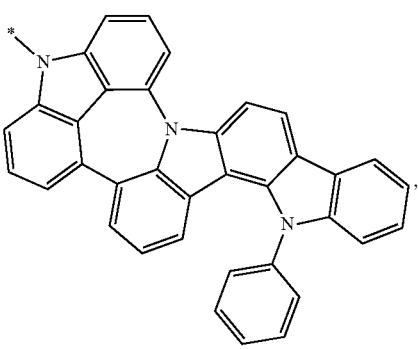

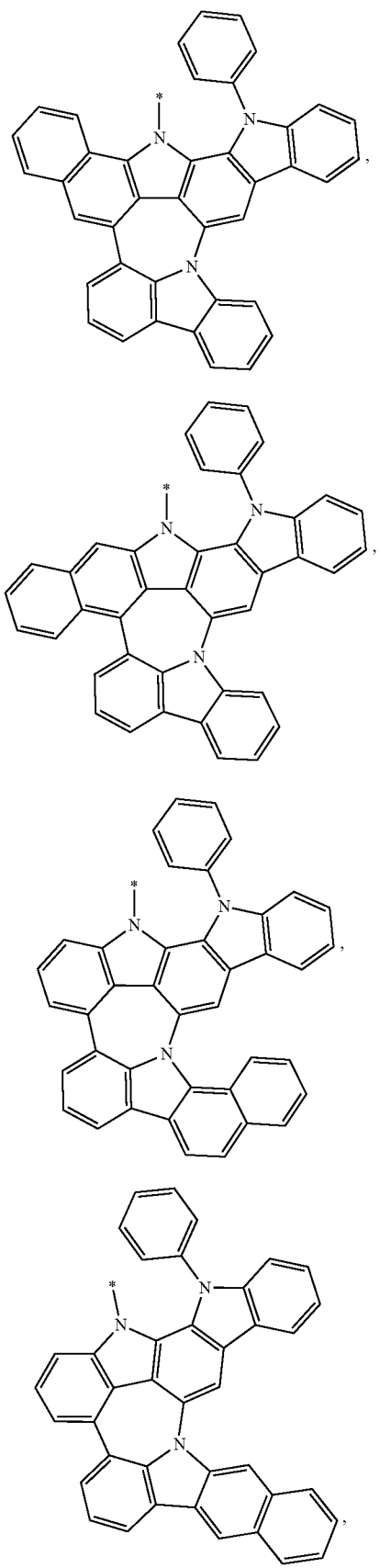
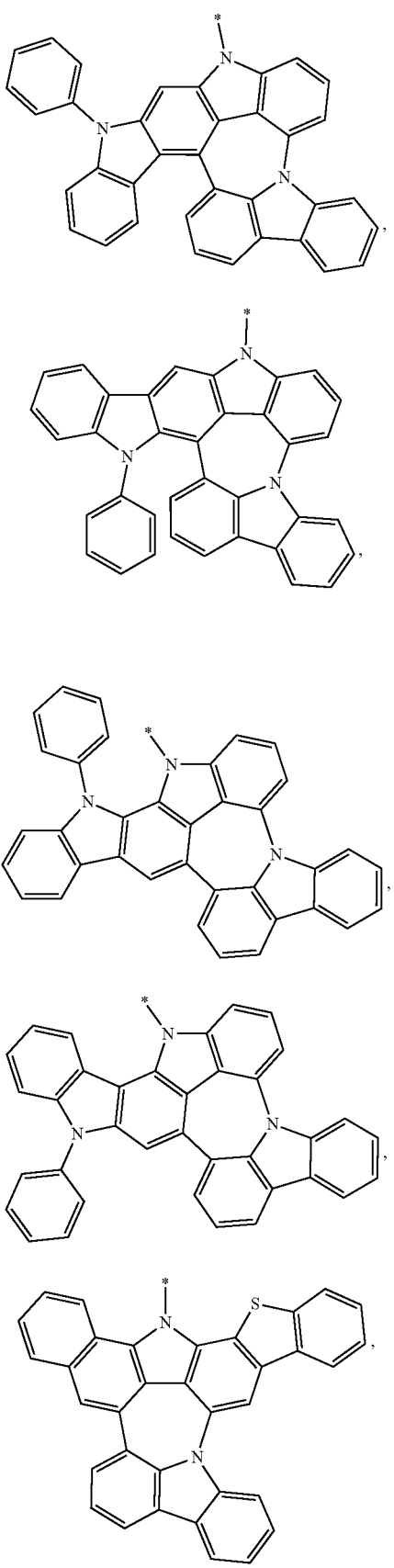

H-92
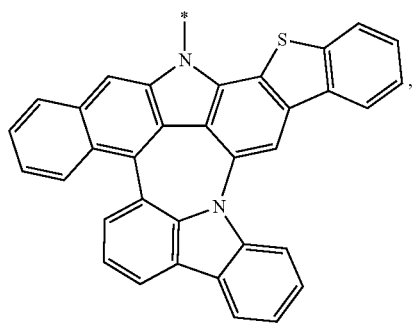
H-93
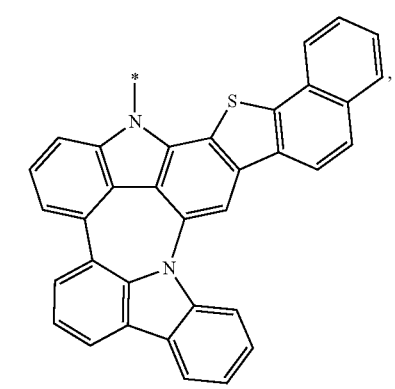
H-94
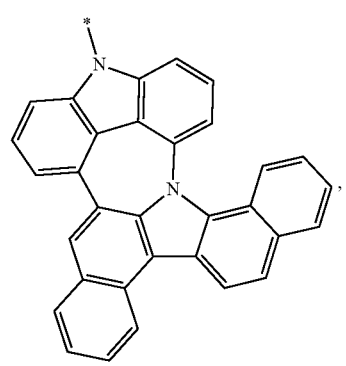
H-95
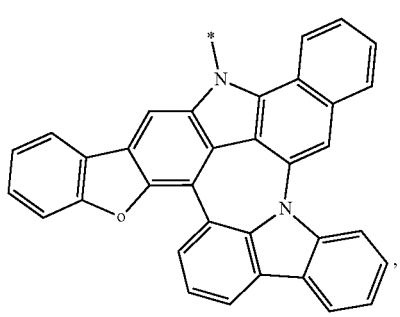
H-96
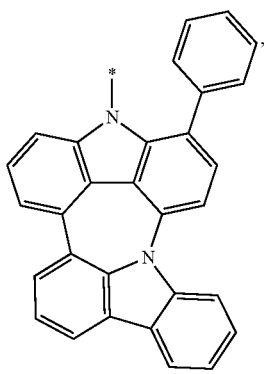
H-97
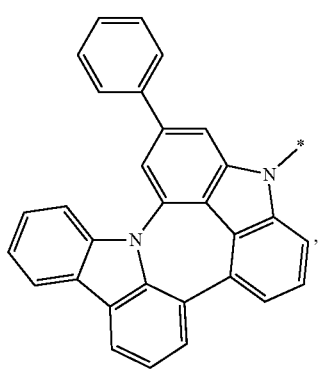
H-98
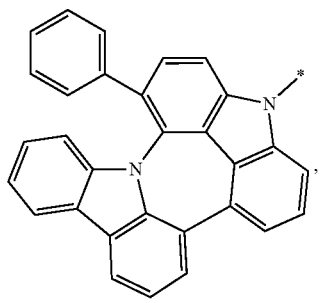
H-99
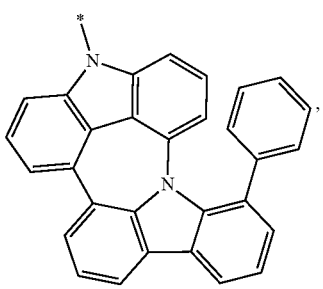

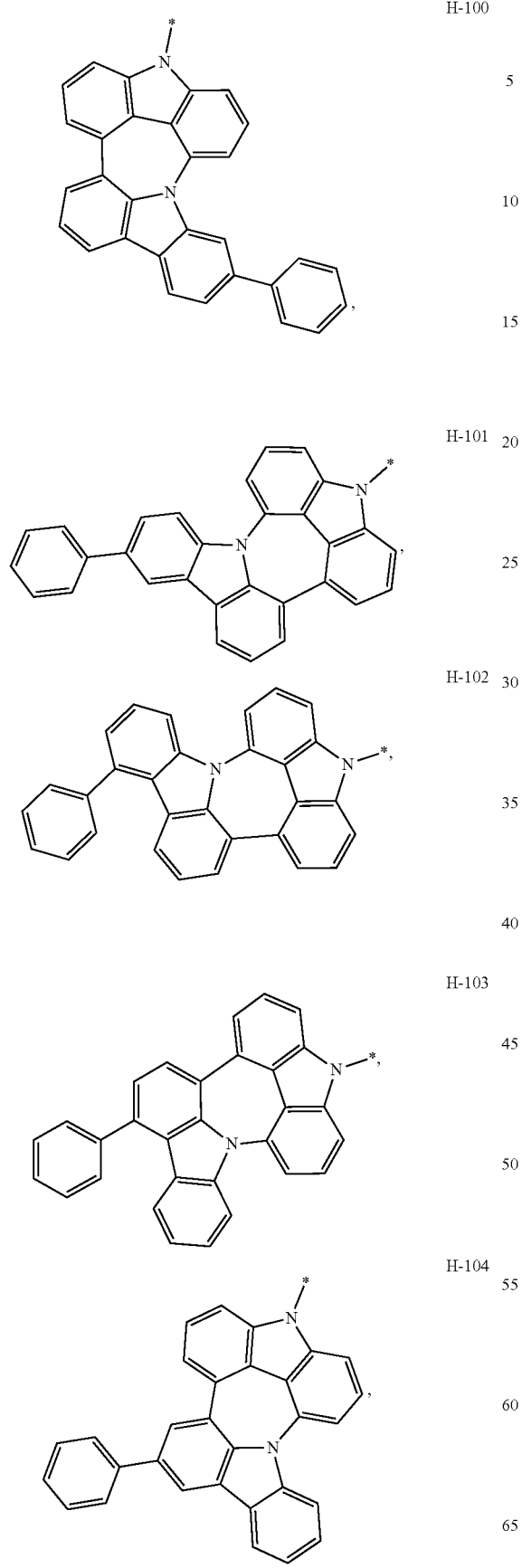

H-110
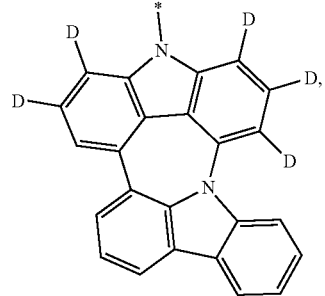
H-111
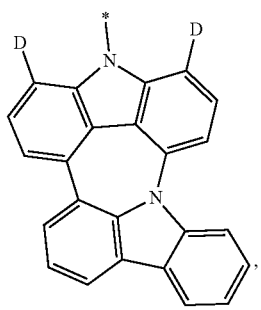
H-112
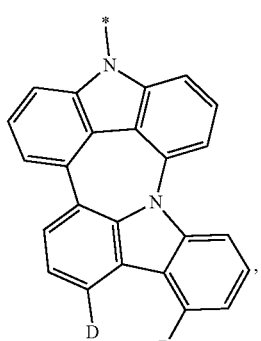
H-113
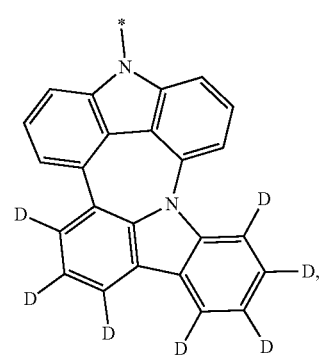
H-114
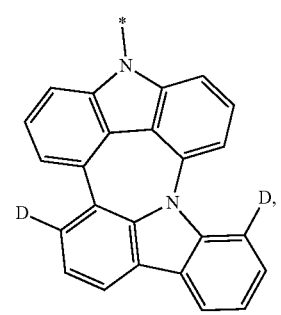
H-115
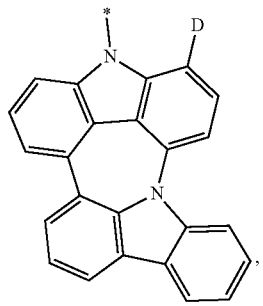
H-116
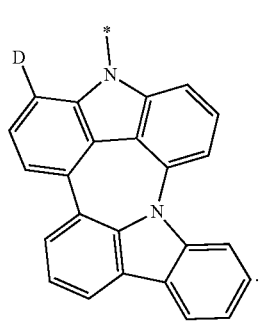
In this embodiment, * represents the position where H is joined to $L_1$.
According to an embodiment of the present disclosure, wherein the E has a structure represented by one of Formula 2-a to Formula 2-f:
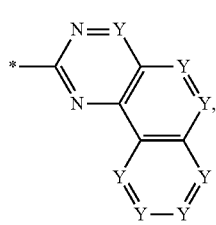
Formula 2-a
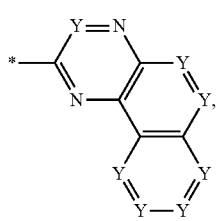
Formula 2-b
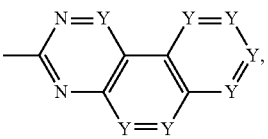
Formula 2-c
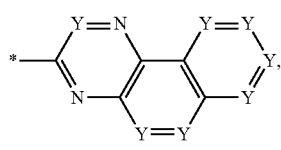
Formula 2-d Formula 2-e

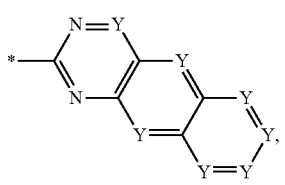

Formula 2-f

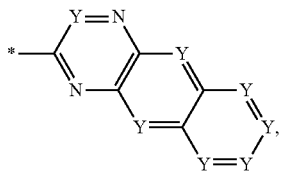

wherein Y is, at each occurrence identically or differently, selected from $CR_y$;

wherein $R_y$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

In this embodiment, * represents the position where E is joined to $L_1$.

According to an embodiment of the present disclosure, wherein the E has a structure represented by one of Formula 2-a to Formula 2-f:

Formula 2-a

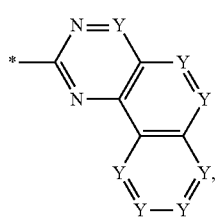

Formula 2-b

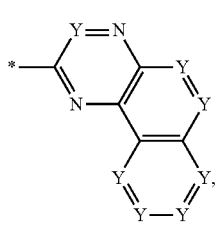

Formula 2-c

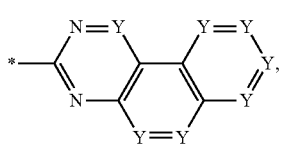

Formula 2-d

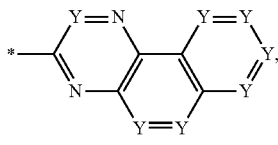

Formula 2-e

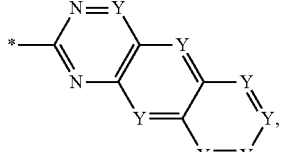

Formula 2-f

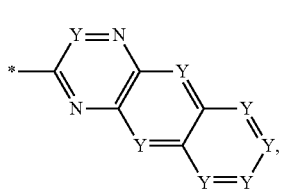

wherein Y is, at each occurrence identically or differently, selected from $CR_y$;

wherein $R_y$ is, at each occurrence identically or differently, selected from the group consisting of: hydrogen, deuterium, halogen, cyano, substituted or unsubstituted aryl having 6 to 30 carbon atoms, substituted or unsubstituted heteroaryl having 3 to 30 carbon atoms and combinations thereof.

In this embodiment, * represents the position where E is joined to $L_1$.

According to an embodiment of the present disclosure, wherein the E has a structure represented by one of Formula 2-a to Formula 2-f:

Formula 2-a

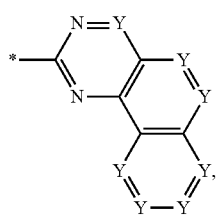

Formula 2-b

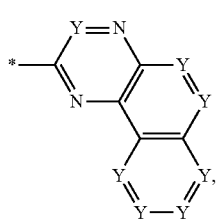

Formula 2-c

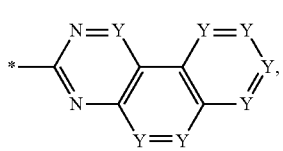

-continued

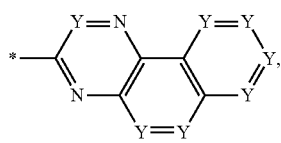
Formula 2-d

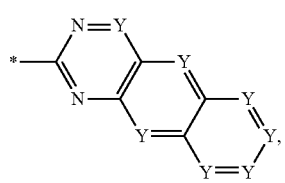
Formula 2-e

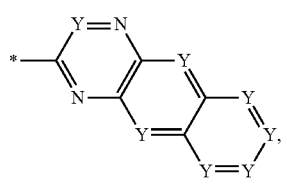
Formula 2-f wherein Y is, at each occurrence identically or differently, selected from $CR_y$; wherein $R_y$ is, at each occurrence identically or differently, selected from the group consisting of hydrogen, deuterium, phenyl, biphenyl, naphthyl, 4-cyanophenyl, dibenzofuryl, dibenzothienyl, triphenylene, carbazolyl, 9-phenylcarbazolyl, 9,9-dimethylfluorenyl, pyridyl and phenylpyridyl.

In this embodiment, * represents the position where E is joined to $L_1$.

According to an embodiment of the present disclosure, in the structure represented by Formula 2-a to Formula 2-f, Y in the aza 6-membered ring is selected from $CR_y$, and the $R_y$ is selected from substituted or unsubstituted aryl having 6 to 30 carbon atoms or substituted or unsubstituted heteroaryl having 3 to 30 carbon atoms.

According to an embodiment of the present disclosure, in the structure represented by Formula 2-a to Formula 2-f, Y in the aza 6-membered ring is selected from $CR_y$, and the $R_y$ is selected from phenyl, biphenyl, naphthyl, 4-cyanophenyl, dibenzofuryl, dibenzothienyl, triphenylene, carbazolyl, 9-phenylcarbazolyl, 9,9-dimethylfluorenyl, pyridyl or phenylpyridyl.

According to an embodiment of the present disclosure, wherein the E is selected from the group consisting of the following structures:

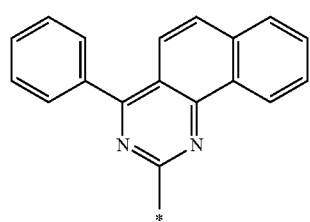
E-1

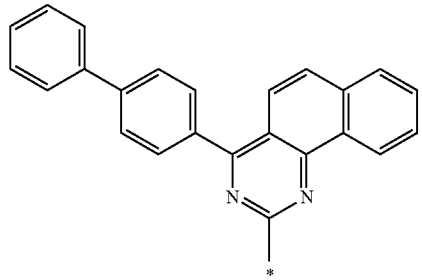
E-2

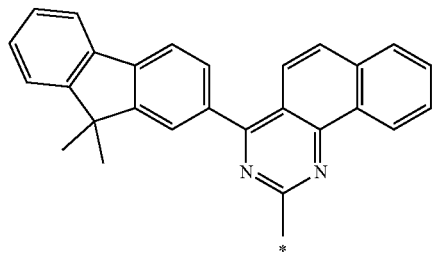
E-3

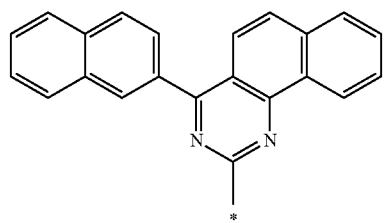
E-4

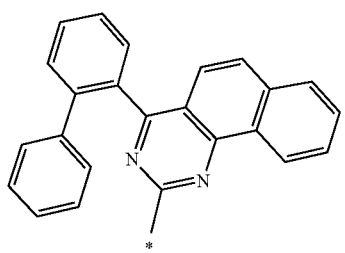
E-5

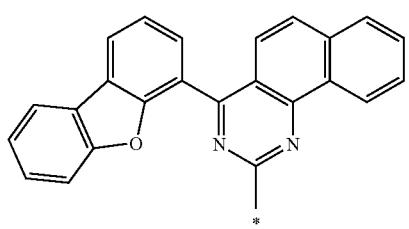
E-6

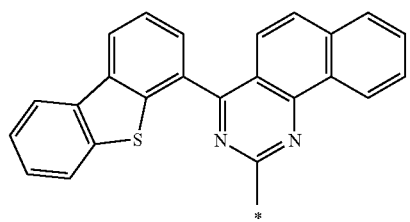
E-7

E-8
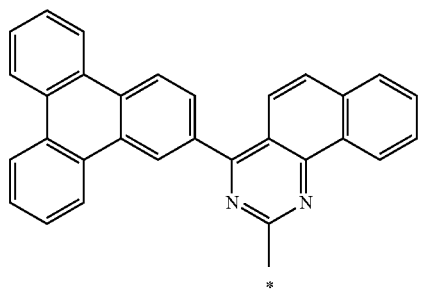
E-9
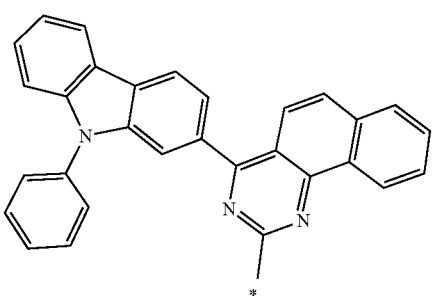
E-10
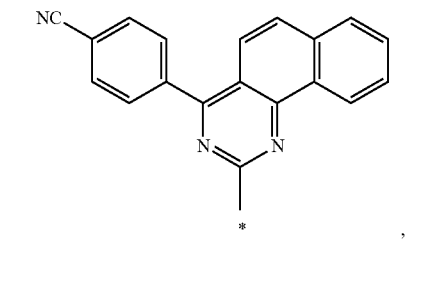
E-11
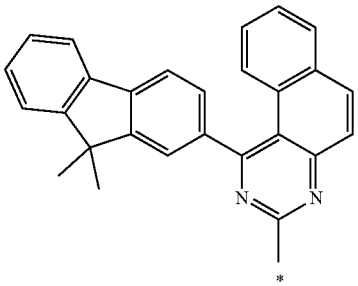
E-12
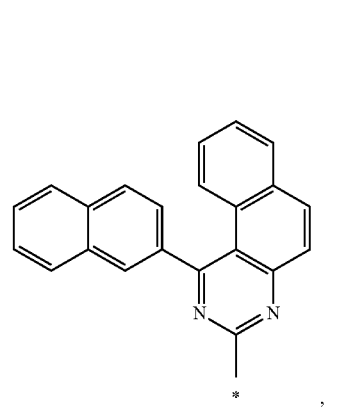
E-13
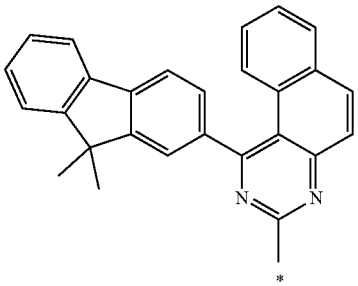
E-14
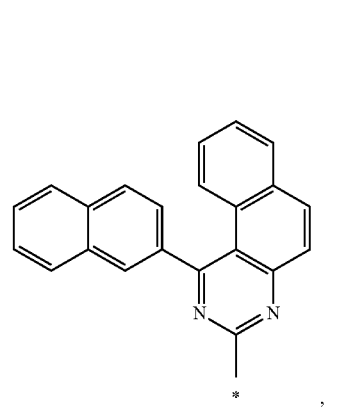
E-15
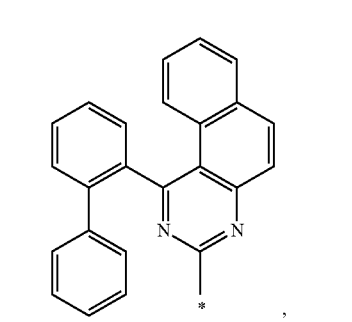
E-16
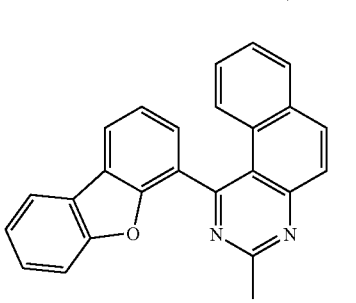
E-17
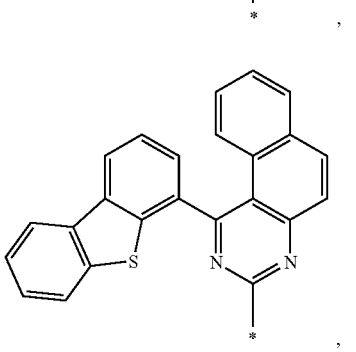

E-18
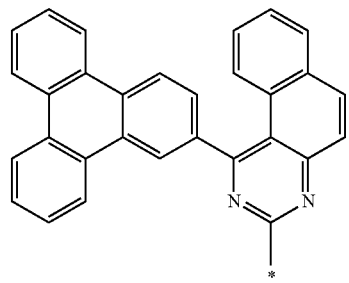
E-19
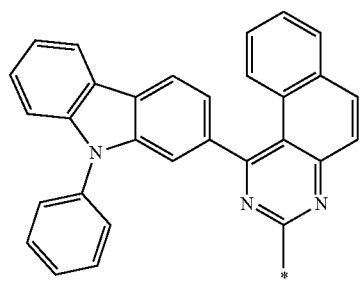
E-20
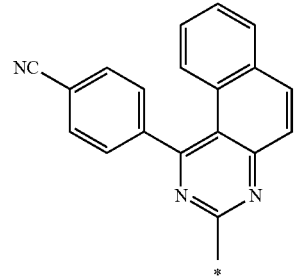
E-21
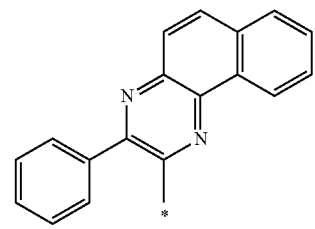
E-22
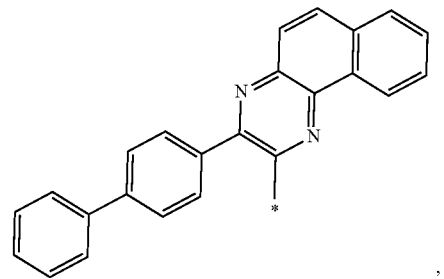
E-23
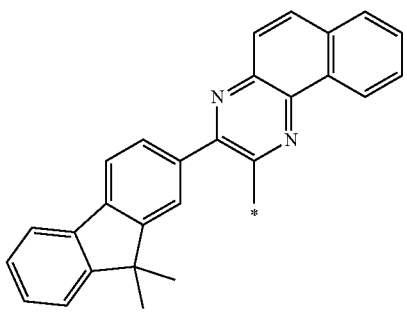
E-24
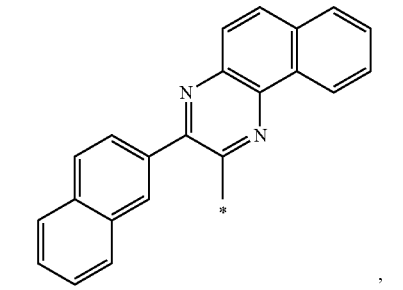
E-25
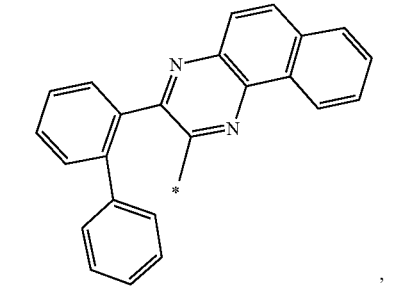
E-26
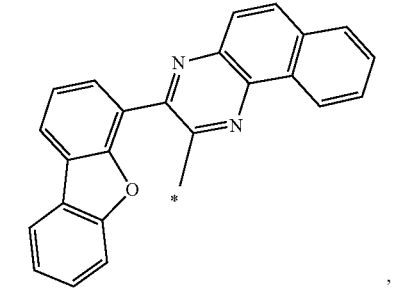
E-27
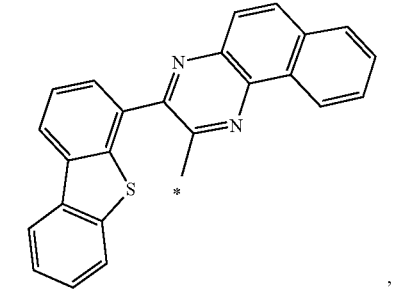

-continued
E-28
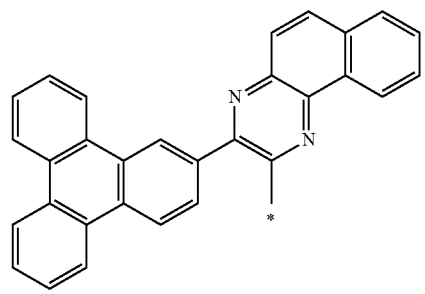
E-29
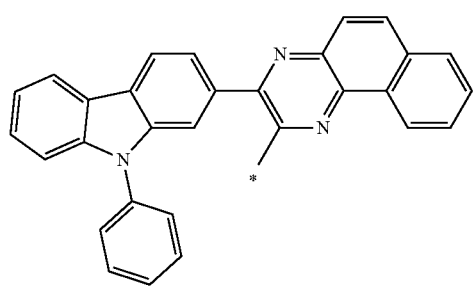
E-30
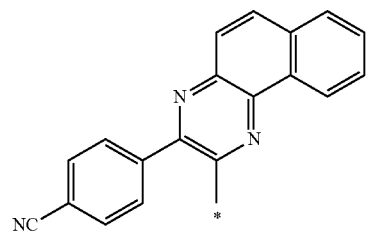
E-31
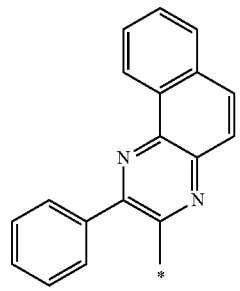
E-32
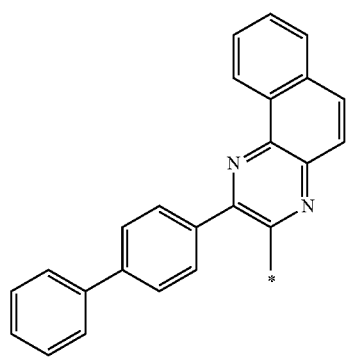
-continued
E-33
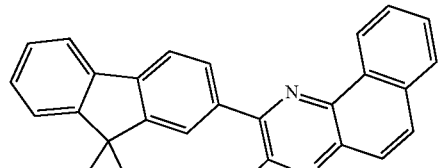
E-34
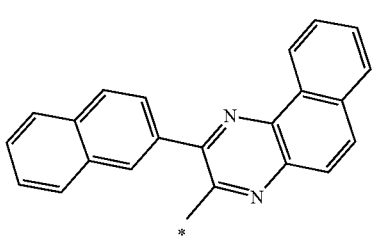
E-35
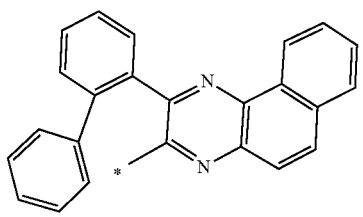
E-36
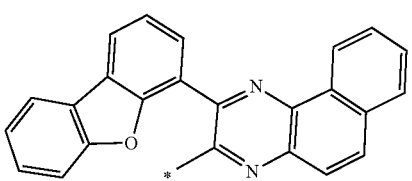
E-37
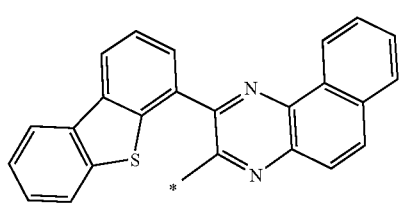
E-38
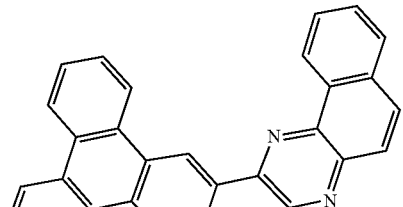
E-39
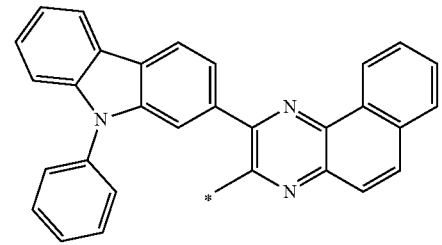

E-40 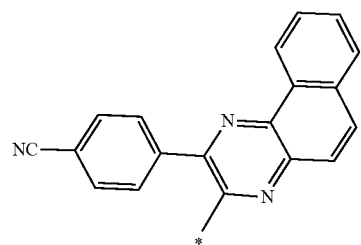,
E-41 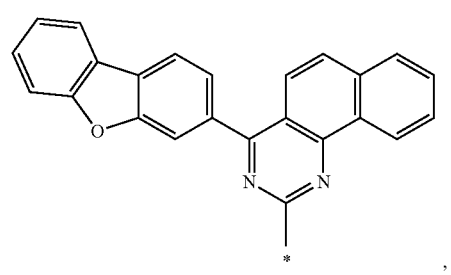,
E-42 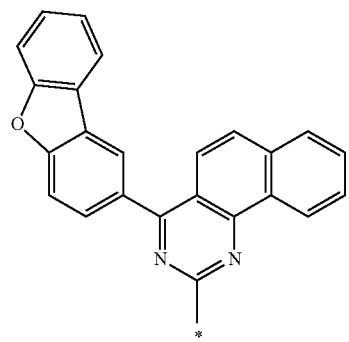,
E-43 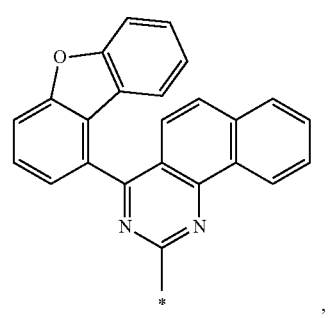,
E-44 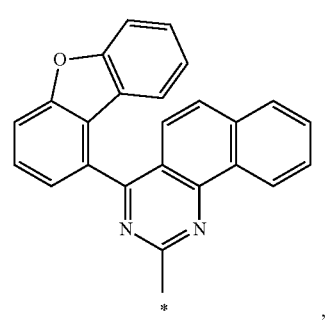,
E-45 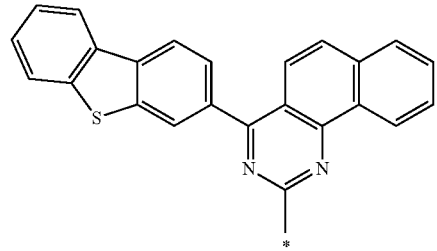,
E-46 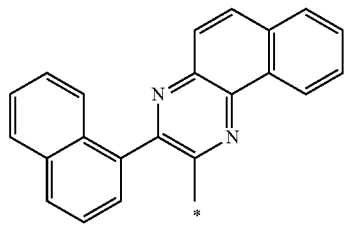,
E-47 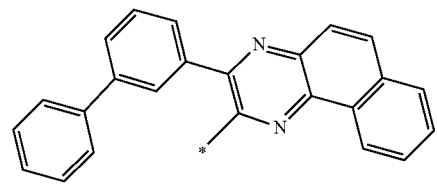,
E-48 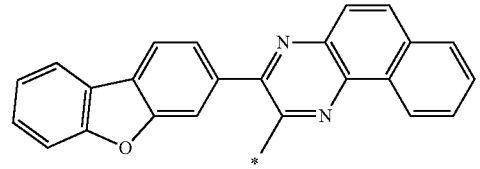,
E-49 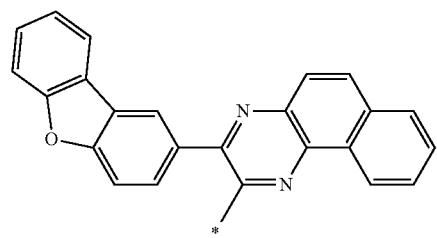,
E-50 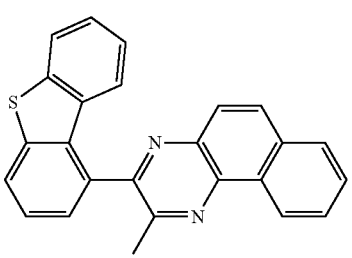,
E-51 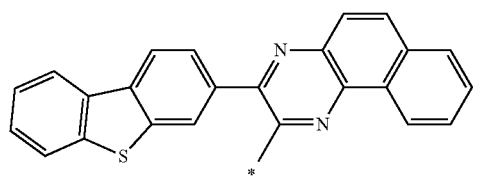, E-52
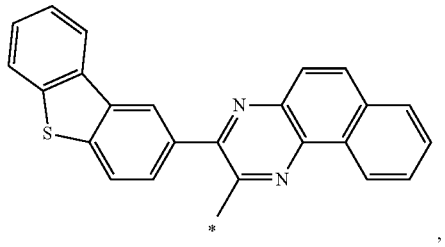
E-53
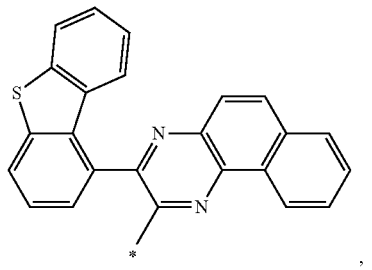
E-54
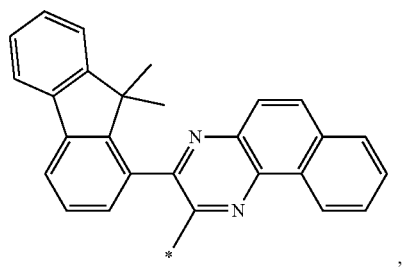
E-55
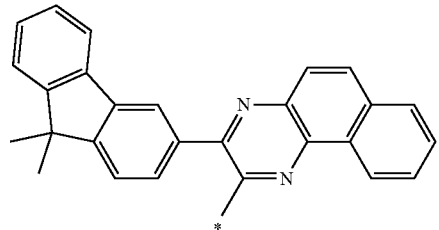
E-56
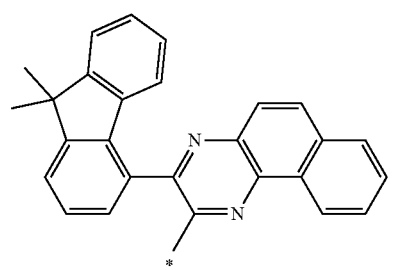
E-57
E-58
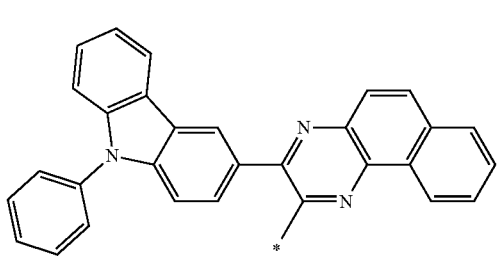
E-59
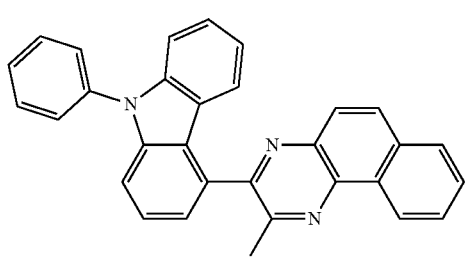
E-60
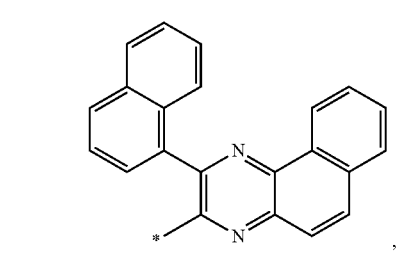
E-61
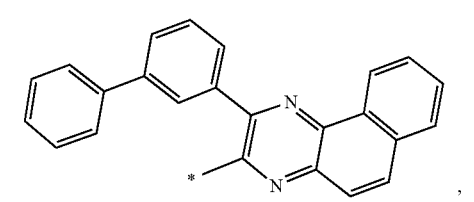
E-62
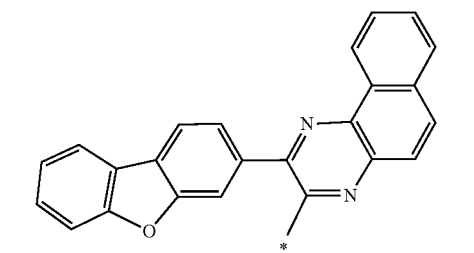
E-63
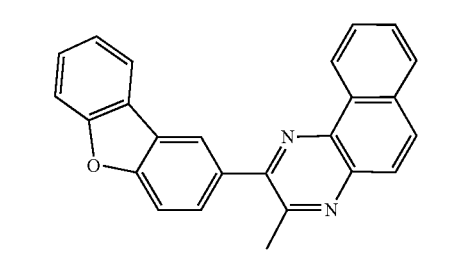

E-64
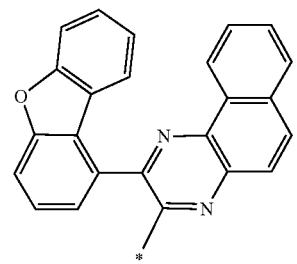
,
E-65
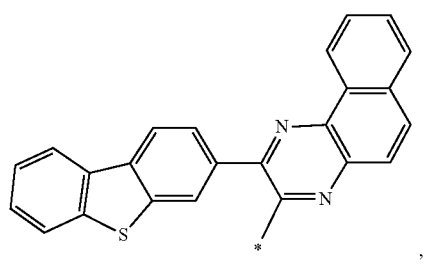
,
E-66
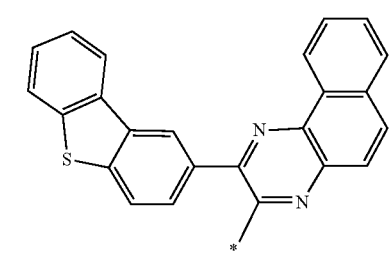
,
E-67
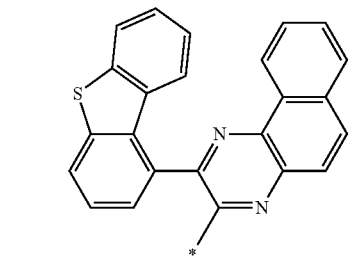
,
E-68
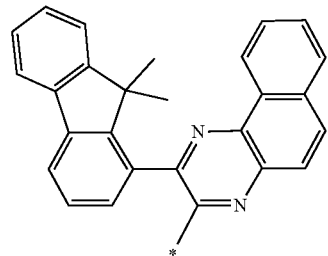
,
E-69
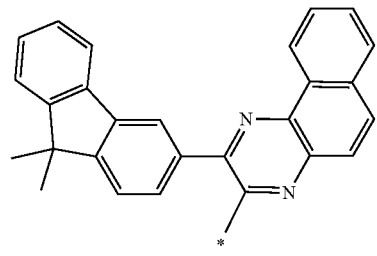
,
E-70
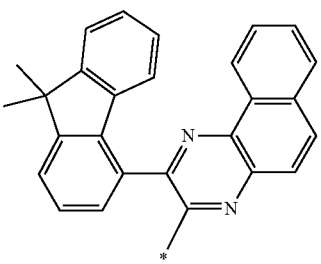
,
E-71
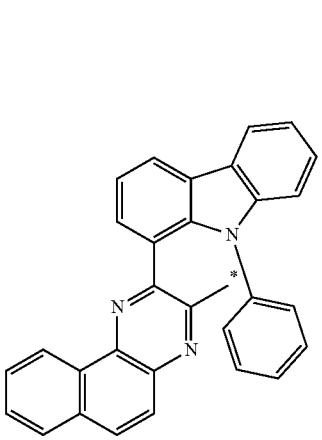
,
E-72
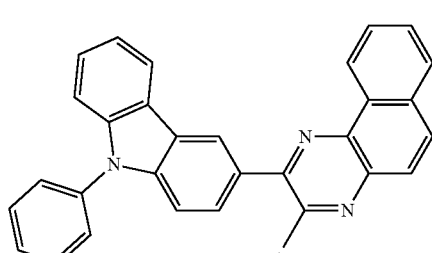
,
E-73
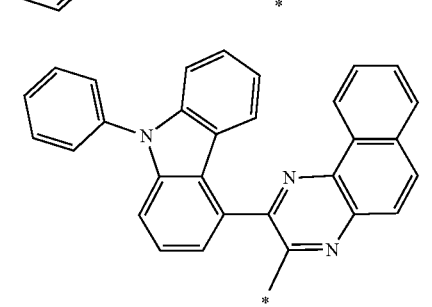
,
E-74
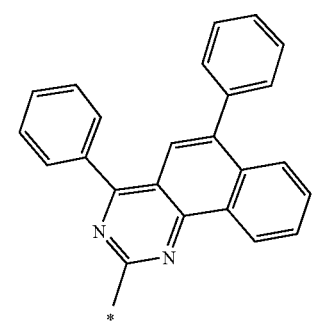
, E-75
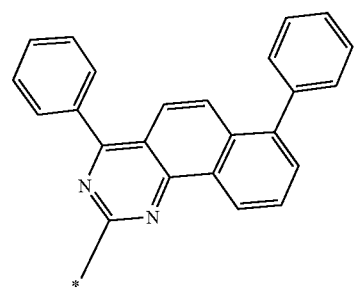
E-76
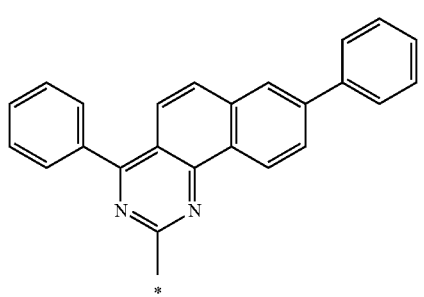
E-77
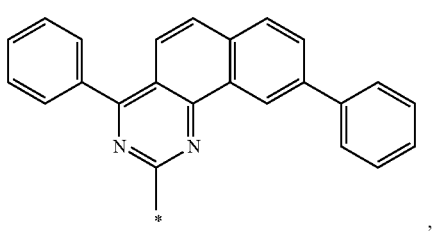
E-78
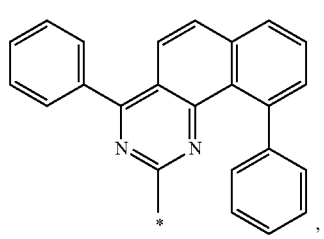
E-79
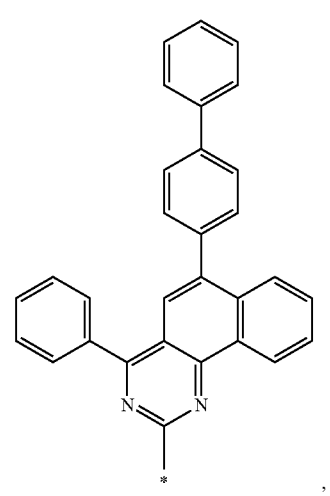
E-80
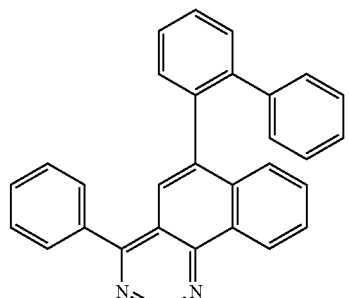
E-81
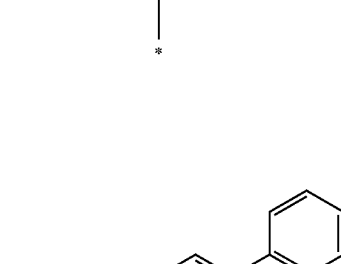
E-82
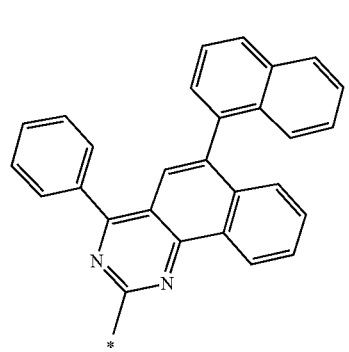
E-83
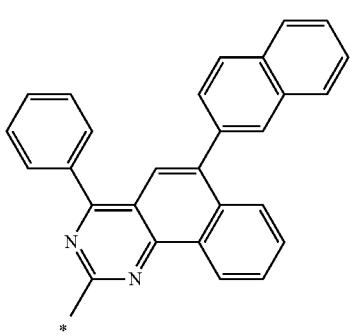

E-84
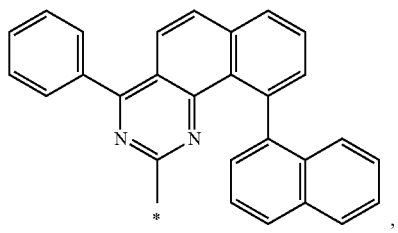
E-85
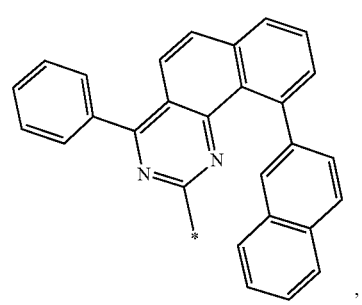
E-86
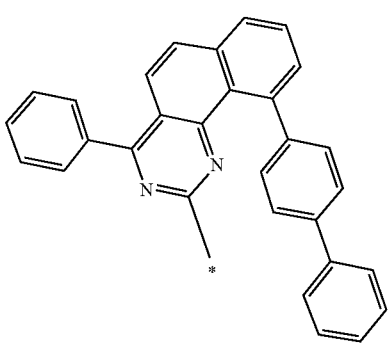
E-87
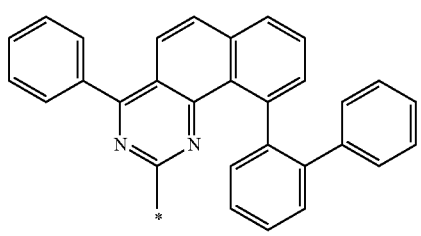
E-88
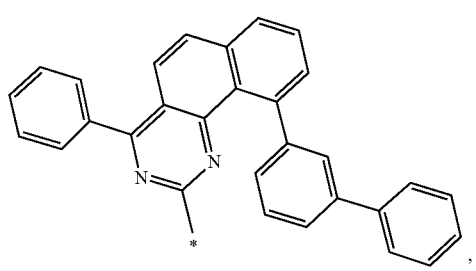
E-89
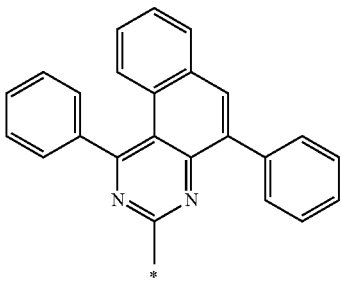
E-90
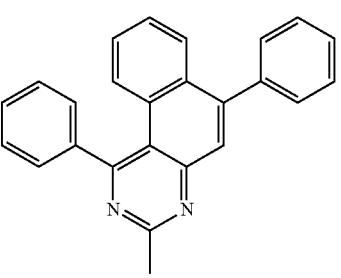
E-91
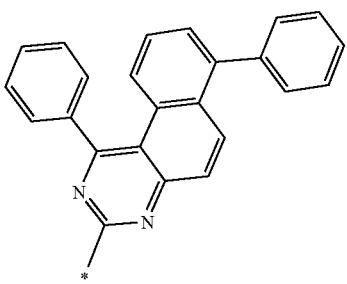
E-92
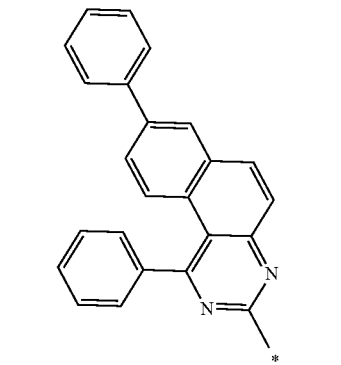
E-93
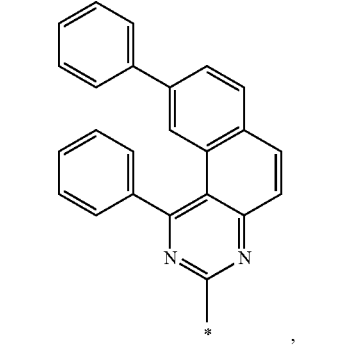

E-94
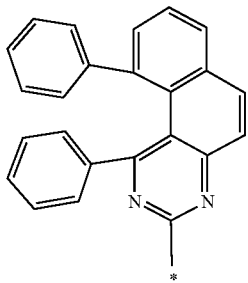
E-95
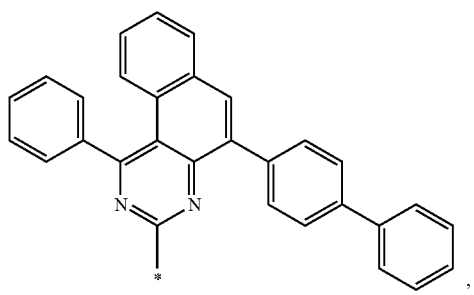
E-96
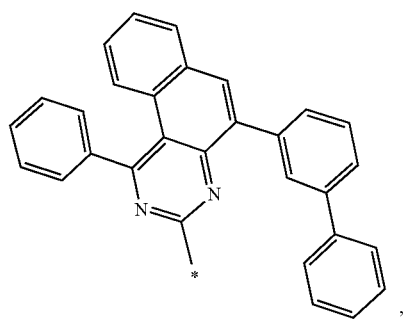
E-97
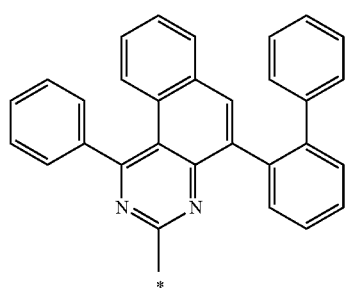
E-98
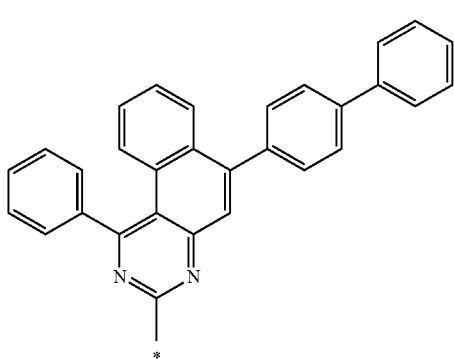
E-99
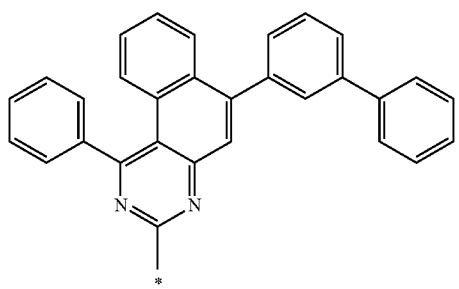
E-100
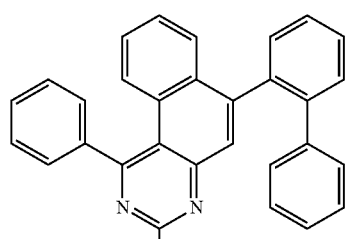
E-101
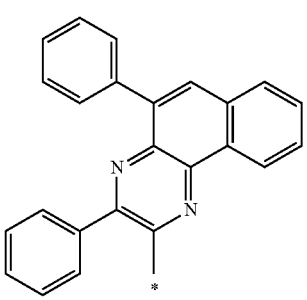
E-102
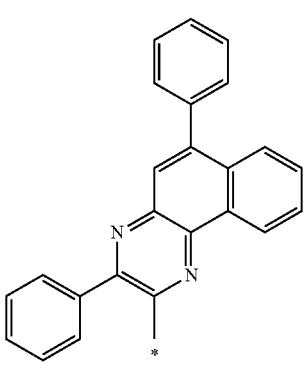
E-103
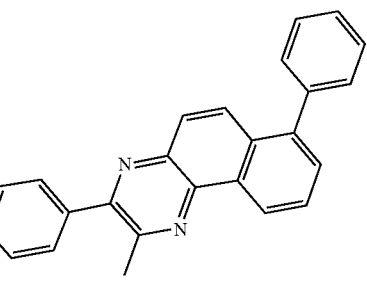

E-104
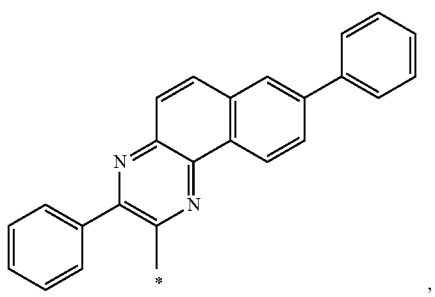
E-105
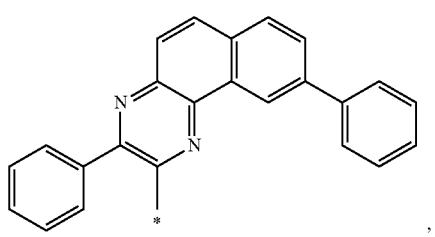
E-106
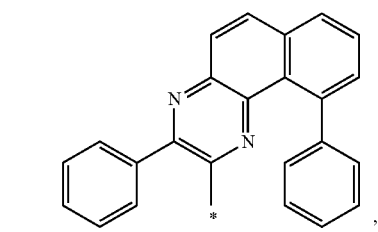
E-107
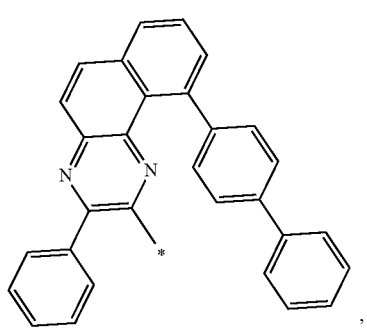
E-108
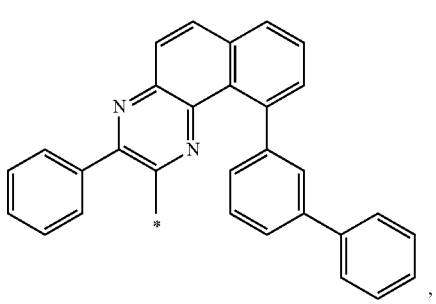
E-109
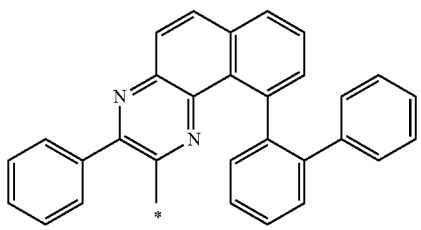
E-110
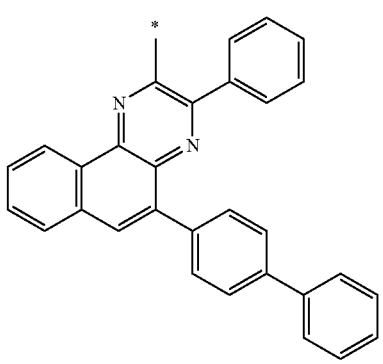
E-111
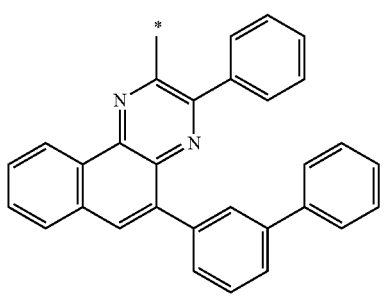
E-112
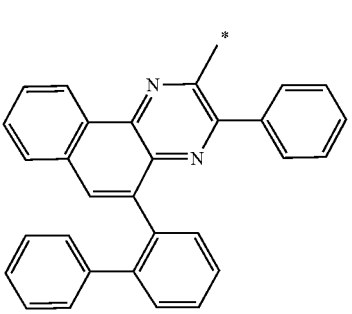
E-113
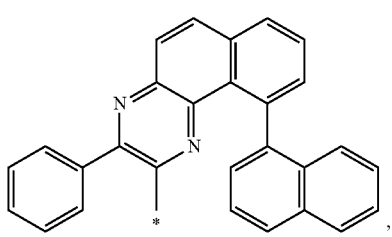

E-114
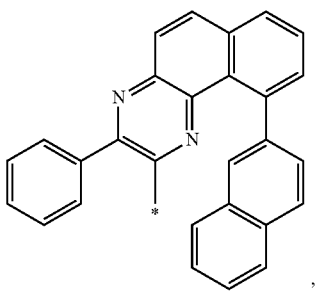
E-115
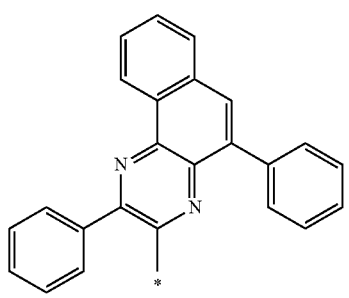
E-116
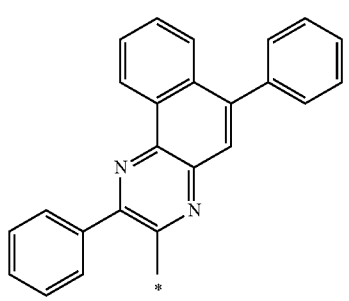
E-117
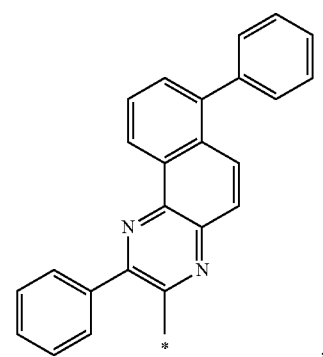
E-118
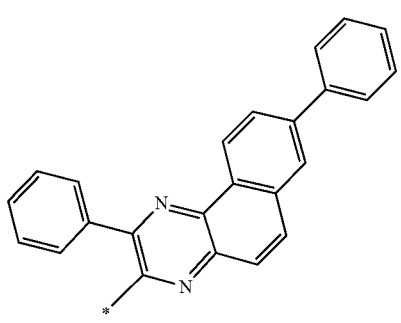
E-119
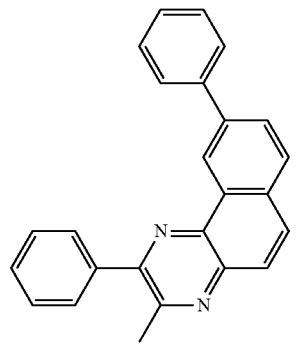
E-120
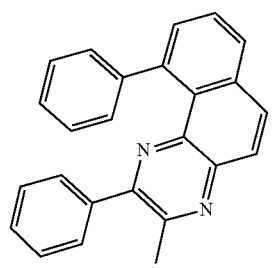
E-121
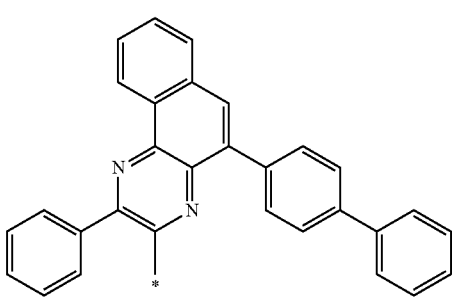
E-122
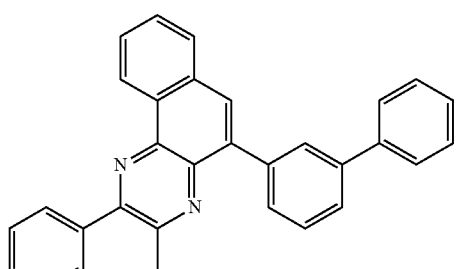
E-123
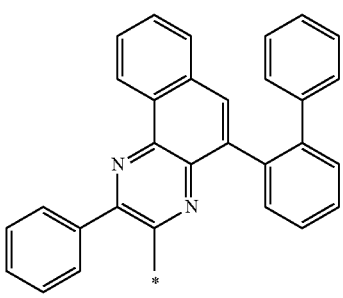

E-124
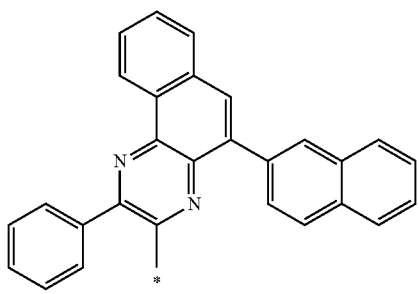
E-125
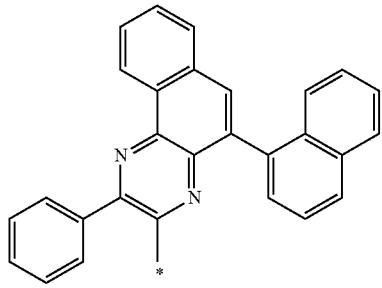
E-126
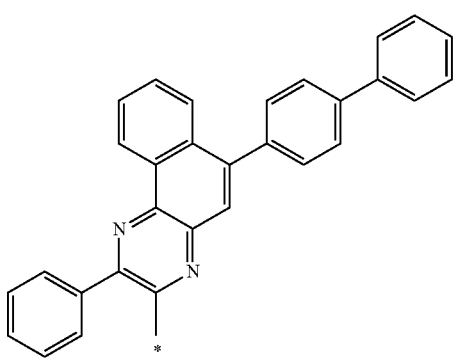
E-127
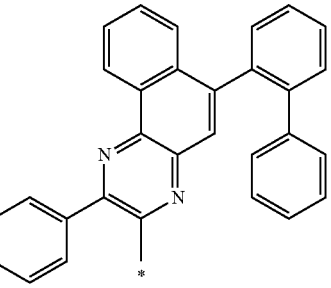
E-128
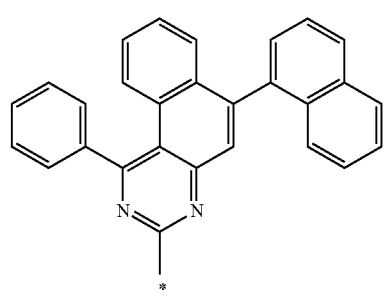
E-129
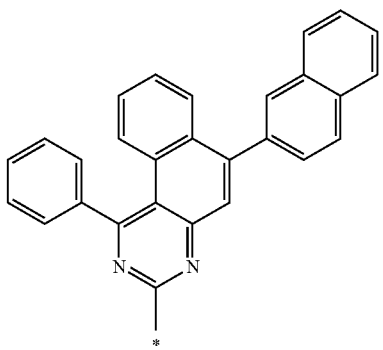
E-130
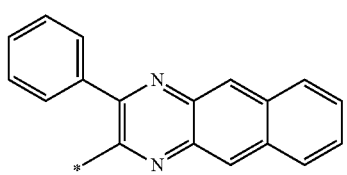
E-131
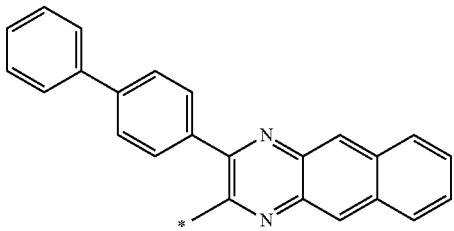
E-132
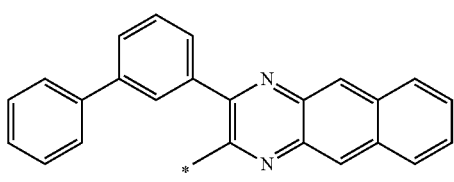
E-133
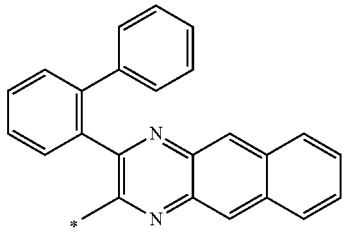
E-134
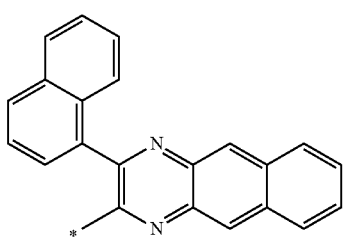

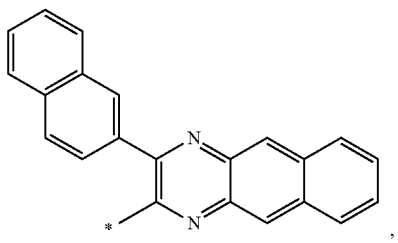
E-135
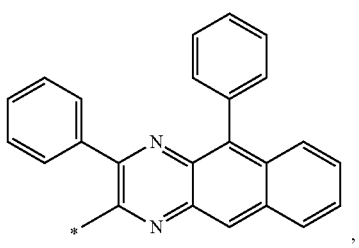
E-140
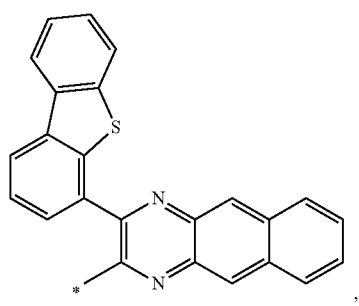
E-136
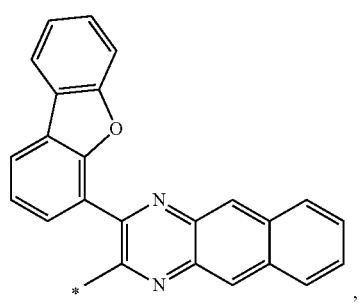
E-137
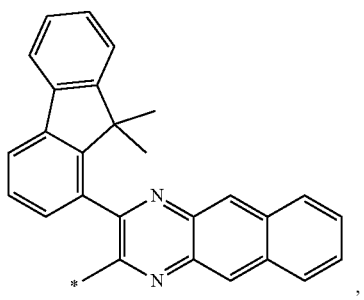
E-138
E-141
E-142
E-143
E-144
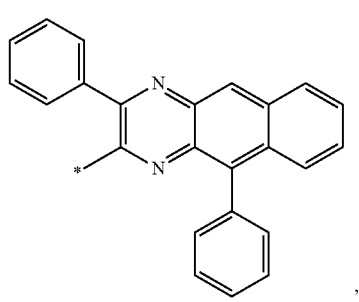
E-139
E-145

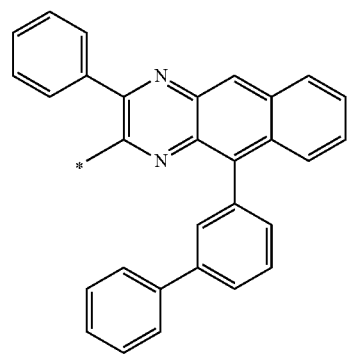
E-146
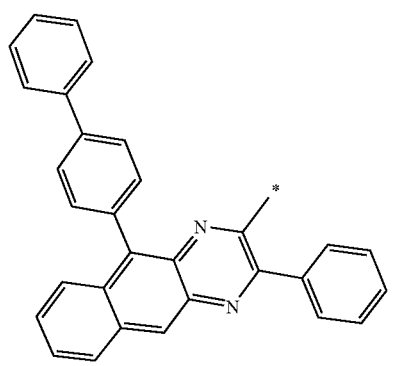
E-147
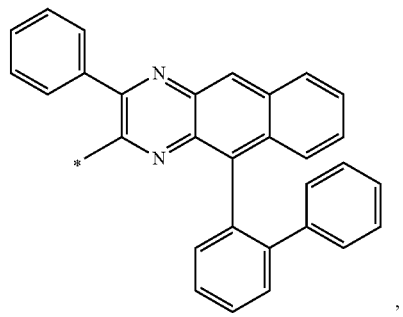
E-148
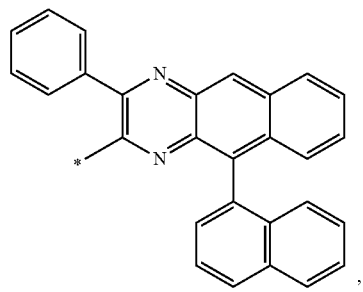
E-149
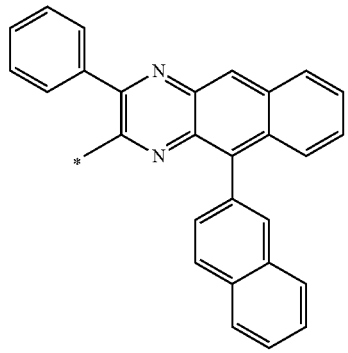
E-150
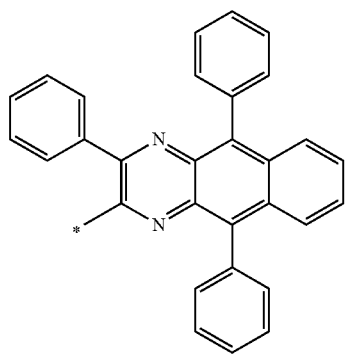
E-151
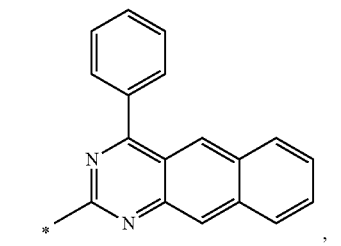
E-152
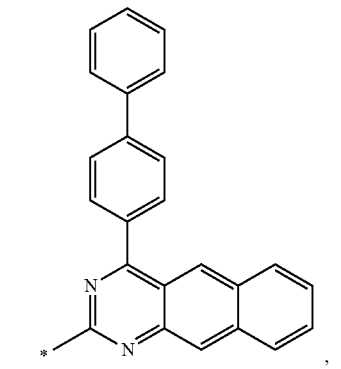
E-153
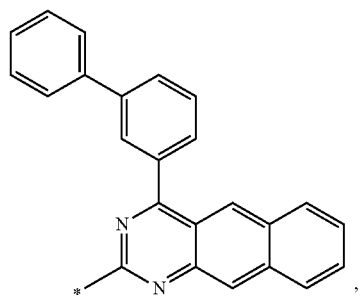
E-154

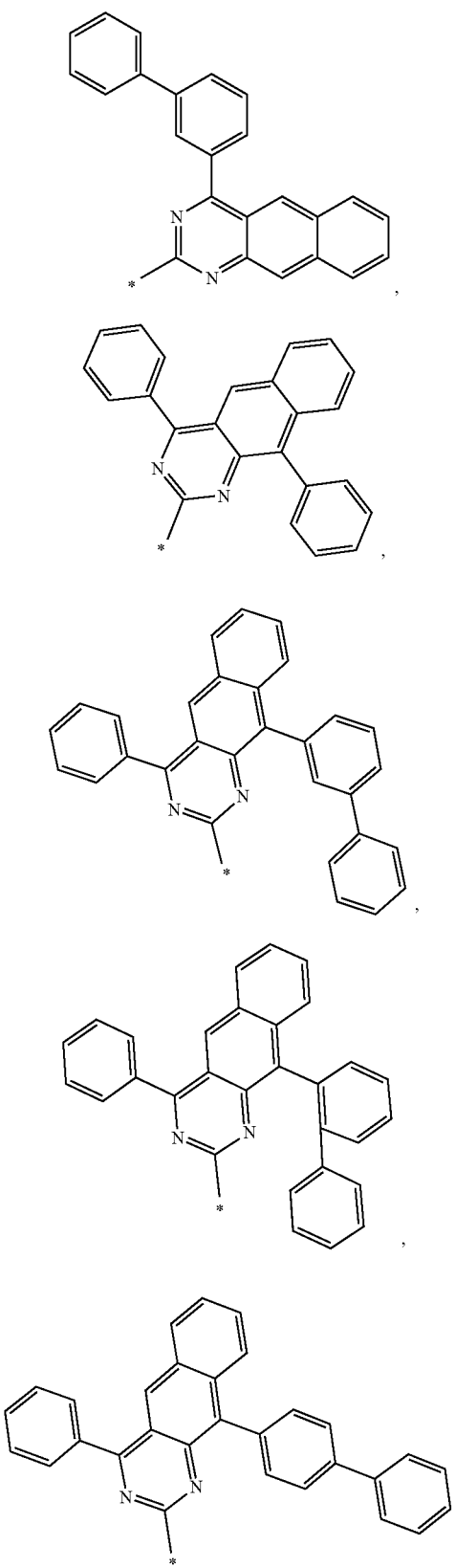

According to an embodiment of the present disclosure, wherein the $L_1$ is selected from the group consisting of: a single bond, phenylene, naphthylene, biphenylene, terphenylene, triphenylene, pyridylene and thienylene.

According to an embodiment of the present disclosure, wherein the $L_1$ is selected from the group consisting of the following structures:

a single bond

L-0,

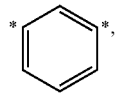 L-1

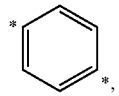 L-2

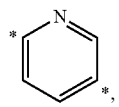 L-3

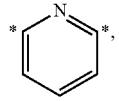 L-4

 L-5

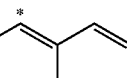 L-6

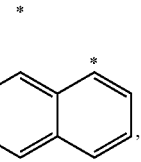 L-7

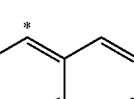 L-8

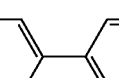 L-9

 L-10

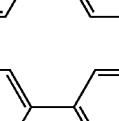 L-11

In this embodiment, * represents the position where E is joined to $L_1$.

-continued

L-12
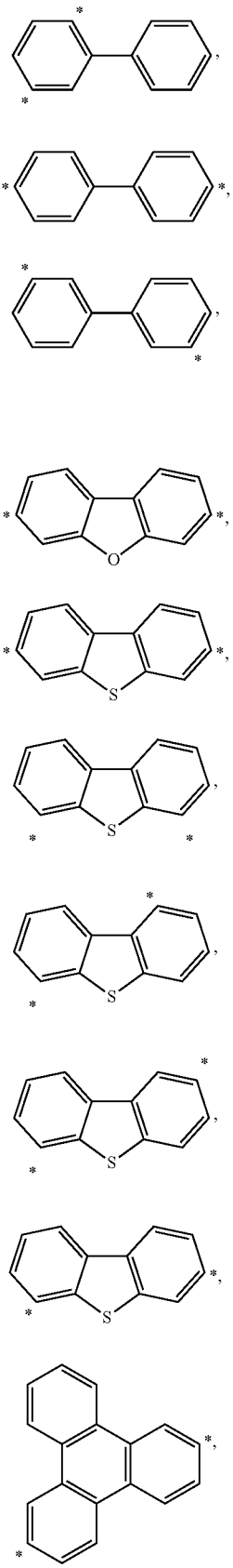
L-13

L-14

L-15

L-16

L-17

L-18

L-19

L-20

L-21

-continued

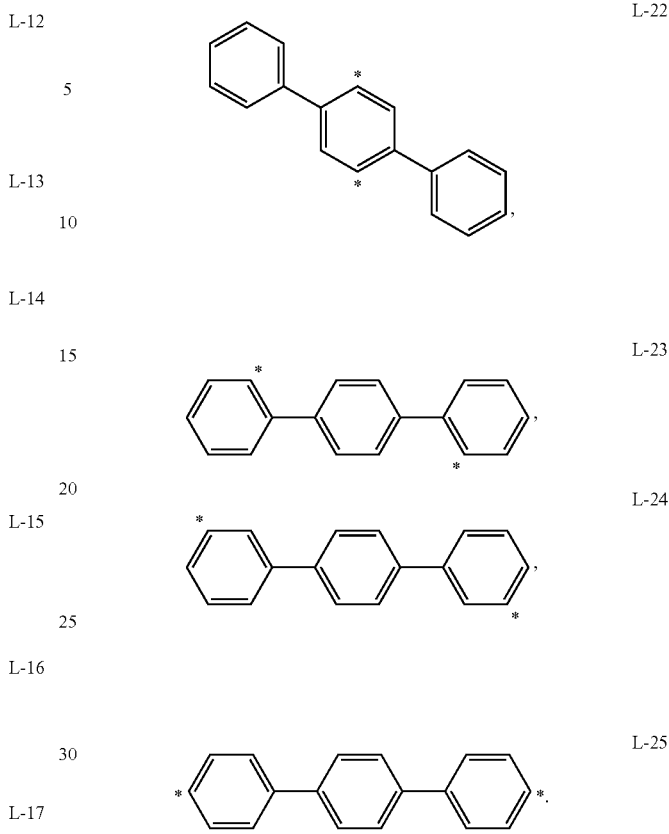

L-22

L-23

L-24

L-25

In this embodiment, * represents the positions where $L_1$ is joined to E and H.

According to an embodiment of the present disclosure, wherein the compound has a structure of H-$L_1$-E, wherein H is selected from the group consisting of H-1 to H-95, $L_1$ is selected from the group consisting of L-0 to L-25, and E is selected from the group consisting of E-1 to E-45.

According to an embodiment of the present disclosure, wherein the compound has a structure of H-$L_1$-E, wherein H is selected from the group consisting of H-1 to H-116, $L_1$ is selected from the group consisting of L-0 to L-25, and E is selected from the group consisting of E-1 to E-159.

According to an embodiment of the present disclosure, wherein the compound is selected from the group consisting of Compound 1-1 to Compound 1-421, where the specific structures of Compound 1-1 to Compound 1-421 are referred to claim 12.

According to an embodiment of the present disclosure, wherein the compound is selected from the group consisting of Compound 1-1 to Compound 1-601, where the specific structures of Compound 1-1 to Compound 1-601 are referred to claim 12.

According to an embodiment of the present disclosure, disclosed is an electroluminescent device, including:

an anode, a cathode, and an organic layer disposed between the anode and the cathode, wherein the organic layer comprises a compound having a structure of H-$L_1$-E;

wherein H has a structure represented by Formula 1:

Formula 1

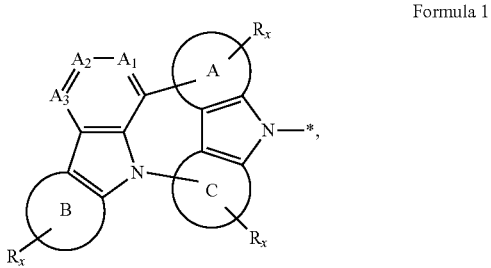

in Formula 1, $A_1$, $A_2$ and $A_3$ are, at each occurrence identically or differently, selected from CR; and the ring A, the ring B and the ring C are, at each occurrence identically or differently, selected from an aromatic ring having 6 to 18 carbon atoms or a hetero-aromatic ring having 3 to 18 carbon atoms;

$R_x$ represents mono-substitution, multiple substitutions or non-substitution; and adjacent substituents R, $R_x$ can be optionally joined to form a ring;

wherein E has a structure represented by Formula 2:

Formula 2

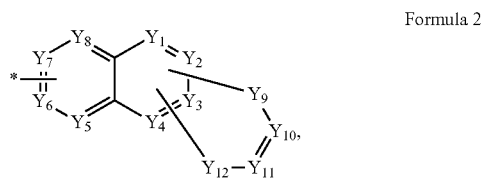

wherein $Y_1$ to $Y_{12}$ are, at each occurrence identically or differently, selected from N, C or $CR_y$; and any two of $Y_5$ to $Y_8$ are selected from nitrogen, the other two of $Y_5$ to $Y_8$ are selected from C or $CR_y$, respectively; and any adjacent two of $Y_1$ to $Y_4$ are C and joined to $Y_9$ and $Y_{12}$, respectively;

$L_1$ is selected from a single bond, substituted or unsubstituted arylene having 6 to 30 carbon atoms, substituted or unsubstituted heteroarylene having 3 to 30 carbon atoms or combinations thereof;

wherein R, $R_x$ and $R_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

In this embodiment, the expression that adjacent substituents R and $R_x$ can be optionally joined to form a ring is intended to mean that adjacent substituents R can be optionally joined to form a ring; also intended to mean that when multiple $R_x$ are present on the ring A, adjacent substituents $R_x$ can be optionally joined to form a ring; also intended to mean that when multiple $R_x$ are present on the ring B, adjacent substituents $R_x$ can be optionally joined to form a ring; also intended to mean that when multiple $R_x$ are present on the ring C, adjacent substituents $R_x$ can be optionally joined to form a ring; and, also intended to mean that adjacent substituents R and $R_x$ can be optionally joined to form a ring. It is obvious for those skilled in the art that adjacent substituents R and $R_x$ may not be joined to form a ring. In this case, adjacent substituents R are not joined to form a ring, adjacent substituents $R_x$ are not joined to form a ring, and adjacent substituents R and $R_x$ are also not joined to form a ring.

According to an embodiment of the present disclosure, in the device, the organic layer is a light-emitting layer, and the compound is a host material.

According to an embodiment of the present disclosure, in the device, the organic layer further comprises a phosphorescent material.

According to an embodiment of the present disclosure, in the device, the phosphorescent material is a metal complex comprising at least one ligand, wherein the ligand comprises any one of the following structures:

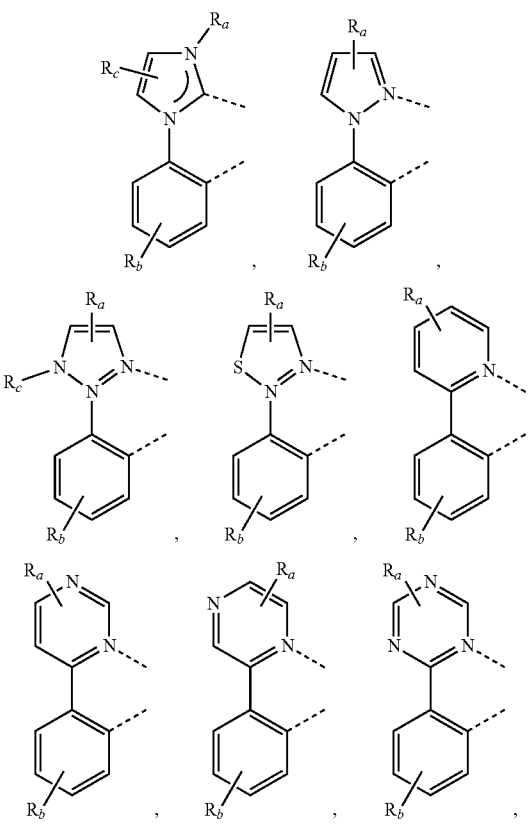

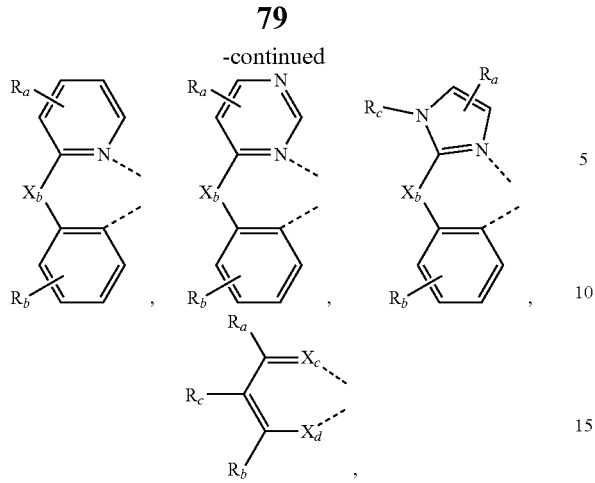

wherein,
- $R_a$, $R_b$, and $R_e$ may represent mono-substitution, multiple substitutions or non-substitution;
- $X_b$ is selected from the group consisting of: O, S, Se, $NR_{N1}$ and $CR_{C1}R_{C2}$;
- $X_c$ and $X_d$ are, at each occurrence identically or differently, selected from the group consisting of: O, S, Se and $NR_{N2}$;
- $R_a$, $R_b$, $R_c$, $R_{N1}$, $R_{N2}$, $R_{C1}$ and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof; and
- in the structure of the ligand, adjacent substituents can be optionally joined to form a ring.

In this embodiment, the expression that adjacent substituents can be optionally joined to form a ring is intended to mean that for groups of adjacent substituents, for example, two substituents $R_a$, two substituents $R_b$, two substituents $R_c$, substituents $R_a$ and $R_b$, substituents $R_a$ and $R_c$, substituents $R_b$ and $R_c$, substituents $R_a$ and $R_{N1}$, substituents $R_b$ and $R_{N1}$, substituents $R_a$ and $R_{C1}$, substituents $R_a$ and $R_{C2}$, substituents $R_b$ and $R_{C1}$, substituents $R_b$ and $R_{C2}$, substituents $R_a$ and $R_{N2}$, substituents $R_b$ and $R_{N2}$, and substituents $R_{C1}$ and $R_{C2}$, any one or more groups of these groups of substituents may be joined to form a ring. Obviously, these substituents may not be joined to form a ring.

According to an embodiment of the present disclosure, in the device, the phosphorescent material is a metal complex comprising at least one ligand, wherein the ligand has the following structure:

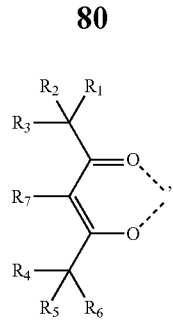

wherein $R_1$ to $R_7$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

According to an embodiment of the present disclosure, in the device, the phosphorescent material is a metal complex comprising at least one ligand, wherein the ligand has the following structure:

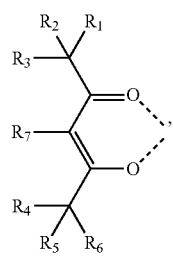

wherein at least one of $R_1$ to $R_3$ is selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms or combinations thereof; and/or at least one of $R_4$ to $R_6$ is selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms or combinations thereof.

According to an embodiment of the present disclosure, in the device, the phosphorescent material is a metal complex comprising at least one ligand, wherein the ligand has the following structure:

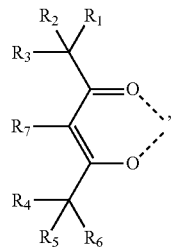

wherein at least two of $R_1$ to $R_3$ are, at each occurrence identically or differently, selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms or combinations thereof; and/or at least two of $R_4$ to $R_6$ are, at each occurrence identically or differently, selected from substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms or combinations thereof.

According to an embodiment of the present disclosure, in the device, the phosphorescent material is a metal complex comprising at least one ligand, wherein the ligand has the following structure:

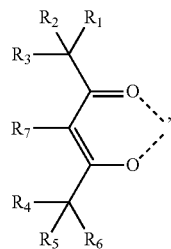

wherein at least two of $R_1$ to $R_3$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms or combinations thereof; and/or at least two of $R_4$ to $R_6$ are, at each occurrence identically or differently, selected from substituted or unsubstituted alkyl having 2 to 20 carbon atoms, substituted or unsubstituted cycloalkyl having 3 to 20 ring carbon atoms, substituted or unsubstituted heteroalkyl having 2 to 20 carbon atoms or combinations thereof.

According to an embodiment of the present disclosure, in the device, wherein the phosphorescent material is an Ir, Pt or Os complex.

According to an embodiment of the present disclosure, in the device, wherein the phosphorescent material is an Ir complex and has a structure of $Ir(L_a)(L_b)(L_c)$; wherein $L_a$, $L_b$ and $L_c$ are, at each occurrence identically or differently, selected from any one of the above ligands.

According to an embodiment of the present disclosure, in the device, wherein the phosphorescent material is selected from the group consisting of the following structures:

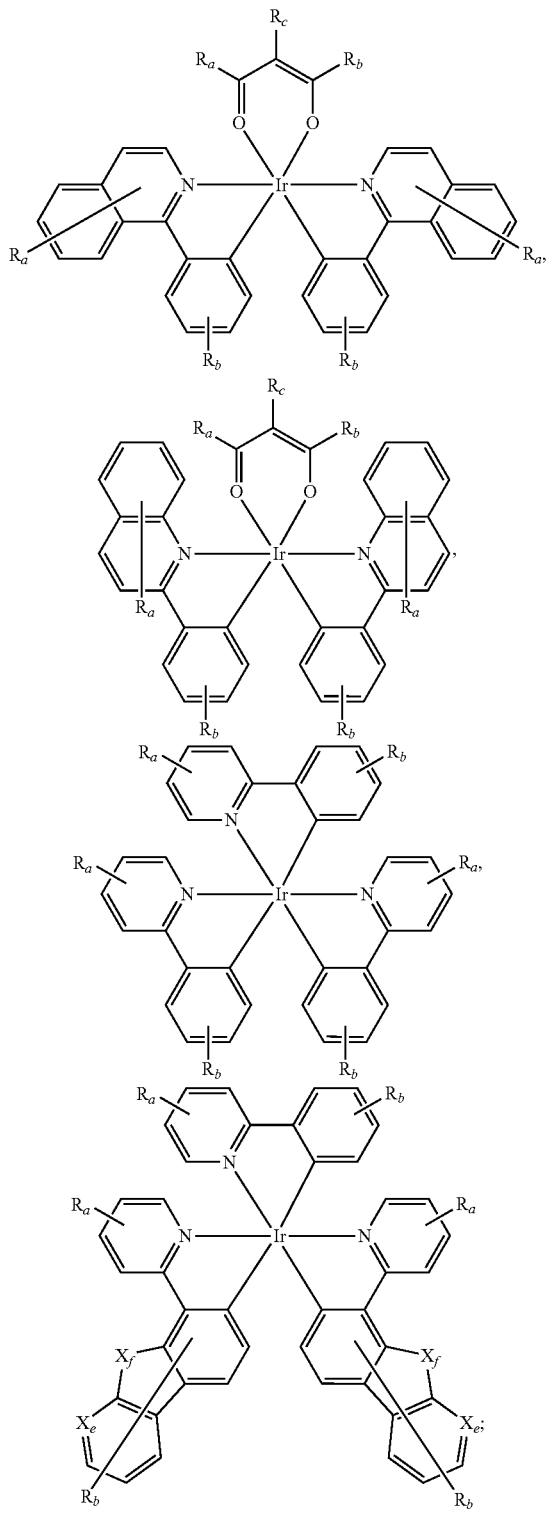

wherein $X_f$ is, at each occurrence identically or differently, selected from the group consisting of O, S, Se, $NR_{N3}$ and $CR_{C3}R_{C4}$;

wherein $X_e$ is $CR_d$ or N;

$R_a$, $R_b$ and $R_e$ may represent mono-substitution, multiple substitutions or non-substitution, and may each be identical or different at each occurrence;

$R_a$, $R_b$, $R_c$, $R_d$, $R_{N3}$, $R_{C3}$ and $R_{C4}$ are, at each occurrence identically or differently, selected from the group consisting of hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

According to another embodiment of the present disclosure, further disclosed is a compound formulation which comprises a compound having a structure of H-$L_1$-E, wherein the specific structure of the compound is as shown in any one of the embodiments described above.

Combination with Other Materials

The materials described in the present disclosure for a particular layer in an organic light emitting device can be used in combination with various other materials present in the device. The combinations of these materials are described in more detail in U.S. Pat. App. No. 20160359122 at paragraphs 0132-0161, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, materials disclosed herein may be used in combination with a wide variety of emissive dopants, hosts, transport layers, blocking layers, injection layers, electrodes and other layers that may be present. The combination of these materials is described in detail in paragraphs 0080-0101 of U.S. Pat. App. No. 20150349273, which is incorporated by reference herein in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatograph-mass spectrometry produced by SHIMADZU, gas chromatograph-mass spectrometry produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this present disclosure.

Material Synthesis Example: The method for preparing a compound in the present disclosure is not limited herein. Typically, the following compounds are taken as examples without limitations, and synthesis routes and preparation methods thereof are described below.

Synthesis Example 1: Synthesis of Compound 1-1

Step 1: Synthesis of Intermediate 1

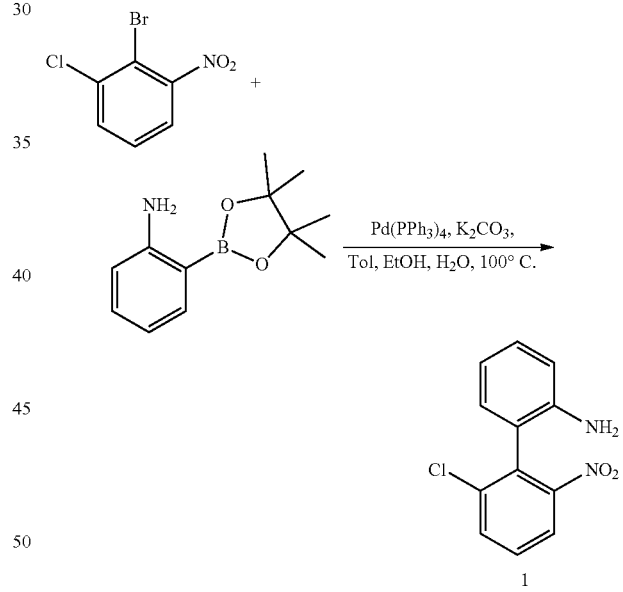

Under nitrogen protection, 2-bromo-3-chloronitrobenzene (100 g, 425.5 mmol), 2-aminophenylboronic acid pinacol ester (102 g, 468.1 mmol), tetrakis(triphenylphosphine) palladium (4.9 g, 4.25 mmol), potassium carbonate (115 g, 852 mmol), toluene (1000 mL), water (200 mL) and ethanol (200 mL) were added to a three-necked flask and reacted at 100° C. for 48 h. After the reaction was complete, the reaction solution was cooled to room temperature, concentrated to remove solvents, and added with distilled water. The mixture was extracted with ethyl acetate. The organic phases were washed with water, dried over anhydrous magnesium sulfate, concentrated to remove the solvent, and purified through column chromatography (PE/EA=4:1) to obtain intermediate 1 as a yellow oil (90 g, yield: 85%).

Step 2: Synthesis of Intermediate 2

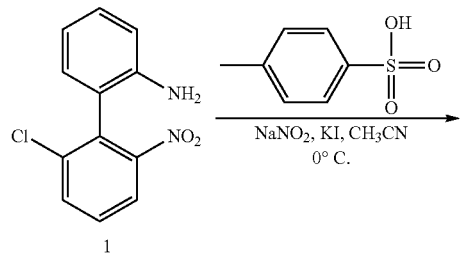

Intermediate 1 (90 g, 363 mmol) and acetonitrile (1000 mL) were put into a three-necked flask, respectively. P-toluenesulfonic acid (193.2 g, 1088 mmol) was added portionwise at 0° C. and stirred for 30 min. At this temperature, a mixed aqueous solution of sodium nitrite (69 g, 726 mmol) and potassium iodide (150.6 g, 907 mmol) was slowly added dropwise. After the dropwise addition was complete, the mixture was slowly warmed to room temperature and reacted for 12 h. After the reaction was complete, a saturated aqueous solution of sodium thiosulfate was added dropwise to quench the reaction. The reaction solution was concentrated and diluted with water. The mixed solution was extracted three times with ethyl acetate. The organic phases were dried over anhydrous sodium sulfate and concentrated to remove solvents. The mixture was isolated through column chromatography (PE/DCM=10/1) to obtain intermediate 2 as a yellow solid (85 g, yield: 65%).

Step 3: Synthesis of Intermediate 4

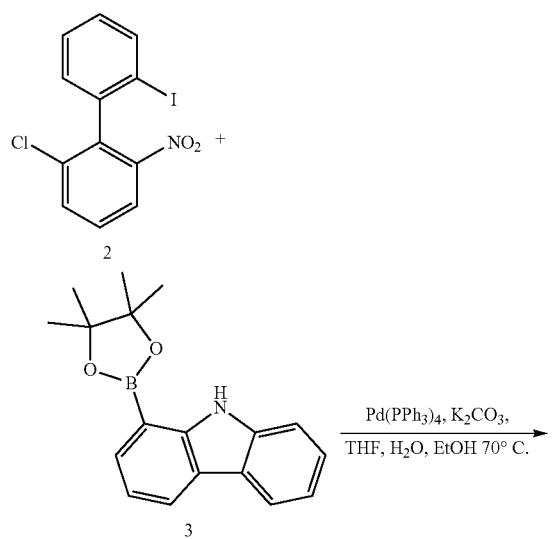

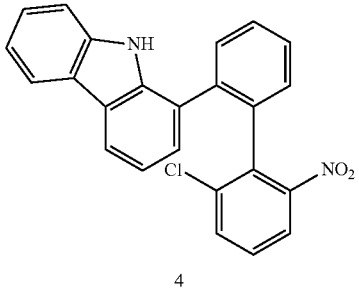

Under nitrogen protection, intermediate 2 (20 g, 55.7 mmol), intermediate 3 (24.5 g, 83.6 mmol), tetrakis(triphenylphosphine)palladium (1.9 g, 1.67 mmol), potassium carbonate (15.4 g, 111.4 mmol), tetrahydrofuran (500 mL), water (100 mL) and ethanol (100 mL) were added to a three-necked flask and reacted at 70° C. for 48 h. After the reaction was complete, the reaction solution was cooled to room temperature, concentrated to remove solvents, and added with distilled water. The mixture was extracted with ethyl acetate. The organic phases were washed with water, dried over anhydrous magnesium sulfate, concentrated to remove the solvent, and purified through column chromatography (PE/EA=4:1) to obtain intermediate 4 as a yellow solid (12 g, yield: 55%).

Step 4: Synthesis of Intermediate 5

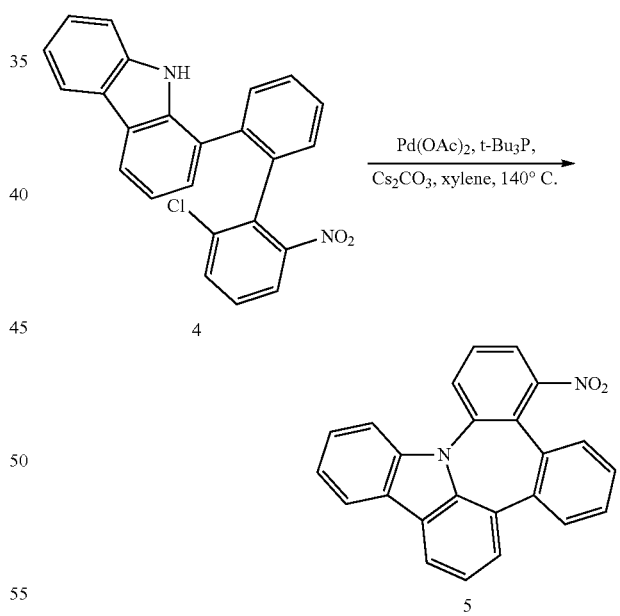

Under nitrogen protection, intermediate 4 (12 g, 30.15 mmol), palladium acetate (338 mg, 1.5 mmol), tri-tert-butylphosphine (606 mg, 3.0 mmol), cesium carbonate (20 g, 60.3 mmol) and xylene (230 mL) were added to a three-necked flask and reacted at 140° C. for 10 h. After the reaction was complete, the reaction solution was cooled to room temperature, concentrated to remove solvents, and added with distilled water. The mixture was extracted with ethyl acetate. The organic phases were washed with water, dried over anhydrous magnesium sulfate, concentrated to remove the solvent, and purified through column chromatography (PE/EA=6:1) to obtain intermediate 5 as a yellow solid (9 g, yield: 80%).

Step 5: Synthesis of Intermediate 6

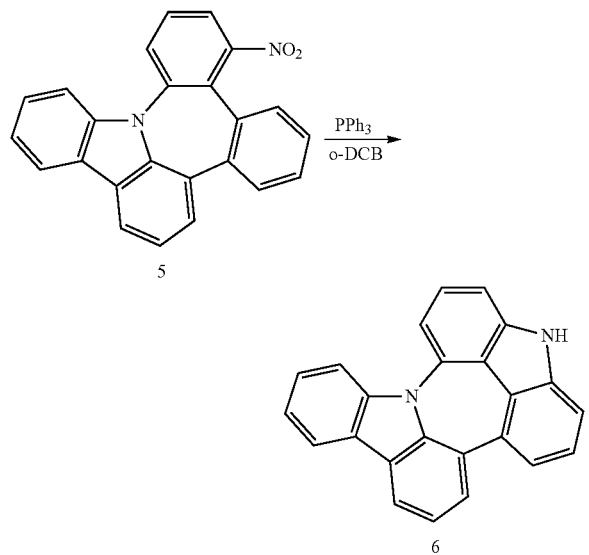

Under nitrogen protection, intermediate 5 (9 g, 24.9 mmol), triphenylphosphine (19.6 g, 74.7 mmol) and o-dichlorobenzene (o-DCB) (100 mL) were added to a three-necked flask and reacted at 200° C. for 12 h. After the reaction was complete, the reaction solution was concentrated to remove the solvent, and the crude product was isolated through column chromatography to obtain intermediate 6 as a yellow solid (7 g, yield: 85%).

Step 6: Synthesis of Compound 1-1

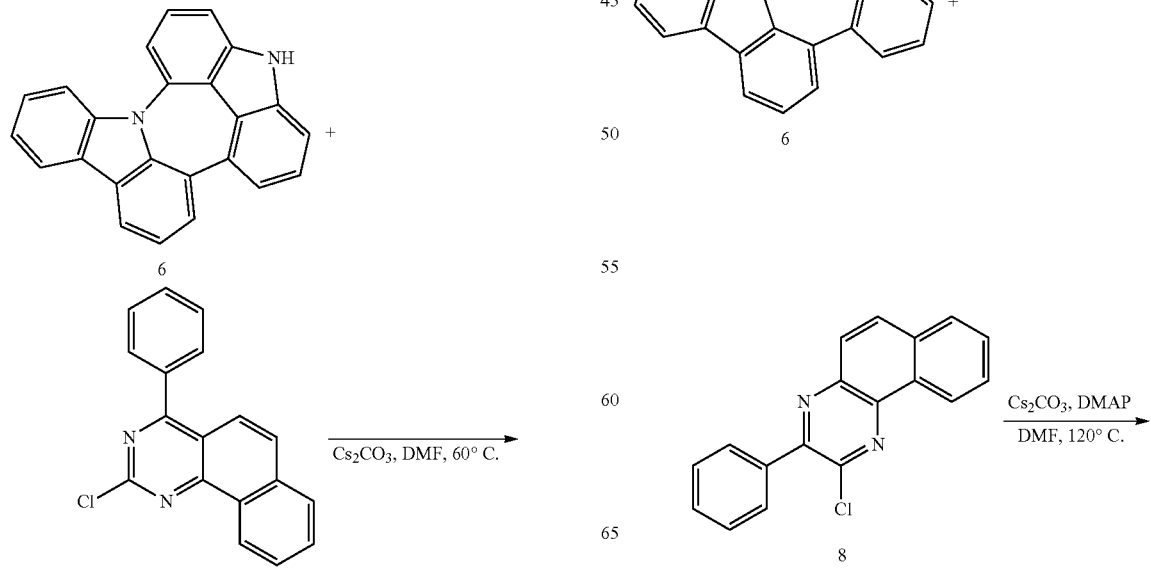

Under nitrogen protection, intermediate 6 (3 g, 9.1 mmol), intermediate 7 (2.64 g, 9.1 mmol), cesium carbonate (5.9 g, 18.2 mmol) and DMF (60 mL) were added to a three-necked flask and reacted at 60° C. for 16 h. After the reaction was complete, the reaction solution was cooled to room temperature, added with distilled water, and filtered to obtain a solid. The solid was washed three times with ethanol and ethyl acetate respectively. The crude product was washed twice with pentanone and toluene respectively to obtain Compound 1-1 as a yellow solid (3.3 g, yield: 56%). The product was confirmed as the target product with a molecular weight of 584.2.

Synthesis Example 2: Synthesis of Compound 1-253

Step 1: Synthesis of Compound 1-253

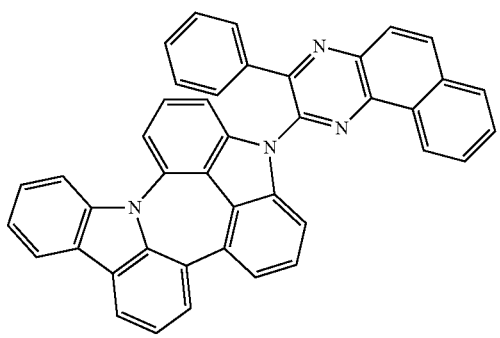

1-253

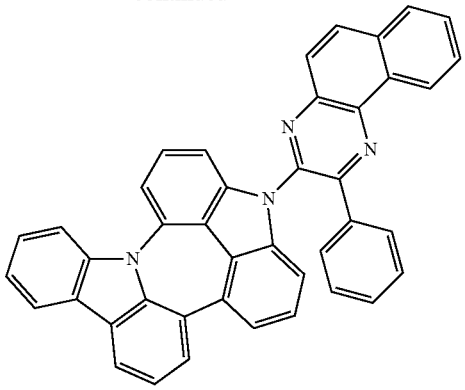

1-348

Under nitrogen protection, intermediate 6 (1 g, 3.03 mmol), intermediate 8 (880 mg, 3.03 mmol), 4-(dimethylamino)pyridine (DMAP) (366 mg, 3.03 mmol), cesium carbonate (2.0 g, 6.06 mmol) and DMF (30 mL) were added to a three-necked flask and reacted at 120° C. for 6 h. After the reaction was complete, the reaction solution was cooled to room temperature, added with distilled water to precipitate a solid, and filtered to collect the solid. The solid was purified through column chromatography (PE/EA=2:1) to obtain Compound 1-253 as a yellow solid (1.3 g, 76%). The product was confirmed as the target product with a molecular weight of 584.2.

Synthesis Example 3: Synthesis of Compound 1-348

Step 1: Synthesis of Compound 1-348

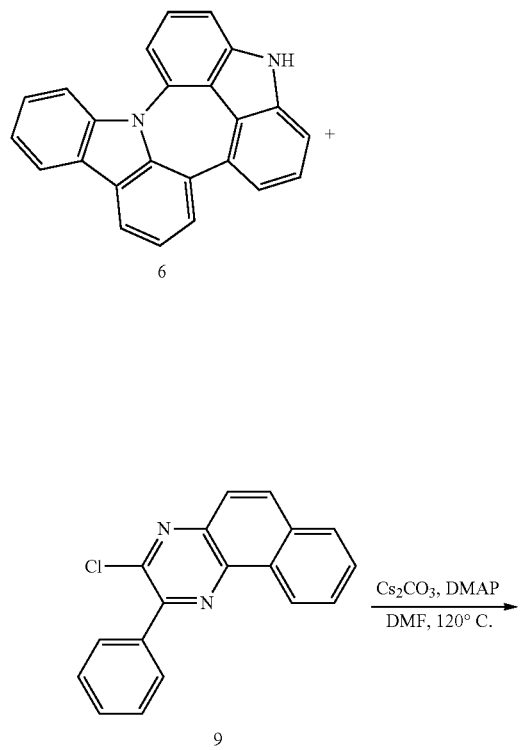

Under nitrogen protection, intermediate 6 (2 g, 6.06 mmol), intermediate 9 (1.8 g, 6.06 mmol), DMAP (733 mg, 6.06 mmol), cesium carbonate (3.9 g, 12.12 mmol) and DMF (40 mL) were added to a three-necked flask and reacted at 120° C. for 6 h. After the reaction was complete, the reaction solution was cooled to room temperature, added with distilled water to precipitate a solid, and filtered to collect the solid. The solid was purified through column chromatography (PE/EA=2:1) to obtain Compound 1-348 as a yellow solid (2.4 g, 68%). The product was confirmed as the target product with a molecular weight of 584.2.

Those skilled in the art will appreciate that the above preparation methods are merely illustrative. Those skilled in the art can obtain other compound structures of the present disclosure through the modifications of the preparation methods.

DEVICE EXAMPLE

Device Example 1

First, a glass substrate having an Indium Tin Oxide (ITO) anode with a thickness of 120 nm was cleaned and then treated with oxygen plasma and UV ozone. After the treatment, the substrate was dried in a nitrogen-filled glovebox to remove moisture and then mounted on a substrate holder and placed in a vacuum chamber. Organic layers specified below were sequentially deposited through vacuum thermal evaporation on the ITO anode at a rate of 0.01 to 5 Å/s at a vacuum degree of about $10^{-8}$ torr. Compound HI was used as a hole injection layer (HIL) with a thickness of 100 Å. Compound HT was used as a hole transporting layer (HTL) with a thickness of 400 Å. Compound EB was used as an electron blocking layer (EBL) with a thickness of 50 Å. Then, Compound 1-1 of the present disclosure as a host and Compound RD as a dopant were co-deposited as an emissive layer (EML) with a thickness of 400 Å. Compound HB was used as a hole blocking layer (HBL) with a thickness of 50 Å. On the HBL, Compound ET and 8-hydroxyquinolinolato-lithium (Liq) were co-deposited as an electron transporting layer (ETL) with a thickness of 350 Å. Finally, 8-hydroxyquinolinolato-lithium (Liq) with a thickness of 10 Å was deposited as an electron injection layer (EIL), and Al with a thickness of 1200 Å was deposited as a cathode. The device was transferred back to the glovebox and encapsulated with a glass lid to complete the device.

Device Comparative Example 1

The implementation mode in Device Comparative Example 1 was the same as that in Device Example 1, except that Compound 1-1 of the present disclosure in the emissive layer (EML) was replaced with Compound A to serve as a host material.

Detailed structures and thicknesses of layers of the devices are shown in the following table. A layer using more than one material is obtained by doping different compounds at their weight ratios as described.

TABLE 1

Device structures in the device example and the comparative example

| Device ID | HIL | HTL | EBL | EML (400 Å) Host | EML (400 Å) Dopant | HBL | ETL |
|---|---|---|---|---|---|---|---|
| Example 1 | Compound HI (100 Å) | Compound HT (400 Å) | Compound EB (50 Å) | Compound 1-1 (97%) | Compound RD (3%) | Compound HB (50 Å) | Compound ET: Liq (40:60) (350 Å) |
| Comparative Example 1 | Compound HI (100 Å) | Compound HT (400 Å) | Compound EB (50 Å) | Compound A (97%) | Compound RD (3%) | Compound HB (50 Å) | Compound ET: Liq (40:60) (350 Å) |

Structures of the materials used in the devices are shown as follows:

Compound HI

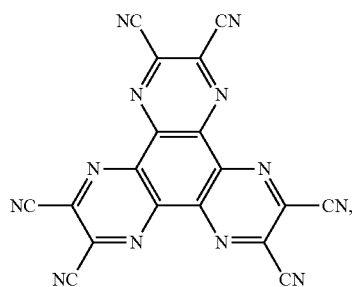

Compound EB

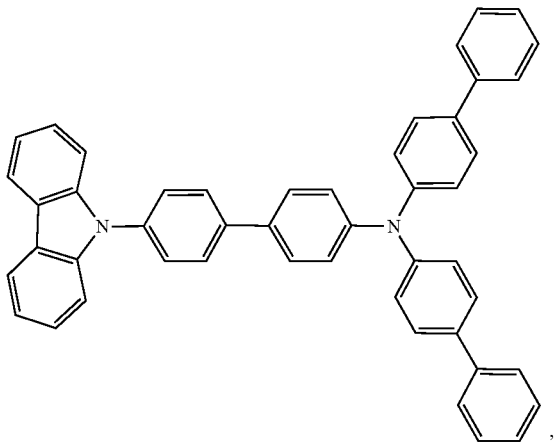

Compound HT

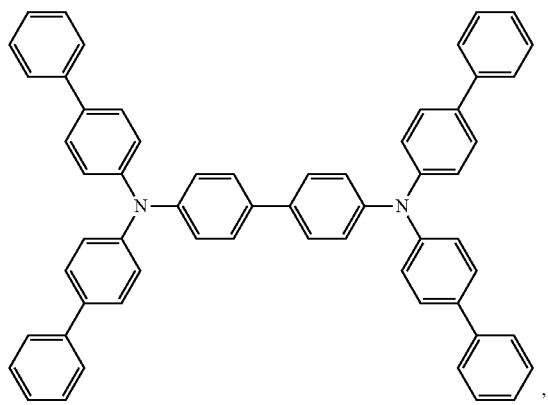

Compound RD

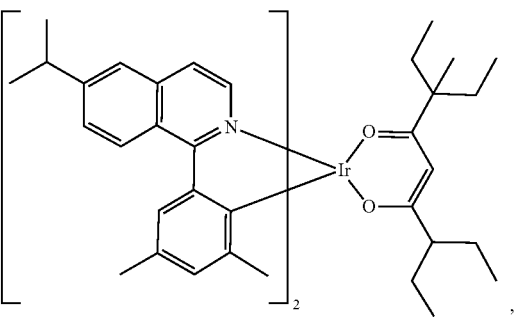

Compound HB

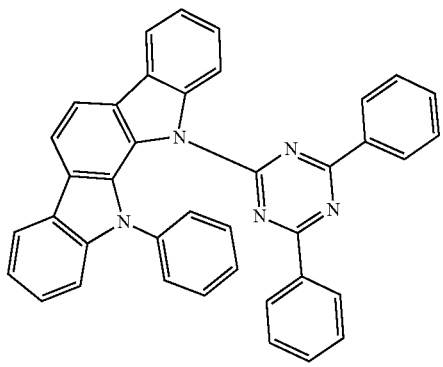

Compound ET

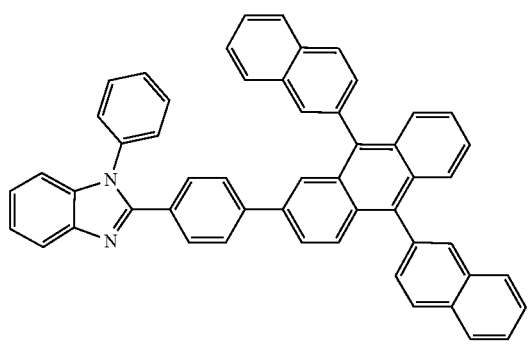

Liq

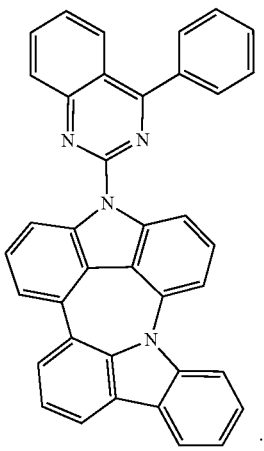

A

I-1

Current efficiency (CE), maximum wavelength ($\lambda_{max}$) and external quantum efficiency (EQE) measured at 15 mA/cm² are listed in Table 2.

TABLE 2

| | Device data | | |
| --- | --- | --- | --- |
| | At 15 mA/cm² | | |
| Device ID | $\lambda_{max}$ (nm) | CE [cd/A] | EQE (%) |
| Example 1 | 628 | 16 | 20.35 |
| Comparative Example 1 | 627 | 15 | 18.8 |

Discussion:

As shown in Table 2, the EQE of Example 1 measured at a current density of 15 mA/cm² is 20.35%, which is 8% higher than the EQE (18.8%) of Comparative Example 1; the CE of Example 1 is slightly higher than the CE of Comparative Example 1; $\lambda_{max}$ is basically the same in Example 1 and Comparative Example 1; but the light-emitting efficiency of Example 1 is greatly improved. That is, the compound of the present disclosure which comprises a hole transporting unit that is formed by fusing indole and pyrrole with an azamacrocycle and is bonded with an electron transporting unit of benzoquinazoline or benzoquinoxaline and similar structures thereof has better electron transporting stability than Compound A where an electron transporting unit of quinazoline is bonded. The compound of the present disclosure can make hole transporting and electron transporting in the emissive layer reach a more balanced state, and thus has significantly improved efficiency.

Device Example 2

The implementation mode in Device Example 2 was the same as that in Device Example 1, except that Compound 1-1 of the present disclosure in the emissive layer (EML) was replaced with Compound 1-253 to serve as a host to be co-deposited with Compound RD (at a weight ratio of 98:2).

Device Example 3

The implementation mode in Device Example 3 was the same as that in Device Example 1, except that Compound 1-1 of the present disclosure in the emissive layer (EML) was replaced with Compound 1-348 to serve as a host to be co-deposited with Compound RD (at a weight ratio of 98:2).

Device Comparative Example 2

The implementation mode in Device Comparative Example 2 was the same as that in Device Example 1, except that Compound 1-1 of the present disclosure in the emissive layer (EML) was replaced with Compound B to serve as a host to be co-deposited with Compound RD (at a weight ratio of 98:2).

Detailed structures and thicknesses of layers of the devices are shown in the following table. A layer using more than one material is obtained by doping different compounds at their weight ratios as described.

TABLE 3

Device structures in the device examples and the comparative example

| Device ID | HIL | HTL | EBL | EML (400 Å) Host | EML (400 Å) Dopant | HBL | ETL |
|---|---|---|---|---|---|---|---|
| Example 2 | Compound HI (100 Å) | Compound HT (400 Å) | Compound EB (50 Å) | Compound 1-253 (98%) | Compound RD (2%) | Compound HB (50 Å) | Compound ET: Liq (40:60) (350 Å) |
| Example 3 | Compound HI (100 Å) | Compound HT (400 Å) | Compound EB (50 Å) | Compound 1-348 (98%) | Compound RD (2%) | Compound HB (50 Å) | Compound ET: Liq (40:60) (350 Å) |
| Comparative Example 2 | Compound HI (100 Å) | Compound HT (400 Å) | Compound EB (50 Å) | Compound B (98%) | Compound RD (2%) | Compound HB (50 Å) | Compound ET: Liq (40:60) (350 Å) |

Structures of the new materials used in the devices are shown as follows:

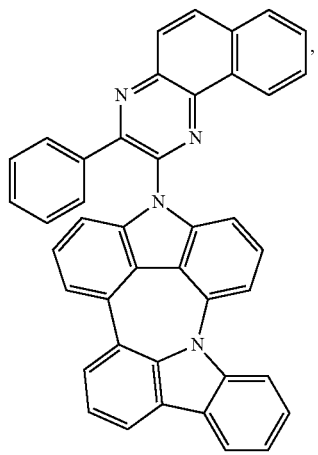

1-253

-continued

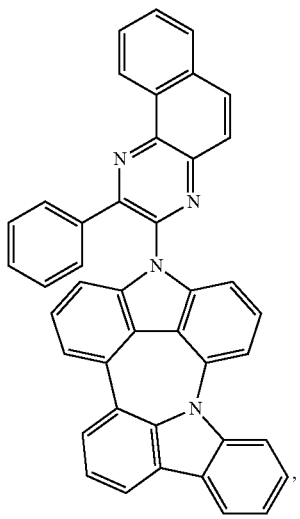

1-348

-continued

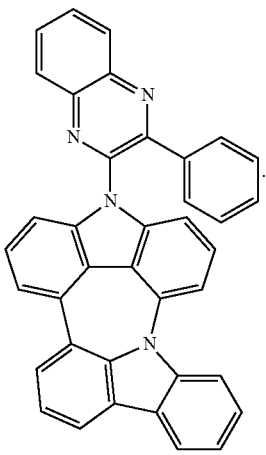

B

Current efficiency (CE) and maximum wavelength ($\lambda_{max}$) measured at 15 mA/cm² and lifetimes measured at 80 mA/cm² are listed in Table 4.

TABLE 4

| | Device data | | |
|---|---|---|---|
| | At 15 mA/cm² | | At 80 mA/cm² |
| Device ID | $\lambda_{max}$ (nm) | CE [cd/A] | LT97 (h) |
| Example 2 | 628 | 19 | 65 |
| Example 3 | 625 | 18 | 67 |
| Comparative Example 2 | 625 | 19 | 41 |

Discussion:

As shown in Table 4, Example 2 and Example 3 have substantially the same current efficiency as Comparative Example 2. However, the lifetime of Example 2 is 65 h, which is 58% longer than the lifetime of Comparative Example 2, and the lifetime of Example 3 has been improved by up to 63% than the lifetime of Comparative Example 2. It proves that the compound of the present disclosure can significantly improve the lifetime of the device compared with Compound B in the prior art.

In summary, the compound disclosed in the present disclosure, which comprises a hole transporting unit that is formed by fusing indole and pyrrole with an azamacrocycle and is bonded with an electron transporting unit of benzoquinazoline or benzoquinoxaline and similar structures thereof, has better electron transporting stability than Compound A and Compound B where an electron transporting unit of quinazoline or quinoxaline is bonded. The compound of the present disclosure can make hole transporting and electron transporting in the emissive layer reach a more balanced state, and thus has significant improvements in efficiency and/or lifetime.

It should be understood that various embodiments described herein are examples and not intended to limit the scope of the present disclosure. Therefore, it is apparent to those skilled in the art that the present disclosure as claimed may include variations of specific embodiments and preferred embodiments described herein. Many of the materials and structures described herein may be replaced with other materials and structures without departing from the spirit of the present disclosure. It should be understood that various theories as to why the present disclosure works are not intended to be limitative.

What is claimed is:
1. A compound, having a structure of H-L₁-E;
wherein H has a structure represented by Formula 1:

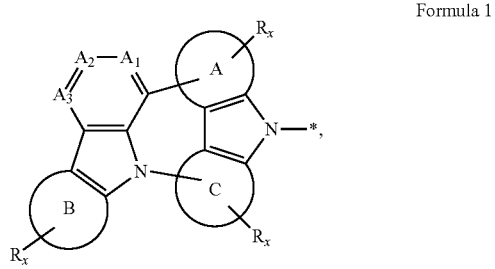

Formula 1 in Formula 1, A₁, A₂ and A₃ are, at each occurrence identically or differently, selected from CR; and the ring A, the ring B and the ring C are, at each occurrence identically or differently, selected from an aromatic ring having 6 to 18 carbon atoms or a hetero-aromatic ring having 3 to 18 carbon atoms;
R$_x$ represents mono-substitution, multiple substitutions or non-substitution; and
adjacent substituents R, R$_x$ can be optionally joined to form a ring;
wherein E has a structure represented by Formula 2-b, Formula 2-d, or Formula 2-f:

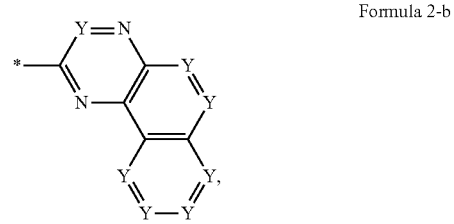

Formula 2-b

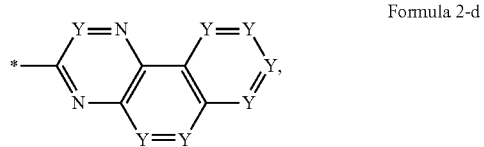

Formula 2-d

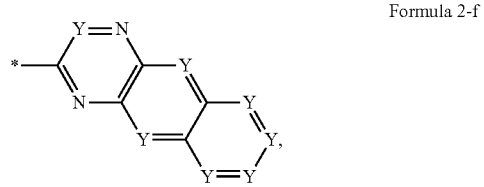

Formula 2-f wherein Y is, at each occurrence identically or differently, selected from CR$_y$;
L₁ is selected from a single bond, substituted or unsubstituted arylene having 6 to 30 carbon atoms, substituted or unsubstituted heteroarylene having 3 to 30 carbon atoms or combinations thereof;
wherein R, R$_x$ and R$_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

2. The compound of claim 1, wherein the H has a structure represented by Formula 1-a:

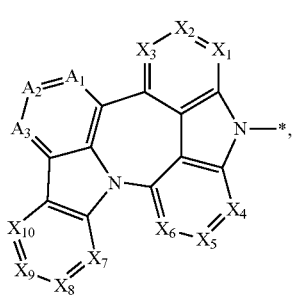

Formula 1-a wherein $A_1$ to $A_3$ are, at each occurrence identically or differently, selected from CR; and $X_1$ to $X_{10}$ are, at each occurrence identically or differently, selected from $CR_x$; wherein R and $R_x$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof; and wherein adjacent substituents R, $R_x$ can be optionally joined to form a ring.

3. The compound of claim 2, wherein R and $R_x$ are, at each occurrence identically or differently, selected from the group consisting of: hydrogen, deuterium, halogen, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted amino having 0 to 20 carbon atoms, a cyano group, an isocyano group, a sulfanyl group and combinations thereof; and adjacent substituents R, $R_x$ can be optionally joined to form a ring.

4. The compound of claim 2, wherein at least one of R and $R_x$ is selected from deuterium, substituted or unsubstituted aryl having 6 to 30 carbon atoms, or substituted or unsubstituted heteroaryl having 3 to 30 carbon atoms.

5. The compound of claim 2, wherein for adjacent substituents R in $A_1$ to $A_3$, adjacent substituents $R_x$ in $X_1$ to $X_3$, adjacent substituents $R_x$ in $X_4$ to $X_6$, and adjacent substituents $R_x$ in $X_7$ to $X_{10}$, at least one of these groups of adjacent substituents is joined to form a ring.

6. The compound of claim 1, wherein the H is selected from the group consisting of the following structures:

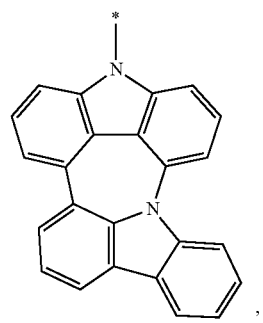

H-1

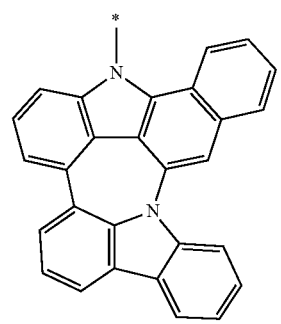

H-2

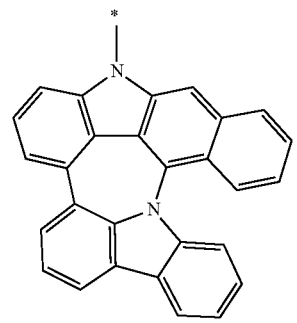

H-3

,

H-4
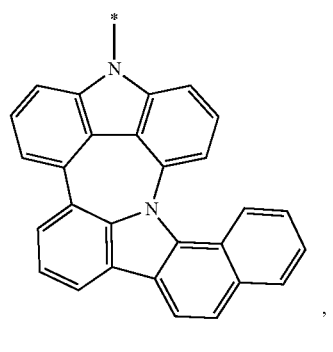
H-5
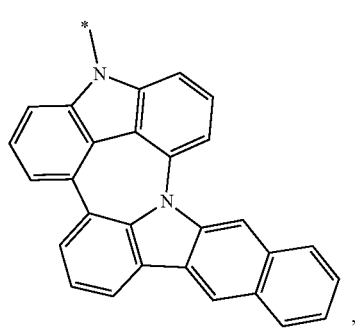
H-6
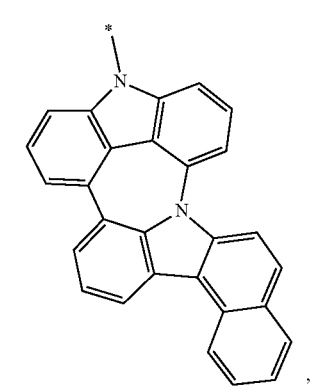
H-7
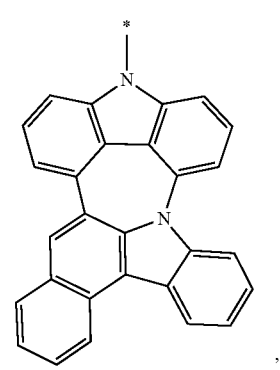
H-8
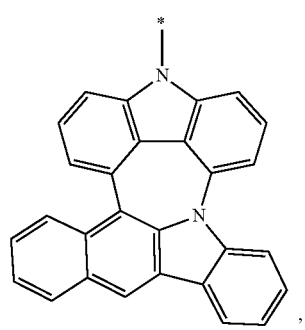
H-9
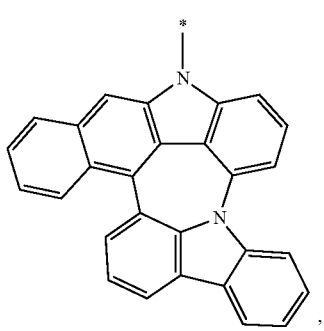
H-10
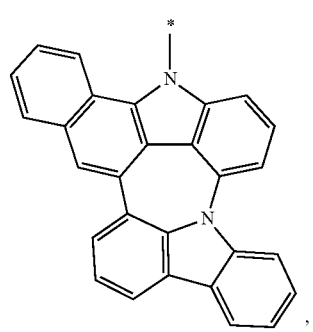
H-11
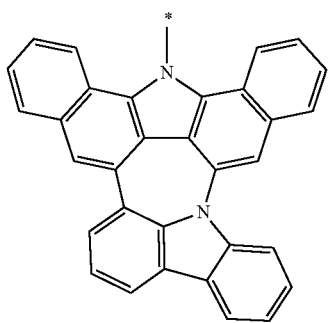

-continued
H-12
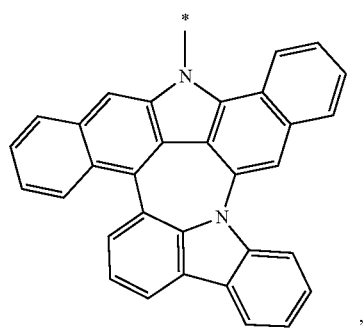
H-13
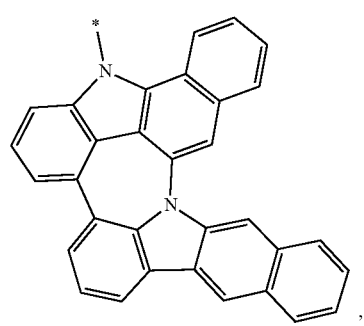
H-14
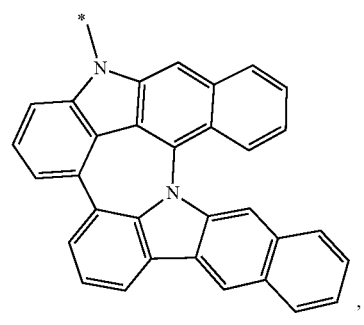
H-15
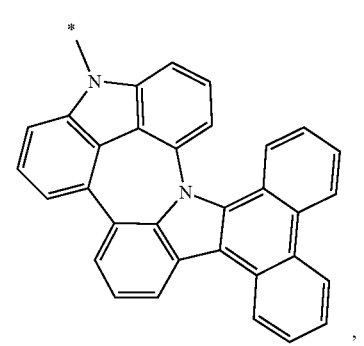
-continued
H-16
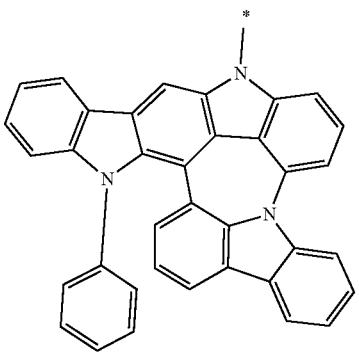
H-17
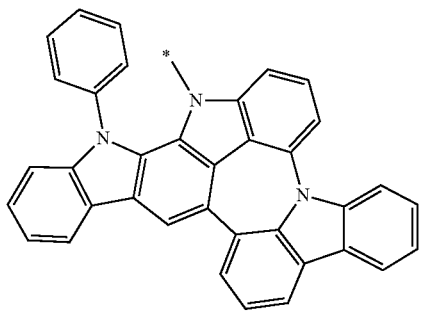
H-18
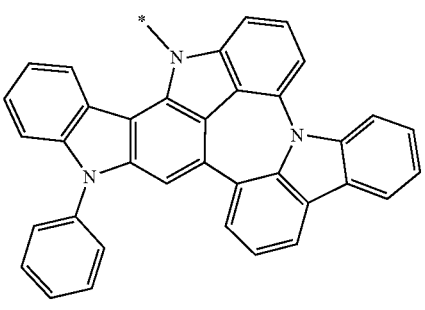
H-19
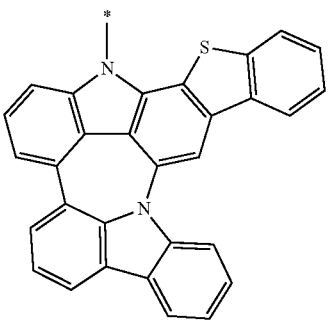

H-20
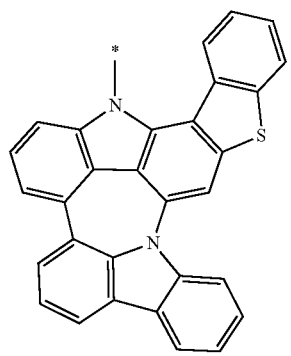
H-21
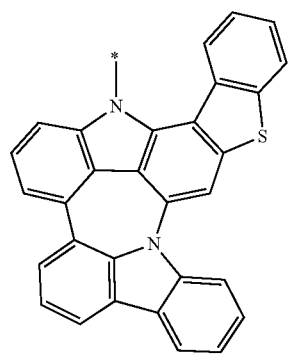
H-22
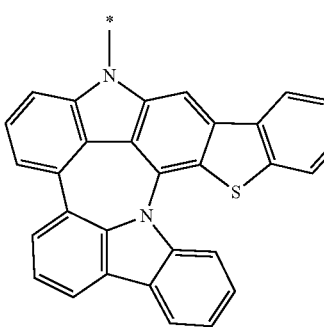
H-23
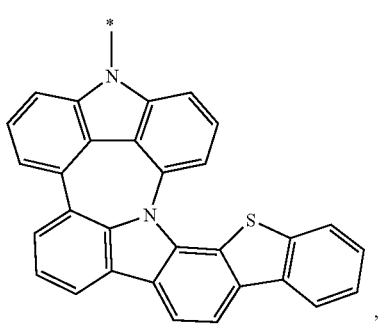
H-24
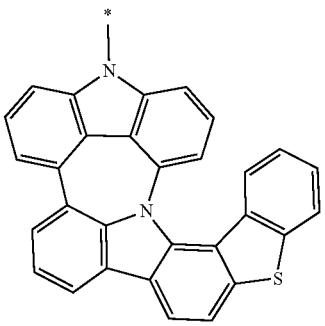
H-25
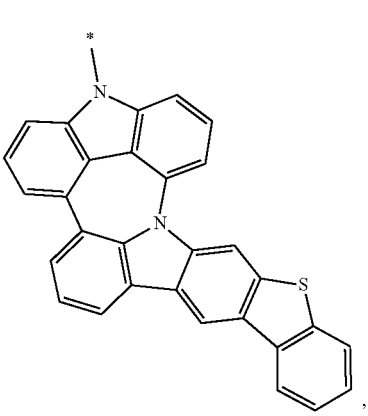
H-26
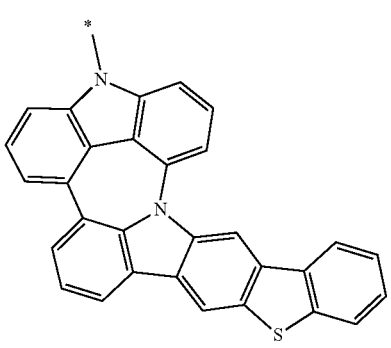
H-27
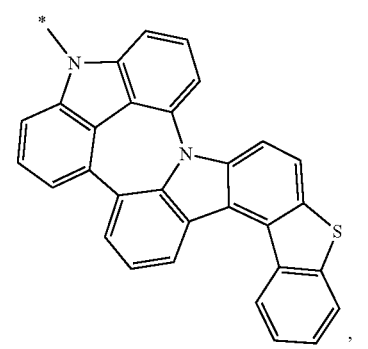

H-28
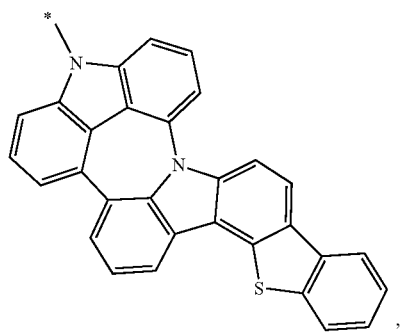
H-29
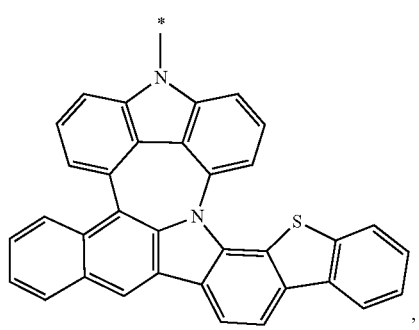
H-30
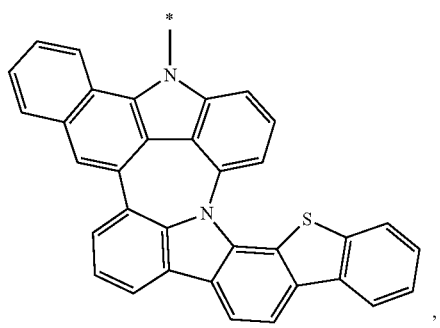
H-31
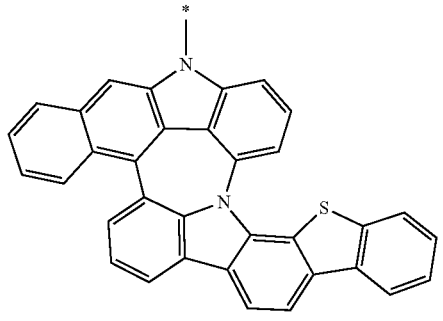
H-32
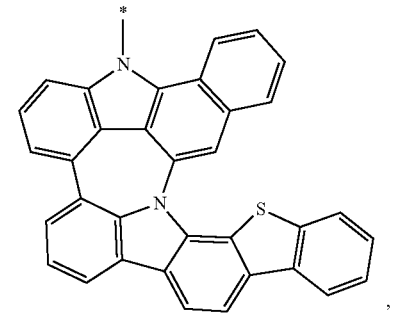
H-33
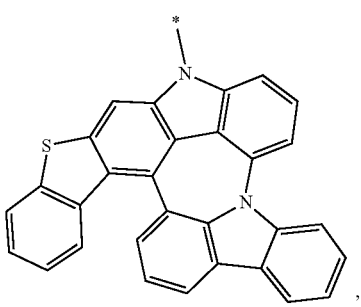
H-34
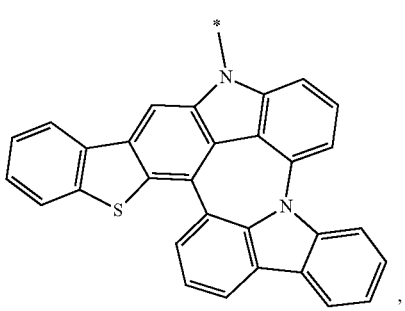
H-35
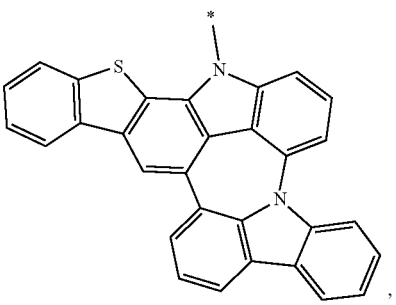
H-36
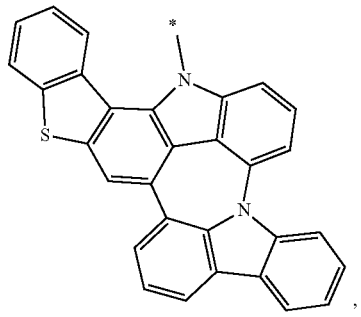
H-37
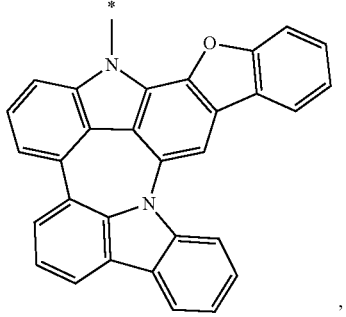

-continued
H-38
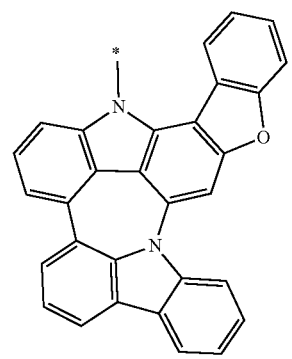
H-39
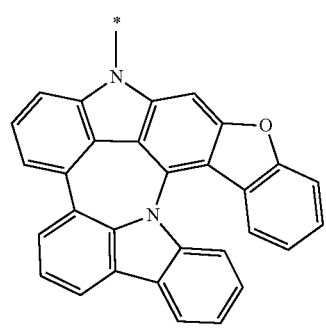
H-40
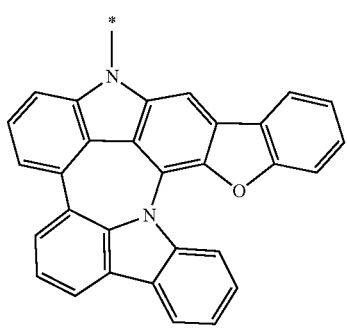
H-41
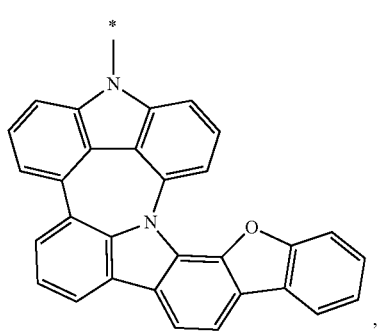
-continued
H-42
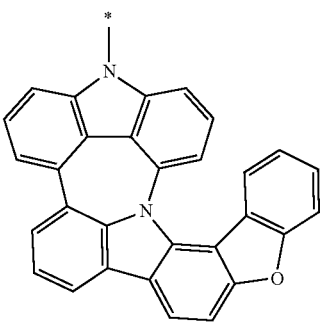
H-43
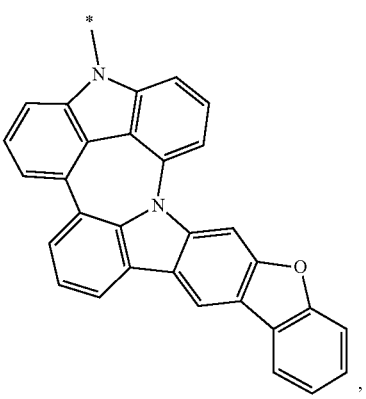
H-44
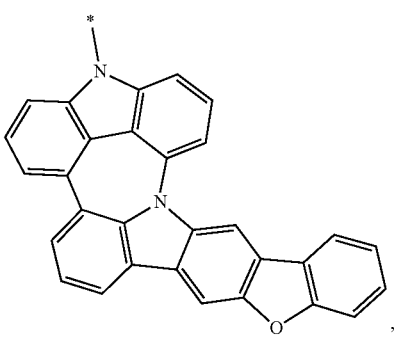
H-45
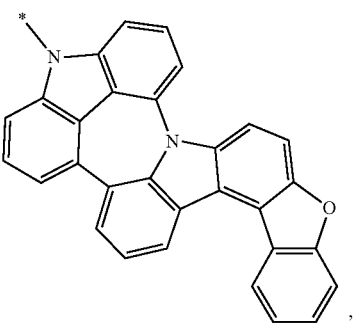

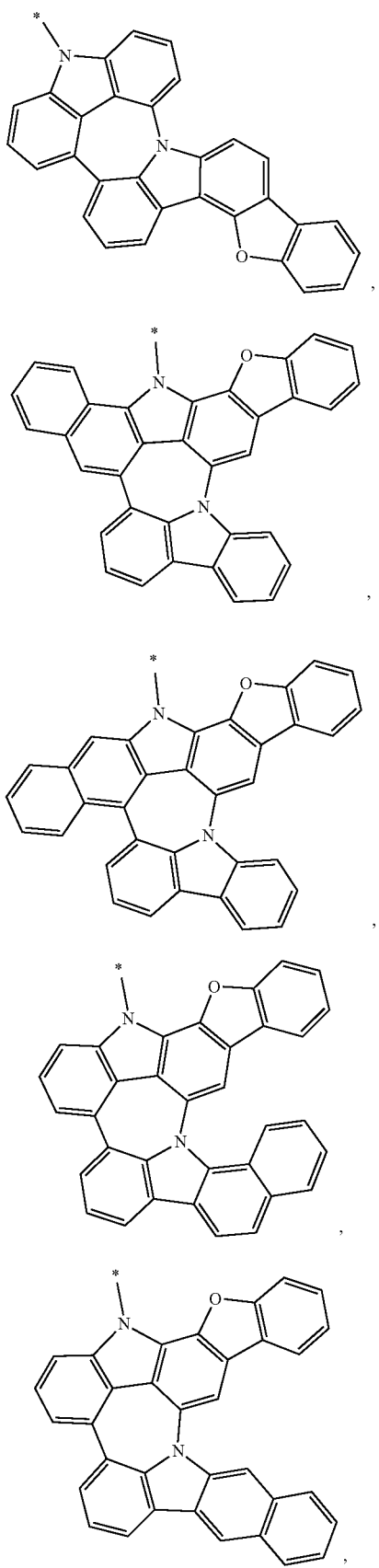
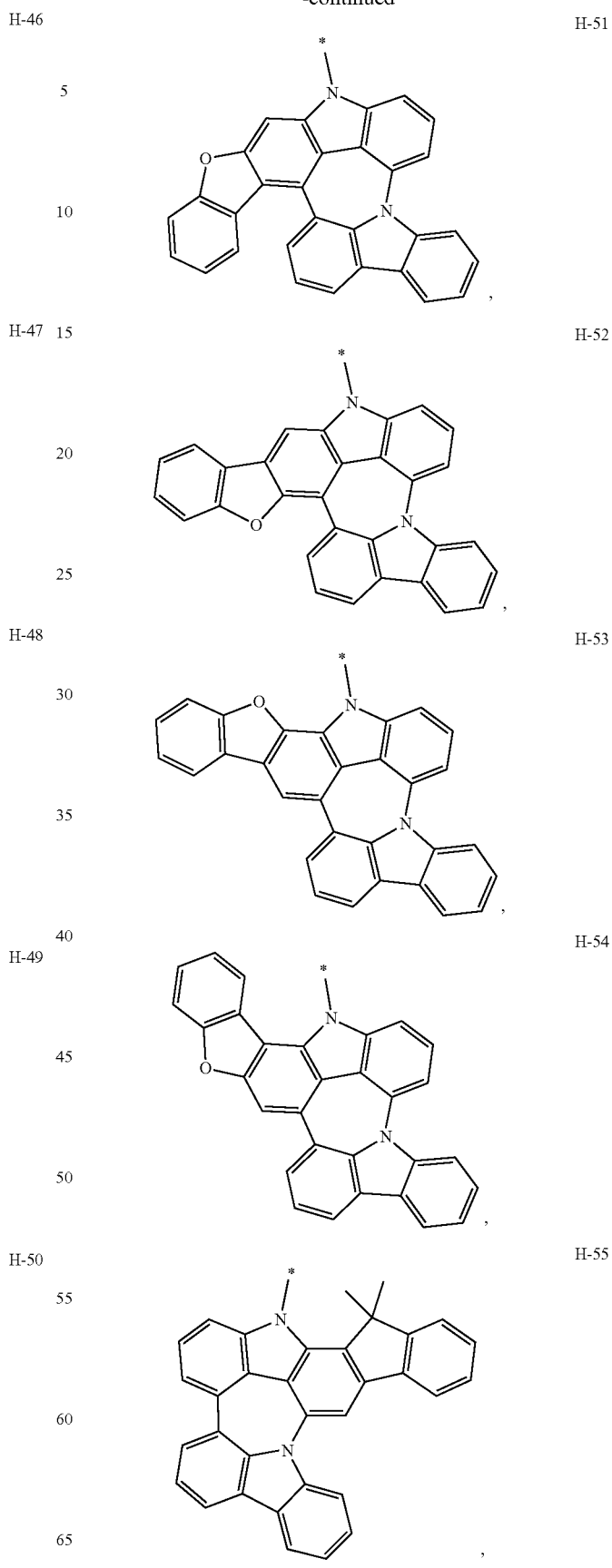

H-56
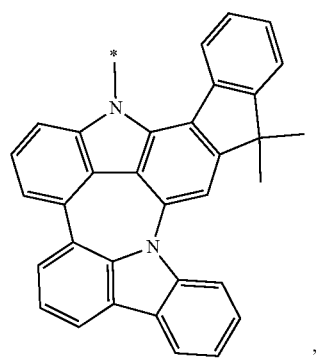
H-57
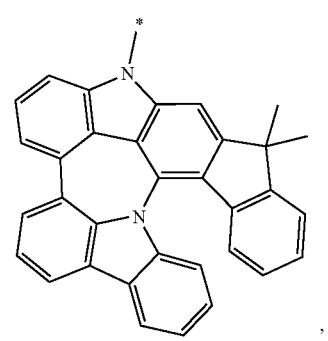
H-58
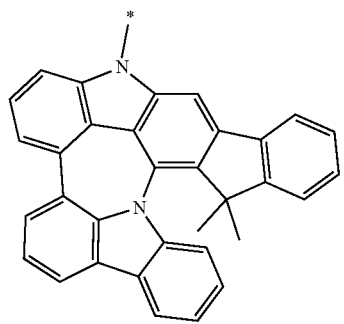
H-59
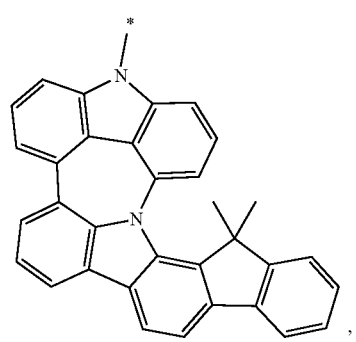
H-60
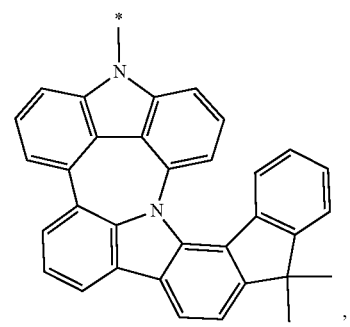
H-61
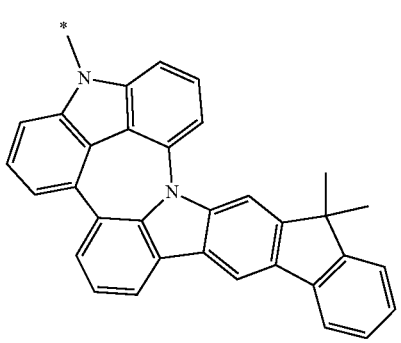
H-62
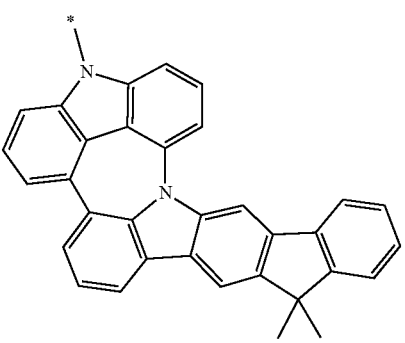
H-63
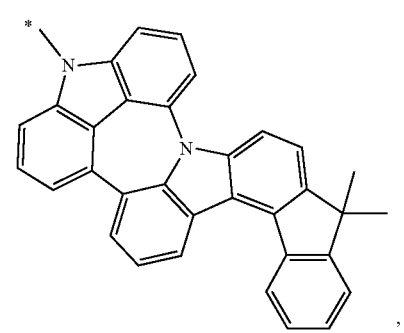

H-64
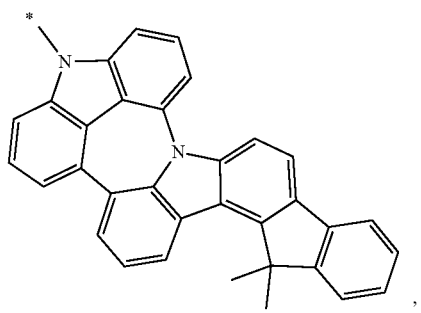
H-65
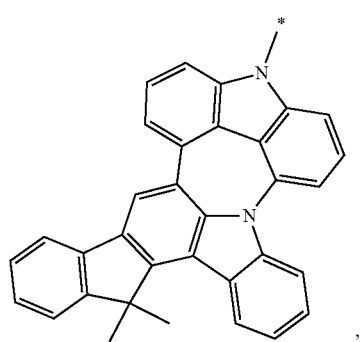
H-66
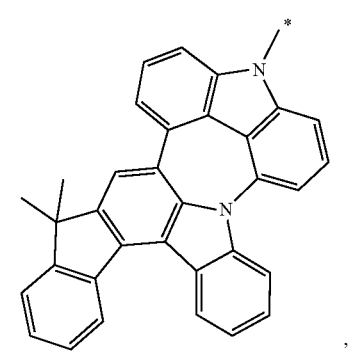
H-67
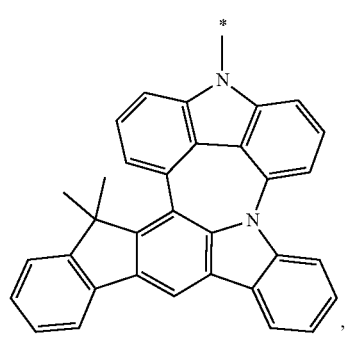
H-68
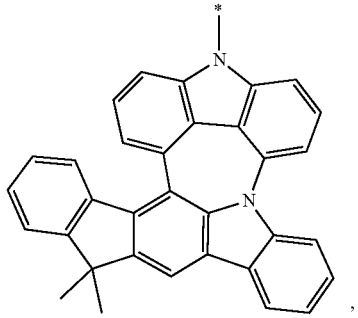
H-69
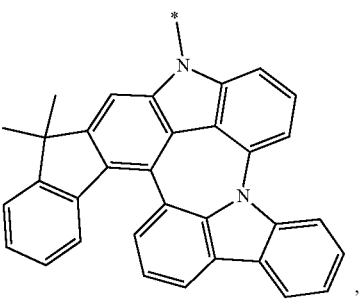
H-70
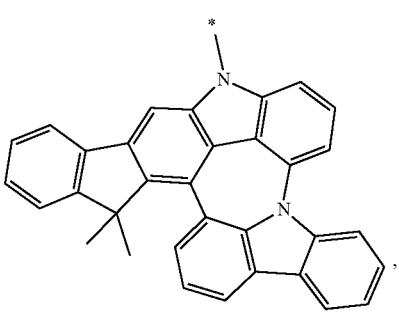
H-71
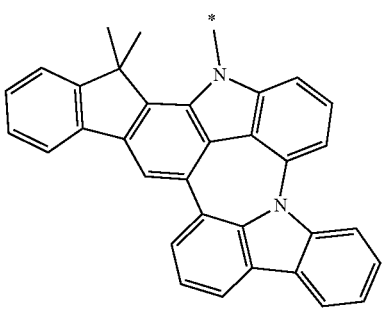
H-72
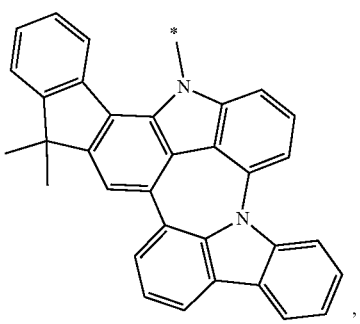

-continued
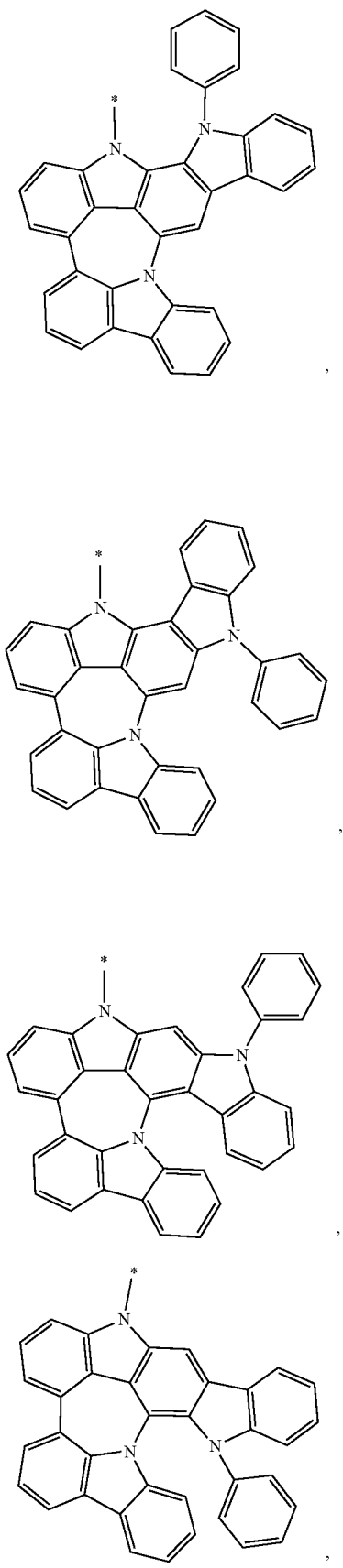
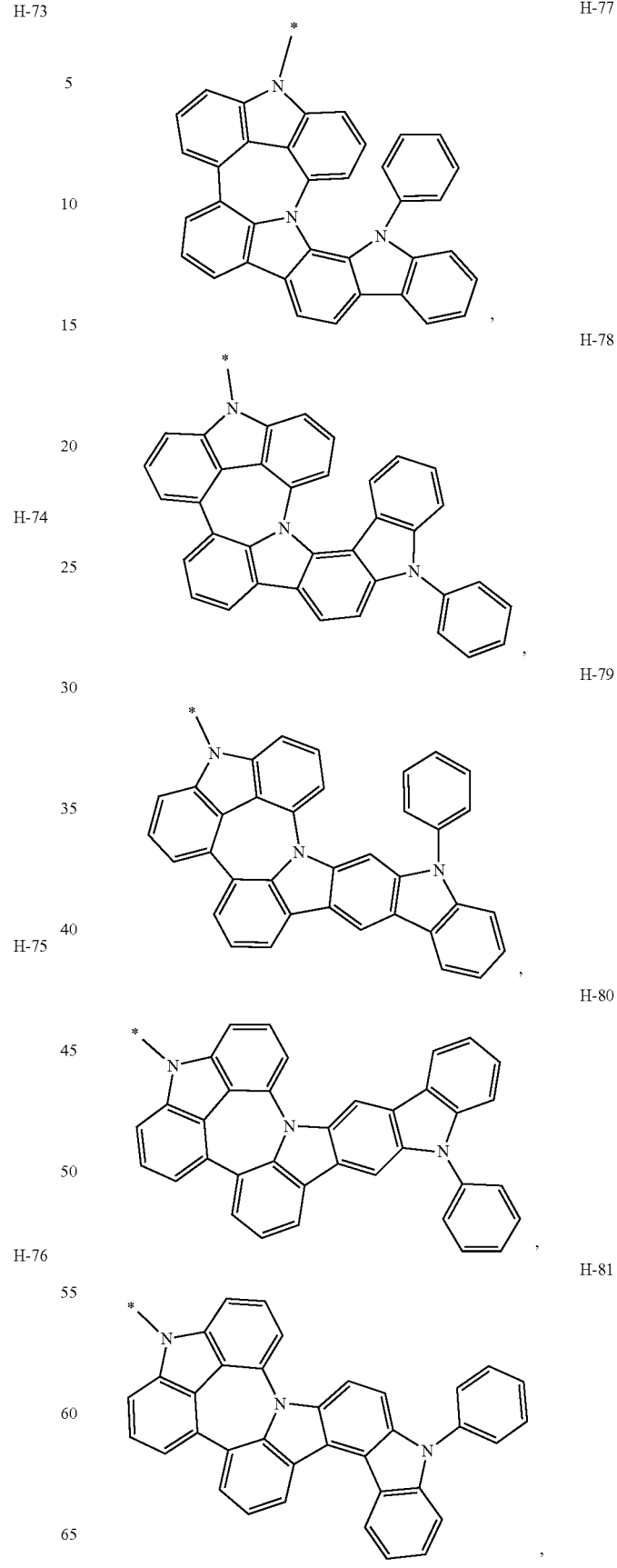

-continued
H-82
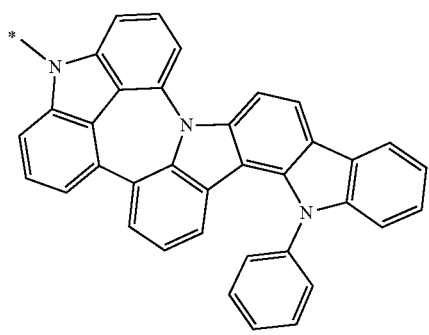
H-83
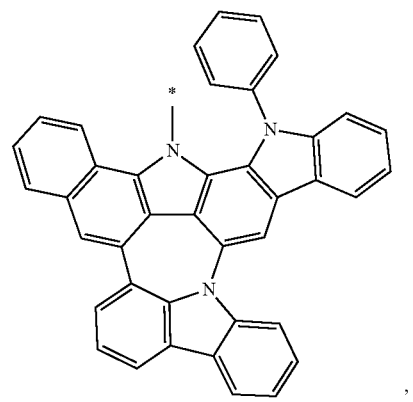
H-84
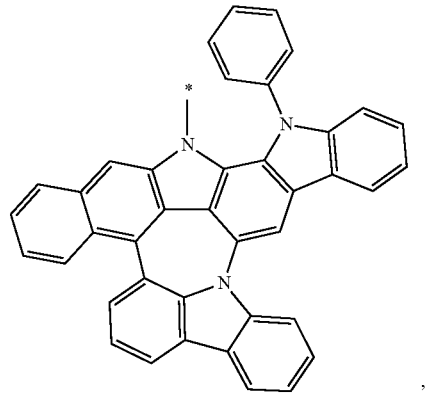
H-85
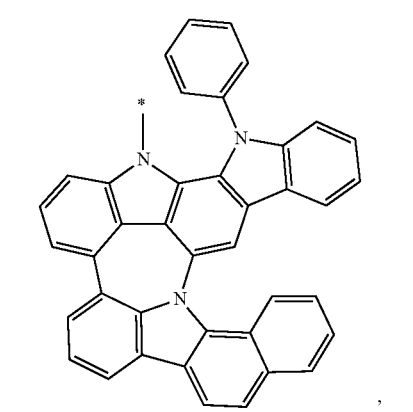
-continued
H-86
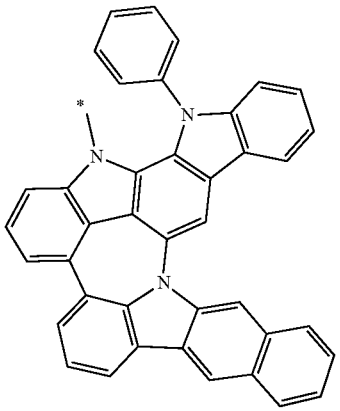
H-87
H-88
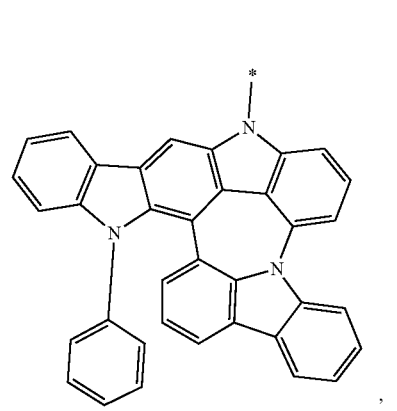
H-89
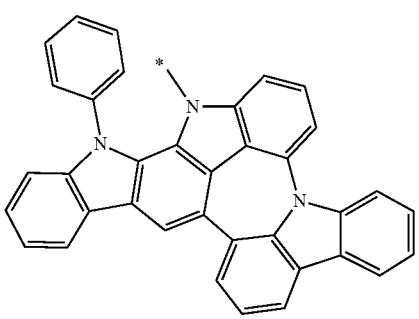

121
-continued
H-90
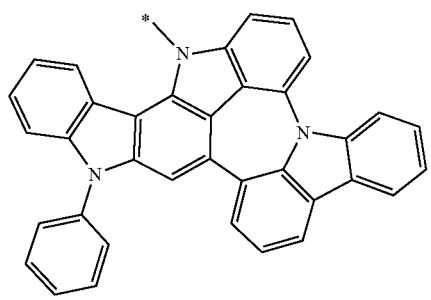
H-91
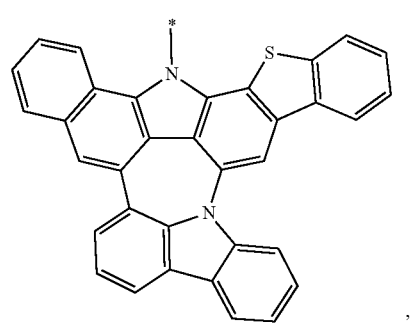
H-92
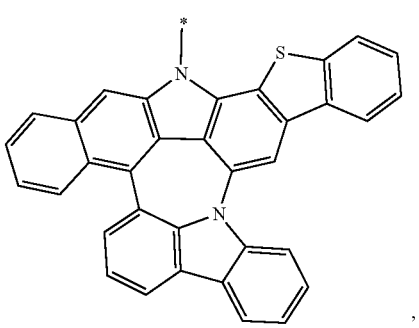
H-93
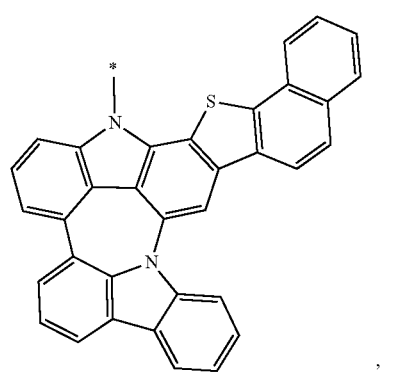
122
-continued
H-94
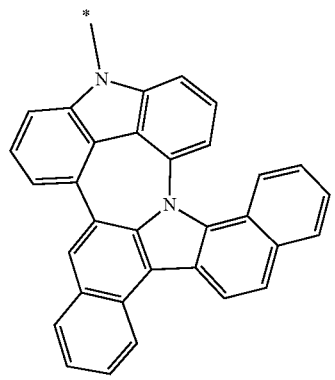
H-95
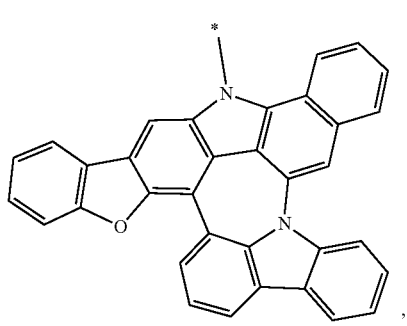
H-96
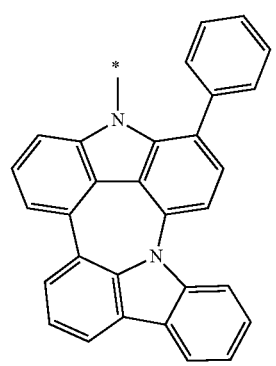
H-97
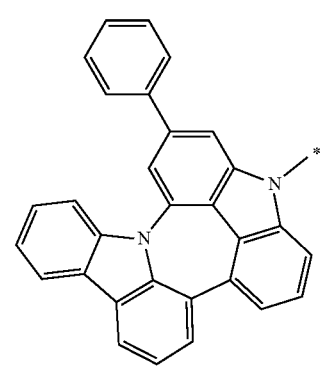

H-98
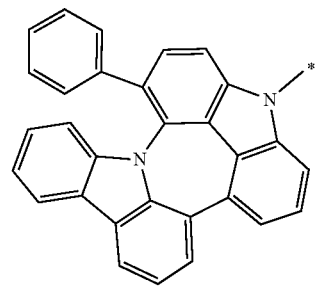
H-99
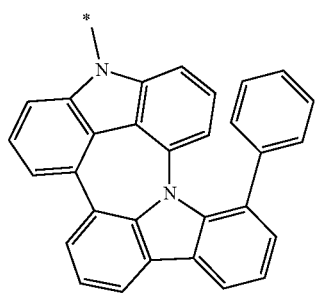
H-100
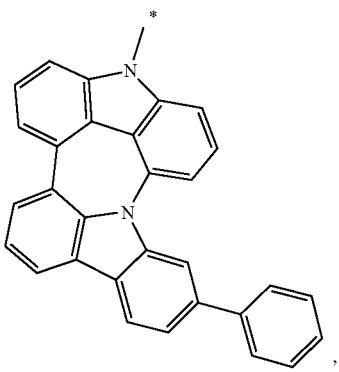
H-101
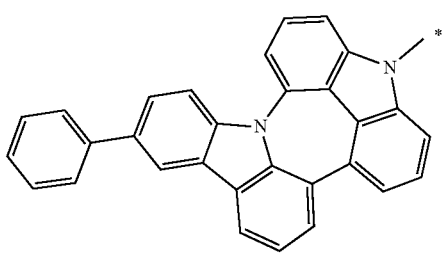
H-102
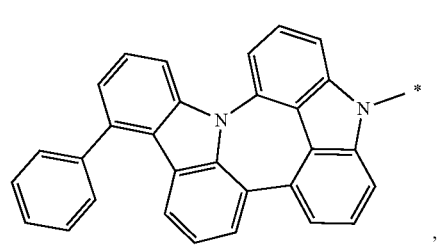
H-103
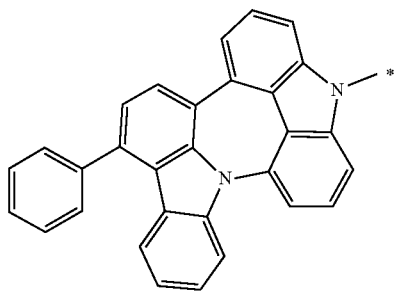
H-104
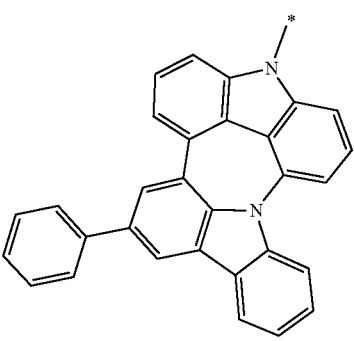
H-105
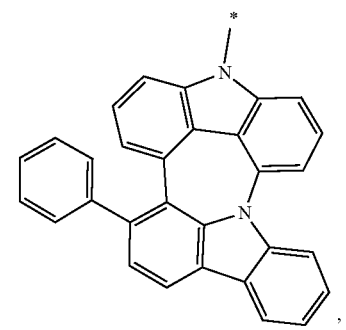
H-106
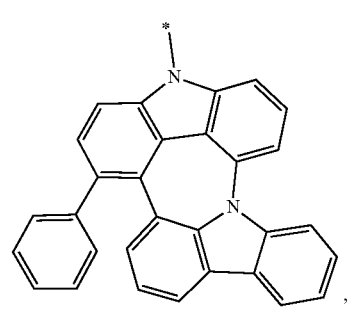
H-107
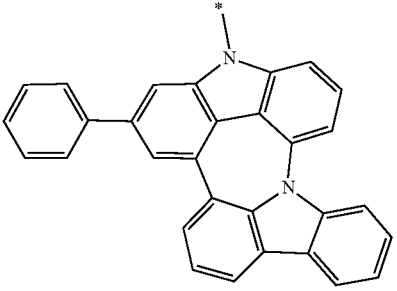

-continued
H-108
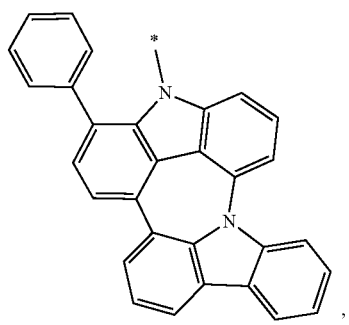
H-109
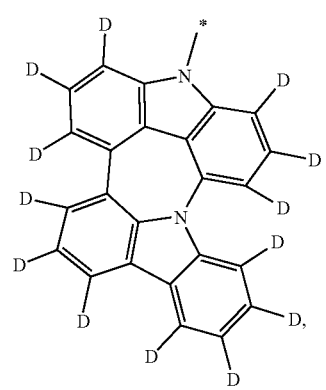
H-110
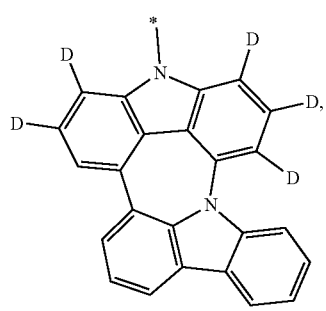
H-111
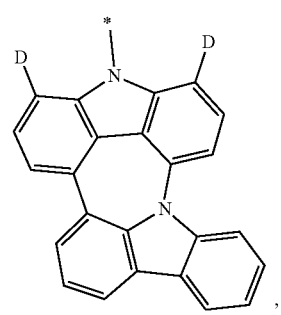
-continued
H-112
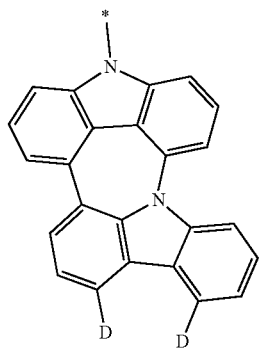
H-113
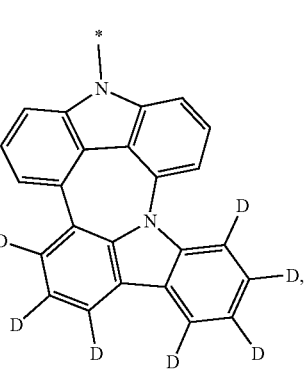
H-114
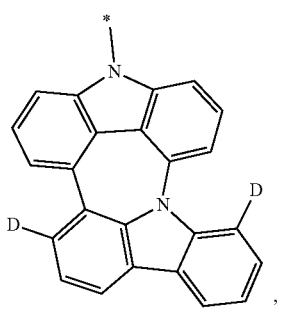
H-115
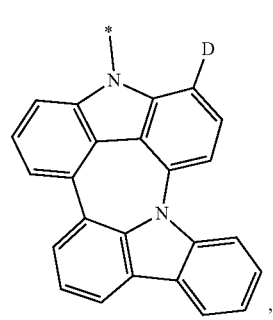

H-116

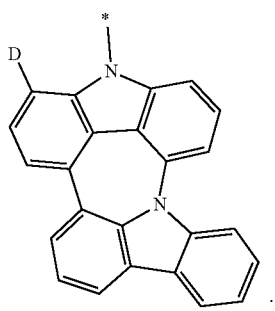

7. The compound of claim 1,
wherein $R_y$ is, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, a cyano group, and combinations thereof.

8. The compound of claim 1, wherein in the structure represented by to Formula 2-b, Formula 2-d, or Formula 2-f, Y in the aza 6-membered ring is selected from $CR_y$, and the $R_y$ is selected from substituted or unsubstituted aryl having 6 to 30 carbon atoms or substituted or unsubstituted heteroaryl having 3 to 30 carbon atoms.

9. The compound of claim 6, wherein the E is selected from the group consisting of the following structures:

E-21

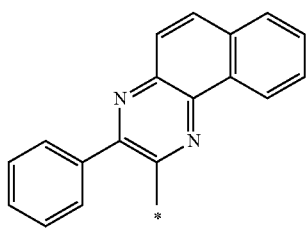

E-22

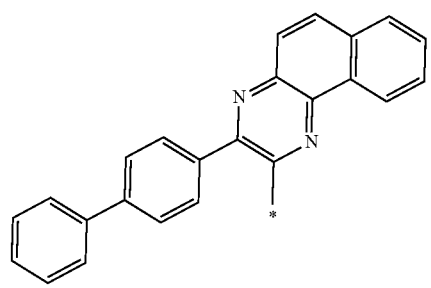

E-23

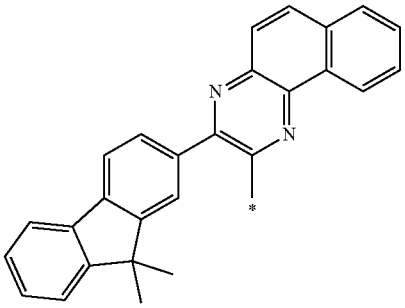

E-24

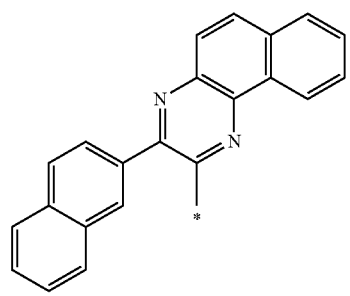

E-25

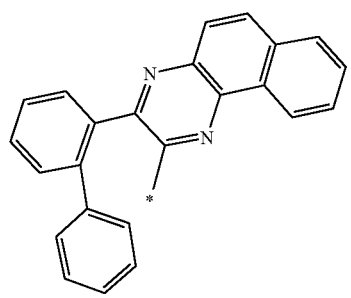

E-26

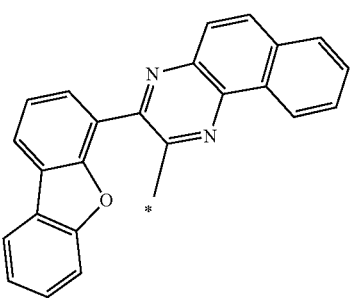

E-27

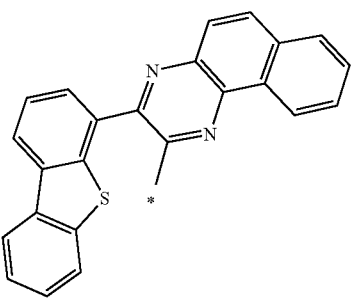

E-28
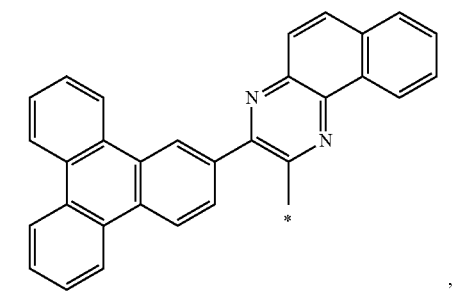
E-29
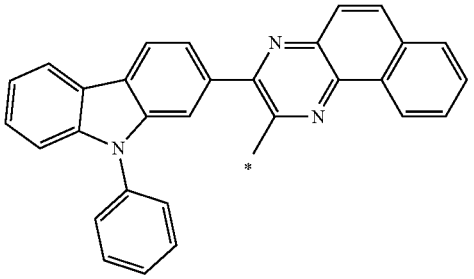
E-30
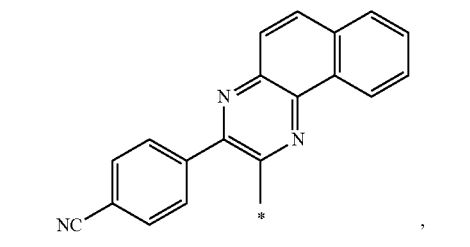
E-31
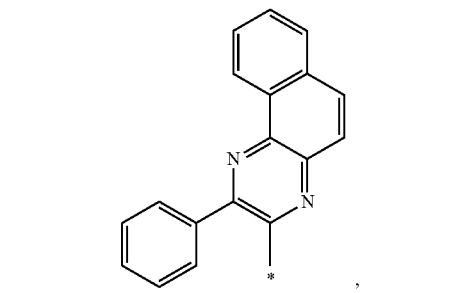
E-32
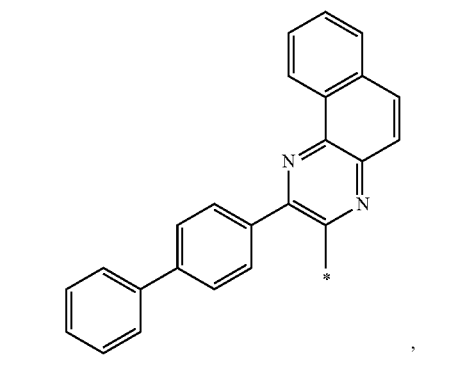
E-33
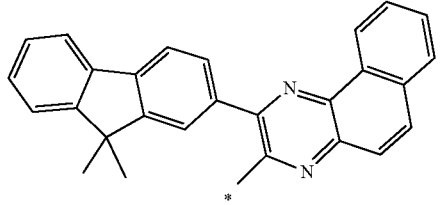
E-34
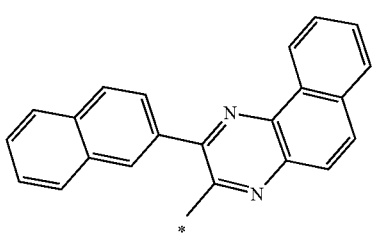
E-35
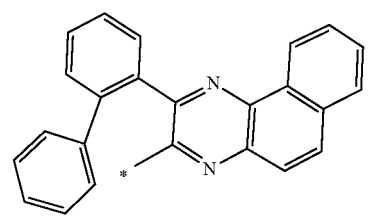
E-36
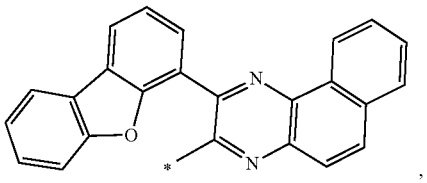
E-37
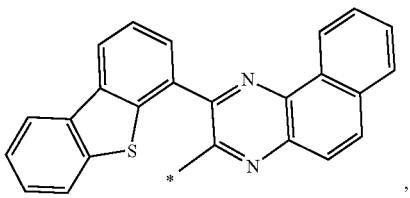
E-38
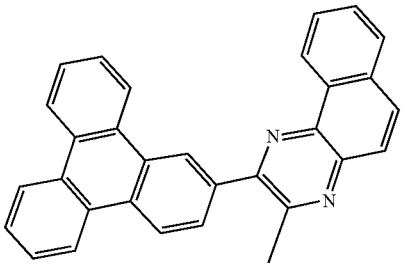
E-39
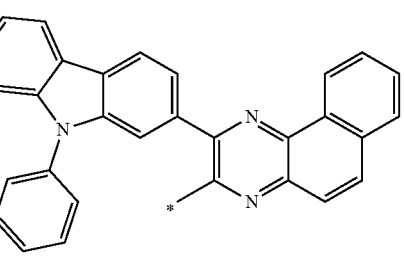

-continued

E-40, E-46, E-47, E-48, E-49, E-50, E-51, E-52, E-53, E-54, E-55, E-56, E-57

E-58
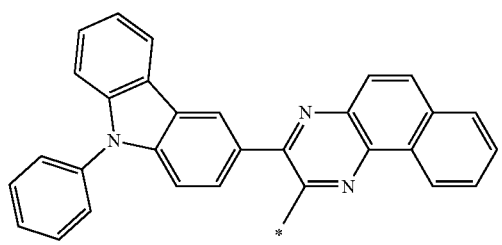
E-59
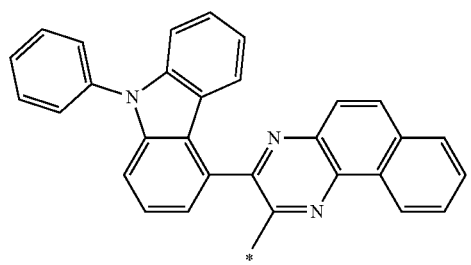
E-60
E-61
E-62
E-63
E-64
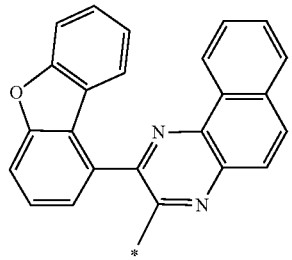
E-65
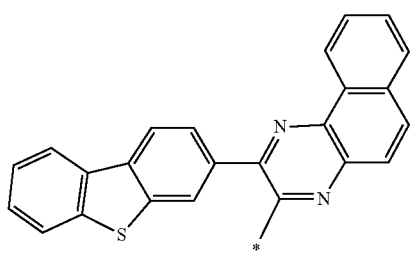
E-66
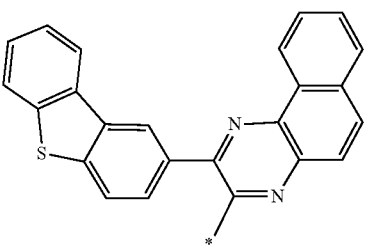
E-67
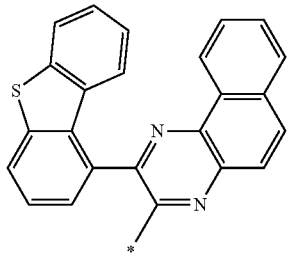
E-68
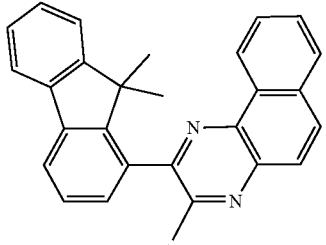
E-69
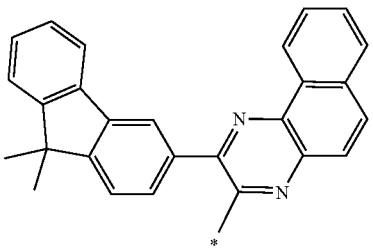

-continued
E-70
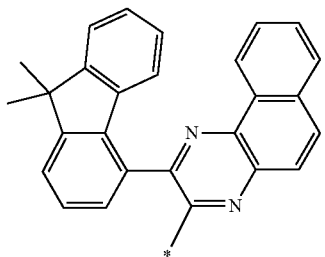,
E-71
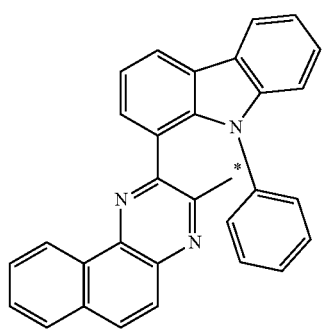,
E-72
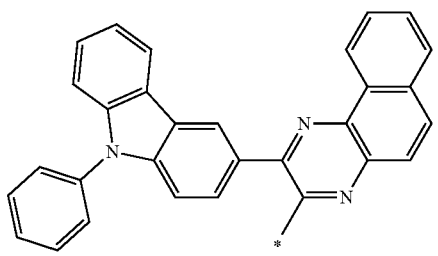,
E-73
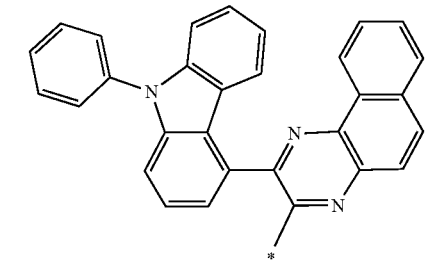,
E-101
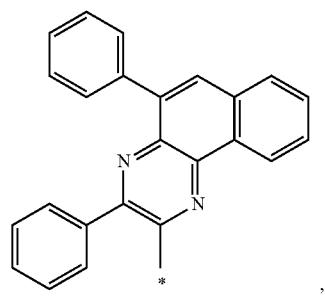,
-continued
E-102
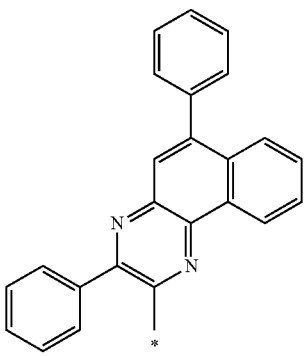,
E-103
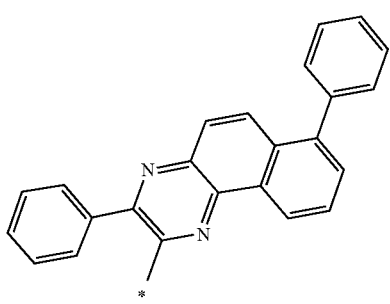,
E-104
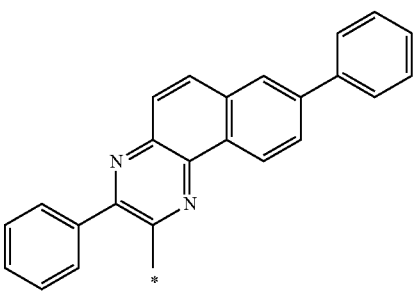,
E-105
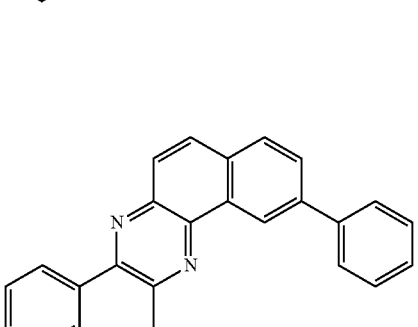,
E-106
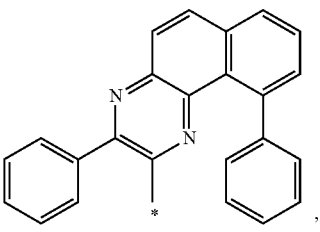, E-107
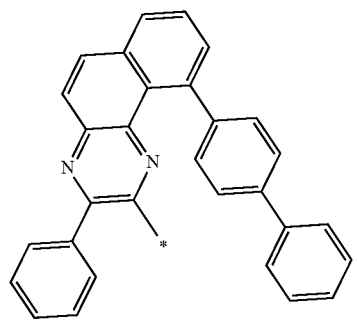
E-108
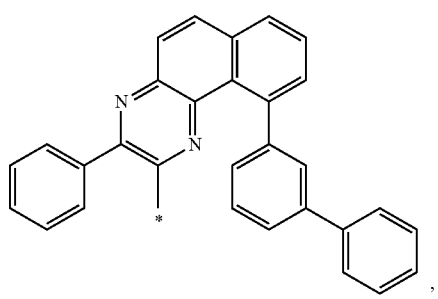
E-109
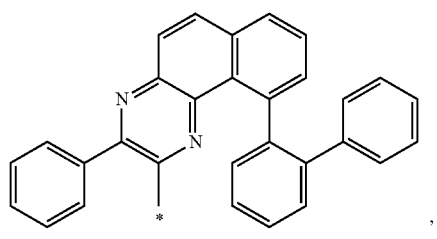
E-110
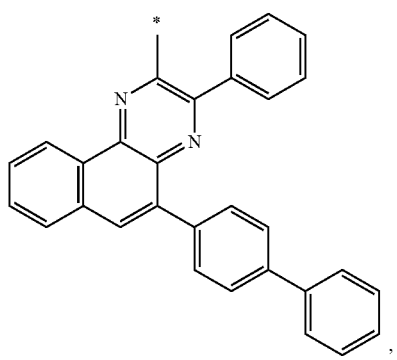
E-111
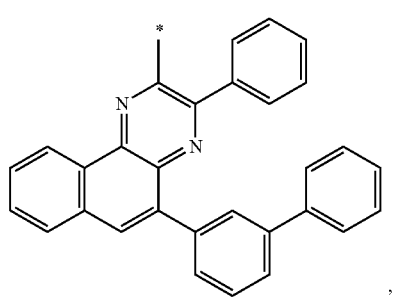
E-112
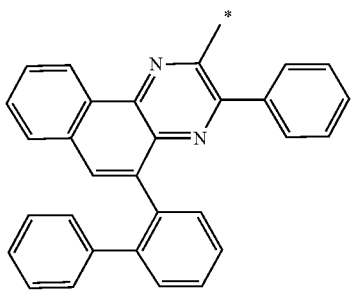
E-113
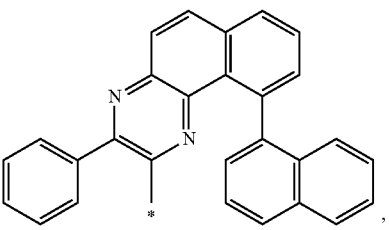
E-114
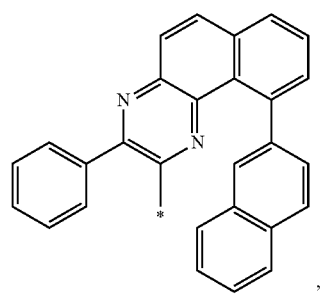
E-115
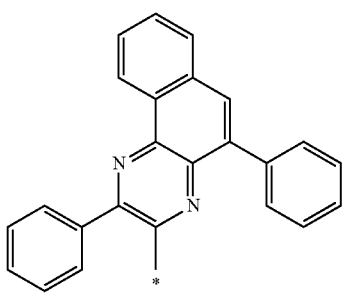
E-116
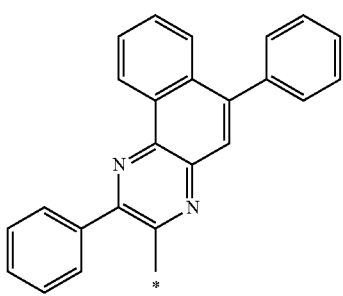

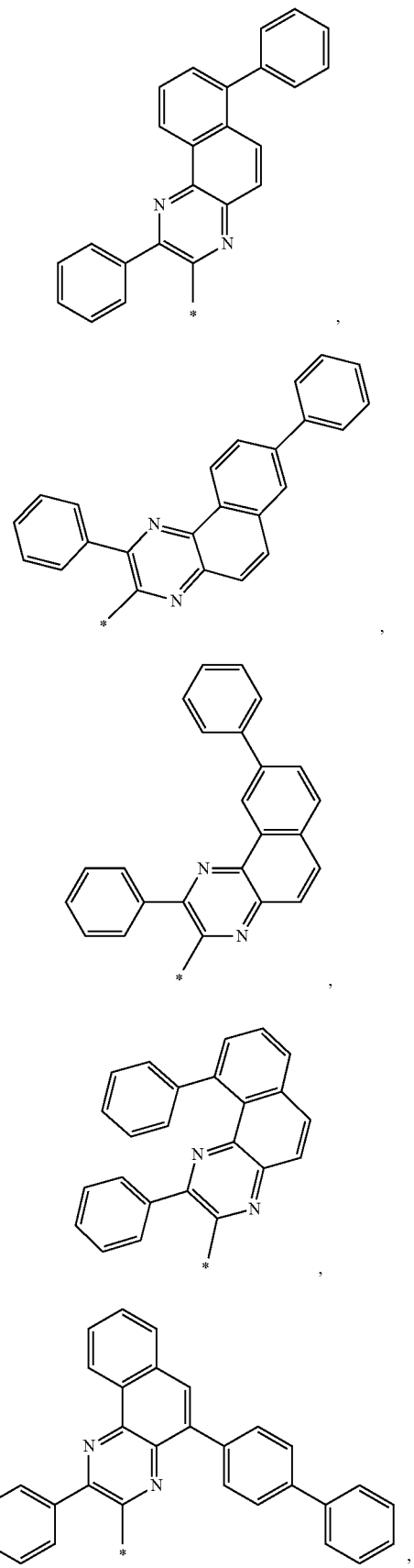
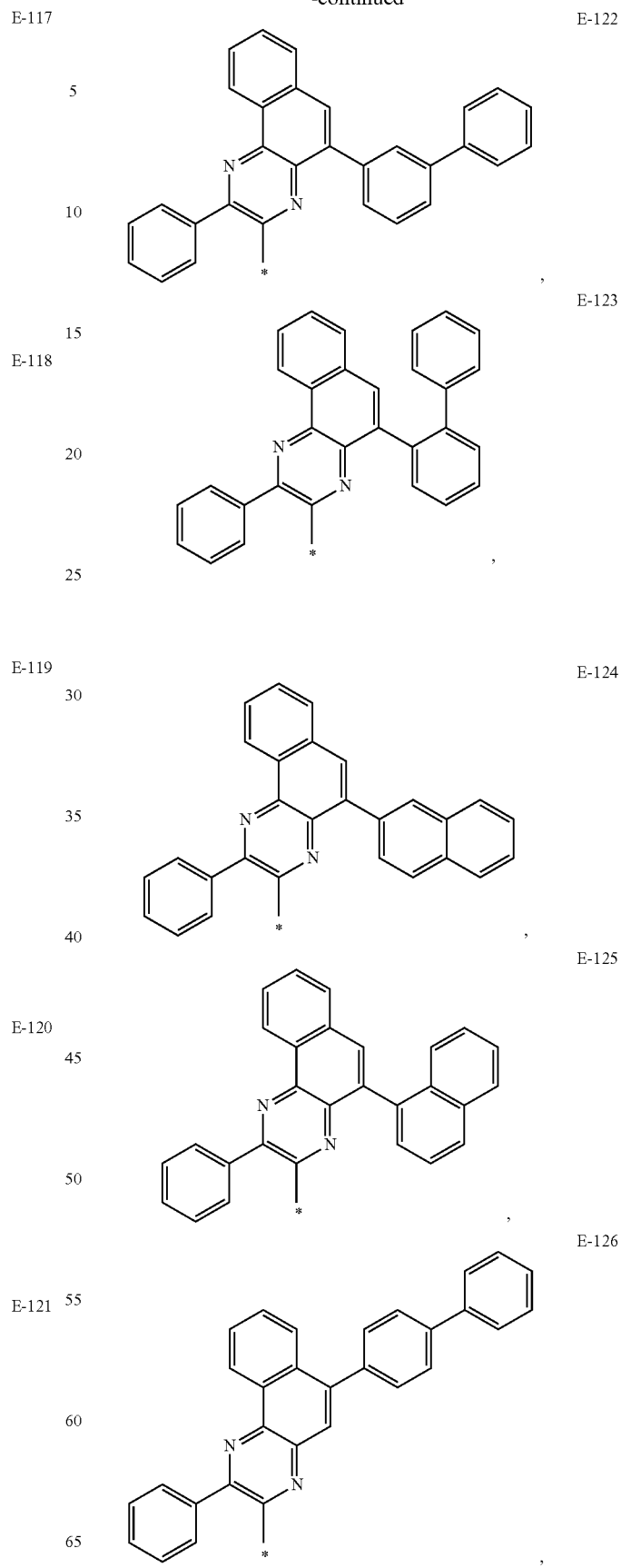

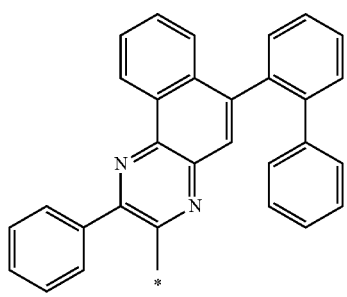

-continued
E-137
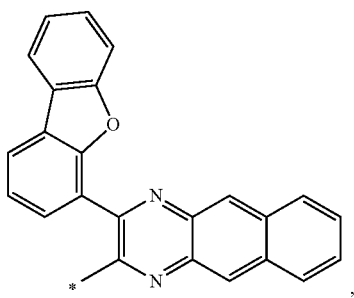
E-138
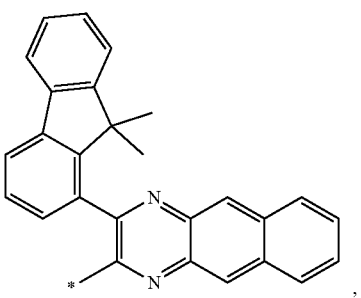
E-139
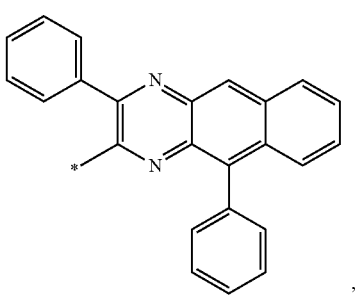
E-140
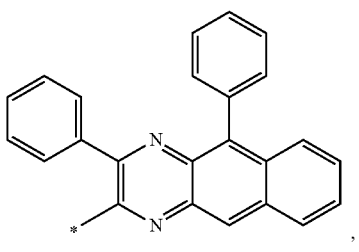
E-141
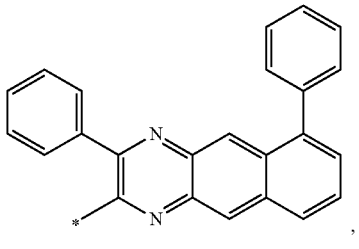
E-142
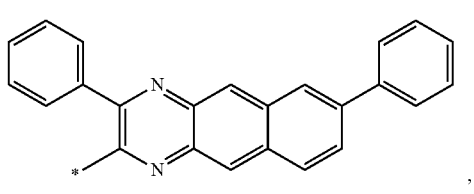
-continued
E-143
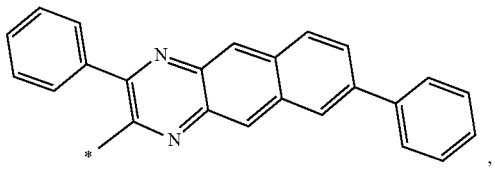
E-144
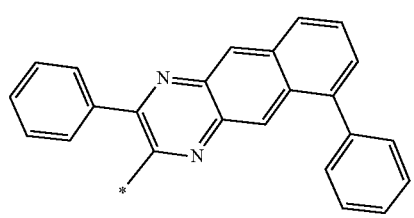
E-145
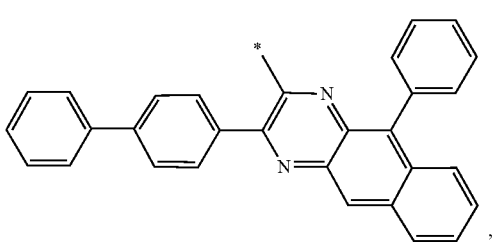
E-146
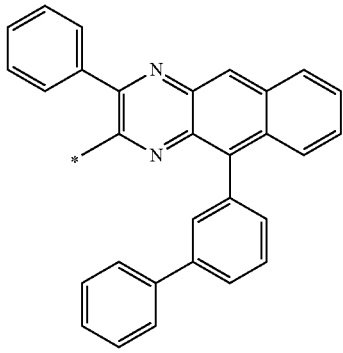
E-147
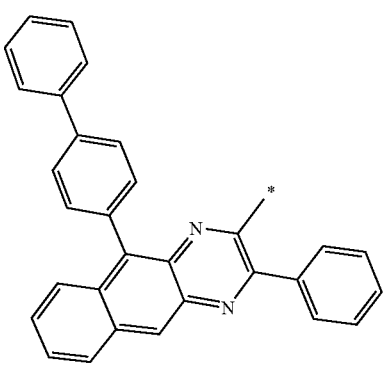

E-148
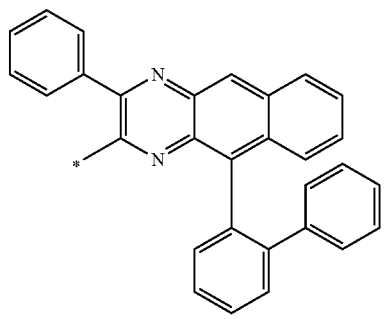
E-149
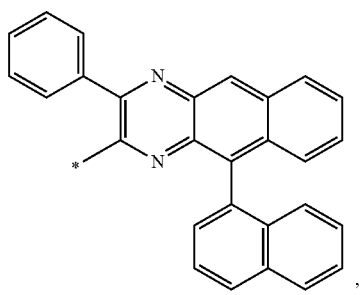
E-150
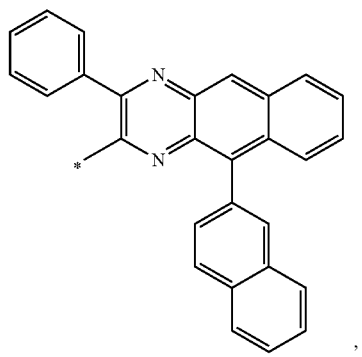
E-151
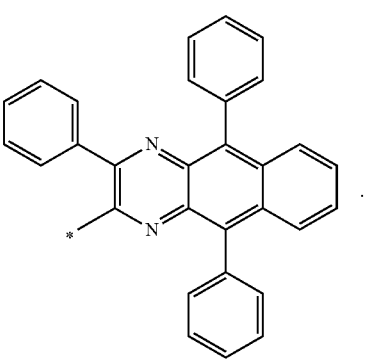
10. The compound of claim 1, wherein L₁ is selected from the group consisting of the following structures:
L-0  a single bond
L-1  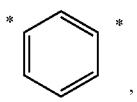
L-2  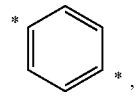
L-3  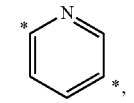
L-4  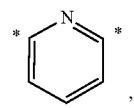
L-5  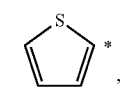
L-6  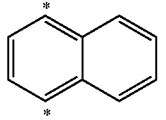
L-7  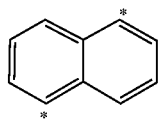
L-8  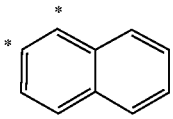
L-9  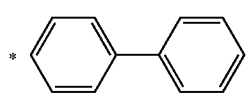
L-10 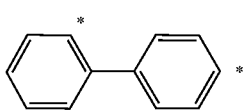
L-11 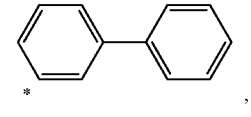
L-12 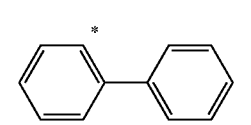
L-13 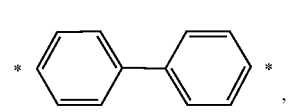

L-14
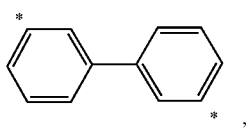

L-15
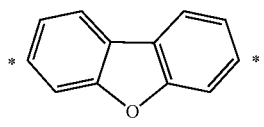

L-16
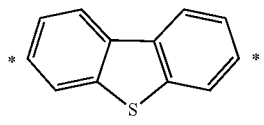

L-17
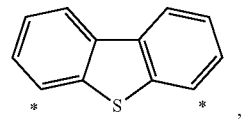

L-18
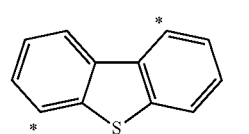

L-19
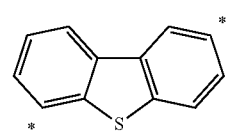

L-20
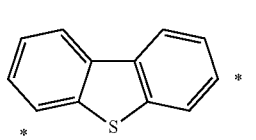

L-21
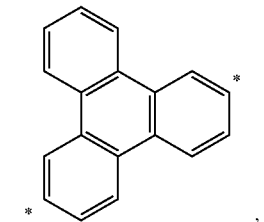

L-22
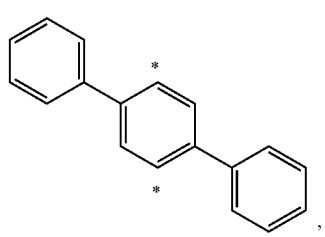

L-24
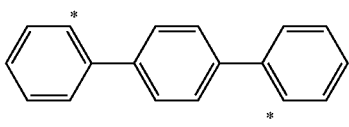

L-25
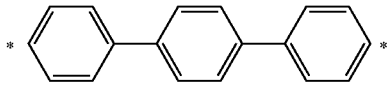

11. The compound of claim 10, wherein the compound has a structure of H-L$_1$-E, wherein H is selected from the group consisting of H-1 to H-116, L$_1$ is selected from the group consisting of L-0 to L-25, and E is selected from the group consisting of E-21 to E-40, E-46 to E-73, E-101 to E-127, E-130 to E-151.

12. The compound of claim 1, wherein the compound is selected from the group consisting of the following structures:

1-253
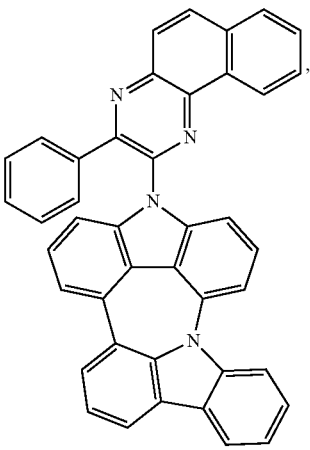

1-254
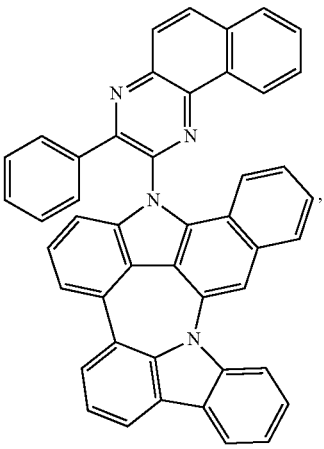

1-255
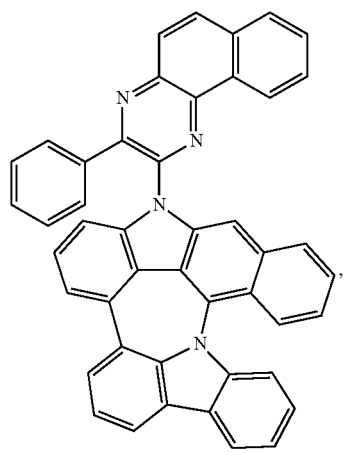
1-256
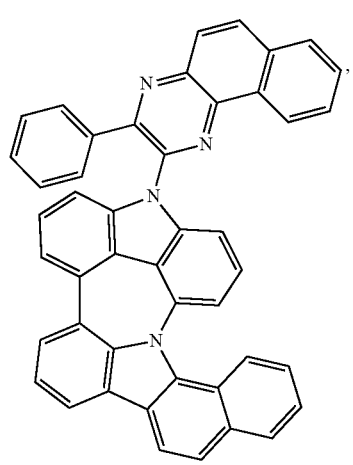
1-257
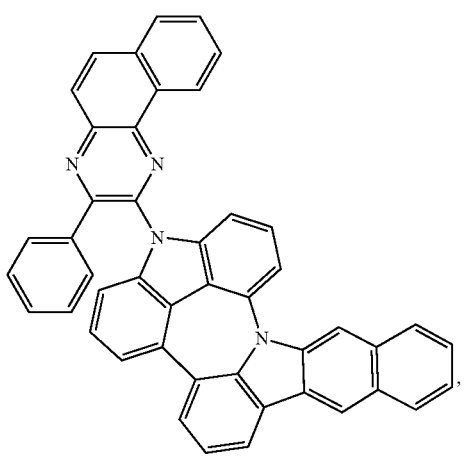
1-258
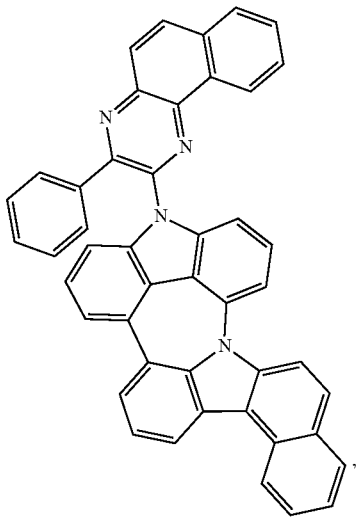
1-259
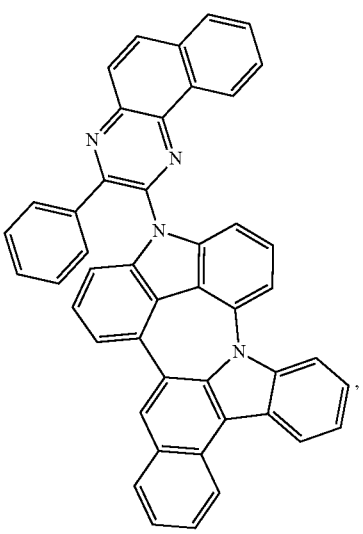
1-260
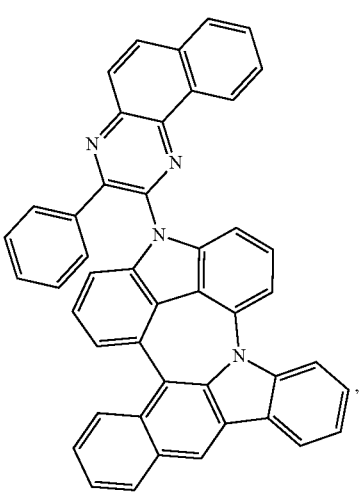

1-261
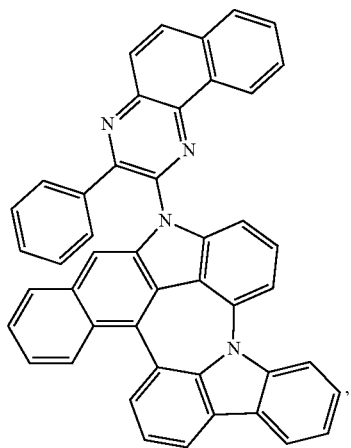
1-262
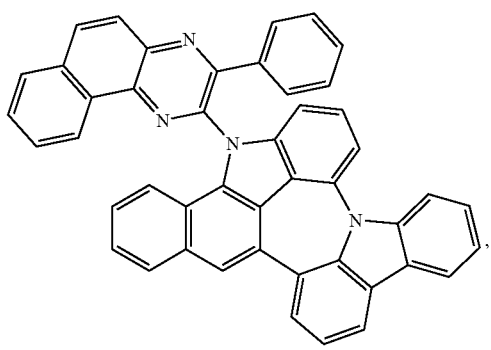
1-263
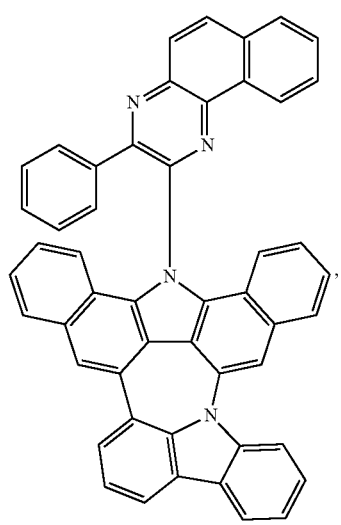
1-264
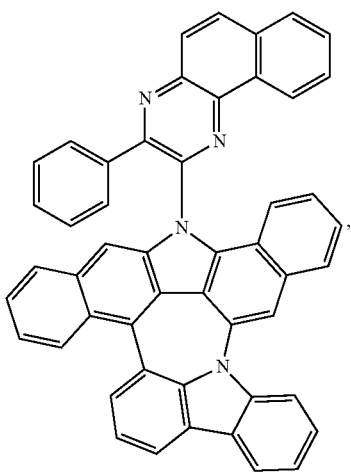
1-265
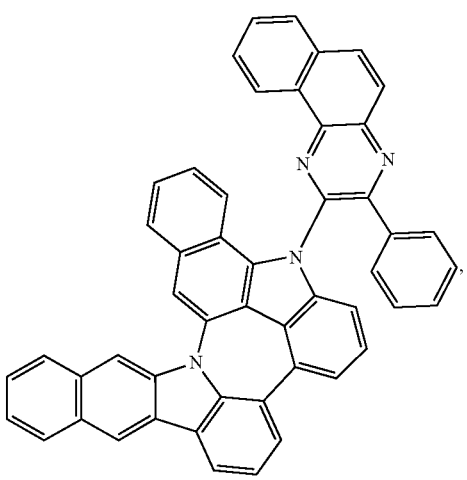
1-266
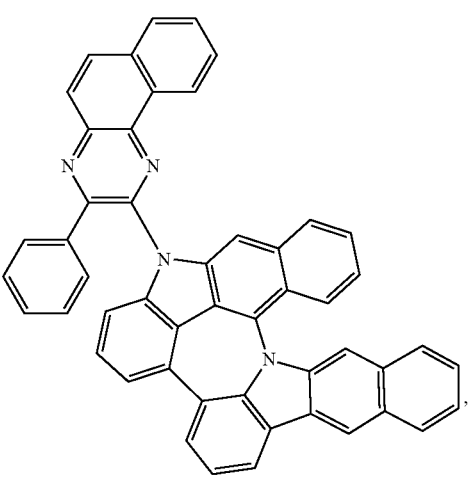

1-267
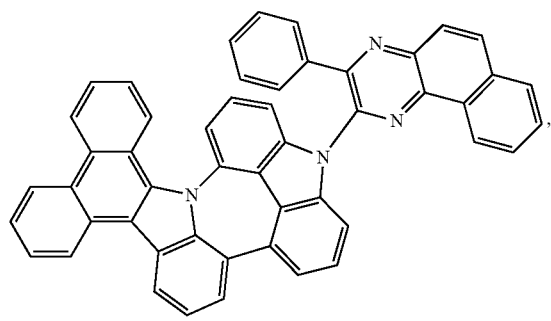
1-268
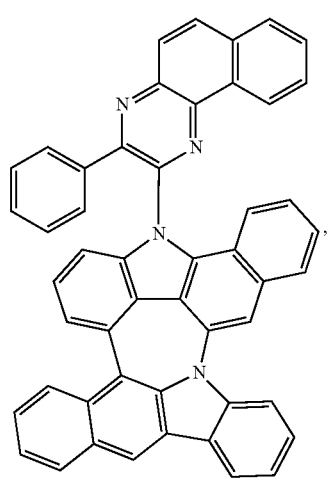
1-269
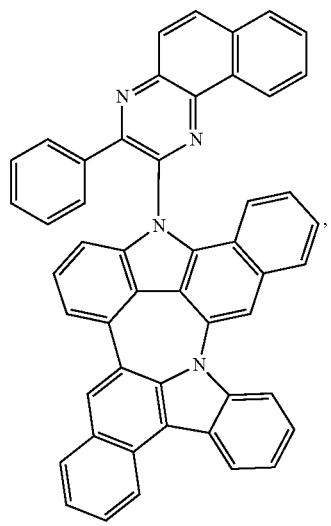
1-270
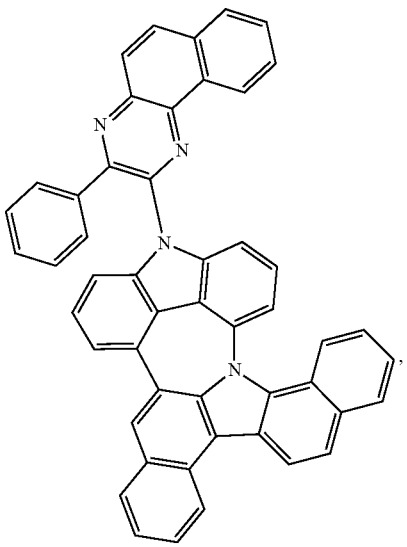
1-271
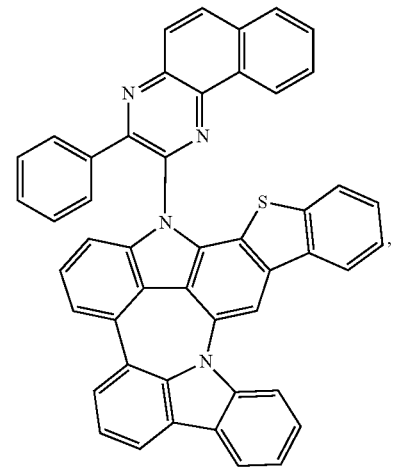
1-272
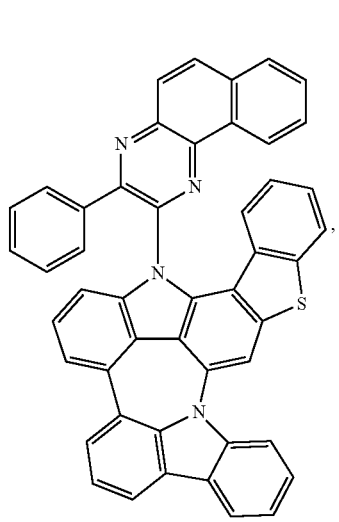

1-273
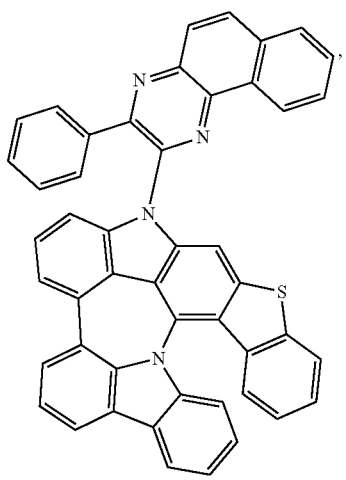
1-274
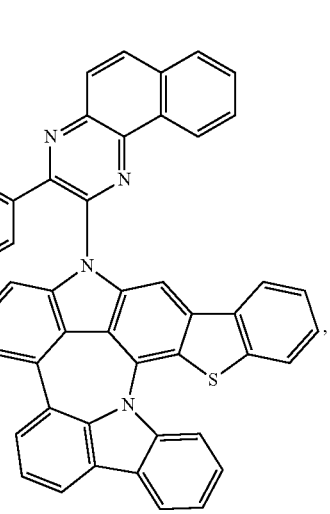
1-275
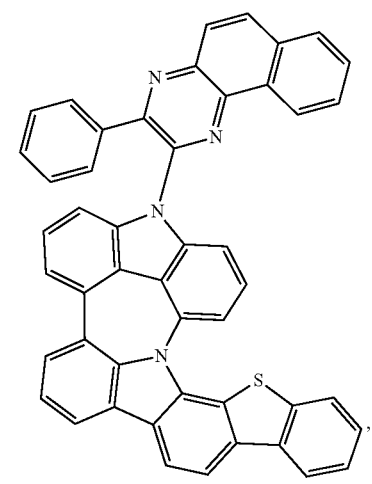
1-276
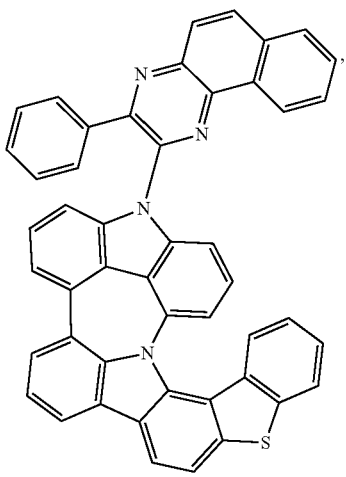
1-277
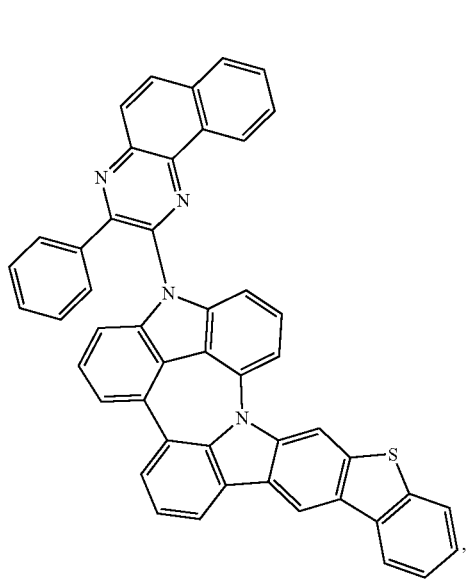
1-278
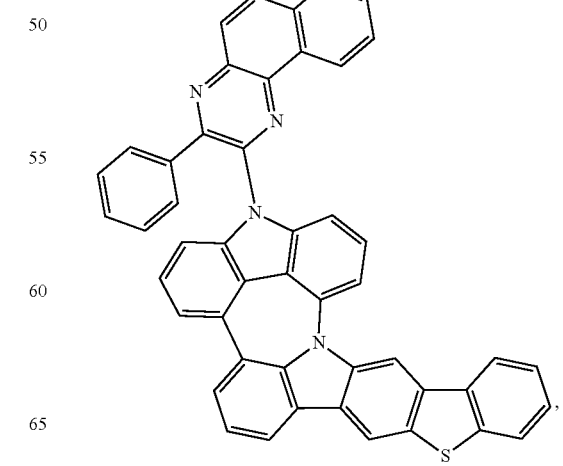

1-279
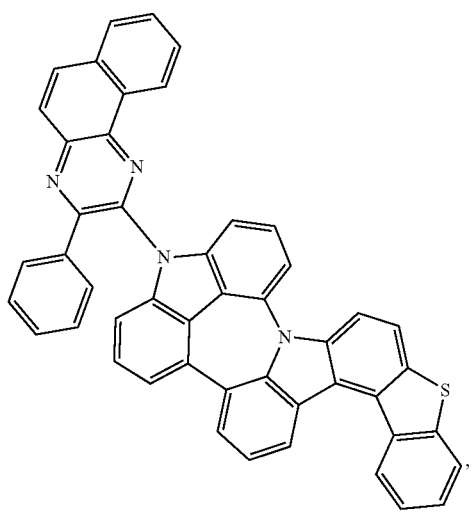
1-280
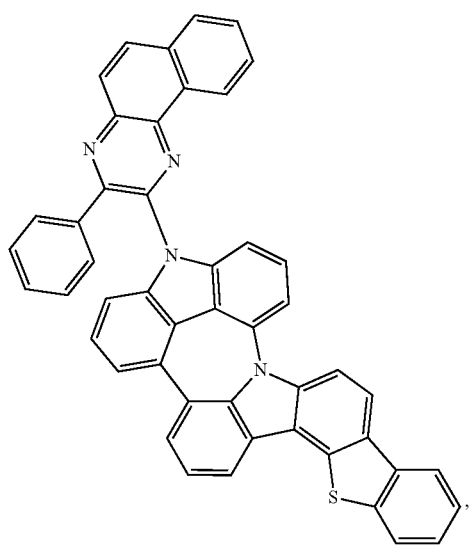
1-281
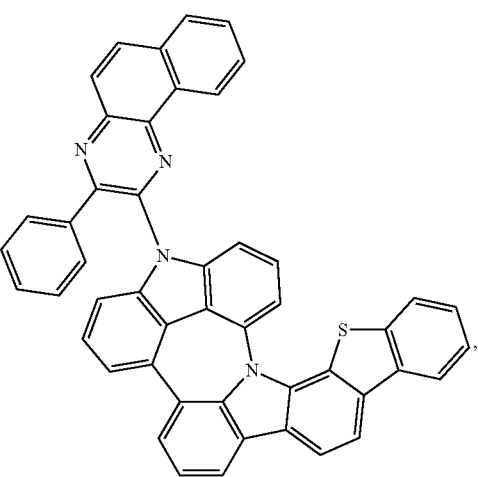
1-282
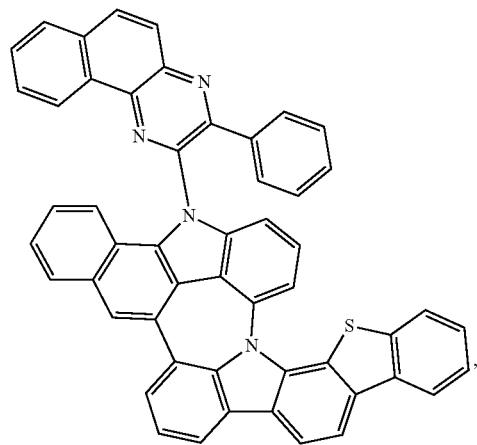
1-283
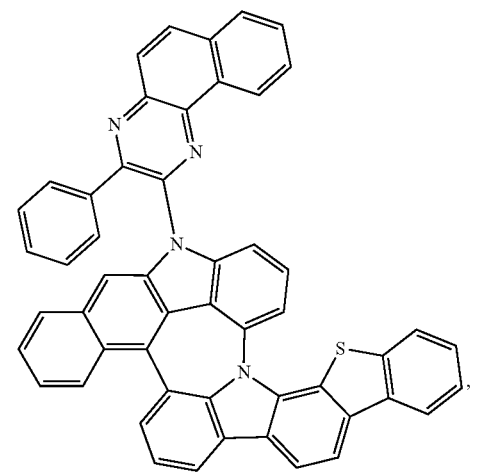
1-284
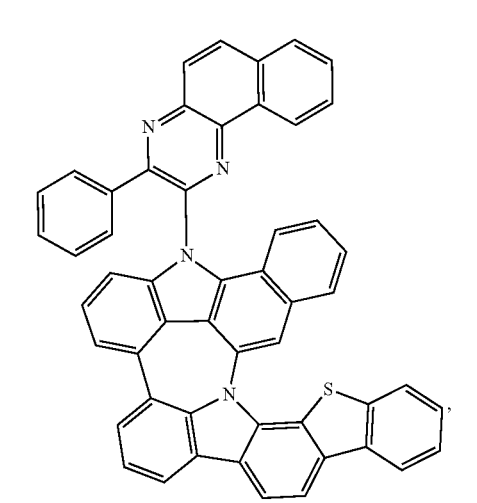

1-285
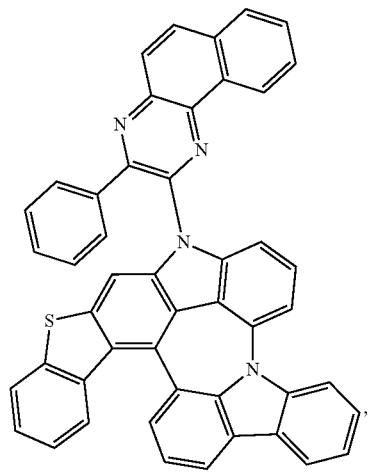
1-286
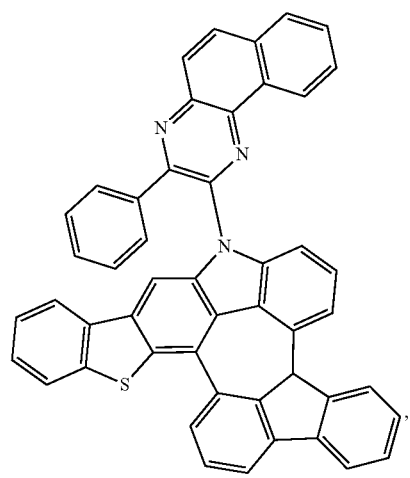
1-287
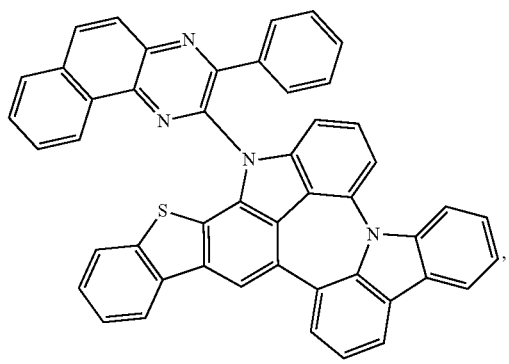
1-288
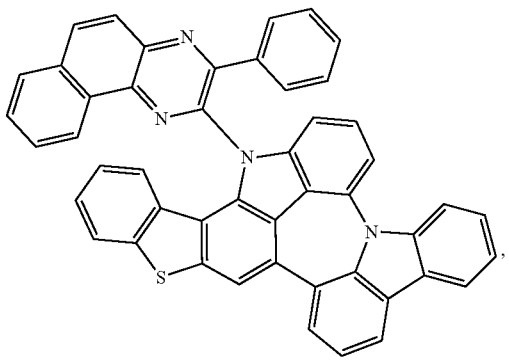
1-289
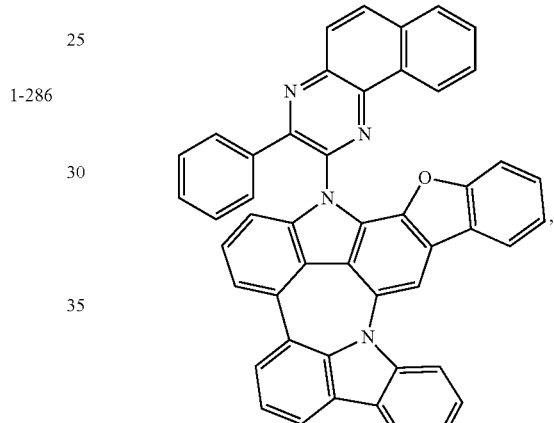
1-290
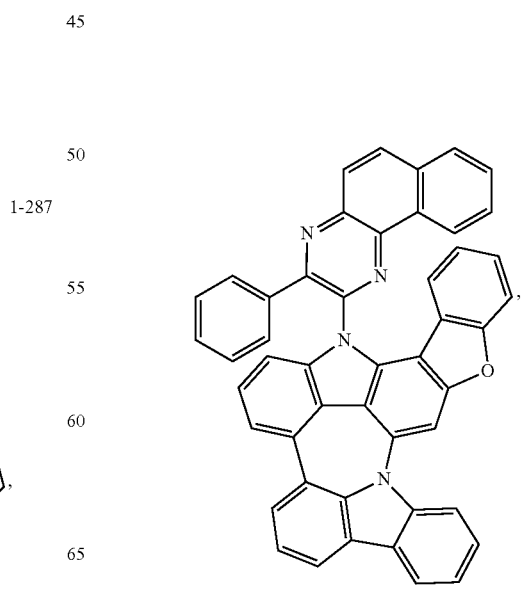

1-291
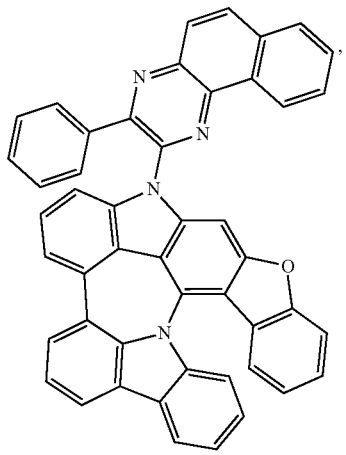
1-292
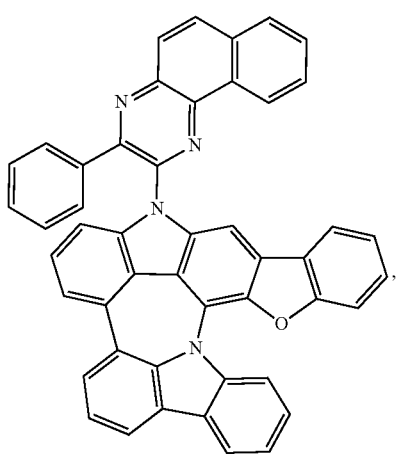
1-293
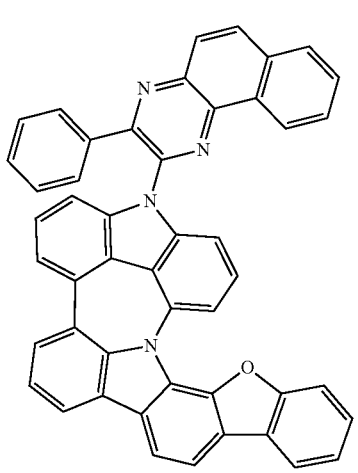
1-294
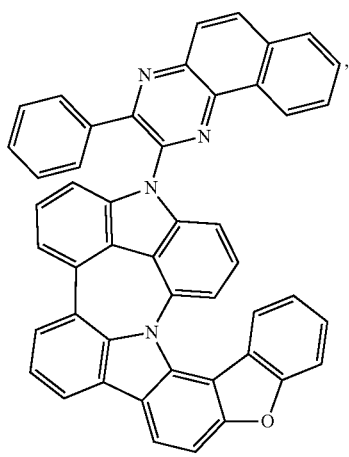
1-295
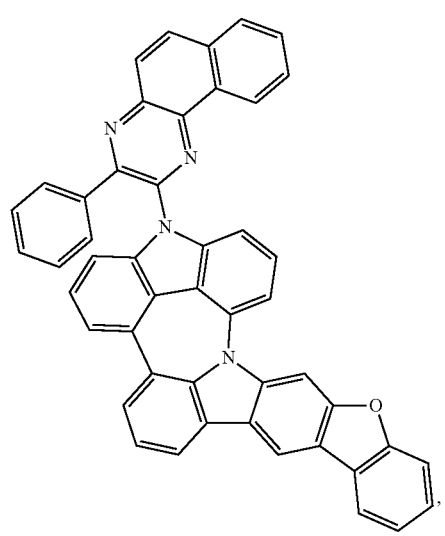
1-296
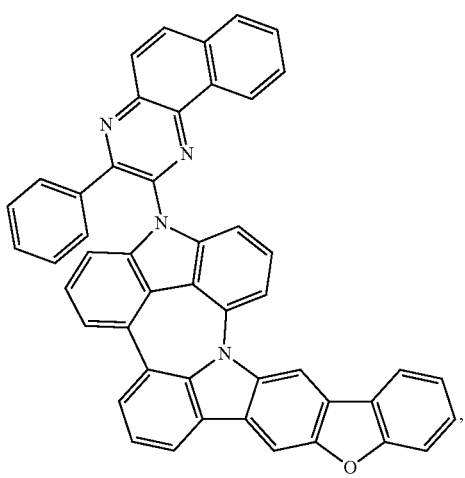

1-297
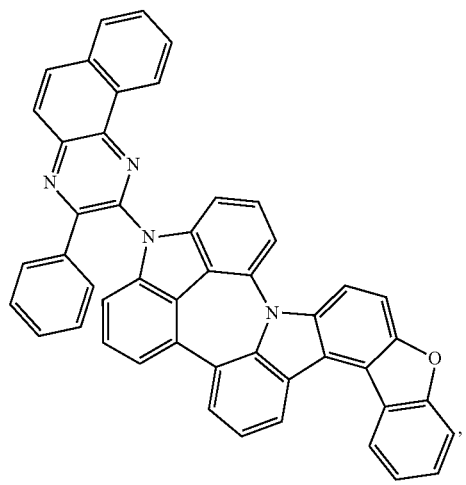
1-298
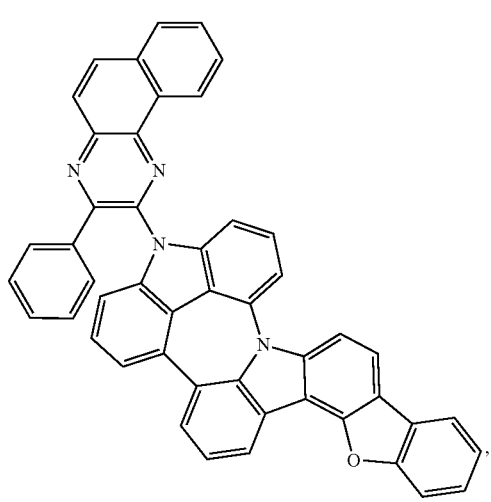
1-299
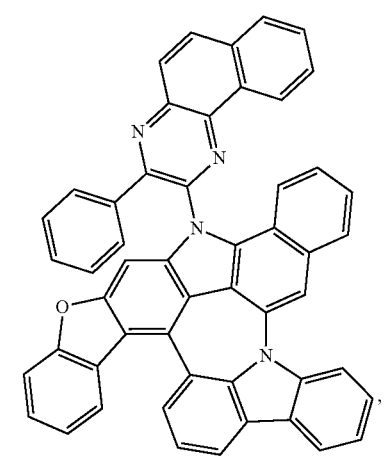
1-300
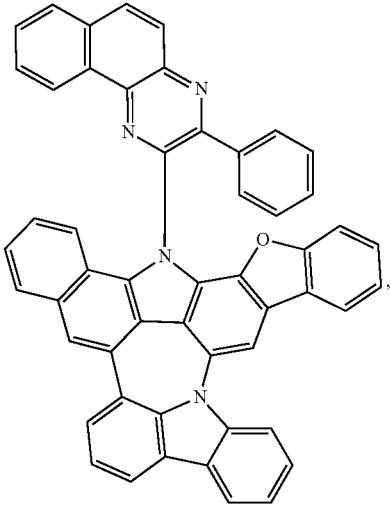
1-301
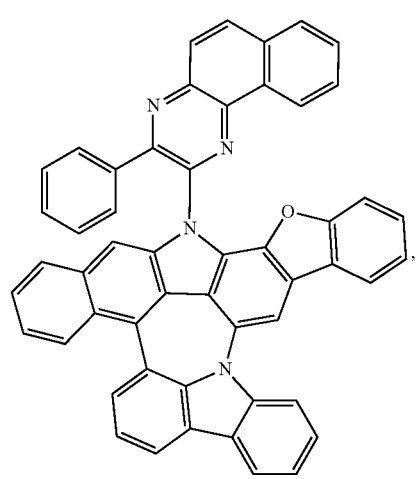
1-302
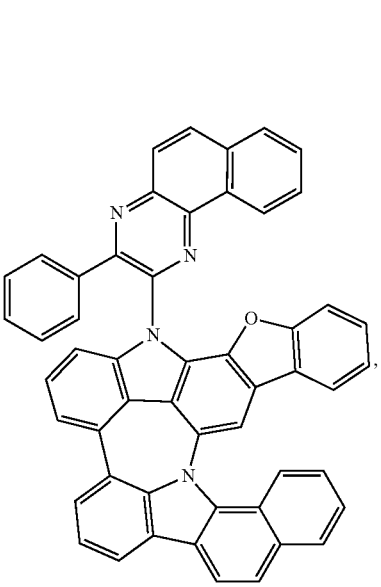

-continued
1-303
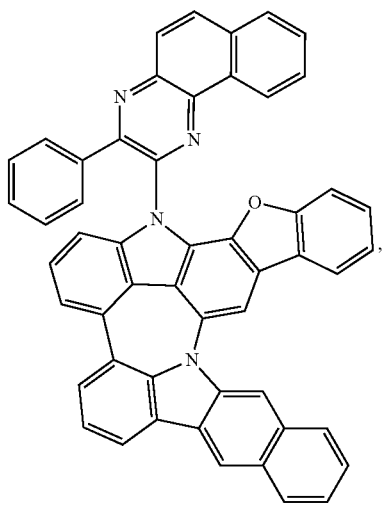
1-304
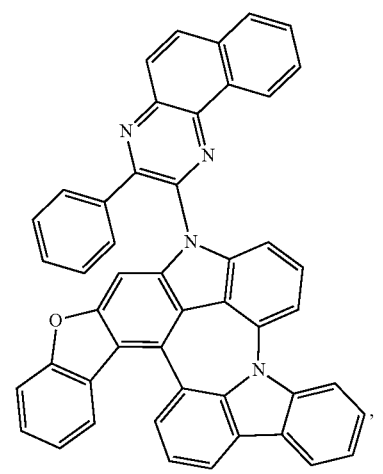
1-305
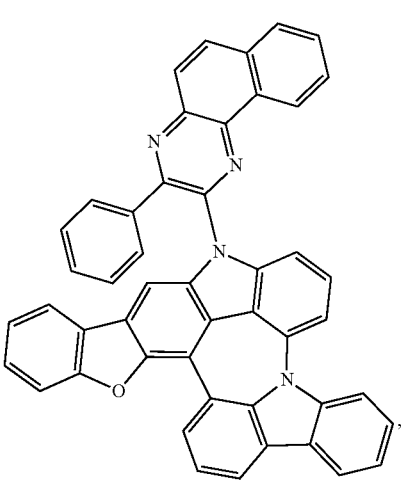
1-306
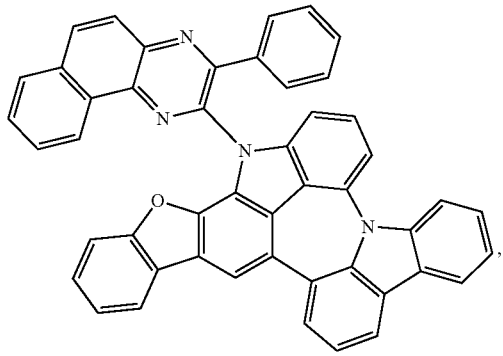
1-307
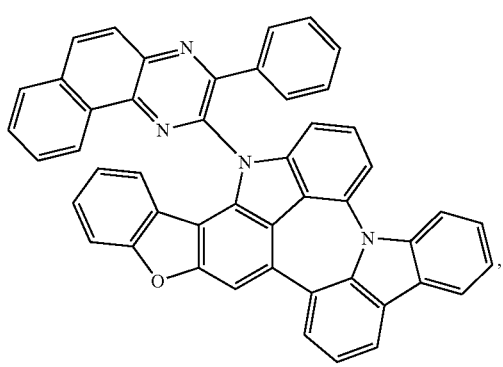
1-308
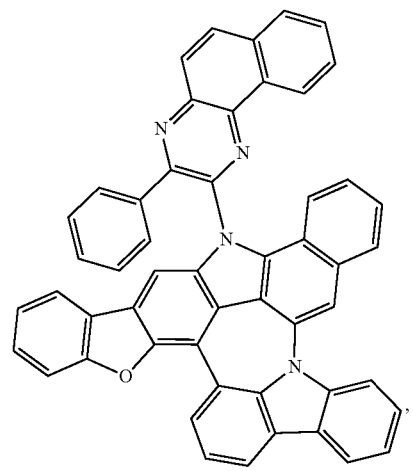

1-309
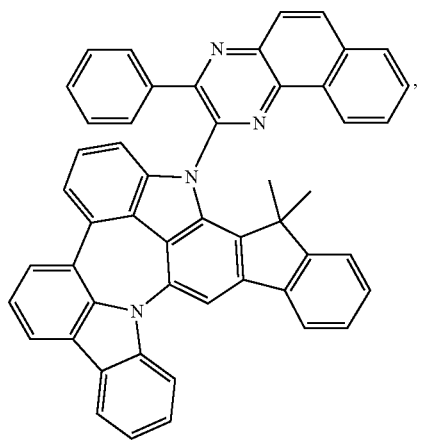
1-310
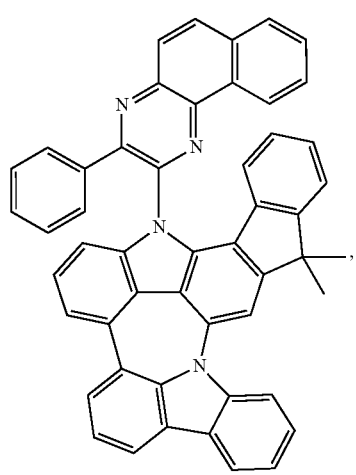
1-311
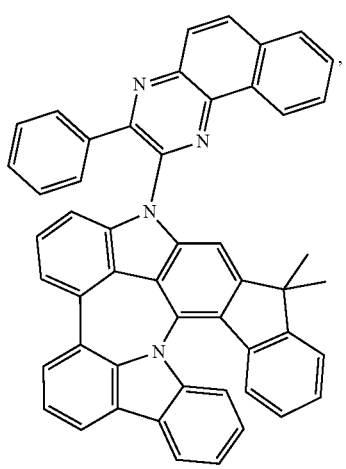
1-312
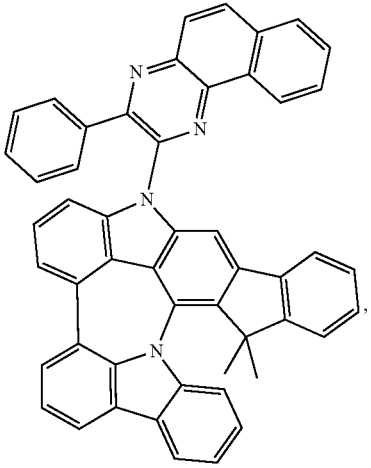
1-313
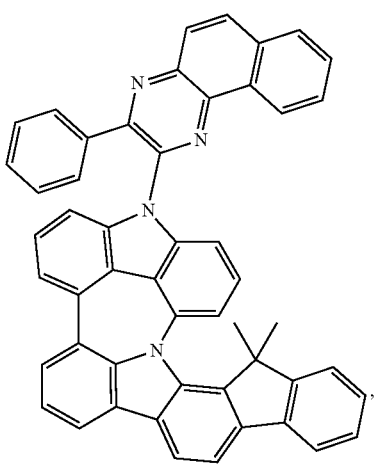
1-314
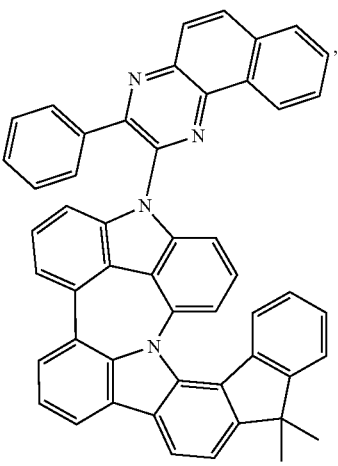

-continued
1-315
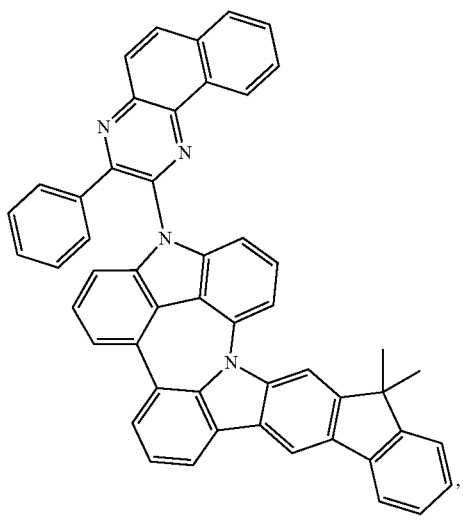
1-316
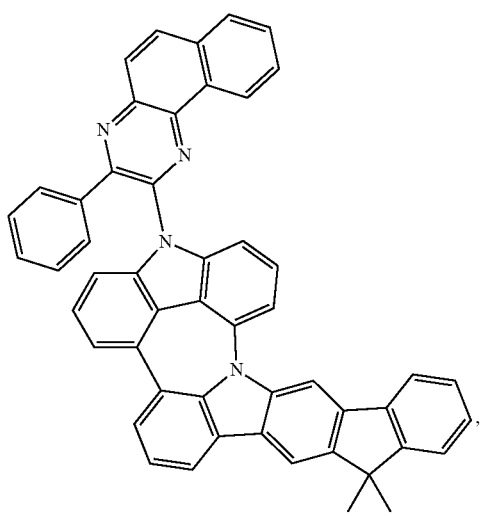
1-317
-continued
1-318
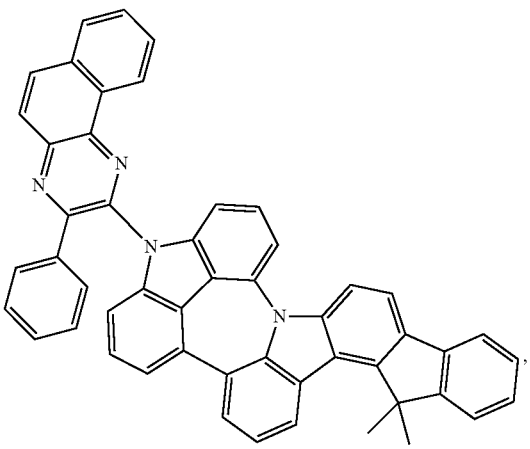
1-319
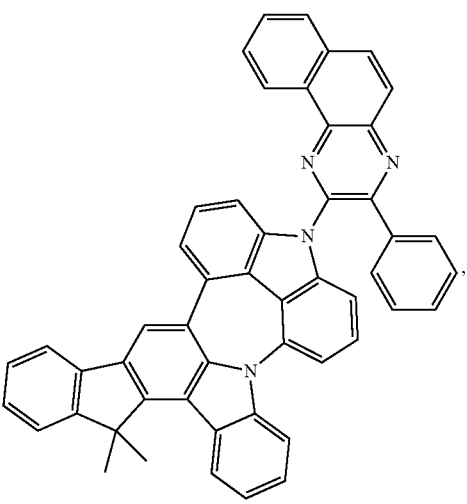
1-320
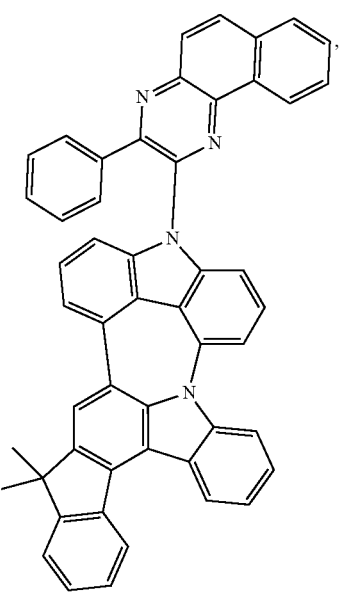

1-321
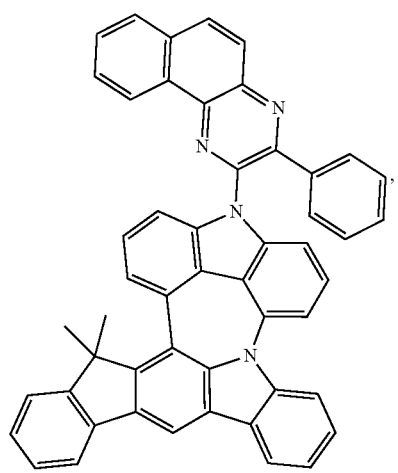
1-322
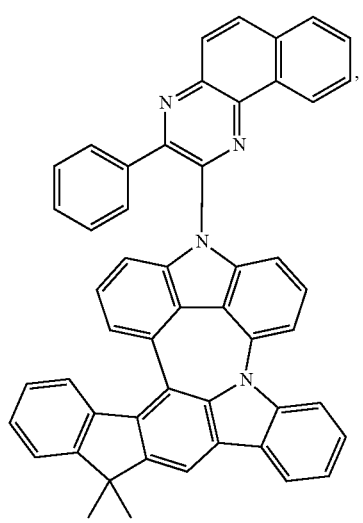
1-323
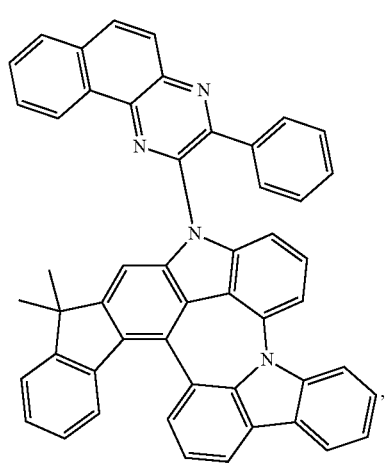
1-324
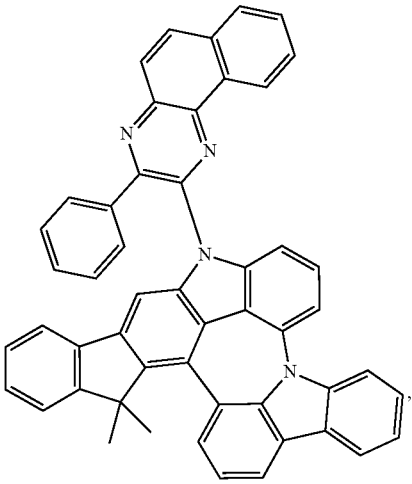
1-325
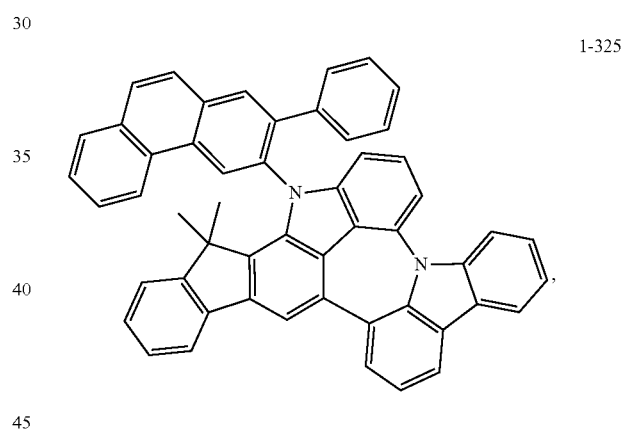
1-326
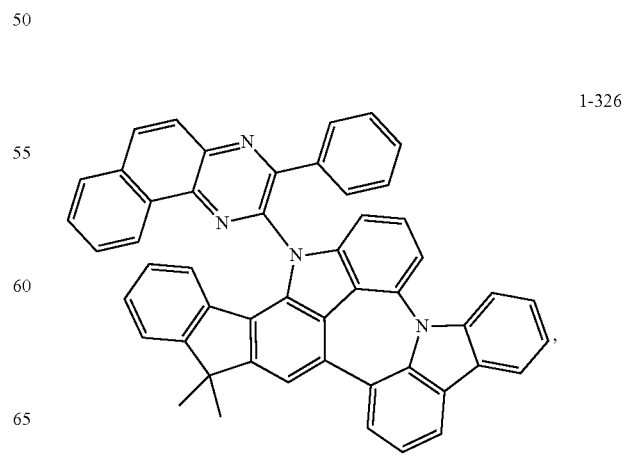

-continued
1-327
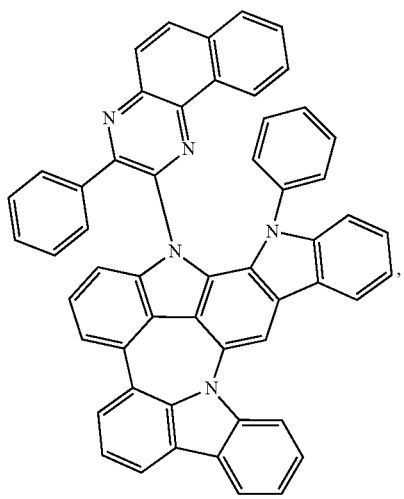
1-328
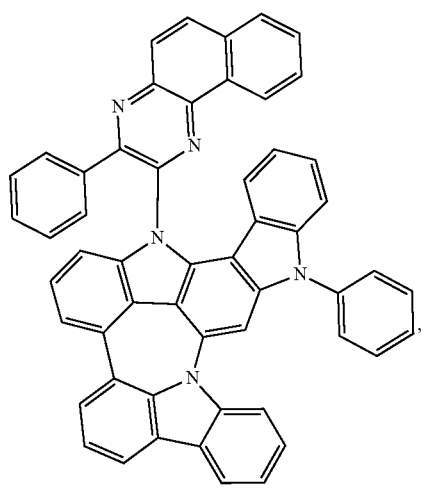
1-329
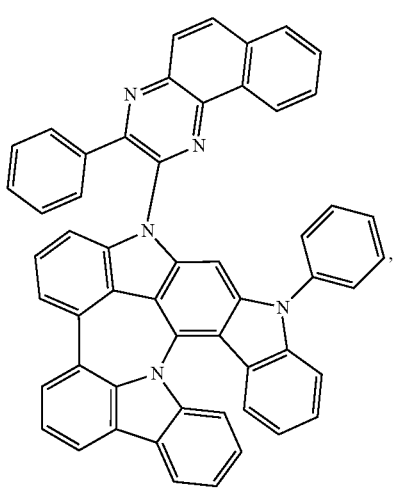
-continued
1-330
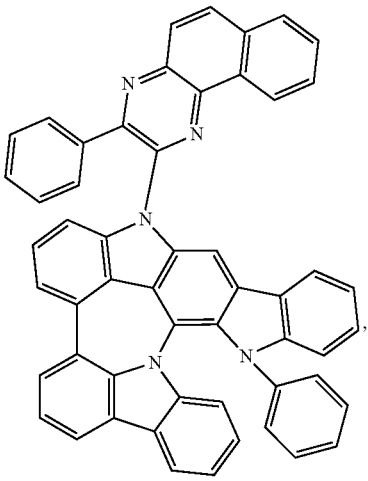
1-331
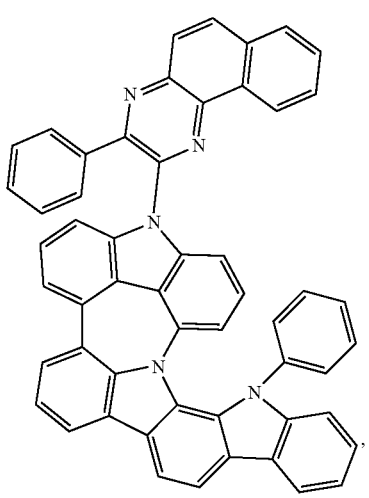
1-332
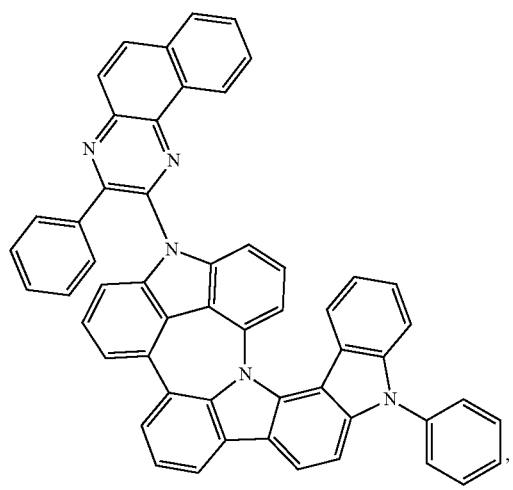

1-333
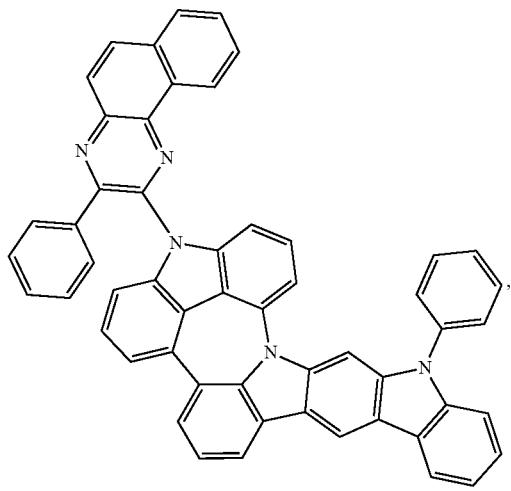
1-334
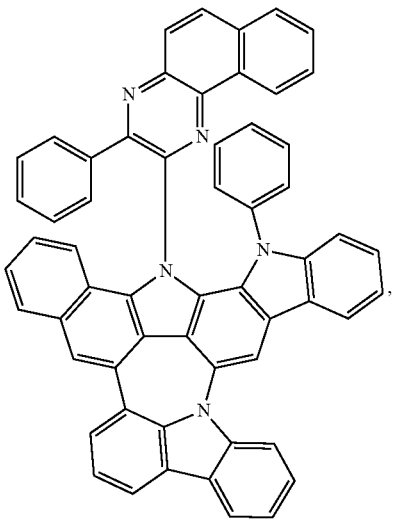
1-336
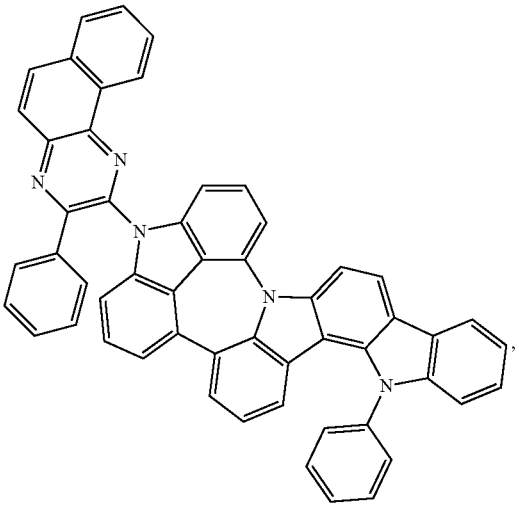
1-337
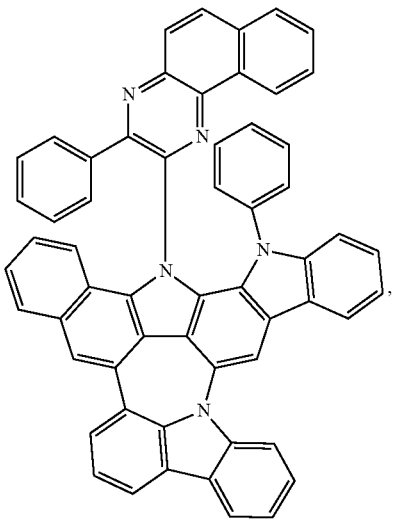
1-338
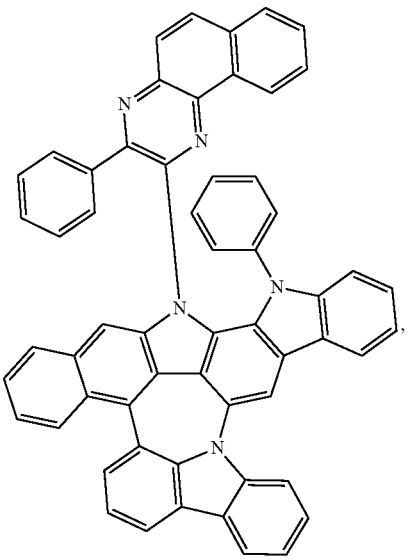

1-339
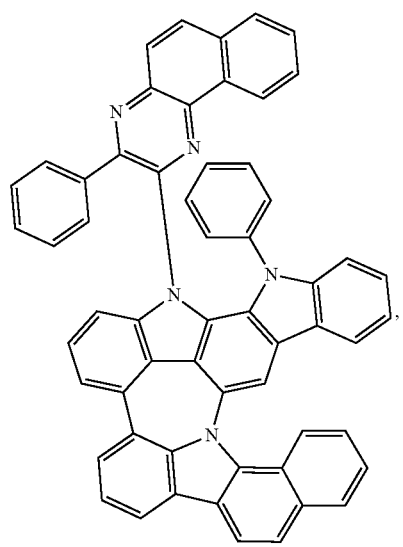
1-340
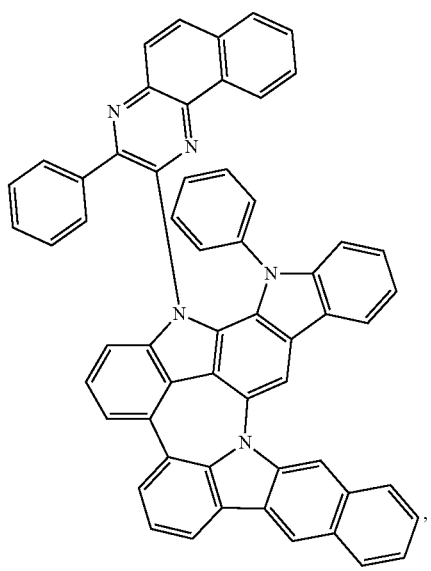
1-341
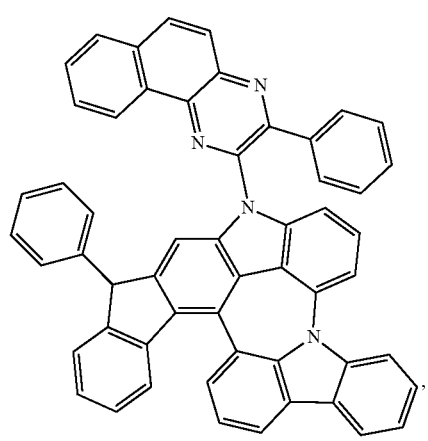
1-342
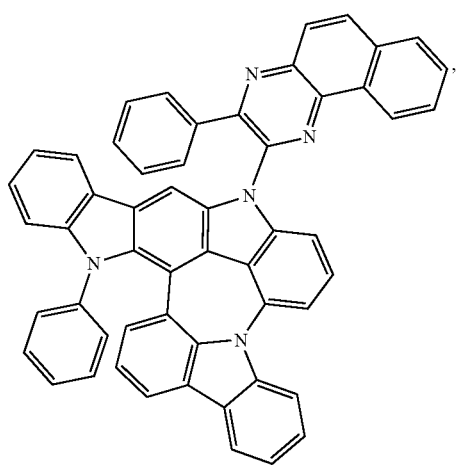
1-343
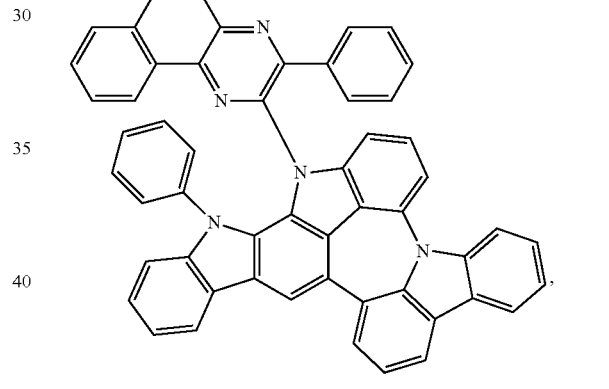
1-344
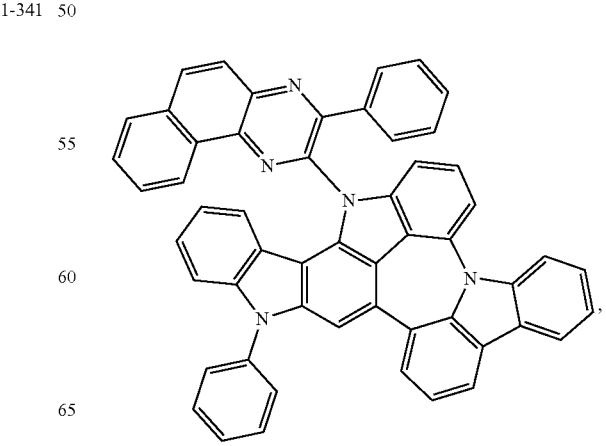

1-345
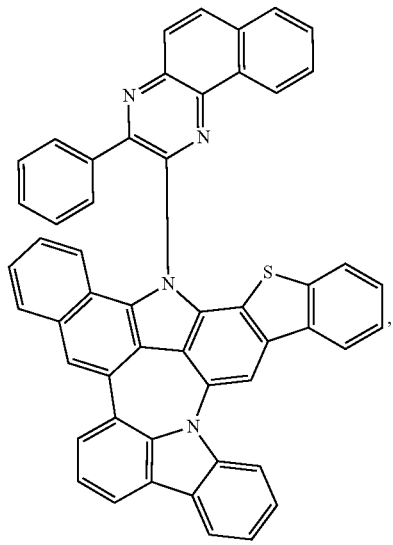
1-346
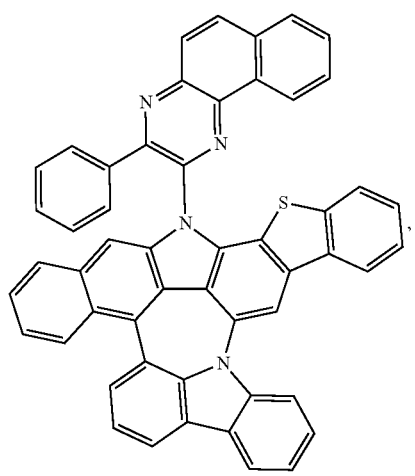
1-347
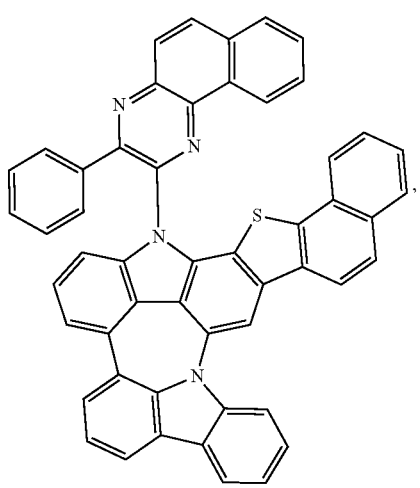
1-348
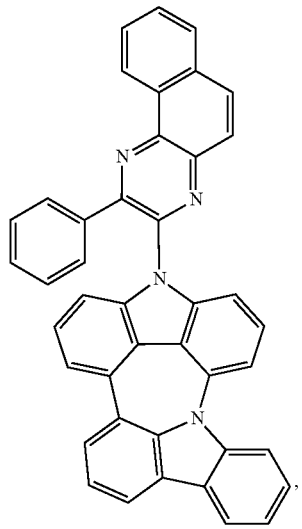
1-349
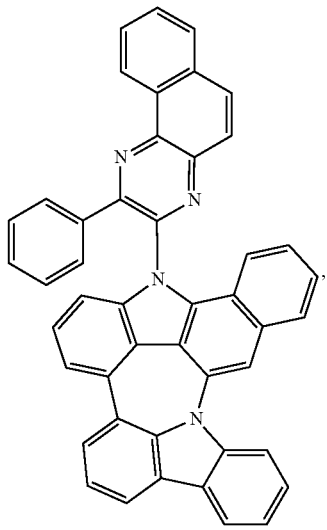
1-350
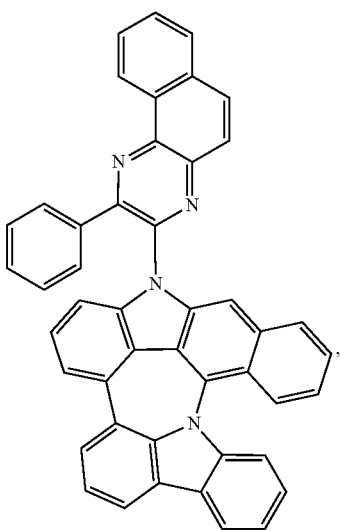

1-351
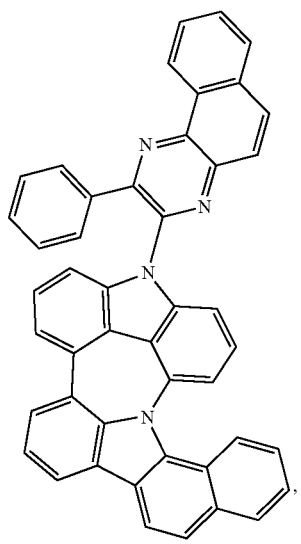
1-352
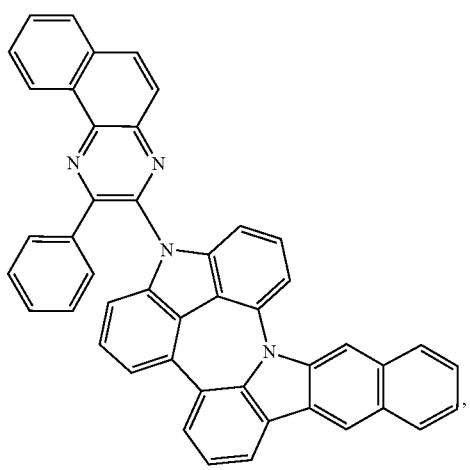
1-353
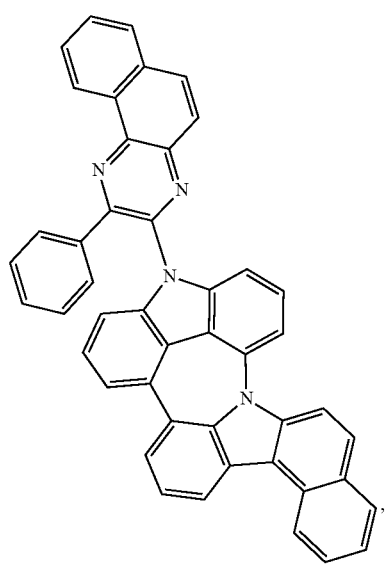
1-354
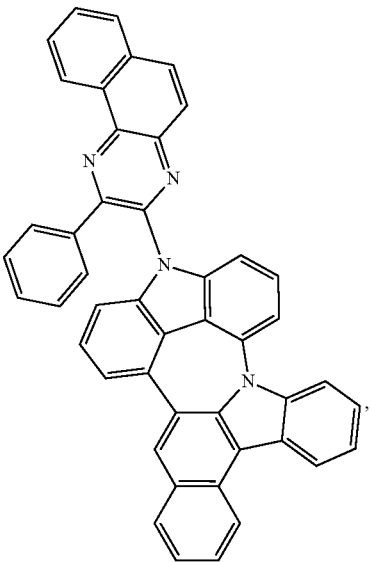
1-355
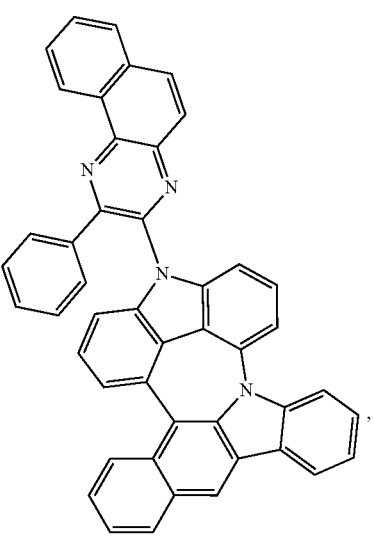
1-356
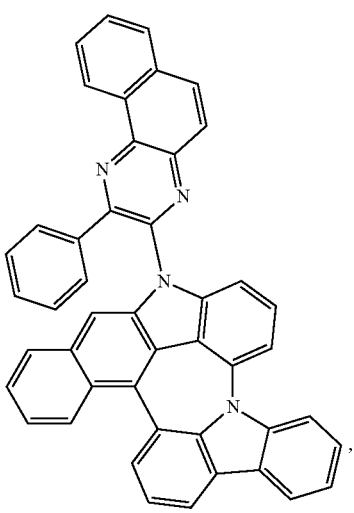

-continued
1-357
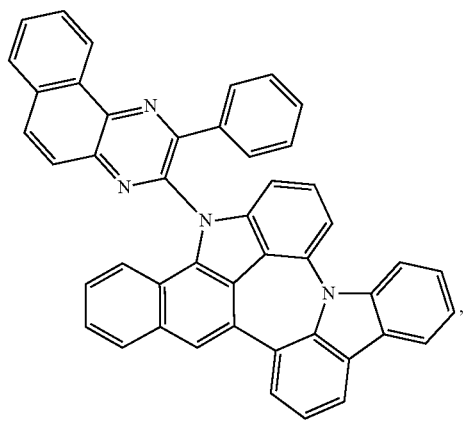
1-358
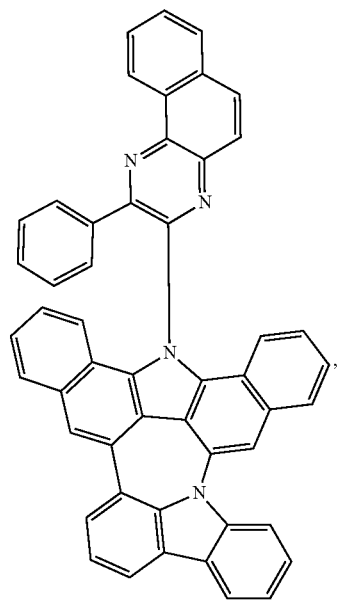
1-359
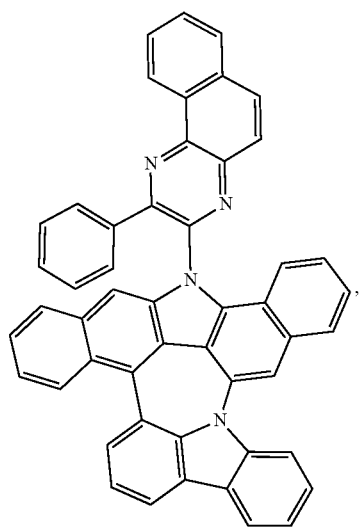
-continued
1-360
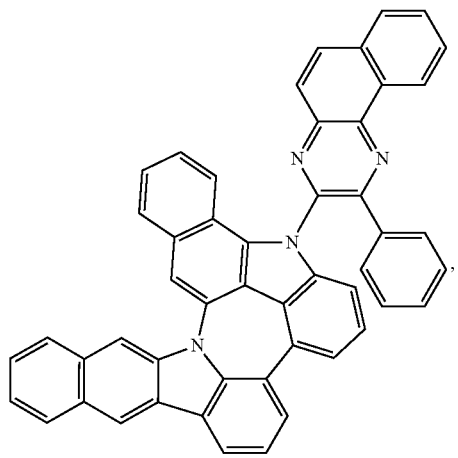
1-361
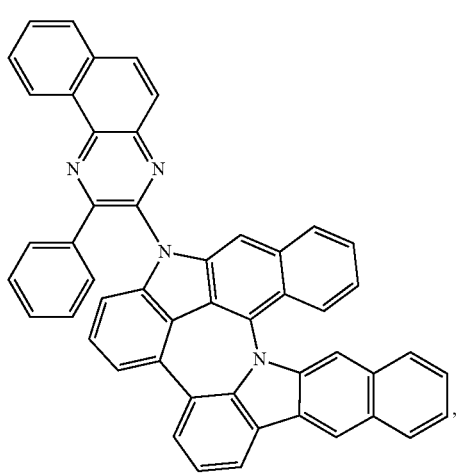
1-362
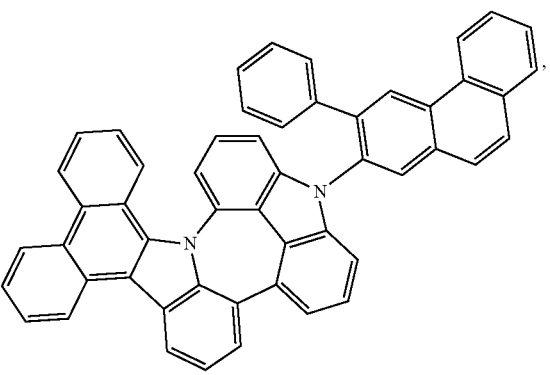

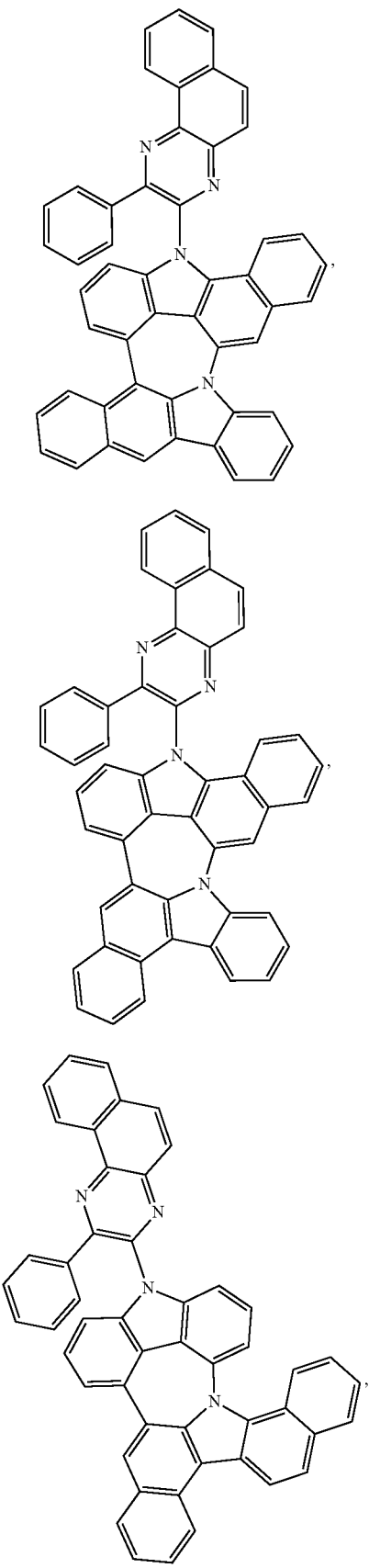
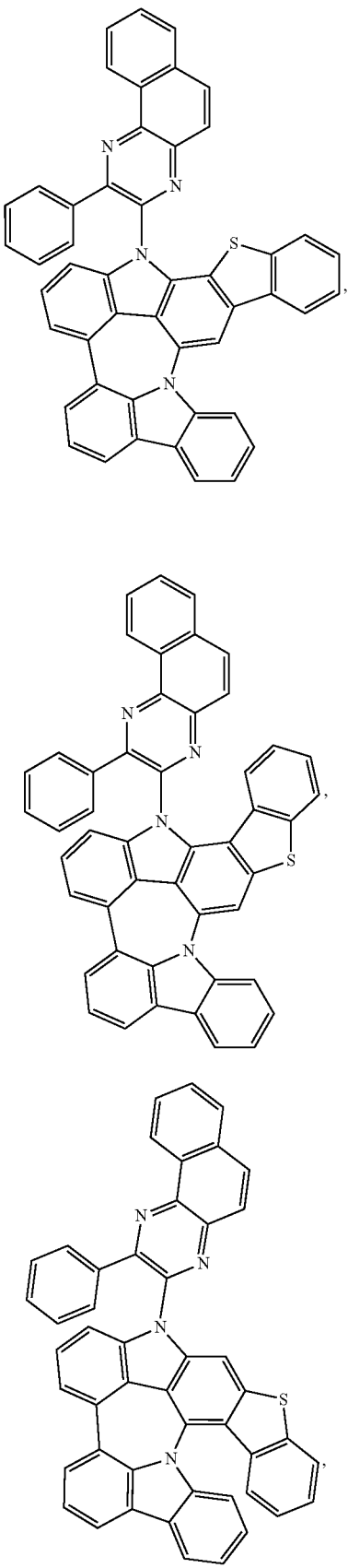

1-369
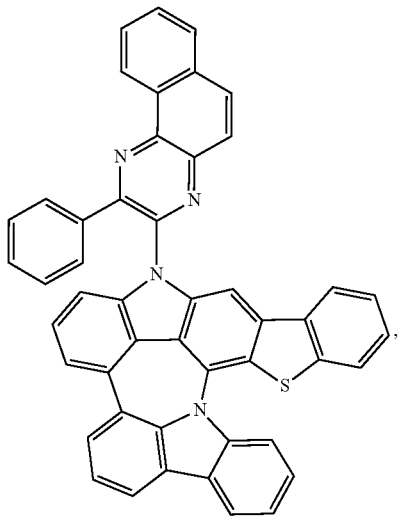
1-370
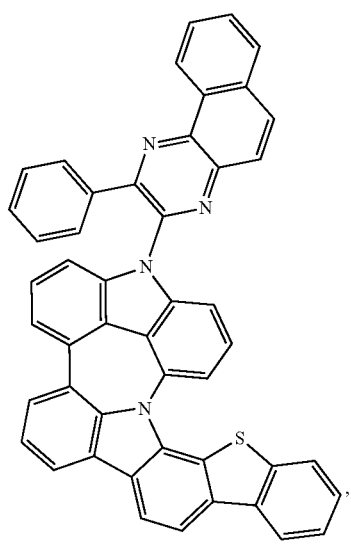
1-371
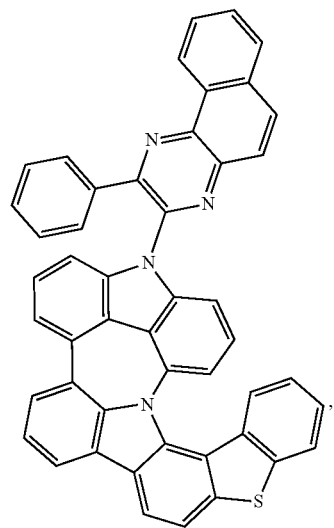
1-372
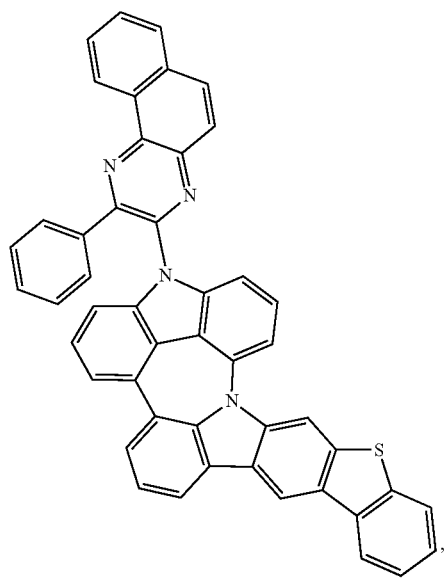
1-373
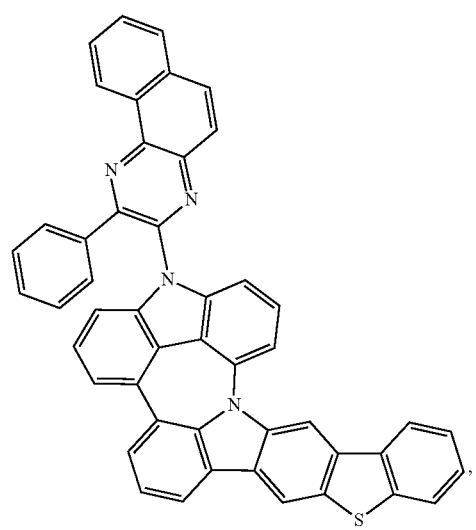
1-374
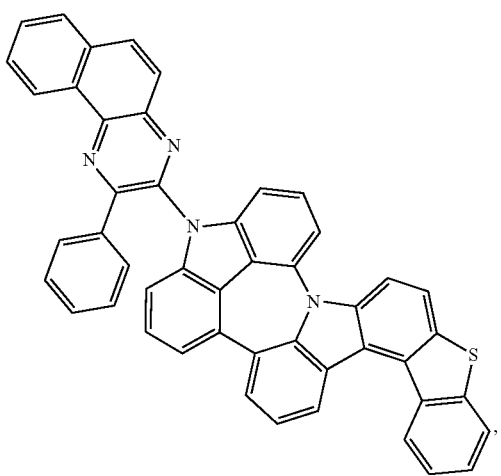

-continued
1-375
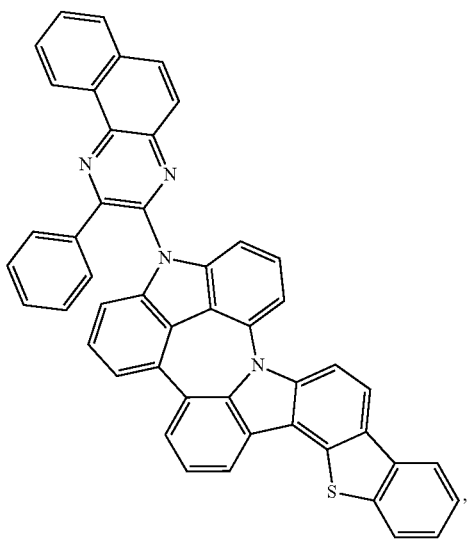
1-376
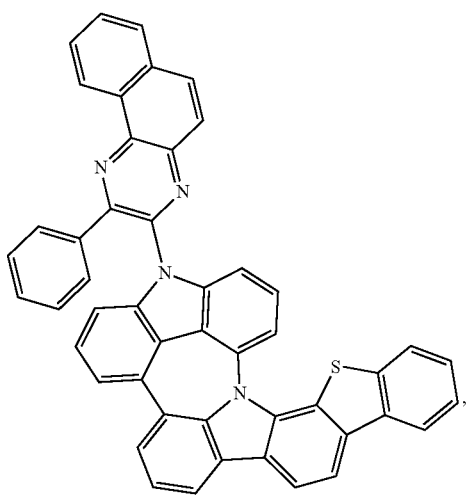
1-377
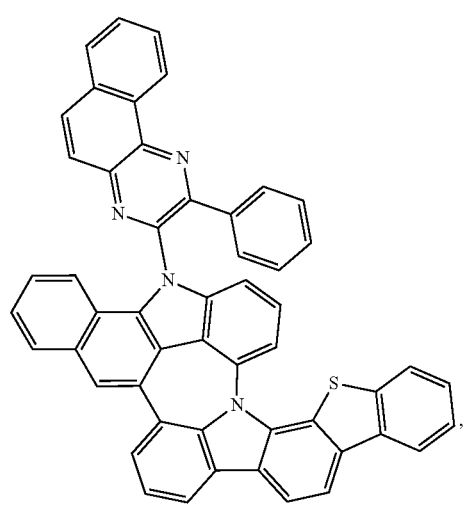
-continued
1-378
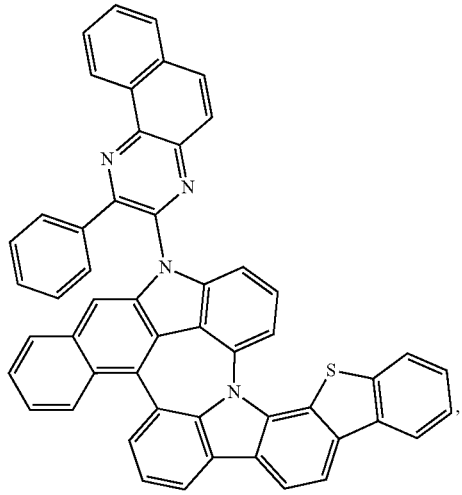
1-379
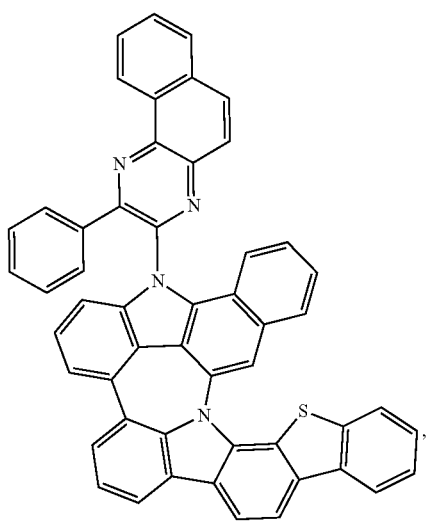
1-380
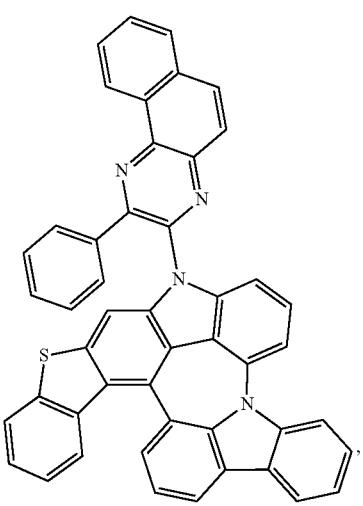

1-381
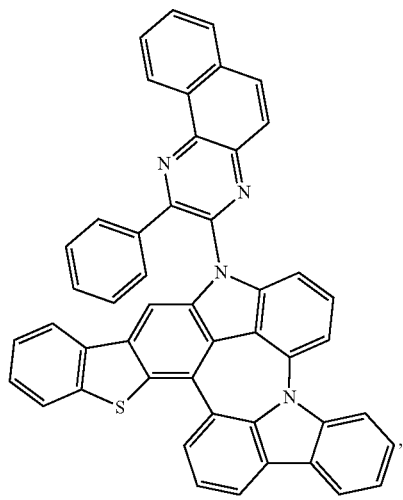
1-382
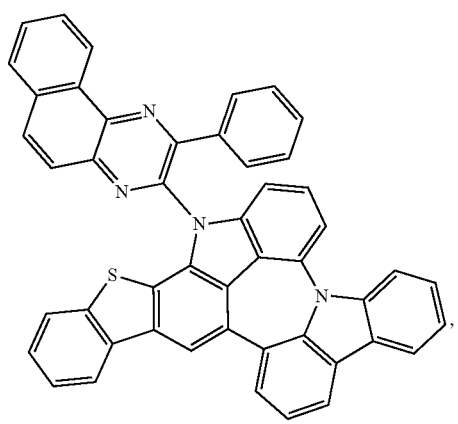
1-383
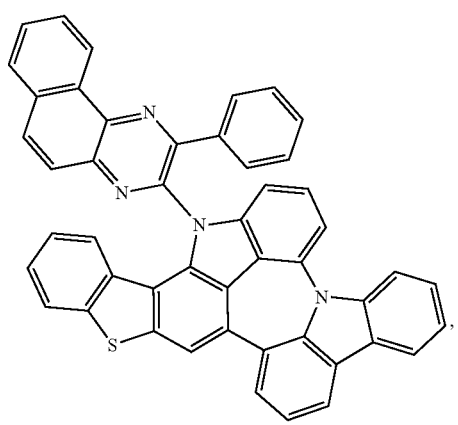
1-384
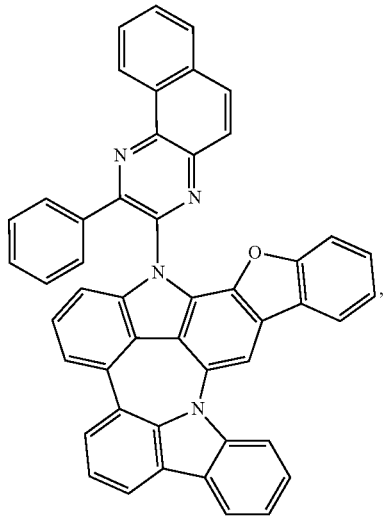
1-385
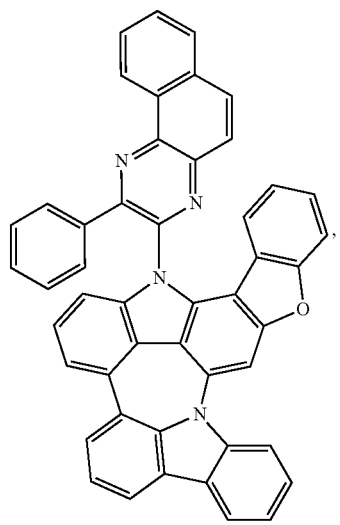
1-386
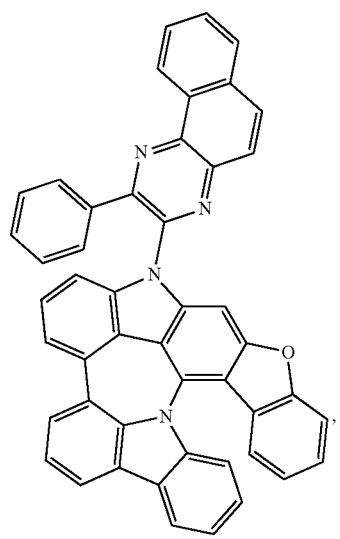

1-387
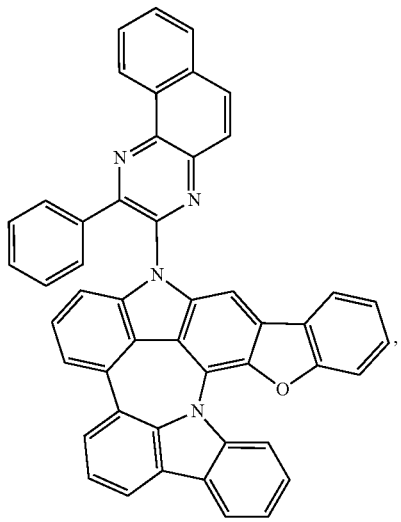
1-388
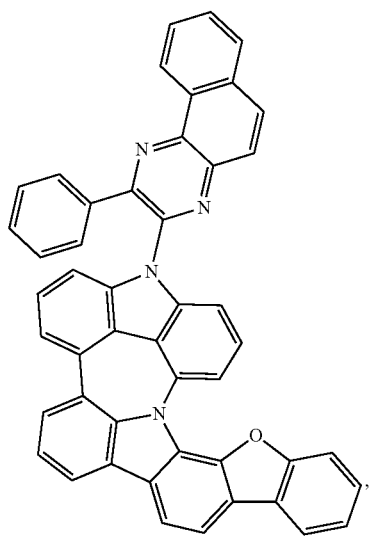
1-389
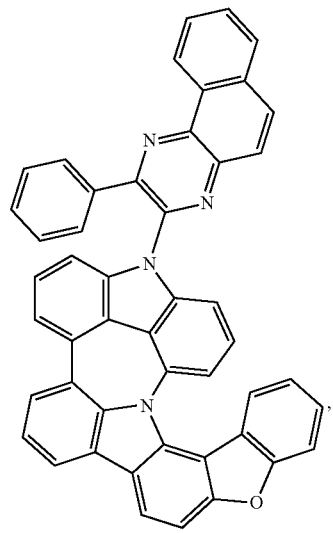
1-390
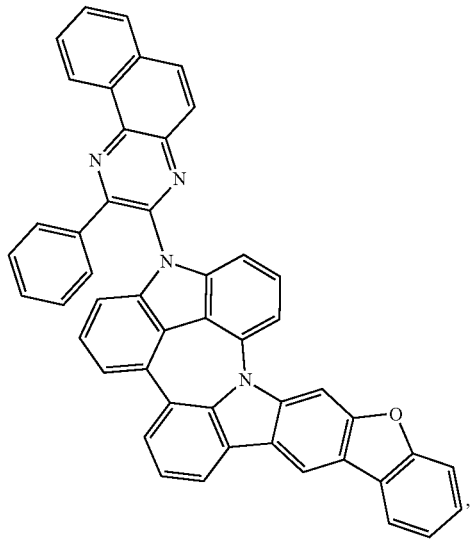
1-391
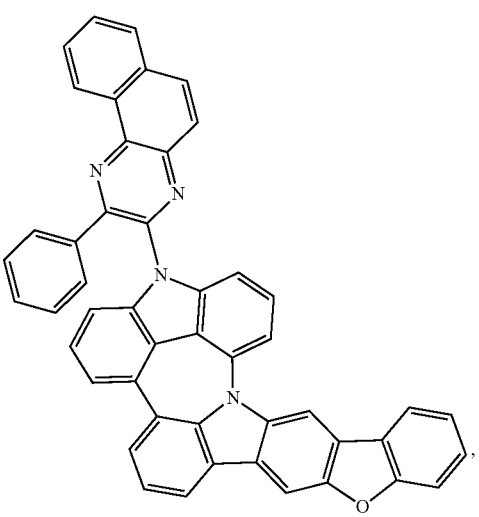
1-392
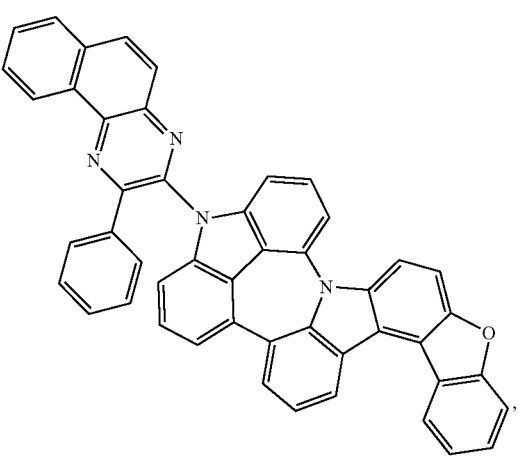

1-393
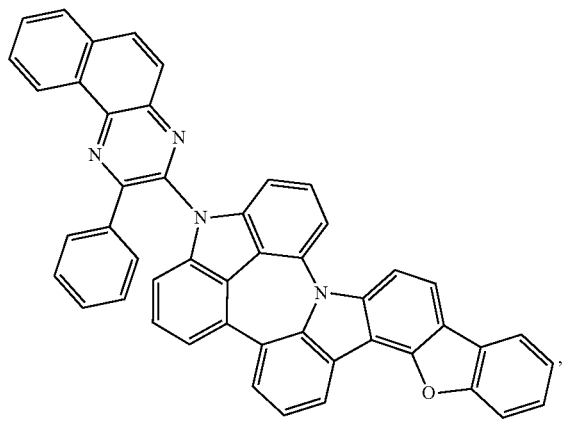
1-394
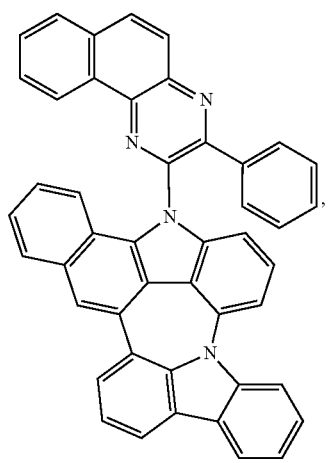
1-395
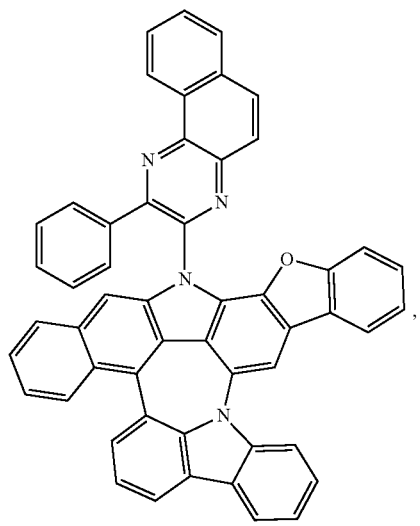
1-396
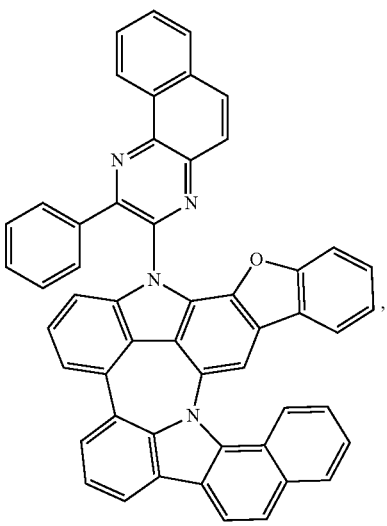
1-397
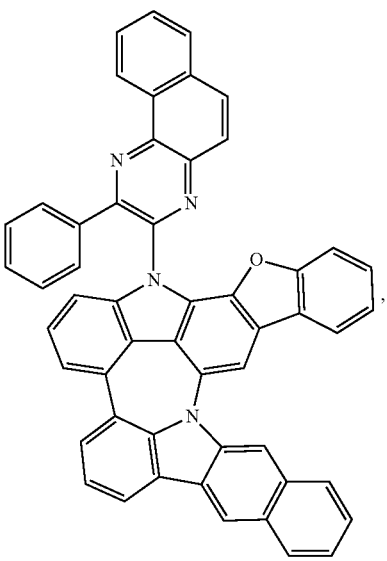
1-398
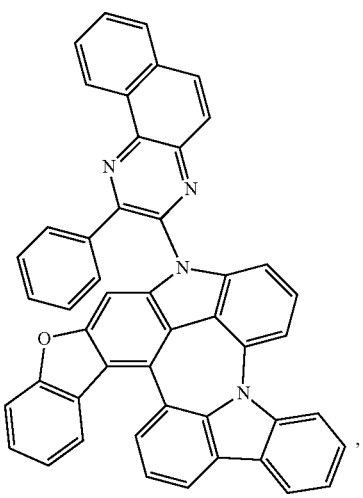

1-399
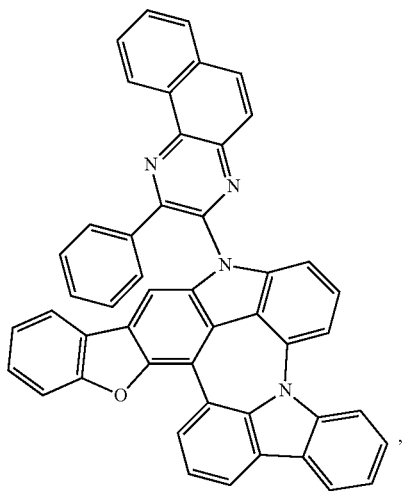
1-400
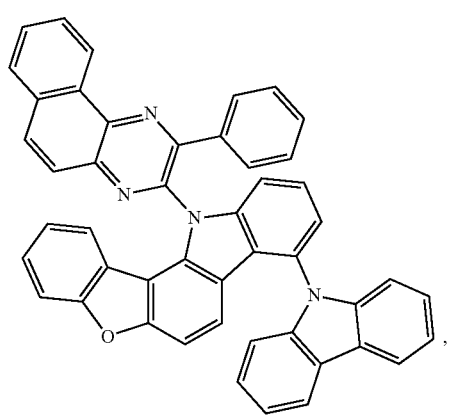
1-401
1-402
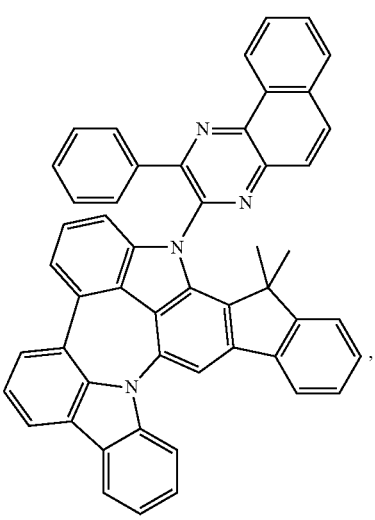
1-403
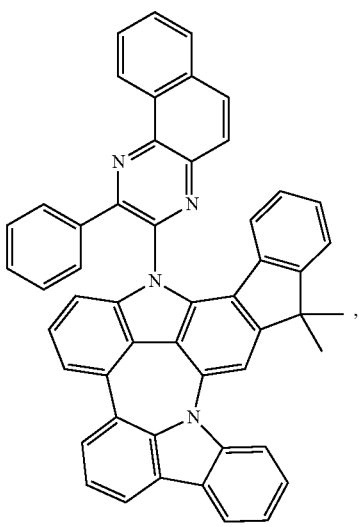
1-404
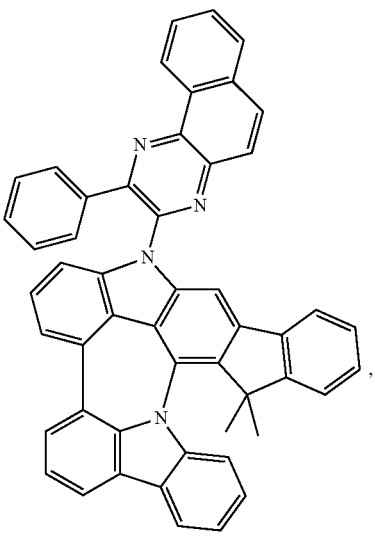

1-405
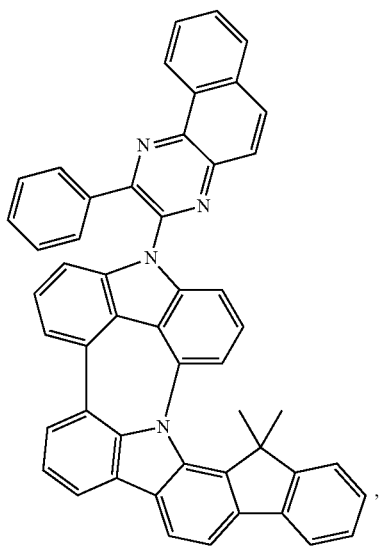
1-406
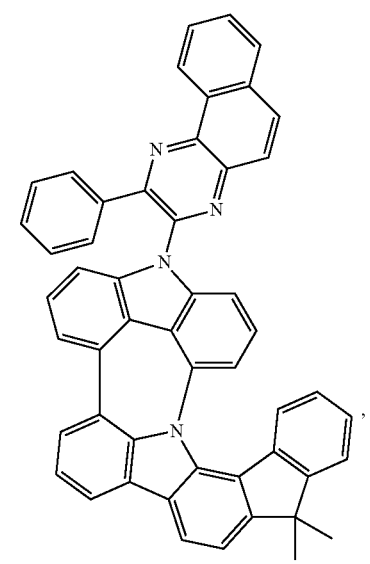
1-407
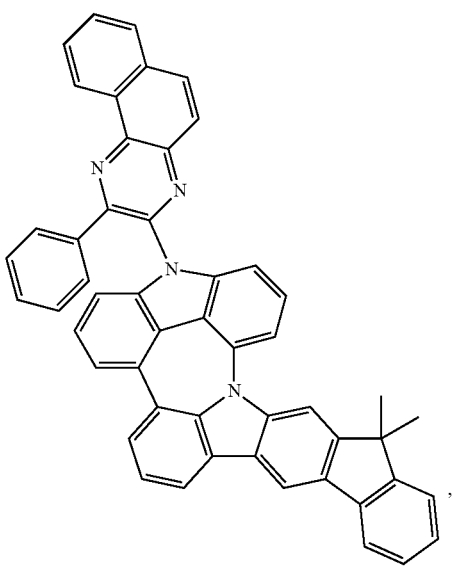
1-408
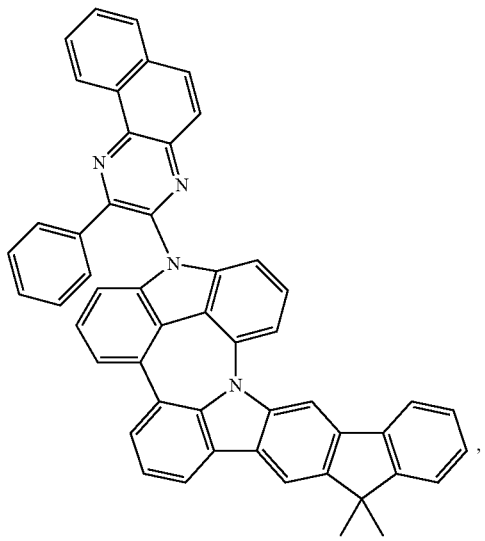
1-409
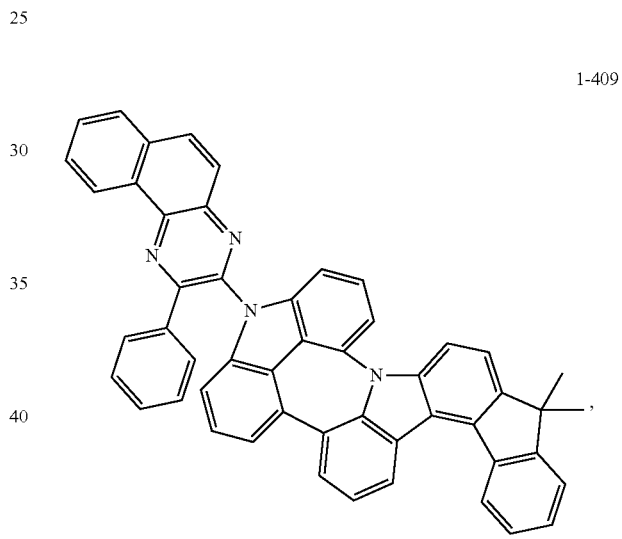
1-410
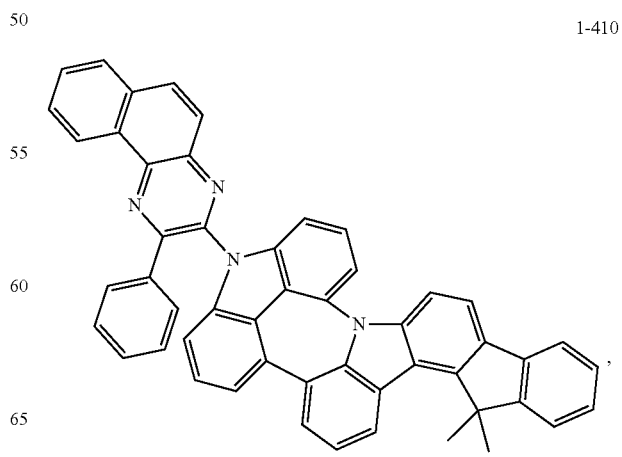

-continued
1-411
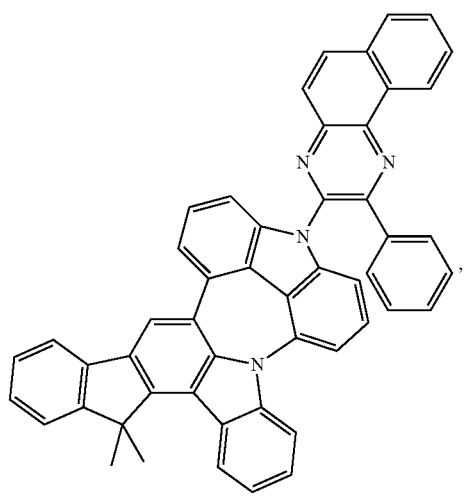
1-412
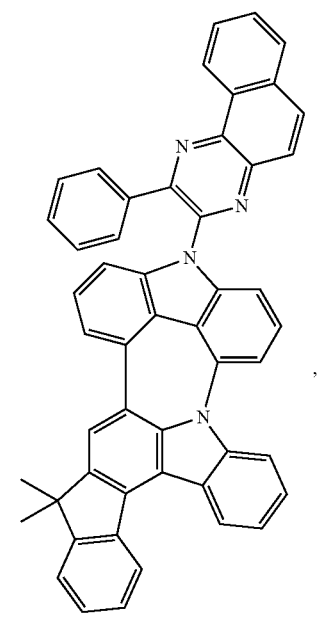
1-413
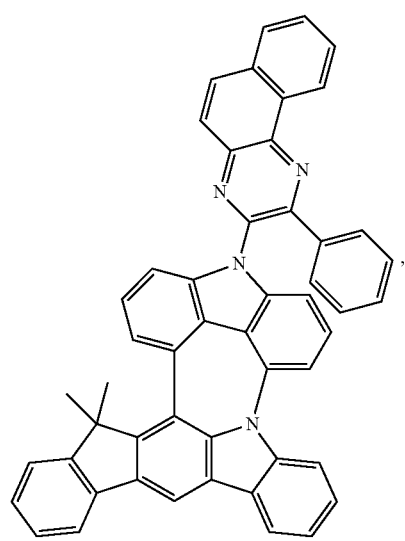
-continued
1-414
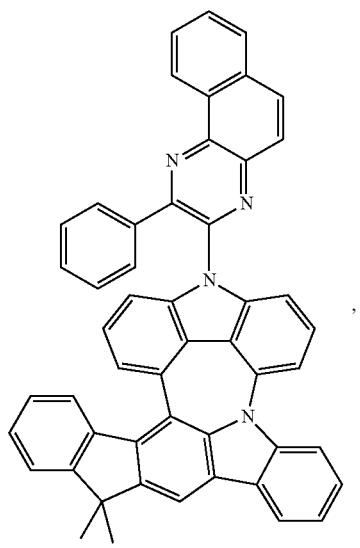
1-415
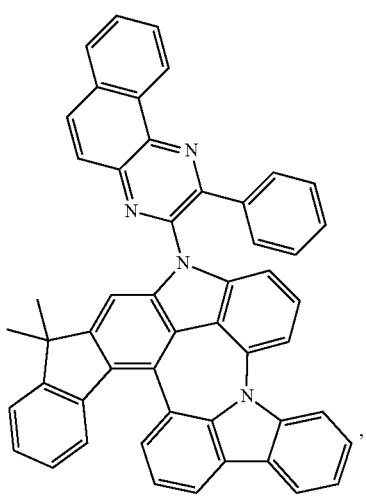
1-416
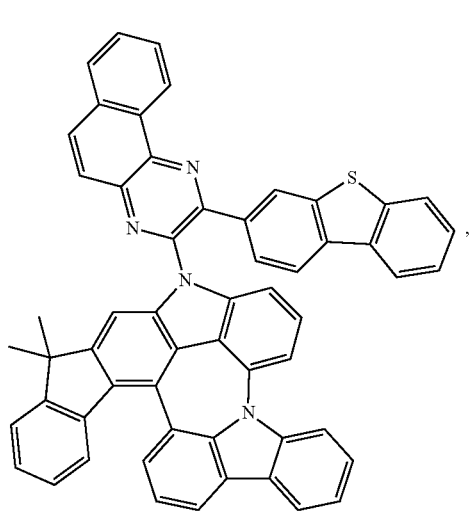

-continued
1-417
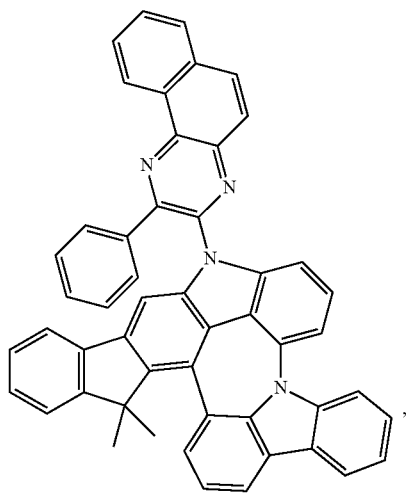
1-418
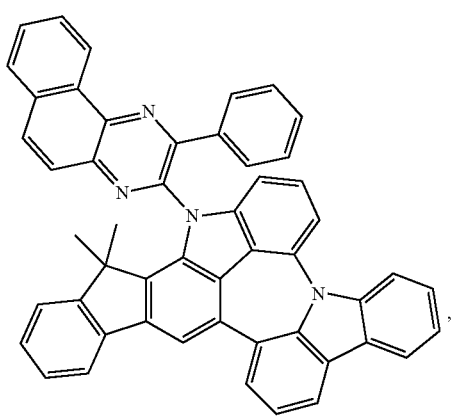
1-419
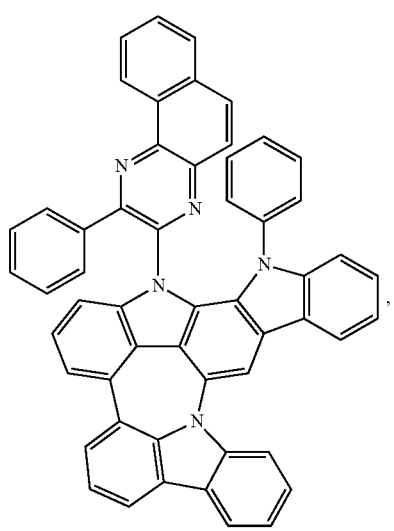
1-420
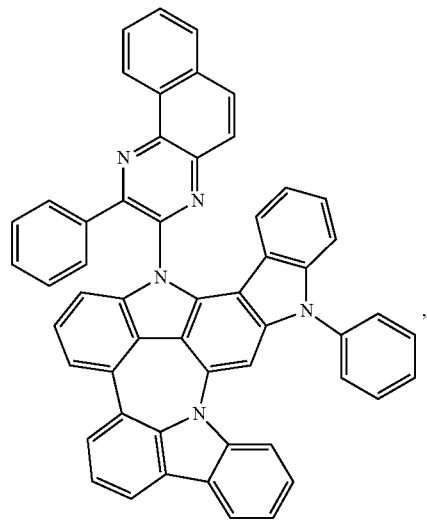
1-421
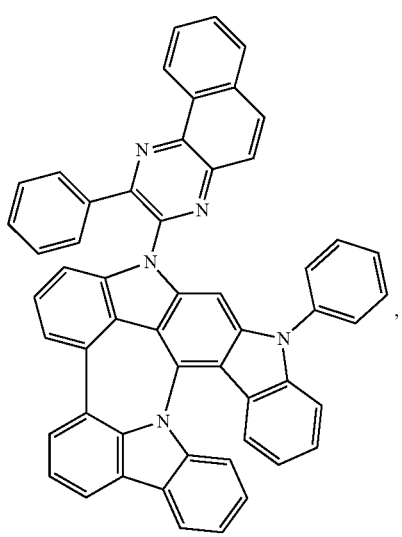
1-422
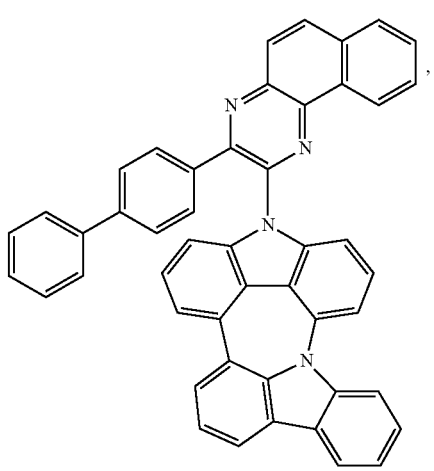

-continued
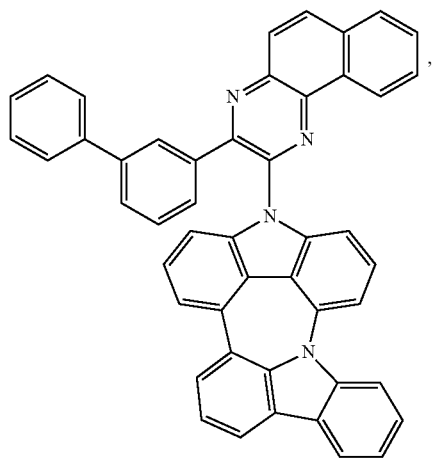
1-423
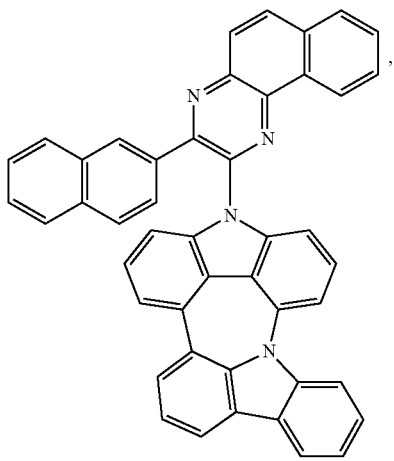
1-426
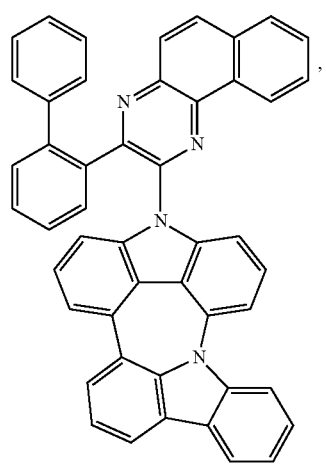
1-424
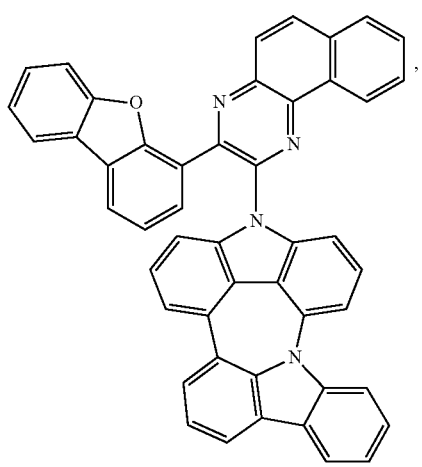
1-427
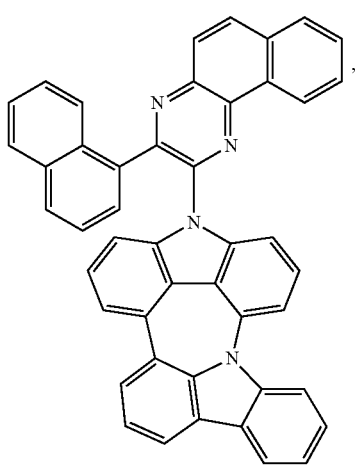
1-425
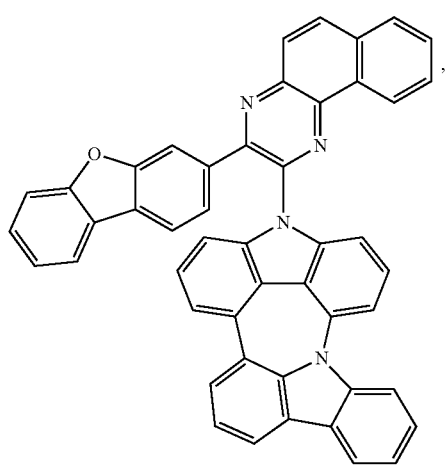
1-428

-continued
1-429
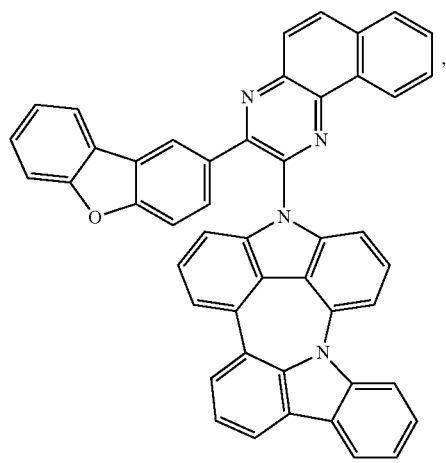
1-430
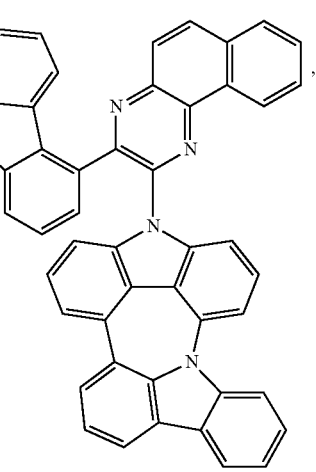
1-431
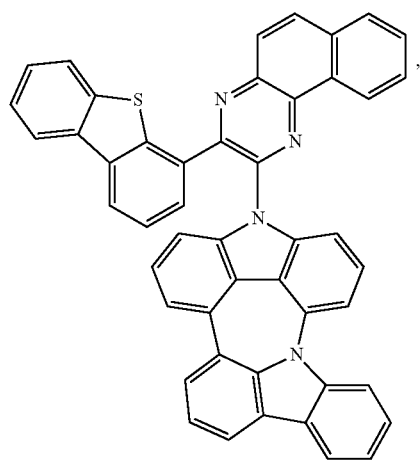
-continued
1-432
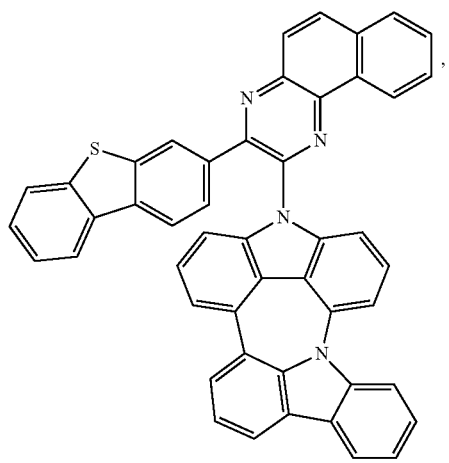
1-433
1-434
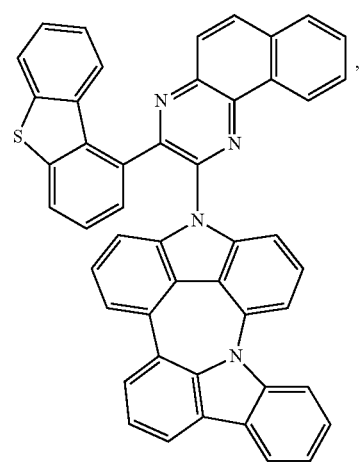

-continued
1-435
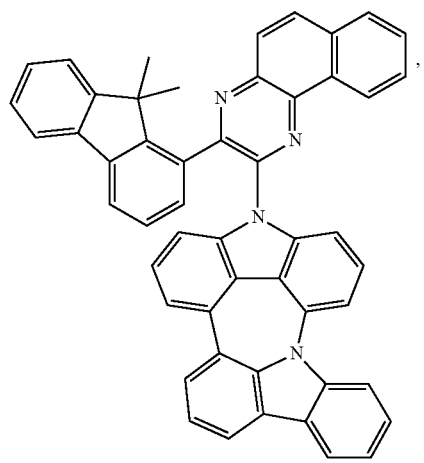
1-436
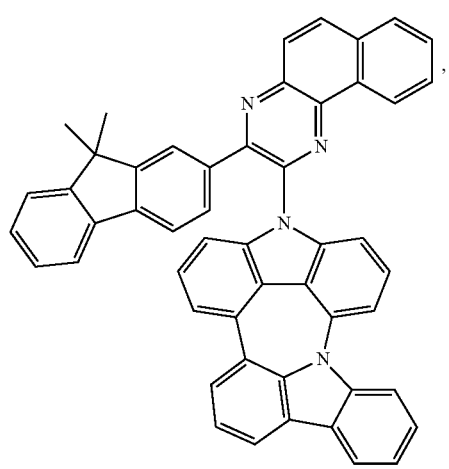
1-437
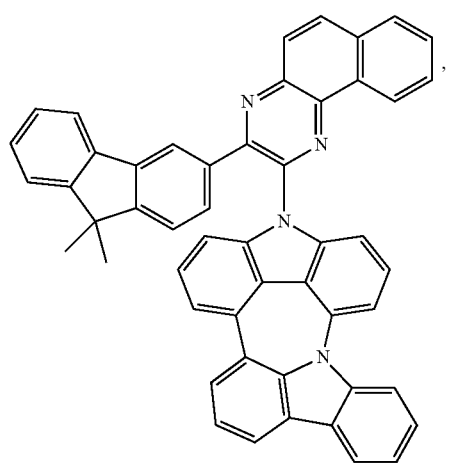
-continued
1-438
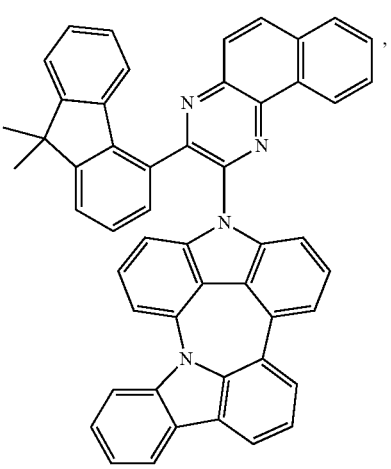
1-439
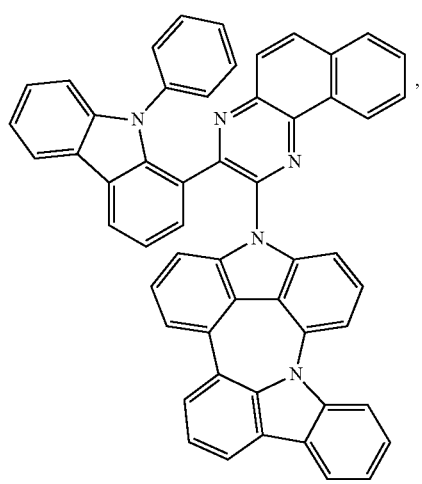
1-440
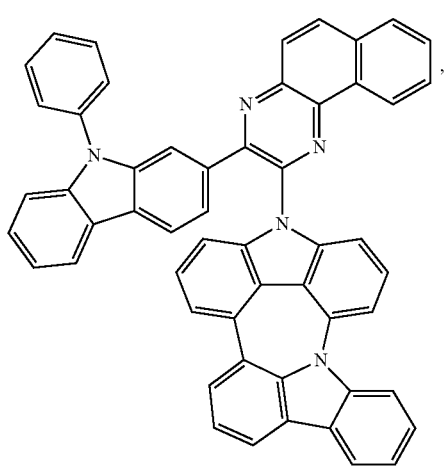

-continued
1-441
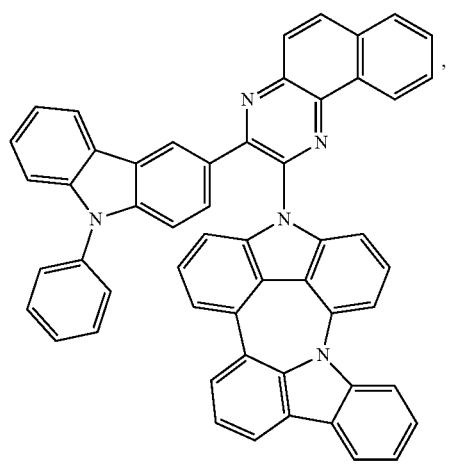
1-442
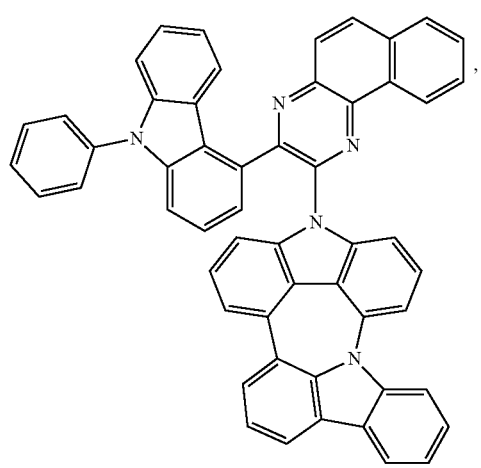
1-443
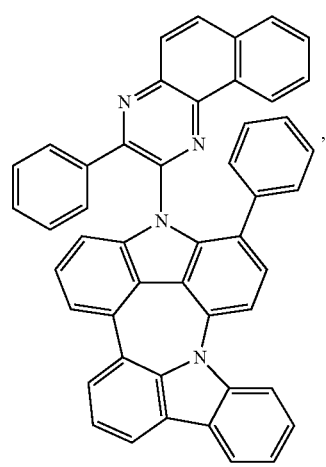
-continued
1-444
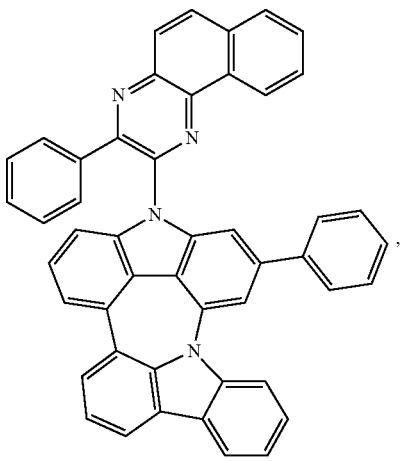
1-445
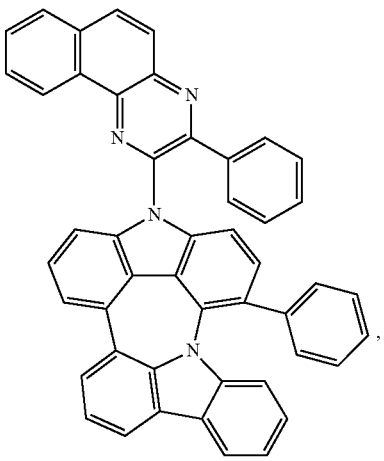
1-446
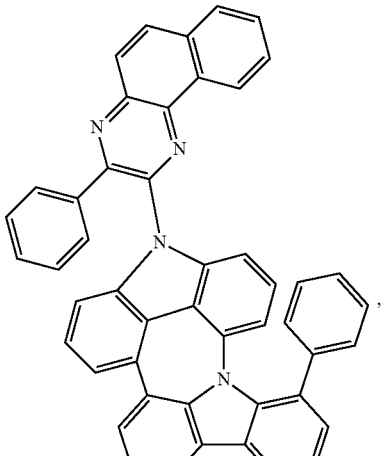

-continued
1-447
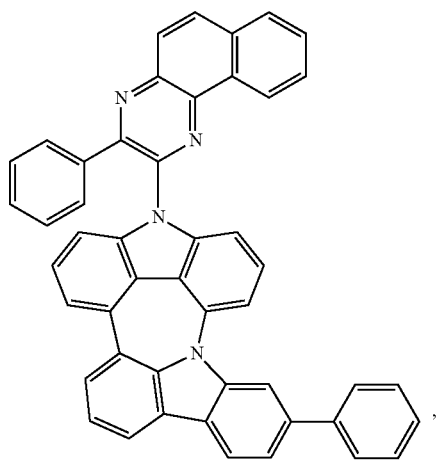
1-448
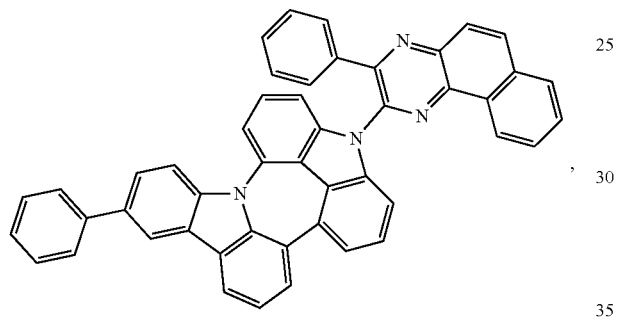
1-449
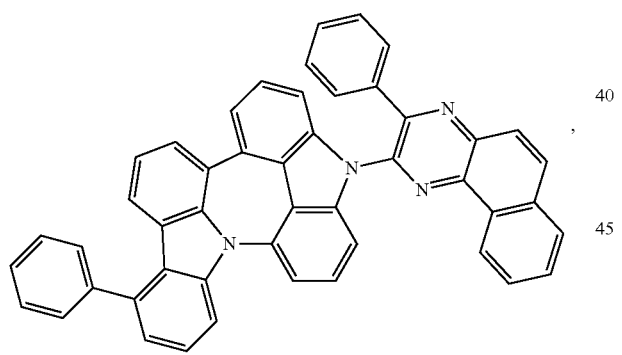
1-450
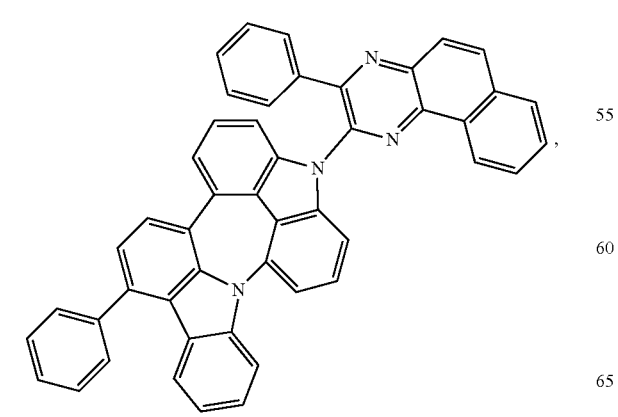
-continued
1-451
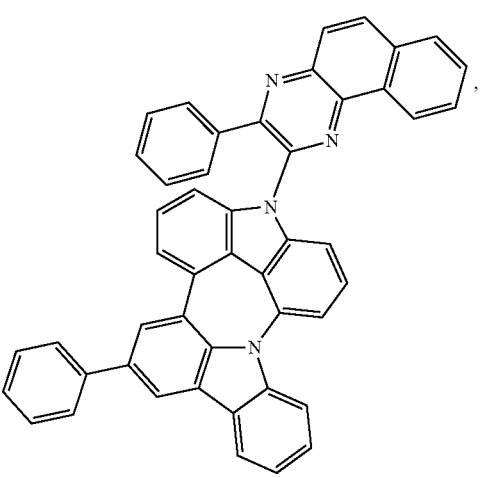
1-452
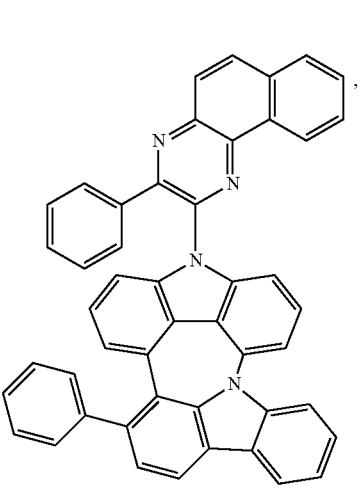
1-453
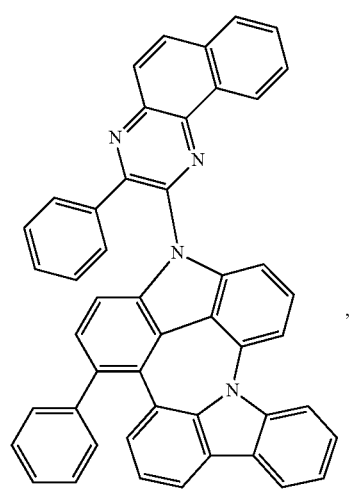

1-454
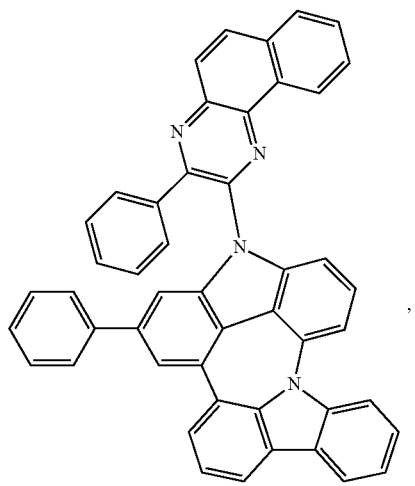
1-455
1-456
1-457
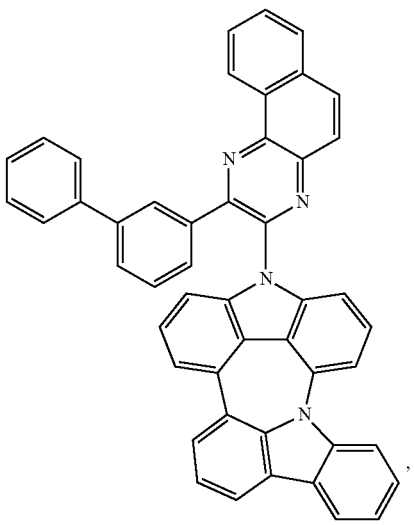
1-458
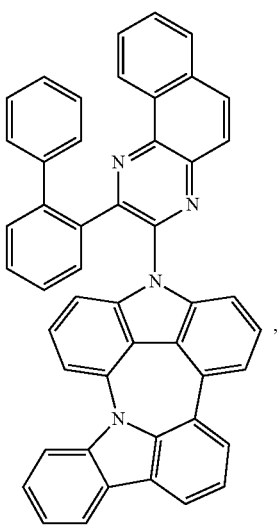
1-459
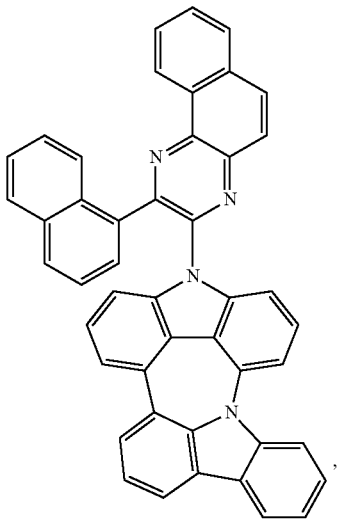

1-460 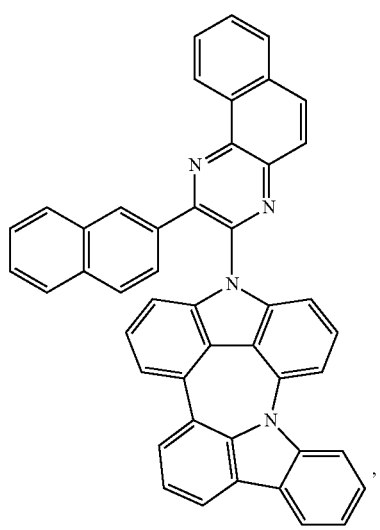
1-461 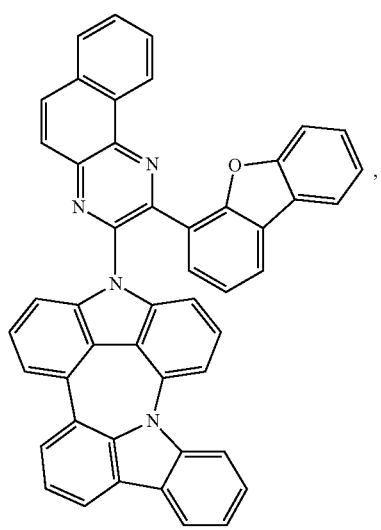
1-462 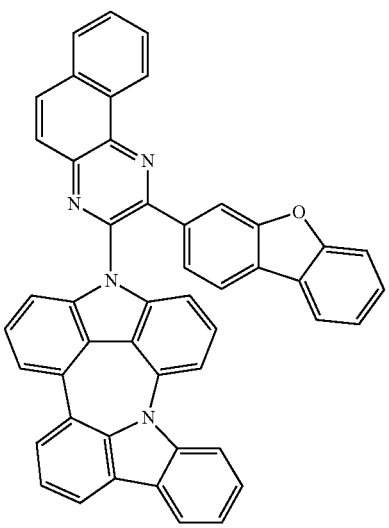
1-463 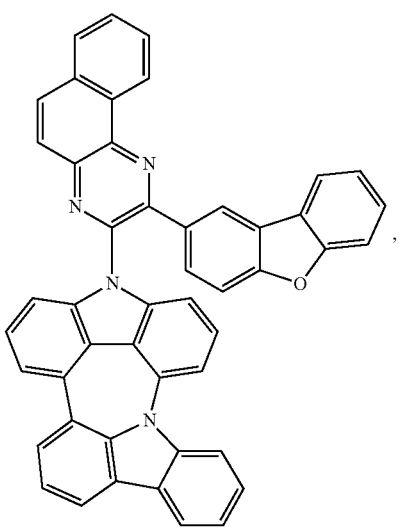
1-464 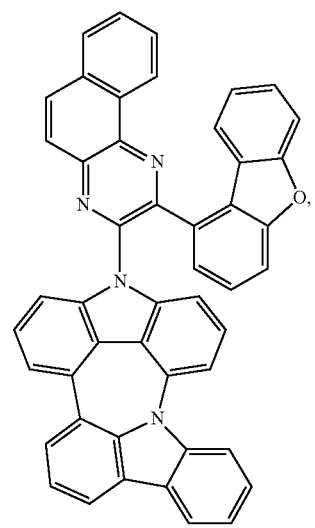
1-465 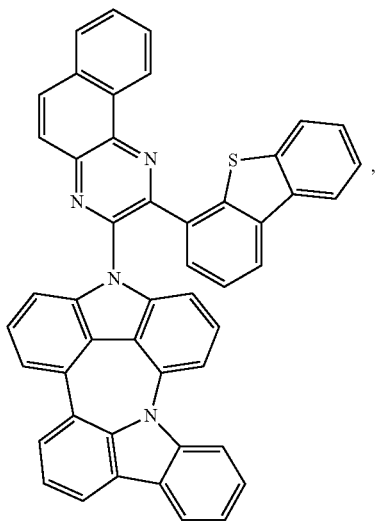

1-466
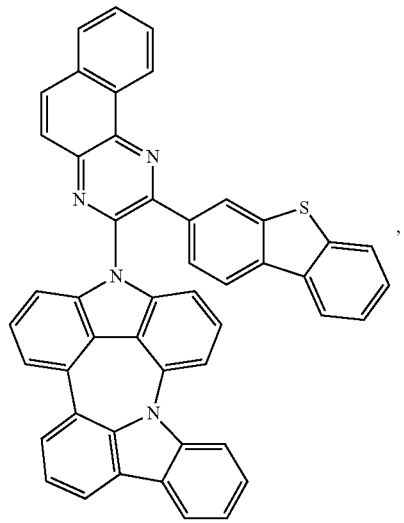
1-467
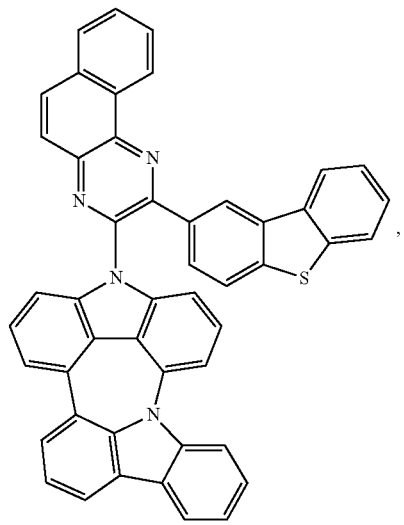
1-468
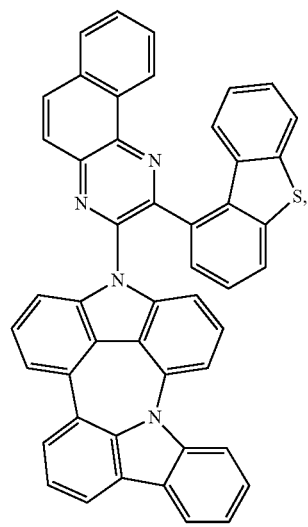
1-469
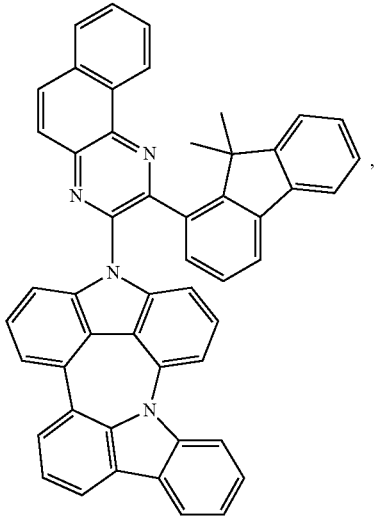
1-470
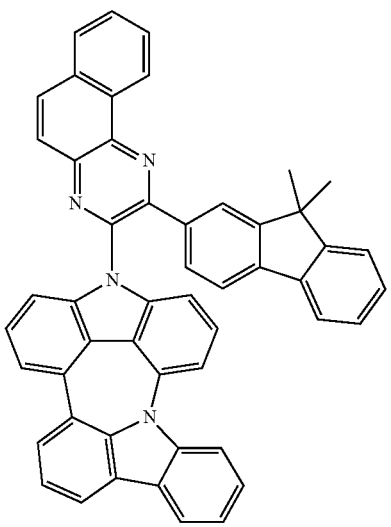
1-471
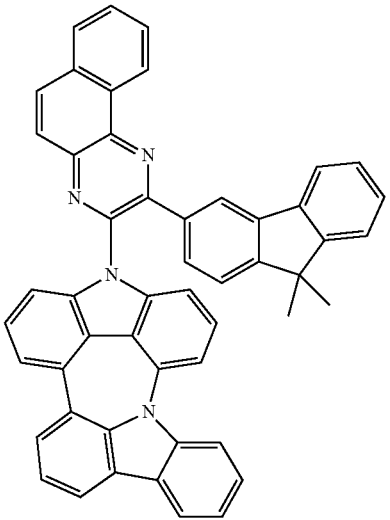

221
-continued
1-472
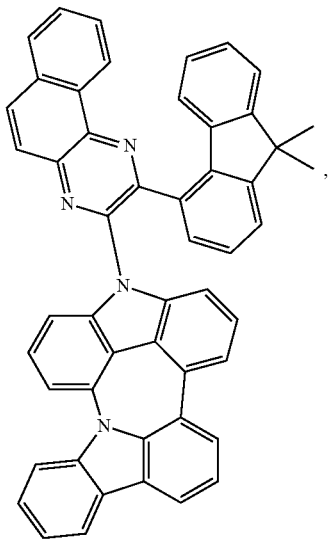
1-473
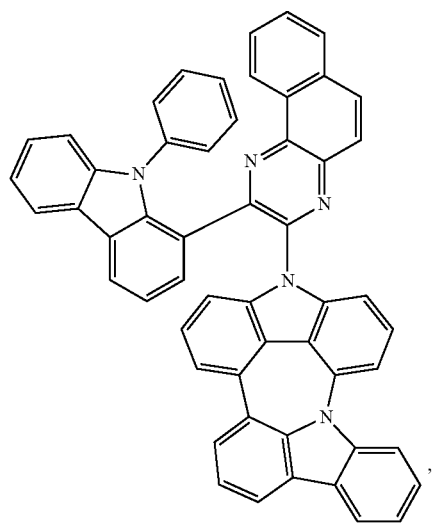
1-474
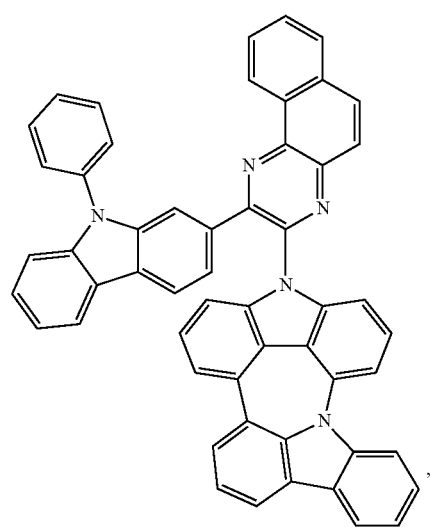
222
-continued
1-475
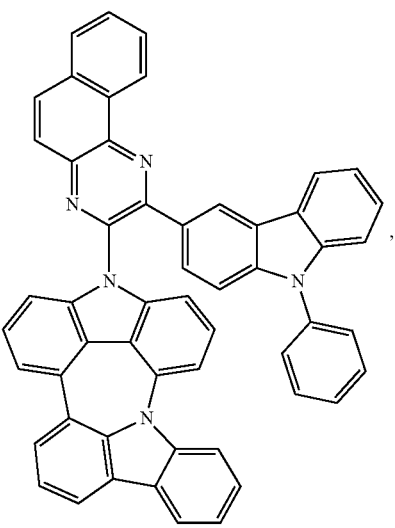
1-476
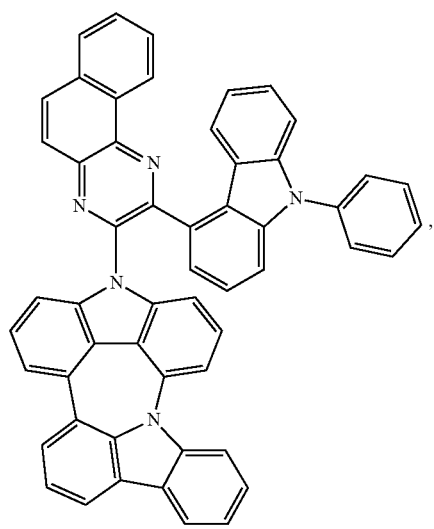
1-477
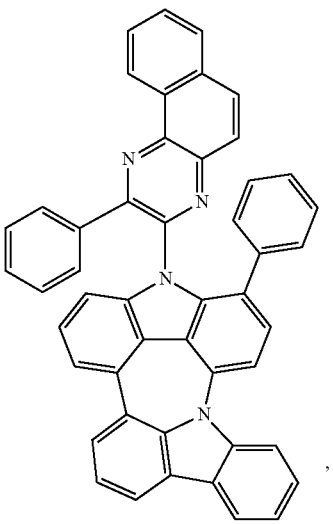

1-478
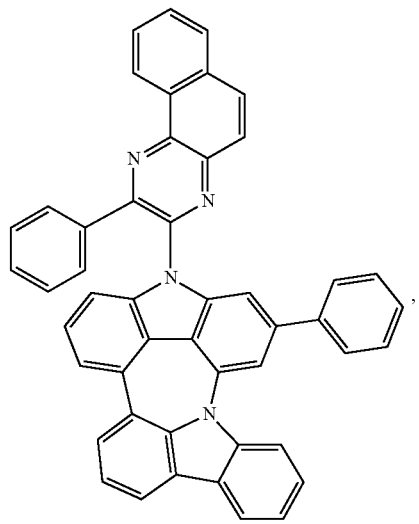
1-479
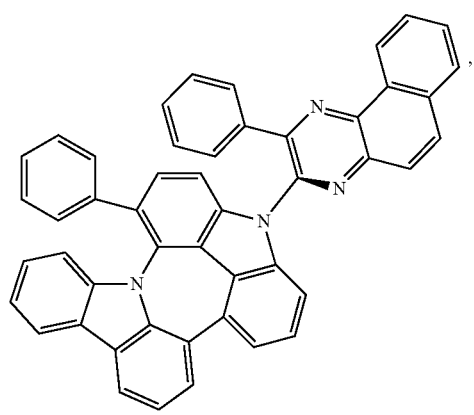
1-480
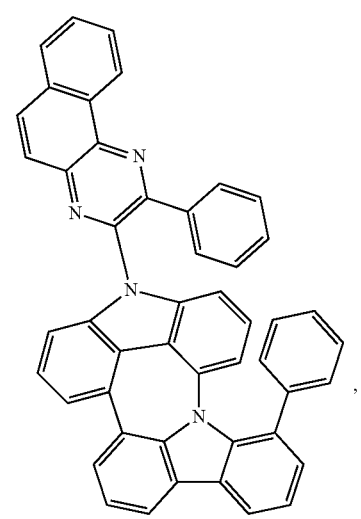
1-481
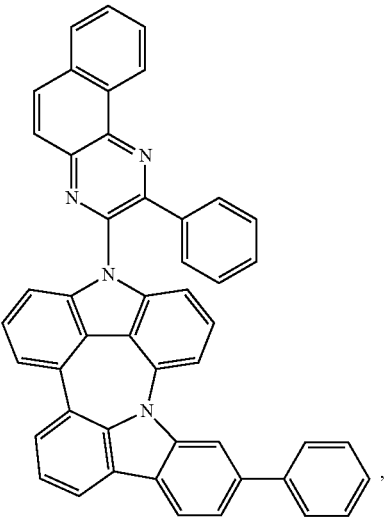
1-482
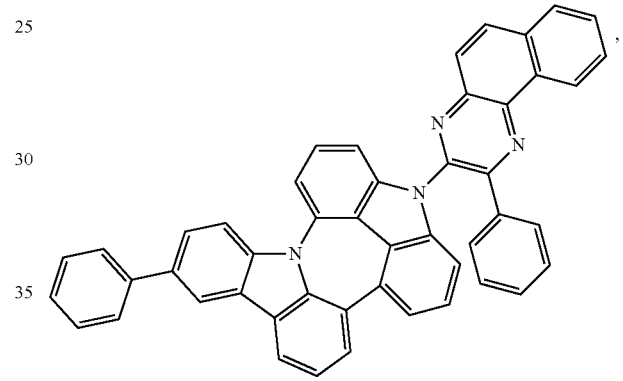
1-483
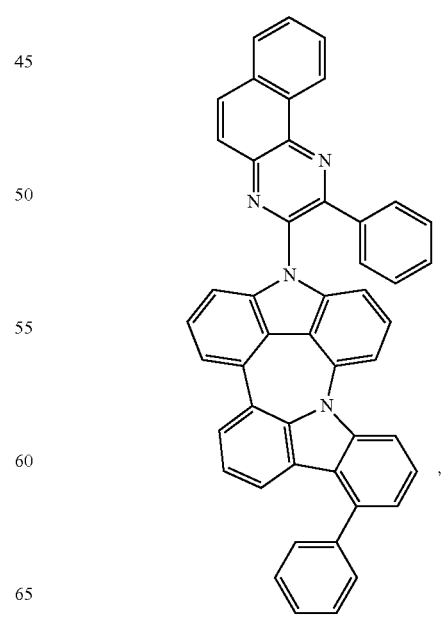

1-484
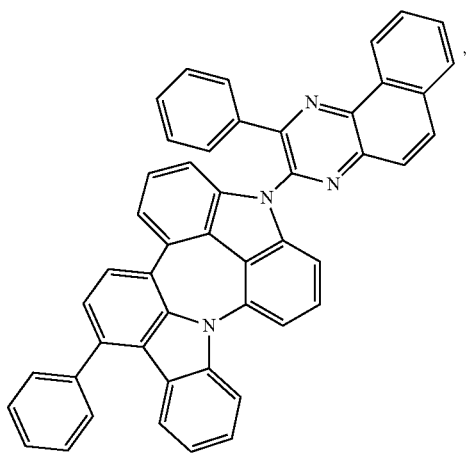
1-485
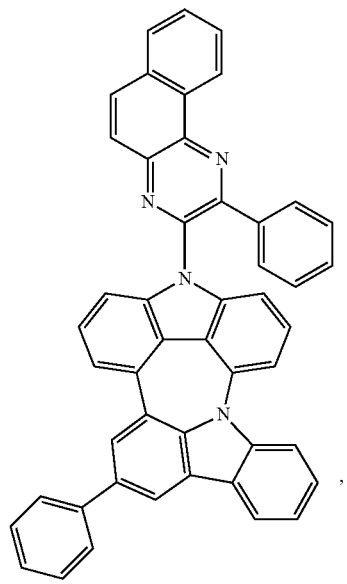
1-486
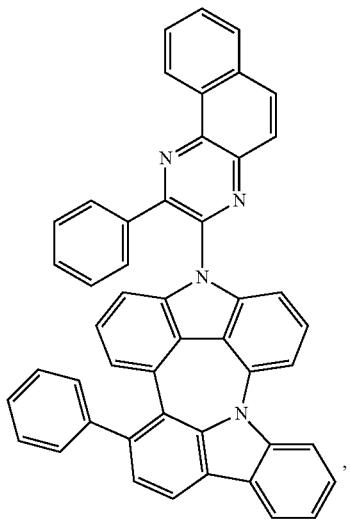
1-487
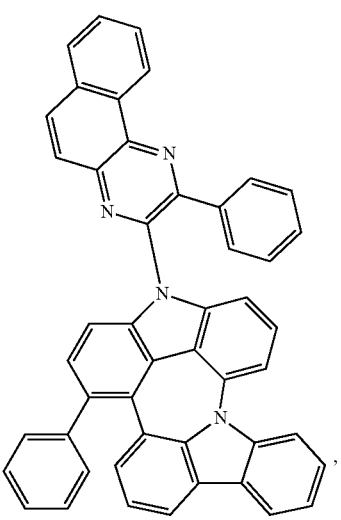
1-488
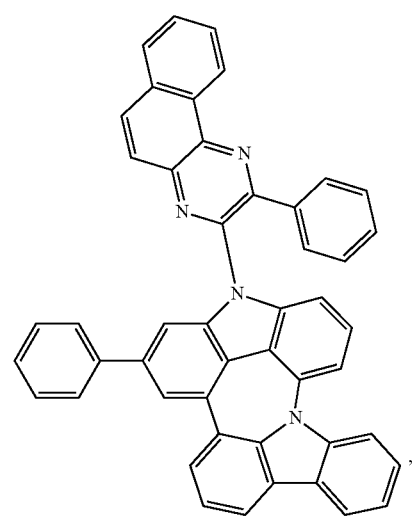
1-489
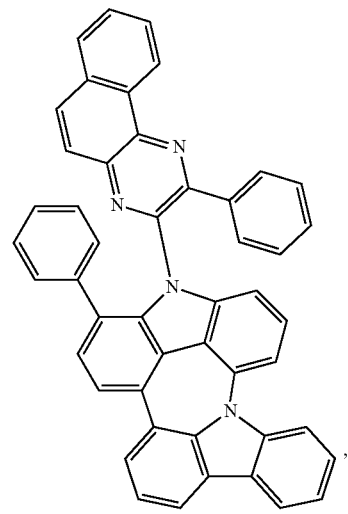

-continued
1-531
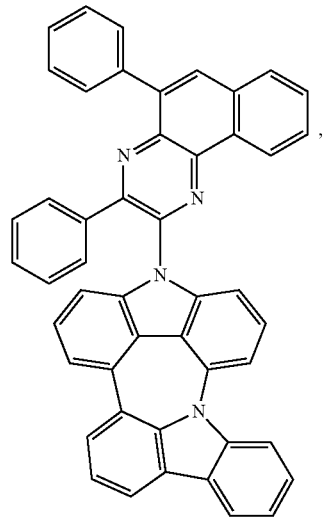
1-532
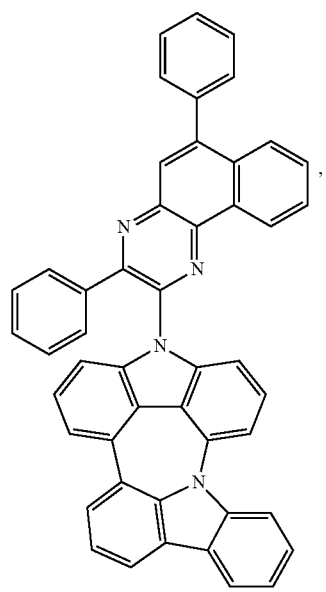
-continued
1-533
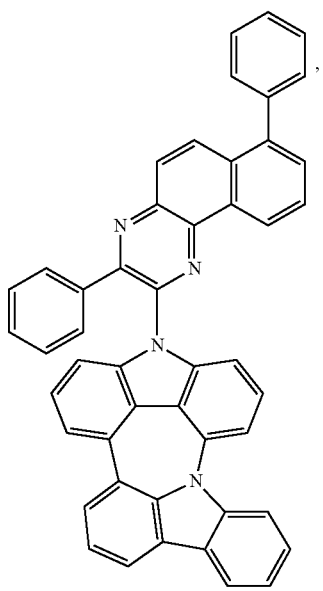
1-534
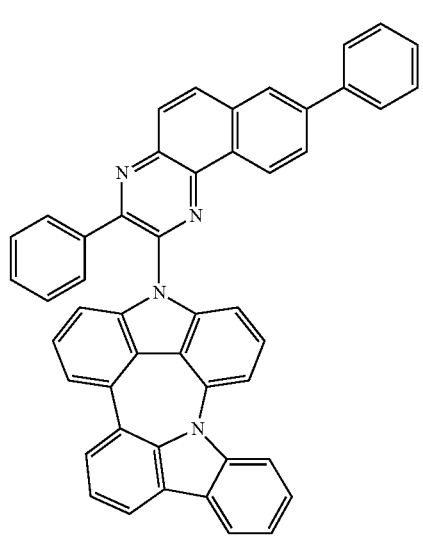
1-535
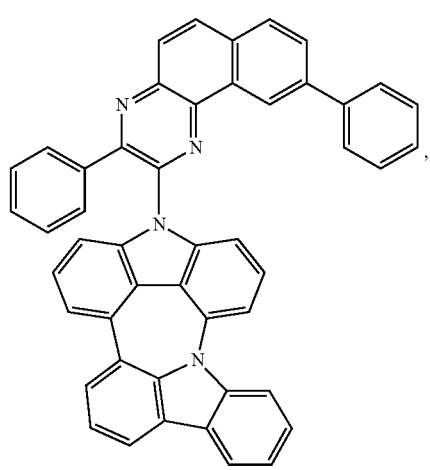

1-536
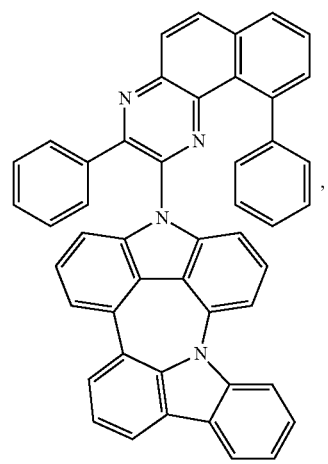
1-537
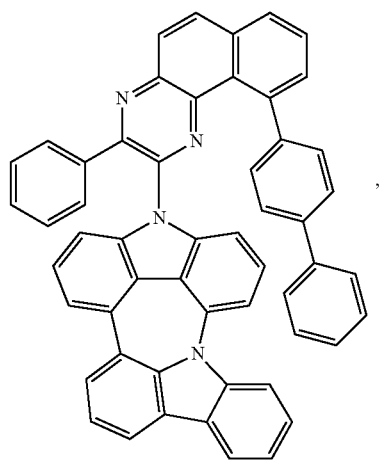
1-538
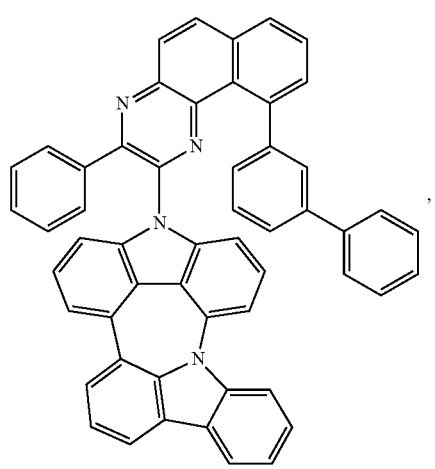
1-539
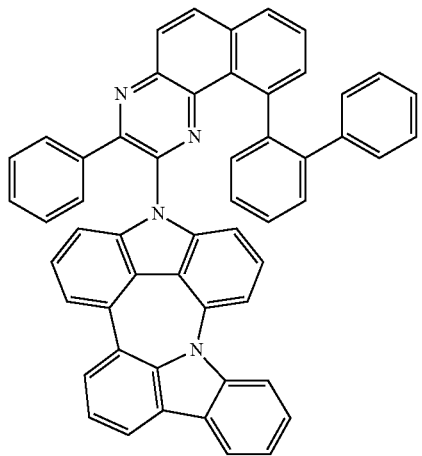
1-540
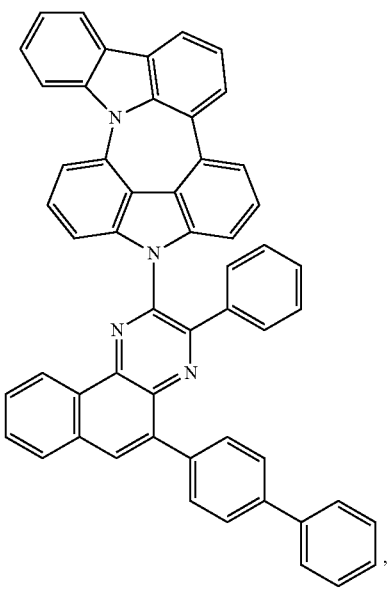
1-541
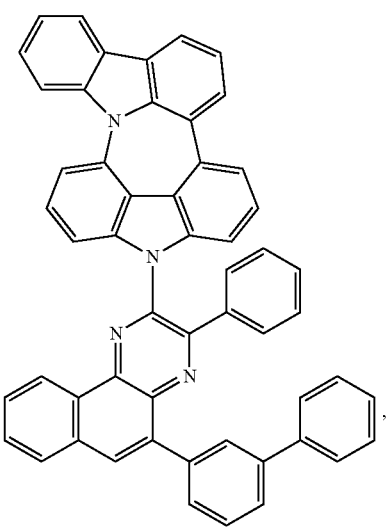

1-542
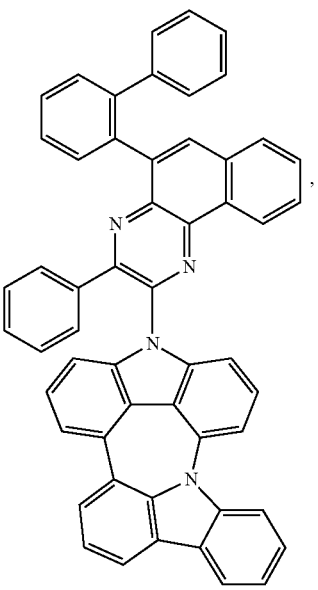
1-543
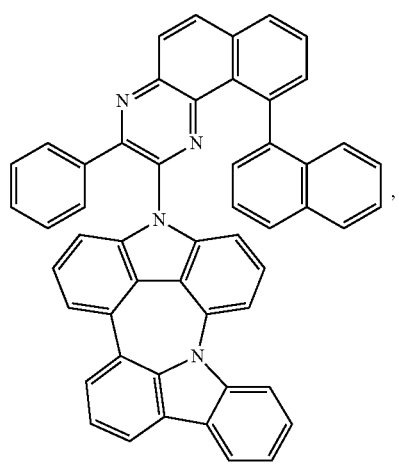
1-544
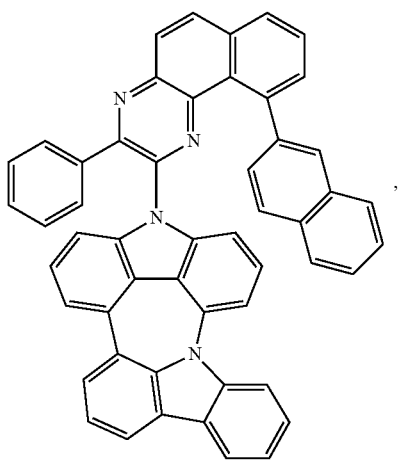
1-545
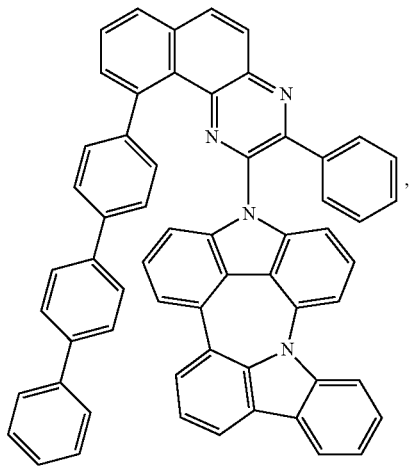
1-546
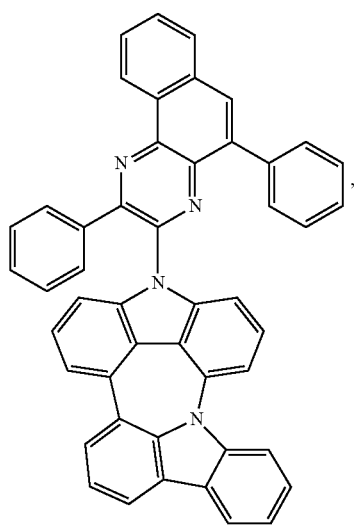
1-547
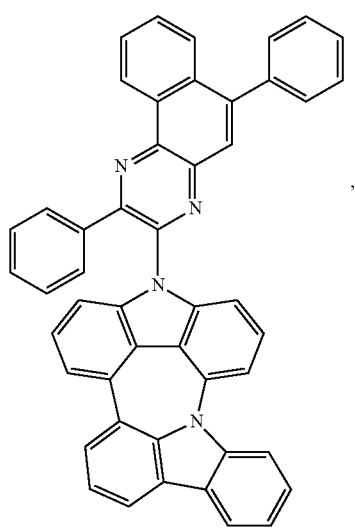

1-548
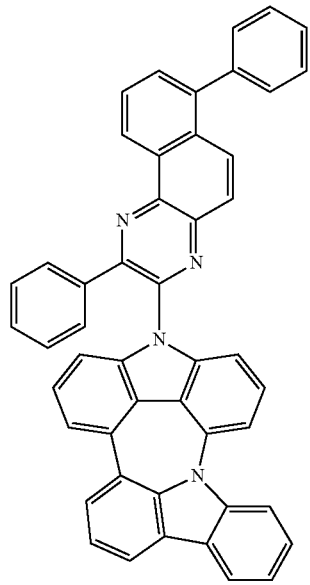
1-549
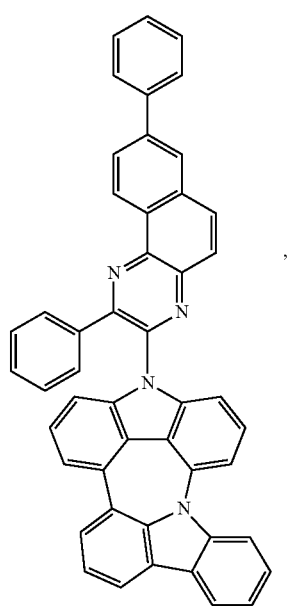
1-550
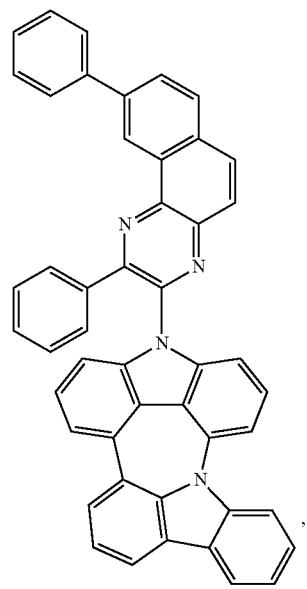
1-551
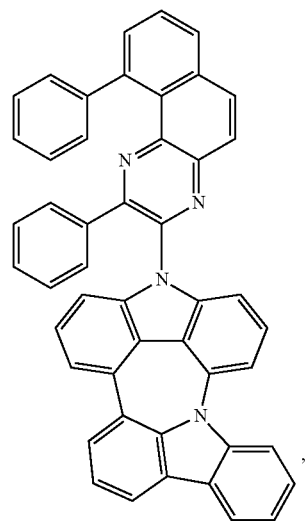
1-552
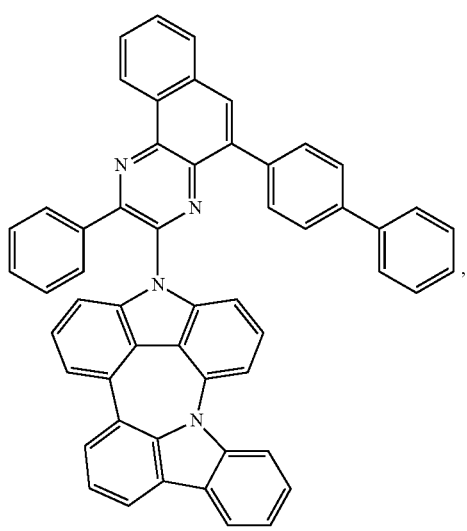

-continued
1-553
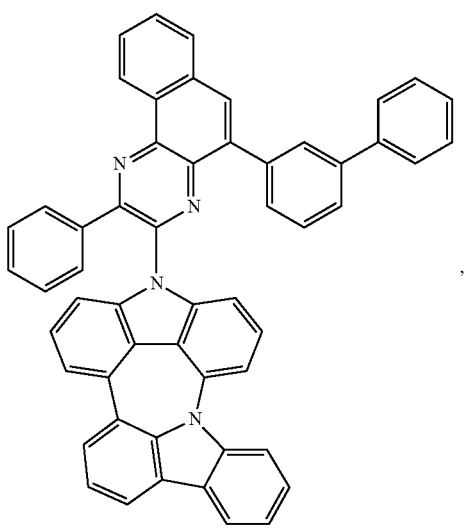
1-554
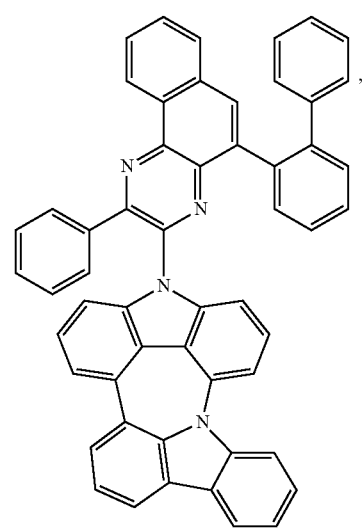
1-555
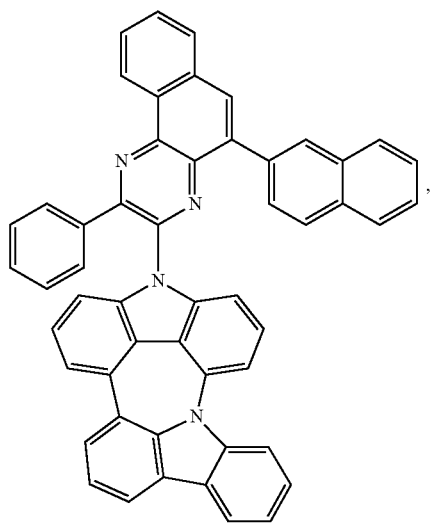
-continued
1-556
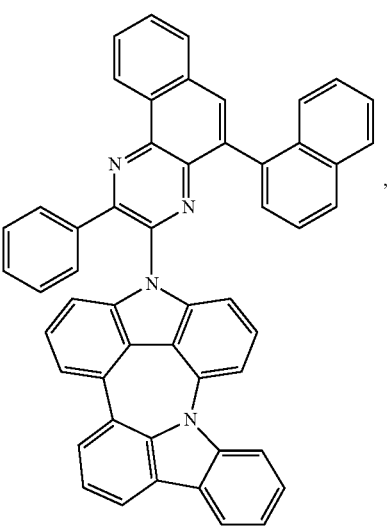
1-557
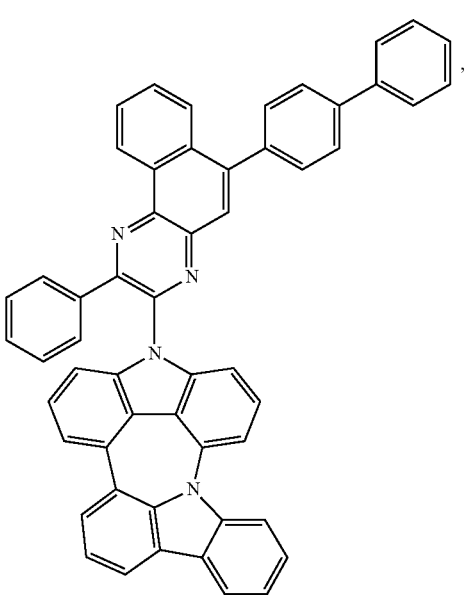
1-558
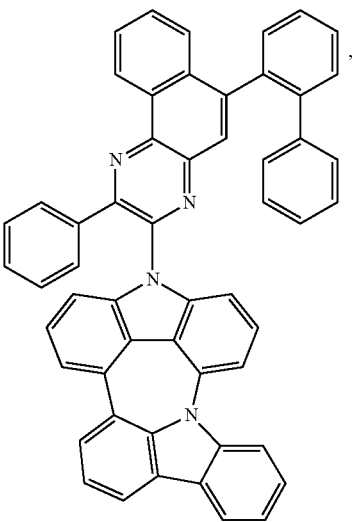

1-559
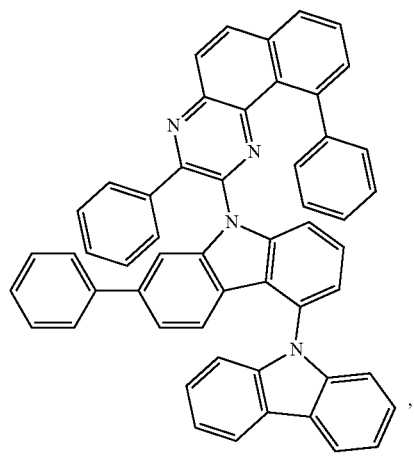
1-560
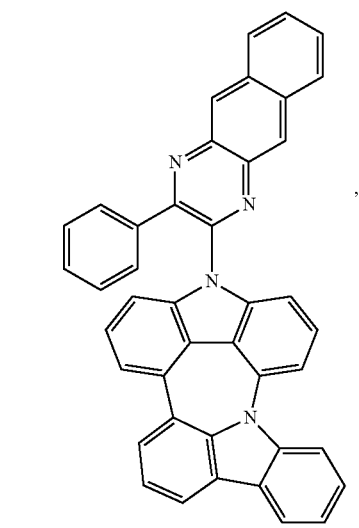
1-561
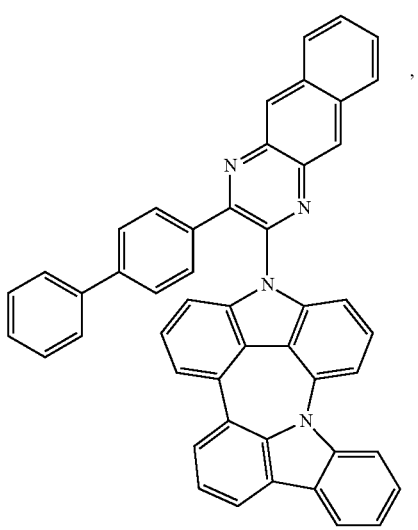
1-562
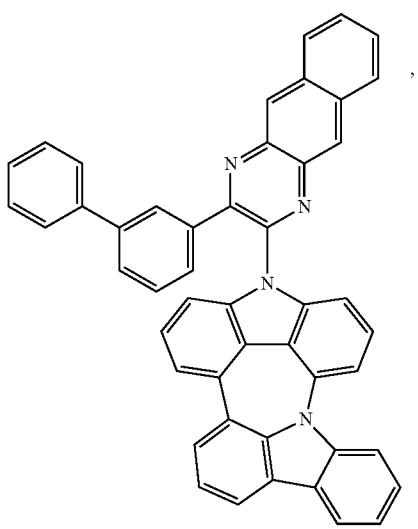
1-563
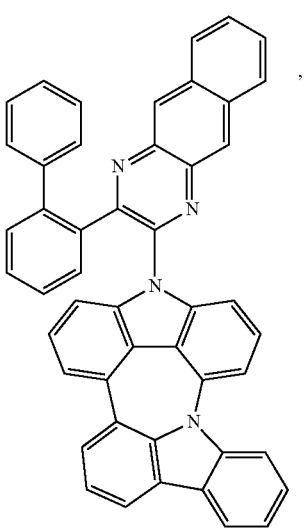
1-564
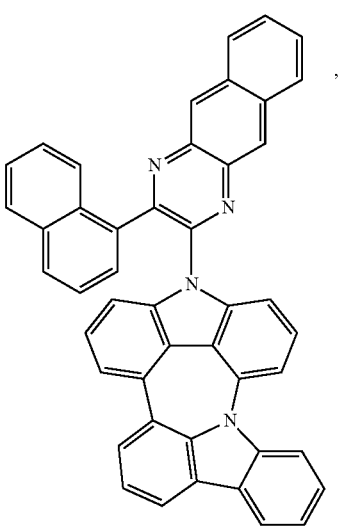

1-565
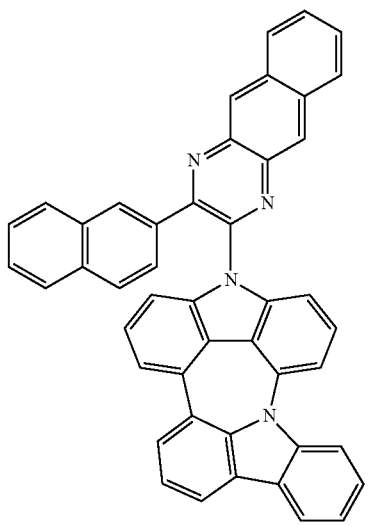
1-566
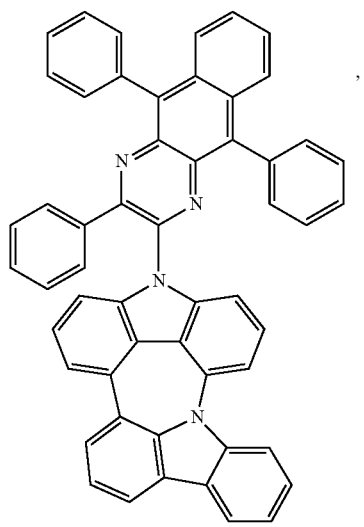
1-567
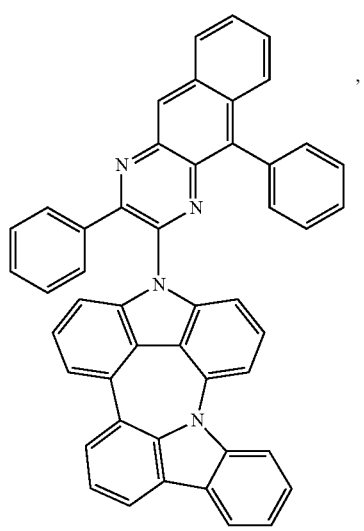
1-568
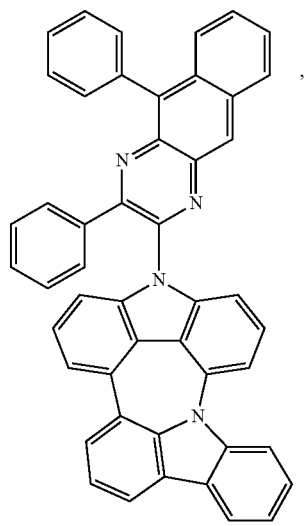
1-569
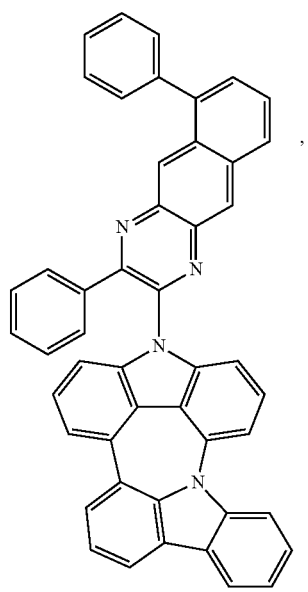

-continued
1-570
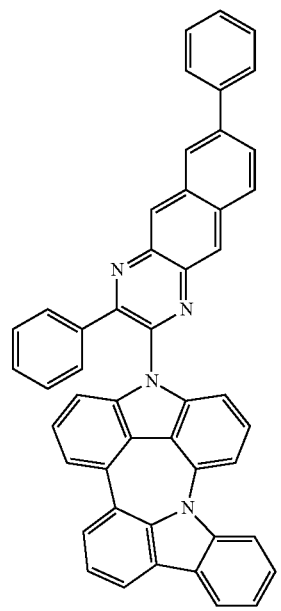
1-571
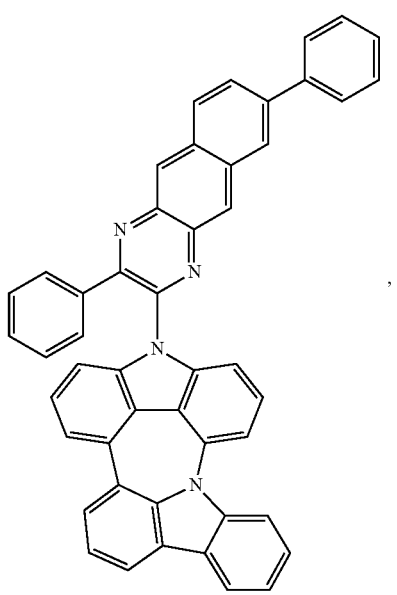
1-572
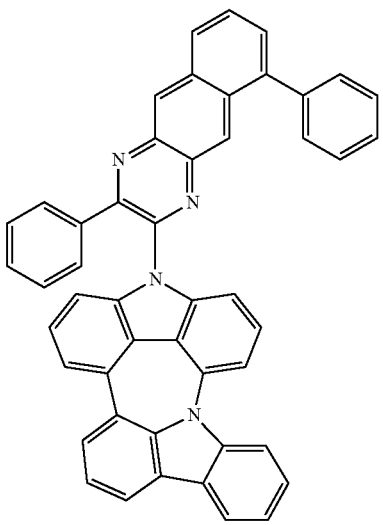
1-573
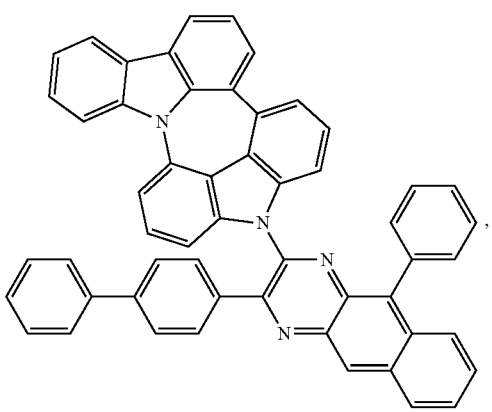
1-575
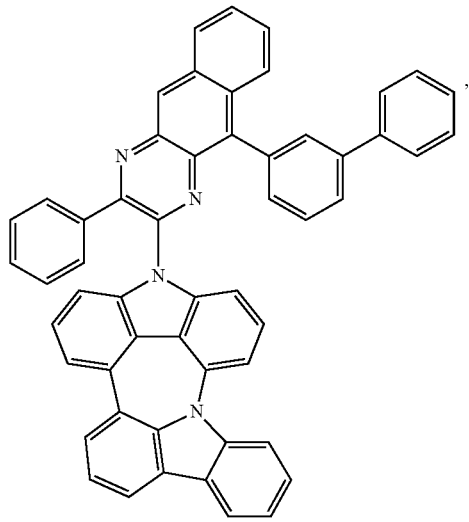

1-576
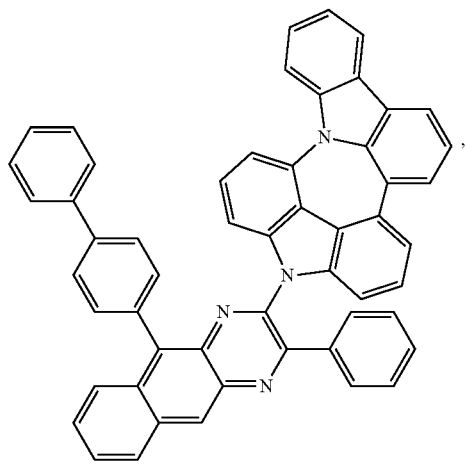
1-577
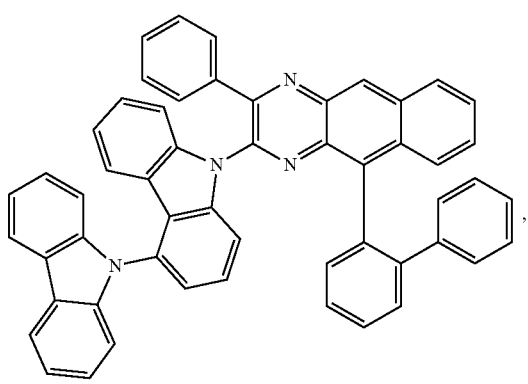
1-578
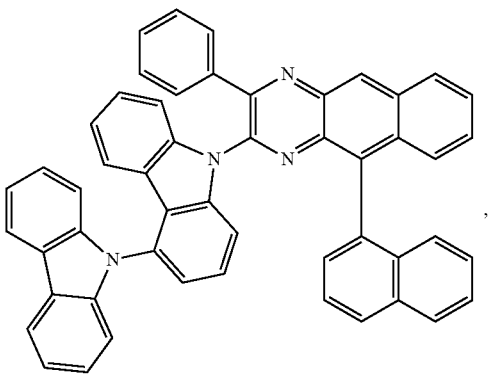
1-579
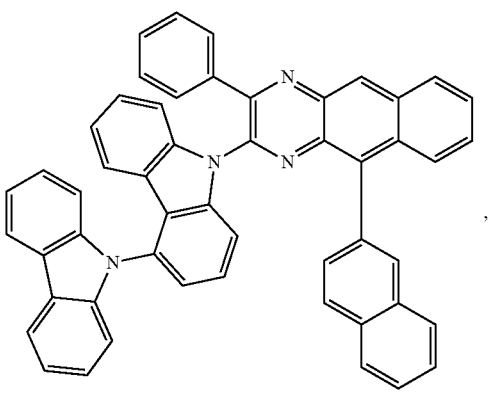
1-580
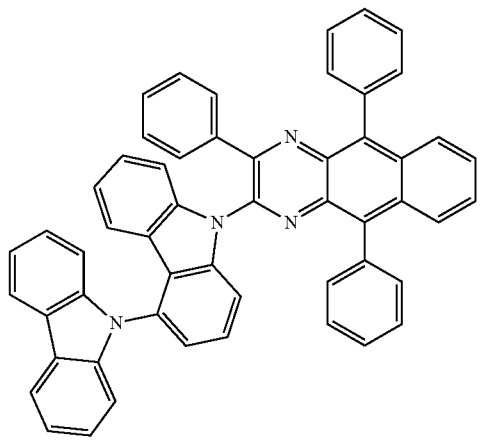
1-594
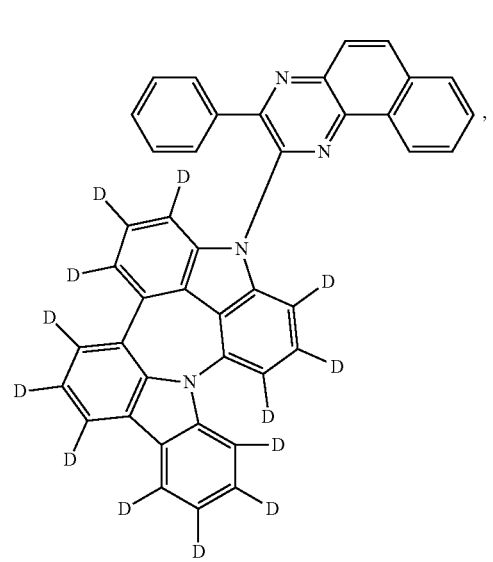
1-595
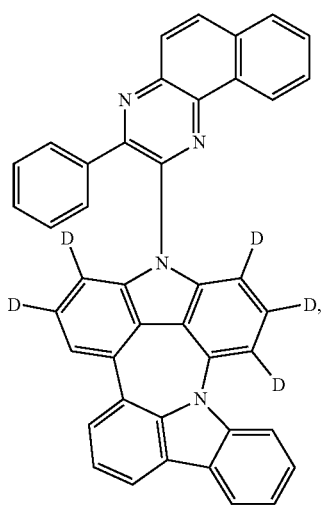

1-596 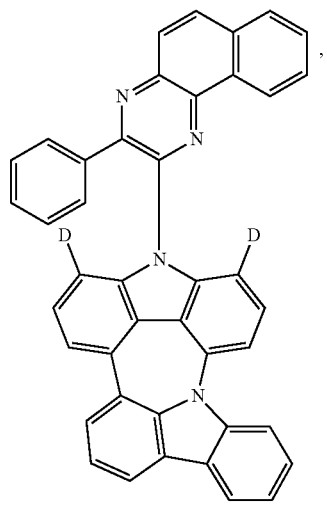
1-597 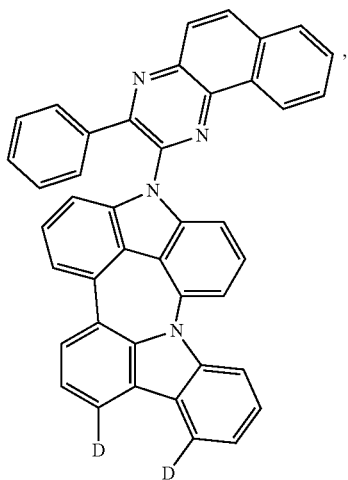
1-598 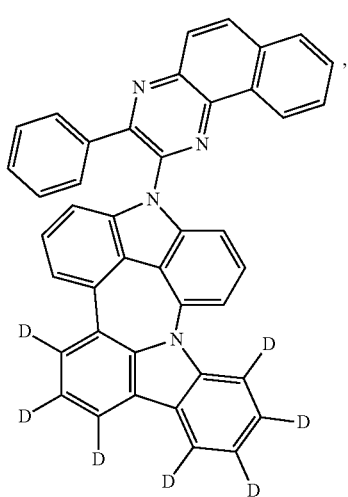
1-599 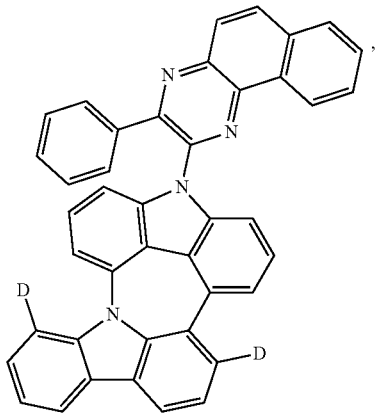
1-600 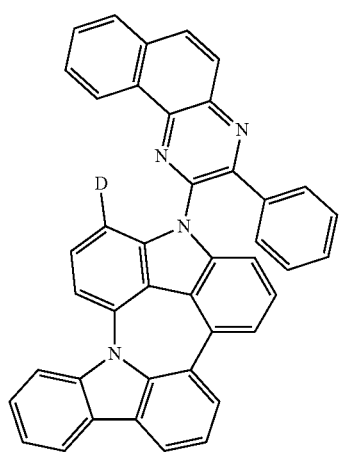
1-601 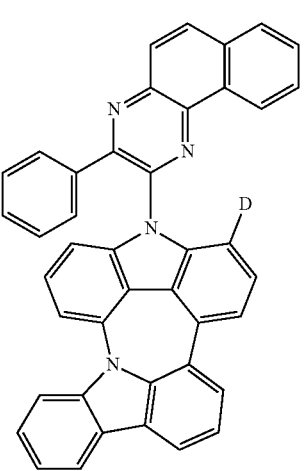

13. An electroluminescent device, comprising:
an anode,
a cathode, and
an organic layer disposed between the anode and the cathode, wherein the organic layer comprises a compound having a structure of H-L$_1$-E;
wherein H has a structure represented by Formula 1:

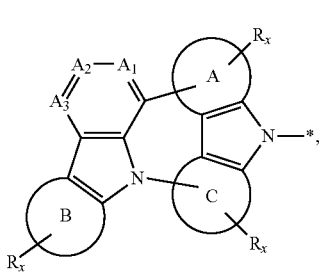

Formula 1 in Formula 1, A$_1$, A$_2$ and A$_3$ are, at each occurrence identically or differently, selected from CR; and the ring A, the ring B and the ring C are, at each occurrence identically or differently, selected from an aromatic ring having 6 to 18 carbon atoms or a hetero-aromatic ring having 3 to 18 carbon atoms;
R$_x$ represents mono-substitution, multiple substitutions or non-substitution; and
adjacent substituents R, R$_x$ can be optionally joined to form a ring;
wherein E has a structure represented by Formula 2-b, Formula 2-d, or Formula 2-f:

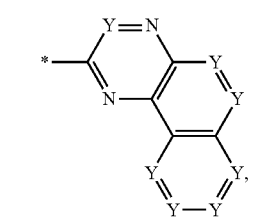

Formula 2-b

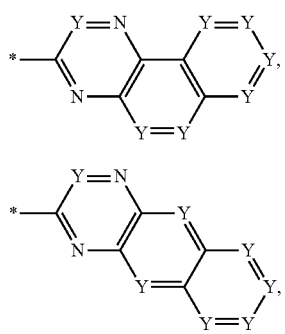

Formula 2-d

Formula 2-f wherein Y is, at each occurrence identically or differently, selected from CR$_y$;
L$_1$ is selected from a single bond, substituted or unsubstituted arylene having 6 to 30 carbon atoms, substituted or unsubstituted heteroarylene having 3 to 30 carbon atoms or combinations thereof;
wherein R, R$_x$ and R$_y$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

14. The electroluminescent device of claim 13, wherein the organic layer is a light-emitting layer, and the compound is a host material.

15. The electroluminescent device of claim 14, wherein the light-emitting layer further comprises a phosphorescent material.

16. The electroluminescent device of claim 15, wherein the phosphorescent material is a metal complex comprising at least one ligand, wherein the ligand comprises any one of the following structures:

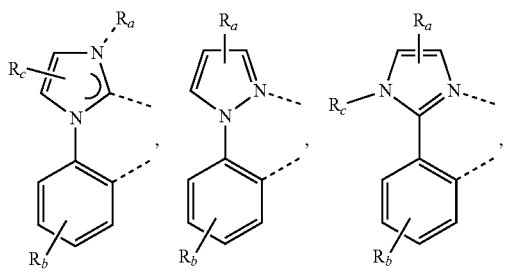

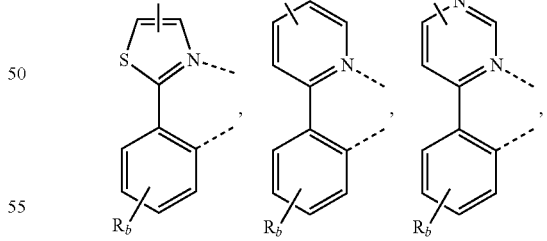

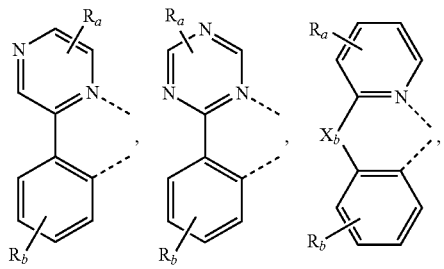

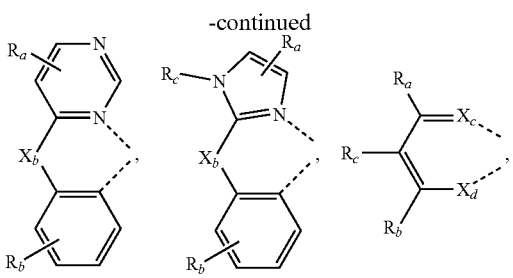

wherein $R_a$, $R_b$ and $R_c$ may represent mono-substitution, multiple substitutions or non-substitution, and may each be identical or different at each occurrence;

$X_b$ is selected from the group consisting of: O, S, Se, $NR_{N1}$ and $CR_{C1}R_{C2}$;

$X_c$ and $X_d$ are, at each occurrence identically or differently, selected from the group consisting of: O, S, Se and $NR_{N2}$;

$R_a$, $R_b$, $R_c$, $R_{N1}$, $R_{N2}$, $R_{C1}$ and $R_{C2}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof; and in the structure of the ligand, adjacent substituents can be optionally joined to form a ring.

17. The electroluminescent device of claim 16, wherein the metal complex comprises at least one ligand, wherein the ligand has the following structure:

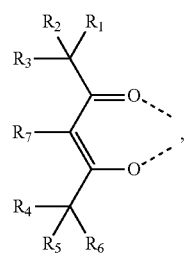

wherein $R_1$ to $R_7$ are each independently selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

18. The electroluminescent device of claim 16, wherein the phosphorescent material is an Ir, Pt or Os complex.

19. The electroluminescent device of claim 18, wherein the phosphorescent material is an Ir complex and has a structure of $Ir(L_a)(L_b)(L_c)$;

wherein $L_a$, $L_b$ and $L_c$ are, at each occurrence identically or differently, selected from any one of the above ligands.

20. The electroluminescent device of claim 15, wherein the phosphorescent material is selected from the group consisting of the following structures:

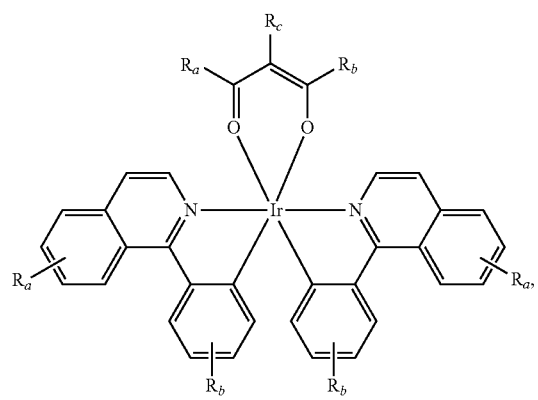

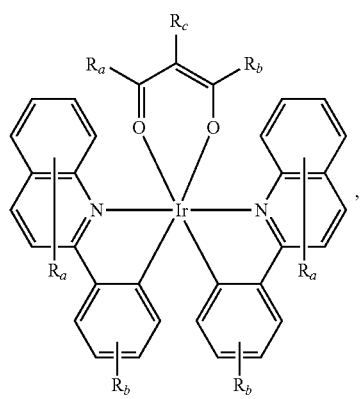

-continued

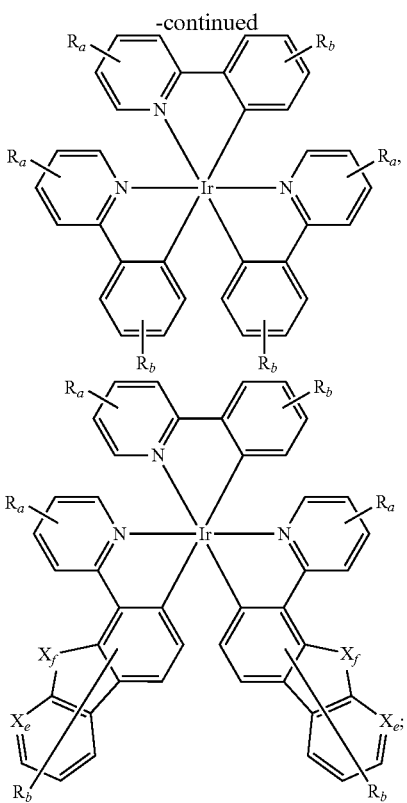

wherein $X_f$ is, at each occurrence identically or differently, selected from the group consisting of: O, S, Se, $NR_{N3}$ and $CR_{C3}R_{C4}$;

wherein $X_c$ is $CR_d$ or N;

$R_a$, $R_b$ and $R_c$ may represent mono-substitution, multiple substitutions or non-substitution, and may each be identical or different at each occurrence;

$R_a$, $R_b$, $R_c$, Rd, $R_{N3}$, $R_{C3}$ and $R_{C4}$ are, at each occurrence identically or differently, selected from the group consisting of: hydrogen, deuterium, halogen, substituted or unsubstituted alkyl having 1 to 20 carbon atoms, substituted or unsubstituted cycloalkyl having 3 to 20 ring carbon atoms, substituted or unsubstituted heteroalkyl having 1 to 20 carbon atoms, substituted or unsubstituted arylalkyl having 7 to 30 carbon atoms, substituted or unsubstituted alkoxy having 1 to 20 carbon atoms, substituted or unsubstituted aryloxy having 6 to 30 carbon atoms, substituted or unsubstituted alkenyl having 2 to 20 carbon atoms, substituted or unsubstituted aryl having 6 to 30 carbon atoms, substituted or unsubstituted heteroaryl having 3 to 30 carbon atoms, substituted or unsubstituted alkylsilyl having 3 to 20 carbon atoms, substituted or unsubstituted arylsilyl having 6 to 20 carbon atoms, substituted or unsubstituted amino having 0 to 20 carbon atoms, an acyl group, a carbonyl group, a carboxylic acid group, an ester group, a cyano group, an isocyano group, a sulfanyl group, a sulfinyl group, a sulfonyl group, a phosphino group and combinations thereof.

21. A compound formulation, comprising the compound of claim 1.

22. The compound of claim 4, wherein at least one of R and $R_x$ is selected from deuterium, phenyl, biphenyl or pyridyl.

23. The compound of claim 1, wherein $R_y$ is, at each occurrence identically or differently, selected from the group consisting of: hydrogen, deuterium, halogen, cyano, substituted or unsubstituted aryl having 6 to 30 carbon atoms, substituted or unsubstituted heteroaryl having 3 to 30 carbon atoms and combinations thereof.

24. The compound of claim 1, wherein $R_y$ is, at each occurrence identically or differently, selected from the group consisting of: hydrogen, deuterium, phenyl, biphenyl, naphthyl, 4-cyanophenyl, dibenzofuryl, dibenzothienyl, triphenylene, carbazolyl, 9-phenylcarbazolyl, 9,9-dimethylfluorenyl, pyridyl and phenylpyridyl.

25. The compound of claim 8, wherein the $R_y$ is selected from phenyl, biphenyl, naphthyl, 4-cyanophenyl, dibenzofuryl, dibenzothienyl, triphenylene, carbazolyl, 9-phenylcarbazolyl, 9,9-dimethylfluorenyl, pyridyl or phenylpyridyl.

26. The compound of claim 1, wherein the $L_1$ is selected from the group consisting of: a single bond, phenylene, naphthylene, biphenylene, terphenylene, triphenylene, pyridylene and thienylene.

* * * * *